US012624113B2

(12) United States Patent
Kai et al.

(10) Patent No.: US 12,624,113 B2
(45) Date of Patent: *May 12, 2026

(54) ANTI-HUMAN CCR1 MONOCLONAL ANTIBODY

(71) Applicants: KYOWA KIRIN CO., LTD., Tokyo (JP); KYOTO UNIVERSITY, Kyoto (JP)

(72) Inventors: Masayuki Kai, Tokyo (JP); Shinya Ogawa, Tokyo (JP); Makoto Taketo, Kyoto (JP); Kenji Kawada, Kyoto (JP); Hideyo Hirai, Kyoto (JP); Yoshiharu Sakai, Kyoto (JP); Taira Maekawa, Kyoto (JP)

(73) Assignees: KYOWA KIRIN CO., LTD., Tokyo (JP); KYOTO UNIVERSITY, Kyoto (JP)

( * ) Notice: Subject to any disclaimer, the term of this patent is extended or adjusted under 35 U.S.C. 154(b) by 94 days.

This patent is subject to a terminal disclaimer.

(21) Appl. No.: 18/459,844

(22) Filed: Sep. 1, 2023

(65) Prior Publication Data

US 2024/0026017 A1 Jan. 25, 2024

Related U.S. Application Data

(63) Continuation of application No. 16/631,655, filed as application No. PCT/JP2018/026958 on Jul. 18, 2018, now Pat. No. 11,912,775.

(30) Foreign Application Priority Data

Jul. 18, 2017 (JP) ................................. 2017-139157

(51) Int. Cl.
| | |
|---|---|
| *A61K 39/395* | (2006.01) |
| *A61P 43/00* | (2006.01) |
| *C07K 16/28* | (2006.01) |
| *C12N 5/12* | (2006.01) |
| *G01N 33/577* | (2006.01) |

(52) U.S. Cl.
CPC ........ *C07K 16/2866* (2013.01); *A61K 39/395* (2013.01); *A61P 43/00* (2018.01); *C12N 5/12* (2013.01); *G01N 33/577* (2013.01)

(58) Field of Classification Search
None
See application file for complete search history.

(56) References Cited

U.S. PATENT DOCUMENTS

| | | | |
|---|---|---|---|
| 6,329,510 | B1 | 12/2001 | Qin et al. |
| 6,756,035 | B2 | 6/2004 | Qin et al. |
| 2002/0037539 | A1 | 3/2002 | Qin et al. |
| 2002/0061305 | A1 | 5/2002 | Qin et al. |
| 2003/0099647 | A1 | 5/2003 | Deshpande |
| 2003/0103973 | A1 | 6/2003 | Rockwell |
| 2003/0157104 | A1 | 8/2003 | Waksal |
| 2004/0265304 | A1 | 12/2004 | Qin et al. |
| 2016/0340442 | A1 | 11/2016 | Kufe |
| 2017/0131282 | A1* | 5/2017 | Muller .............. G01N 33/6863 |
| 2017/0349658 | A1 | 12/2017 | Micklem |

FOREIGN PATENT DOCUMENTS

| | | |
|---|---|---|
| AU | 2004200923 | 4/2004 |
| JP | 2003-517810 | 6/2003 |
| WO | 2017-126587 | 7/2017 |

OTHER PUBLICATIONS

Neote et al., "Molecular Cloning, Functional Expression, and Signaling Characteristics of a C—C Chemokine Receptor", Cell, 1993, vol. 72, pp. 415-425.

Horuk, "Targeting CCR1", Chemokine Receptors as Drug Targets, Eds. Martine J. Smit, Sergio A. Lira, and Rob Leurs, 2010, vol. 46, pp. 323-338.

Ono et al., "Chemokines: Roles in leukocyte development, trafficking, and effector function", Journal of Allergy and Clinical Immunology, 2003, vol. 111, pp. 1185-1199.

Berahovich et al., "Proteolytic Activation of Alternative CCR1 Ligands in Inflammation", The Journal of Immunology, 2005, vol. 174, pp. 7341-7351.

Ludeman et al., "The structural role of receptor tyrosine sulfation in chemokine recognition", British Journal of Pharmacology, 2014, vol. 171, pp. 1167-1179.

Su et al., "Preparation of specific polyclonal antibodies to a C—C chemokine receptor, CCR1, and determination of CCR1 expression on various types of leukocytes", Journal of Leukocyte Biology, 1996, vol. 60, pp. 658-666.

Weber et al., "Specialized roles of the chemokine receptors CCR1 and CCR5 in the recruitment of monocytes and $T_H1$-like/CD45RO$^+$ T cells", Blood, 2001, vol. 97, No. 4, pp. 1144-1146.

Phillips et al., "Variations in Eosinophil Chemokine Responses: An Investigation of CCR1 and CCR3 Function, Expression in Atopy, and Identification of a Functional CCR1 Promoter", The Journal of Immunology, 2003, vol. 170, pp. 6190-6201.

(Continued)

*Primary Examiner* — Michael D Pak
(74) *Attorney, Agent, or Firm* — Wenderoth, Lind & Ponack, L.L.P

(57) ABSTRACT

A monoclonal antibody is provided which binds to a human CC chemokine receptor 1 (CCR1) and inhibits activation of the human CCR1, or an antibody fragment thereof. The monoclonal antibody binds to an extracellular region of a human CCR1 and inhibits activation of the human CCR1 by a human CC chemokine ligand 15 (CCL15). An antibody fragment thereof, a hybridoma producing the antibody, a nucleic acid having a nucleotide sequence encoding the antibody or the antibody fragment, a transformant cell containing a vector containing the nucleic acid, a method for producing the antibody or the antibody fragment using the hybridoma or the transformant cell; a therapeutic agent and a diagnostic agent containing the antibody or the antibody fragment, and a method for treating and diagnosing a CCR1-related disease using the antibody or the antibody fragment are also provided.

16 Claims, 7 Drawing Sheets

Specification includes a Sequence Listing.

(56)                    References Cited

OTHER PUBLICATIONS

Cheng et al., "Granulocyte-Macrophage Colony Stimulating Factor Up-Regulates CCR1 in Human Neutrophils", The Journal of Immunology, 2001, vol. 166, pp. 1178-1184.

Corcione et al., "Chemotaxis of human tonsil B lymphocytes to CC chemokine receptor (CCR) 1, CCR2 and CCR4 ligands is restricted to non-germinal center cells", International Immunology, 2002, vol. 14, No. 8, pp. 883-892.

Kitamura et al., "SMAD4-deficient intestinal tumors recruit CCR1+ myeloid cells that promote invasion", Nature genetics, 2007, vol. 39, No. 4, pp. 467-475.

Inamoto et al., "Loss of SMAD4 Promotes Colorectal Cancer Progression by Accumulation of Myeloid-Derived Suppressor Cells through CCL15-CCR1 Chemokine Axis", Clinical Cancer Research, 2015, vol. 22, No. 2, pp. 492-501.

D'Ambrosio et al., "Chemokine receptors in inflammation: an overview", Journal of Immunological Methods, 2003, vol. 273, pp. 3-13.

Schall et al., "Overcoming hurdles in developing successful drugs targeting chemokine receptors", Nature Reviews Immunology, 2011, vol. 11, pp. 355-363.

Lebre et al., "Why CCR2 and CCR5 Blockade Failed and Why CCR1 Blockade Might Still Be Effective in the Treatment of Rheumatoid Arthritis", PLoS One, 2011, vol. 6, No. 7, 7 pages.

Oba et al., "MIP-1α utilizes both CCR1 and CCR5 to induce osteoclast formation and increase adhesion of myeloma cells to marrow stromal cells", Experimental Hematology, 2005, vol. 33, pp. 272-278.

Hwang et al., "Angiogenic activity of human CC chemokine CCL15 in vitro and in vivo", FEBS Letters, 2004, vol. 570, pp. 47-51.

Itatani et al., "Mechanism of metastasis of colorectal cancer to liver through CCL15-CCR1 axis, and expectation of suppressing liver metastasis by CCR1 inhibitor", Journal of Japan Surgical Society, 2013, vol. 114, special extra edition (2), p. 387, with partial translation.

International Search Report issued Oct. 16, 2018 in International (PCT) Patent Application No. PCT/JP2018/026958, with English Translation.

Written Opinion of the International Searching Authority issued Oct. 16, 2018 in International (PCT) Patent Application No. PCT/JP2018/026958, with English Translation.

Zoffmann et al., "Identification of the Extracellular Loop 2 as the Point of Interaction between the N Terminus of the Chemokine MIP-1α and Its CCR1 Receptor", Molecular Pharmacology, 2002, vol. 62, No. 3, pp. 729-736.

Extended European Search Report issued Mar. 3, 2021 in corresponding European Patent Application No. 18836123.2.

Office Action issued Aug. 15, 2022 in corresponding Taiwanese Patent Application No. 107124834, with English language translation.

Office Action issued Feb. 14, 2023 in CN Appln. No. 201880048205.3 (with English translation).

Office Action issued Jul. 18, 2023 in Korean Application No. 10-2020-7001464 (with English translation).

Examination Report No. 2 issued Nov. 11, 2024 in corresponding Australian Patent Application No. 2018302647.

Office Action issued Jun. 17, 2024 in Australian Patent Application No. 2018302647.

Office Action issued Aug. 13, 2024 in Canadian Patent Application No. 3,070,342.

Office Action issued Nov. 22, 2024 in corresponding Taiwanese Patent Application No. 107124834, with machine English translation.

Office Action issued Dec. 3, 2025 in Canadian Patent Application No. 3,070,342.

* cited by examiner

FIG. 4

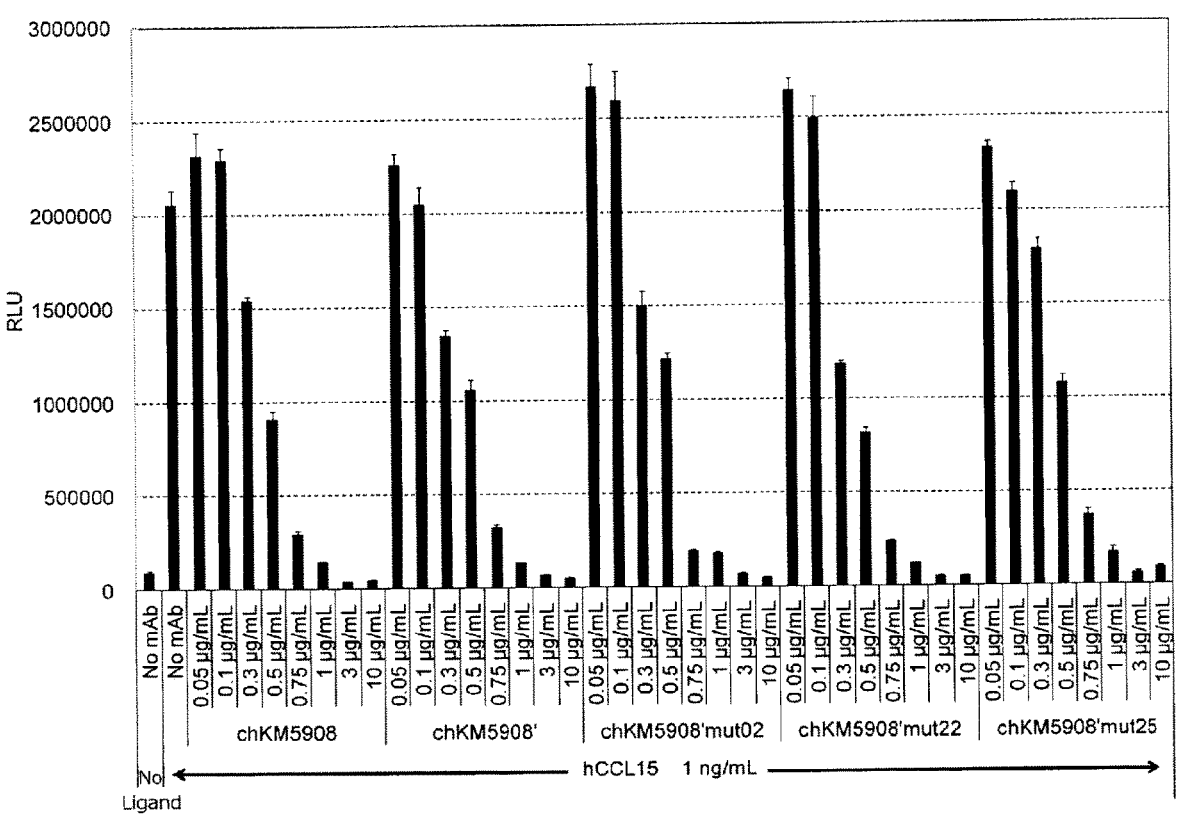

FIG. 5

```
              1234567890123456789 0123 4567890123456789 012345678901234 5678901
mAb5-06 VL   DVVMTQTPLSLPVSLGDQASIFC RSSQSLVHRNGITFFH WYLQKPGQSPKLLIY KISNRFS
LV0          DIVMTQSPLSLPVTPGEPASISC                 WYLQKPGQSPQLLIY
LV1a         DIVMTQSPLSLPVTPGEPASISC                 WYLQKPGQSPKLLIY
LV1b         DIVMTQSPLSLPVTLGEPASISC                 WYLQKPGQSPQLLIY
LV2a         DIVMTQSPLSLPVTLGEPASISC    CDR L1       WYLQKPGQSPKLLIY   CDR L2
LV2b         DIVMTQSPLSLPVTPGEPASISC                 WYLQKPGQSPKLLIY
LV4          DIVMTQSPLSLPVTLGEPASISC                 WYLQKPGQSPKLLIY
LV5          DVVMTQSPLSLPVTLGEPASISC                 WYLQKPGQSPKLLIY
```

```
              2345678901234567890123456789 0123 456789012 3456789012
mAb5-06 VL   GVPDRFSGSGSGTDFTLKISRVAPDDLGVYFC SQGTHVPPT FGGGTKLEIK
LV0          GVPDRFSGSGSGTDFTLKISRVEAEDVGVYYC           FGQGTKVEIK
LV1a         GVPDRFSGSGSGTDFTLKISRVEAEDVGVYYC           FGQGTKVEIK
LV1b         GVPDRFSGSGSGTDFTLKISRVEAEDVGVYYC           FGQGTKVEIK
LV2a         GVPDRFSGSGSGTDFTLKISRVEAEDVGVYYC   CDR L3   FGQGTKVEIK
LV2b         GVPDRFSGSGSGTDFTLKISRVEAEDVGVYFC           FGQGTKVEIK
LV4          GVPDRFSGSGSGTDFTLKISRVEAEDVGVYFC           FGQGTKLEIK
LV5          GVPDRFSGSGSGTDFTLKISRVEAEDVGVYFC           FGQGTKLEIK
```

FIG. 6

```
              123456789012345678901234567890 12345 67890123456789 0123456789012345
mAb5-06 VH    QVQLKQSGPGLVQPSQSLSITCTVSGFSLN NYGVH WVRQPPGKGLEWLG VIWSAGTTVYNAAAIS
HV0           QVQLQESGPGLVKPSQTLSLTCTVSGGSVS       WIRQPPGKGLEWIG
HV14          QVQLQQSGPGLVKPSQTLSITCTVSGFSLN CDR   WVRQPPGKGLEWLG      CDR H2
HV17          QVQLQQSGPGLVKPSQTLSITCTVSGFSLN H1    WVRQPPGKGLEWLG
```

```
              6789012345678901234567890123 4567 89012345678 90123456789
mAb5-06 VH    RLSISKDDSKSQVFFKMNSLQAGDTAIYYCAK DGSRYYTAMDY WGQGTSVTVSS
HV0           RVTISVDTSKNQFSLKLSSVTAADTAVYYCAR             WGQGTLVTVSS
HV14          RLTISKDTSKNQVSFKMSSLTAADTAVYYCAK CDR H3      WGQGTLVTVSS
HV17          RLTISKDDSKSQVSFKMSSLTAADTAIYYCAK             WGQGTLVTVSS
```

FIG. 7

```
              1234567890123456789 0123 4567890123456789 012345678901234 5678901
KM5907 VL     DVLMTQTPLSLPVSLGDQVSISC RSSQSIVHSNGNTFLE WYLKKPGQSPKLLIY KVSSRFS
LV0           DIVMTQTPLSLPVTSGEPASISC                  WYLQKPGQSPQLLIY
LV1a          DIVMTQTPLSLPVTSGEPASISC                  WYLKKPGQSPQLLIY
LV1b          DIVMTQTPLSLPVTSGEPASISC                  WYLQKPGQSPKLLIY
LV1c          DIVMTQTPLSLPVTSGEPVSISC     CDR L1       WYLQKPGQSPQLLIY   CDR L2
LV2a          DIVMTQTPLSLPVTSGEPASISC                  WYLKKPGQSPKLLIY
LV2b          DIVMTQTPLSLPVTSGEPVSISC                  WYLKKPGQSPQLLIY
LV4           DIVMTQTPLSLPVTLGEPVSISC                  WYLKKPGQSPKLLIY
LV6           DVVMTQTPLSLPVTLGEPASISC                  WYLKKPGQSPKLLIY
```

```
              234567890123456789012345678901234567890123 456789012 3456789012
KM5907 VL     GVPDRFSGSGSGTDFTLKIRRVEADDLGVYYC FQGSHIPWT FGGGTNLEIK
LV0           GVPDRFSGSGSGTDFTLKISRVEAEDVGVYYC           FGGGTKVEIK
LV1a          GVPDRFSGSGSGTDFTLKISRVEAEDVGVYYC           FGGGTKVEIK
LV1b          GVPDRFSGSGSGTDFTLKISRVEAEDVGVYYC           FGGGTKVEIK
LV1c          GVPDRFSGSGSGTDFTLKISRVEAEDVGVYYC CDR L3    FGGGTKVEIK
LV2a          GVPDRFSGSGSGTDFTLKISRVEAEDVGVYYC           FGGGTKVEIK
LV2b          GVPDRFSGSGSGTDFTLKISRVEAEDVGVYYC           FGGGTKVEIK
LV4           GVPDRFSGSGSGTDFTLKISRVEAEDVGVYYC           FGGGTKVEIK
LV6           GVPDRFSGSGSGTDFTLKISRVEAEDVGVYYC           FGGGTKLEIK
```

FIG. 8

```
              12345678901234567890123456 7890 12345 67890123456789 01234567890123456
KM5907 VH  EVQVVESGGNLVKPGGSLKLSCSASGFTFS RYGMS WVRQTPDKRLEWVA  SISATFTYTYYTDNVKG
HV0        EVQLLESGGGLVQPGGSLRLSCAASGFTFS       WVRQAPGKGLEWVS
HV1        EVQLLESGGGLVQPGGSLRLSCAASGFTFS       WVRQAPGKRLEWVS
HV2a       EVQLLESGGGLVQPGGSLRLSCAASGFTFS       WVRQAPGKRLEWVS
HV2b       EVQLLESGGGLVQPGGSLRLSCAASGFTFS       WVRQAPGKGLEWVA
HV3a       EVQLLESGGGLVQPGGSLRLSCAASGFTFS  CDR  WVRQAPGKRLEWVS   CDR H2
HV3b       EVQLLESGGGLVQPGGSLRLSCAASGFTFS  H1   WVRQAPGKRLEWVA
HV3c       EVQLLESGGGLVQPGGSLRLSCAASGFTFS       WVRQAPGKRLEWVS
HV4        EVQLLESGGGLVQPGGSLRLSCAASGFTFS       WVRQAPGKGLEWVA
HV7        EVQVLESGGGLVQPGGSLRLSCAASGFTFS       WVRQAPGKRLEWVA
```

```
              7890123456789012345678901234 5678 901234567 89012345678
KM5907 VH  RFTISRDNAKNTLYLQMSSLRSEDTGMYYCTR QDNYAWFDS WGQGTLVTVSA
HV0        RFTISRDNSKNTLYLQMNSLRAEDTAVYYCAK            WGQGTLVTVSS
HV1        RFTISRDNSKNTLYLQMNSLRAEDTAVYYCAK            WGQGTLVTVSS
HV2a       RFTISRDNSKNTLYLQMNSLRAEDTAVYYCAR            WGQGTLVTVSS
HV2b       RFTISRDNSKNTLYLQMNSLRAEDTAVYYCAR            WGQGTLVTVSS
HV3a       RFTISRDNSKNTLYLQMNSLRAEDTGVYYCAR  CDR H3    WGQGTLVTVSS
HV3b       RFTISRDNSKNTLYLQMNSLRAEDTAVYYCTK            WGQGTLVTVSS
HV3c       RFTISRDNSKNTLYLQMNSLRAEDTGVYYCTK            WGQGTLVTVSS
HV4        RFTISRDNSKNTLYLQMNSLRAEDTGVYYCTR            WGQGTLVTVSS
HV7        RFTISRDNSKNTLYLQMNSLRAEDTGMYYCTR            WGQGTLVTVSS
```

FIG. 9

```
             123456789012345678901234 5678901234 567890123456789 0123456
KM5916 VL  DIQMTQSPSSLSASLGGKVTITC KASQDINKYIA WYQHKPGQGPRLLIH YTSSLQP
LV0        DIQMTQSPSSLSASVGDRVTITC             WYQQKPGKAPKLLIH
LV1a       DIQMTQSPSSLSASVGDRVTITC  CDR L1     WYQHKPGKGPKLLIH   CDR L2
```

```
             78901234567890123456789012345678 90123456 7890123456
KM5916 VL  GIPSRFSGSGSGRDYSFSISNLEPEDIATYYC LQYDYTMT FGGGTKLEIR
LV0        GVPSRFSGSGSGTDFSFTISSLQPEDLATYYC          FGGGTKVEIK
LV1a       GVPSRFSGSGSGTDFSFTISSLQPEDLATYYC CDR L3   FGGGTKVEIK
```

FIG.10

```
              1234567890123456789012345678901234567890 12345 67890123456789 01234567890123456
KM5916 VH     DVKLVESGEGLVKPGGSLKLSCAASGFTFS RNAMS WVRQTPEKRLEWVA YISSGSDYIYYADTVKG
HV0           QVQLQESGGGLVKPGGSLKLSCAASGFTFS       WVRQTPDKRLEWVA
HV1           QVQLQESGGGLVKPGGSLKLSCAASGFTFS  CDR  WVRQTPDKRLEWVA        CDR H2
HV3           QVQLQESGGGLVKPGGSLKLSCAASGFTFS  H1   WVRQTPEKRLEWVA
```

```
              78901234567890123456789012345678 901234567890 12345678901
KM5916 VH     RFTVSRDNARNTLYLQMTSLRSEDTAMYFCTR FSYGYGKNAPDY WGQGTSVTVSS
HV0           RFTISRDNAKNTLYLQMSSLKSEDTAMYYCAR              WGQGTMVTVSS
HV1           RFTISRDNAKNTLYLQMSSLKSEDTAMYYCTR  CDR H3      WGQGTMVTVSS
HV3           RFTISRDNAKNTLYLQMSSLRSEDTAMYYCTR              WGQGTMVTVSS
```

FIG. 11

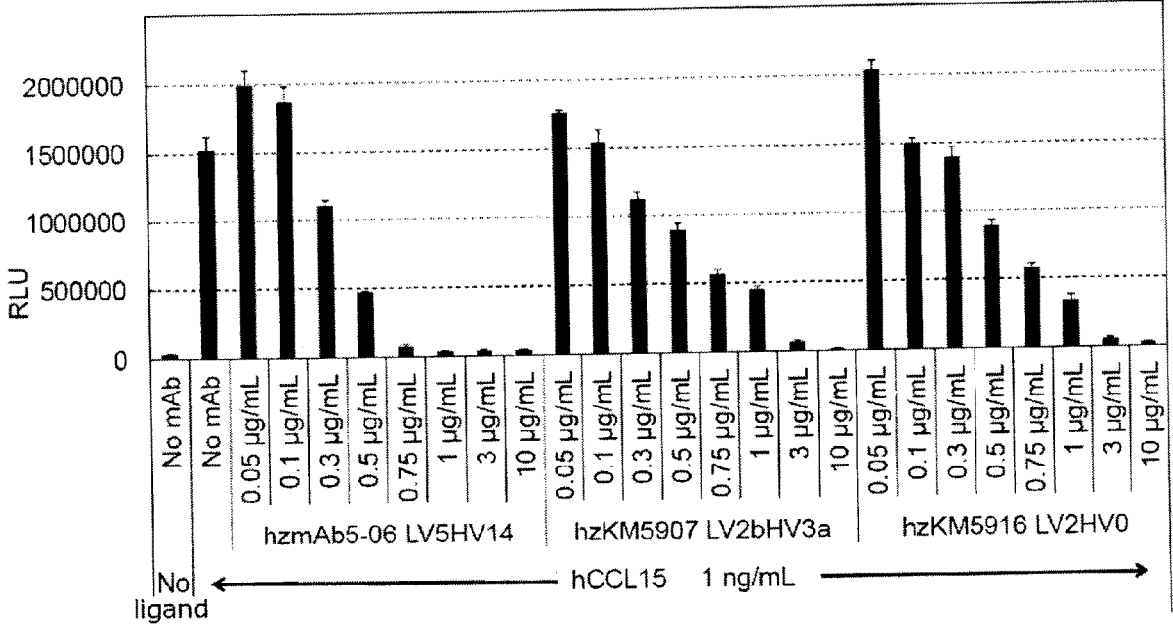

ANTI-HUMAN CCR1 MONOCLONAL ANTIBODY

SEQUENCE LISTING

A sequence listing in electronic (XML file) format is filed with this application and incorporated herein by reference. The name of the XML file is "Sequence Listing.xml"; the file was created on Aug. 29, 2023; the size of the file is 259,647 bytes.

TECHNICAL FIELD

The present invention relates to a monoclonal antibody which binds to an extracellular region of a human CC chemokine receptor 1 (CC chemokine receptor 1, hereinafter, referred to as human CCR1) and inhibits activation of the human CCR1 by a human CC chemokine ligand (hereinafter, referred to as human CCL) 15, or an antibody fragment thereof, a hybridoma producing the antibody, a nucleic acid having a nucleotide sequence encoding the antibody or the antibody fragment, a transformant cell containing a vector containing the nucleic acid, a method for producing the antibody or the antibody fragment using the hybridoma or the transformant cell; a therapeutic agent and a diagnostic agent containing the antibody or the antibody fragment, and a method for treating and diagnosing a CCR1-related disease using the antibody or the antibody fragment.

BACKGROUND ART

CCR1 has other names such as surface antigen classification (cluster of differentiation, CD) 191, CKR-1, HM145, Macrophage inflammatory protein 1α receptor (MIP1α R), CMKBR1, SCYAR1, or the like.

A gene encoding human CCR1 is identified in 1993 (NPT 1). The cDNA sequence (SEQ ID NO: 1) and amino acid sequence (SEQ ID NO: 2) of human CCR1 are publicly available. For example, in National Center for Biotechnology Information (NCBI), the cDNA sequence can be referred to as NM_001295, and the protein amino acid sequence can be referred to as NP_001286. The cDNA sequence (SEQ ID NO: 3) and amino acid sequence (SEQ ID NO: 4) of a mouse CCR1 are also disclosed. In NCBI, the cDNA sequence can be referred to as NM_009912, and the protein amino acid sequence can be referred to as NP_034042.

CCR1 is a G protein-coupled receptor (hereinafter, referred to as GPCR) having a seven-transmembrane structure, and is a membrane protein consisting of a total length of 355 amino acids. As ligands for the human CCR1, human CCL3, CCL5, CCL8, CCL14, CCL15, CCL16, and CCL23 have been reported (NPL 2). Further, as ligands for mouse CCR1, mouse CCL3, CCL5, CCL7, and CCL9 have been reported (NPL 3).

The human CCL15 is a ligand included in the C-C chemokine family and consists of a total of 92 amino acids. CCR1 and CCR3 are known to function as CCL15 receptors. It has been known that CCL15 exhibits stronger activity when an N-terminus thereof is degraded by the action of proteases and becomes an activated form of about 68 amino acids (NPL 4).

The activation of the chemokine receptors including CCR1 is considered to occur through the following two steps (NPL 5). As a step 1, the interaction between the chemokine (ligand) and an N-terminus extracellular region of the receptor is generated. As a step 2, the N-terminus region of the chemokine interacts with the extracellular loop region of the receptor, and as a result of the structural change of the receptor, a signal is transmitted into the cell.

In the intracellular signal transduction of GPCRs, G proteins α, β, and γ trimers associated with a C-terminus of GPCR are activated in response to structural changes in GPCR generated by ligand binding, and α subunits is dissociated from a βγ complex. The α subunit acts on further downstream factors and activates signal transduction pathways. When phospholipase C (hereinafter, referred to as "PLC") is activated by the activation of the α subunit, phosphatidylinositol (4,5) diphosphate [phosphatidylinositol (4,5) bisphosphate, $PIP_2$] is decomposed, and inositol triphosphate ($IP_3$) and diacylglycerol (DAG) are produced.

$IP_3$ acts on an endoplasmic reticulum, releases calcium ions ($Ca^{2+}$) into cells, and causes various cellular responses via calmodulin. This increase in an intracellular calcium concentration can be measured using a fluorescent calcium indicator or the like, and can be used as an index of GPCR activation. For CCR1, it is also possible to measure the activation of intracellular signals by this method.

Expression of the human CCR1 in various blood cells such as neutrophils, eosinophils, basophils, monocytes, macrophages, dendritic cells, NK cells, T cells, and B cells has been reported so far (NPLs 6 to 10). In recent years, it has been reported that cell clusters called immature myeloid cells (hereinafter, referred to as iMC) and myeloid derived suppressor cells (hereinafter, referred to as MDSC) that exist in cancer microenvironment and promote progress of cancer express CCR1 (NPLs 11 and 12).

CCR1 has been suggested to be involved in various autoimmune diseases and inflammatory diseases such as rheumatoid arthritis, multiple sclerosis, and chronic obstructive pulmonary disease (NPL 13). In addition, the expression in iMC and MDSC described above suggests that CCR1 contributes to the progress of cancer and exacerbation process (NPLs 11 and 12).

For example, in human colorectal cancer, it has been known that mutation of SMAD4, which is a tumor suppressor gene, or disappearance of SMAD4 protein is seen at a certain frequency, and deficiency of SMAD4 is considered to be a poor prognostic factor. In recent years, the deficiency of SMAD4 has become a factor that draws CCR1-positive iMC or MDSC into the tumor environment through increased expression of CCL15, and the mechanism by which these cells assist cancer invasion or metastasis by secretion of matrix metalloprotease (MMP) and an immunosuppressive action, and worsens the prognosis of patients (NPLs 11 and 12).

Examples of the existing low molecule CCR1 inhibitor include CP481,715 (Pfizer), MLN3897 (Millennium), BX-471 (Berlex), and CCX-354 (Chemocentryx). These low molecule inhibitors have been tested with patients having autoimmune or inflammatory diseases such as rheumatoid arthritis, multiple sclerosis, and chronic obstructive pulmonary disease; however, none of them have shown effectiveness (NPL 14).

Among the existing anti-CCR1 antibodies, those that have been reported to inhibit CCR1 activation in the literature include 141-2 (MBL, #D063-3) (NPL 15), 53504 (R & D Systems, #MAB145) (NPL 16) and 2D4 (Millennium) (PTL 1).

3

CITATION LIST

Patent Literature

[PTL 1] U.S. Pat. No. 6,756,035

Non-Patent Literature

[NPL 1] Neote, Kuldeep, et al. "Molecular cloning, functional expression, and signaling characteristics of a CC chemokine receptor." Cell 72.3 (1993): 415-425.

[NPL 2] Mannhold, Raimund, Hugo Kubinyi, and Gerd Folkers. Chemokine receptors as drug targets. Eds. Martine J. Smit, Sergio A. Lira, and Rob Leurs. Vol. 46. John Wiley & Sons, 2010.

[NPL 3] Ono, Santa Jeremy, et al. "Chemokines: roles in leukocyte development, trafficking, and effector function." Journal of allergy and clinical immunology 111.6 (2003): 1185-1199.

[NPL 4] Berahovich, Robert D., et al. "Proteolytic activation of alternative CCR1 ligands in inflammation." The Journal of Immunology 174.11 (2005): 7341-7351.

[NPL 5] Ludeman, Justin P., and Martin J. Stone. "The structural role of receptor tyrosine sulfation in chemokine recognition." British journal of pharmacology 171.5 (2014): 1167-1179.

[NPL 6] Su, S. B., et al. "Preparation of specific polyclonal antibodies to a CC chemokine receptor, CCR1, and determination of CCR1 expression on various types of leukocytes." Journal of leukocyte biology 60.5 (1996): 658-666.

[NPL 7] Weber, Christian, et al. "Specialized roles of the chemokine receptors CCR1 and CCR5 in the recruitment of monocytes and TH1-like/CD45RO+ T cells." Blood 97.4 (2001): 1144-1146.

[NPL 8] Phillips, Rhian M., et al. "Variations in eosinophil chemokine responses: an investigation of CCR1 and CCR3 function, expression in atopy, and identification of a functional CCR1 promoter." The Journal of Immunology 170.12 (2003): 6190-6201.

[NPL 9] Cheng, Sara S., et al. "Granulocyte-macrophage colony stimulating factor up-regulates CCR1 in human neutrophils." The Journal of Immunology 166.2 (2001): 1178-1184.

[NPL 10] Corcione, Anna, et al. "Chemotaxis of human tonsil B lymphocytes to CC chemokine receptor (CCR) 1, CCR2 and CCR4 ligands is restricted to non-germinal center cells." International immunology 14.8 (2002): 883-892.

[NPL 11] Kitamura, Takanori, et al. "SMAD4-deficient intestinal tumors recruit CCR1+ myeloid cells that promote invasion." Nature genetics 39.4 (2007): 467-475.

[NPL 12] Inamoto, Susumu, et al. "Loss of SMAD4 Promotes Colorectal Cancer Progression by Accumulation of Myeloid-Derived Suppressor Cells through CCL15-CCR1 Chemokine Axis." Clinical Cancer Research (2015): clincanres-0726.

[NPL 13] D'Ambrosio, Daniele, Paola Panina-Bordignon, and Francesco Sinigaglia. "Chemokine receptors in inflammation: an overview." Journal of immunological methods 273.1 (2003): 3-13.

[NPL 14] Schall, Thomas J., and Amanda EI Proudfoot. "Overcoming hurdles in developing successful drugs targeting chemokine receptors." Nature Reviews Immunology 11.5 (2011): 355-363.

[NPL 15] Lebre, Maria C., et al. "Why CCR2 and CCR5 blockade failed and why CCR1 blockade might still be effective in the treatment of rheumatoid arthritis." PLoS One 6.7 (2011): e21772.

[NPL 16] Oba, Yasuo, et al. "MIP-1α utilizes both CCR1 and CCR5 to induce osteoclast formation and increase adhesion of myeloma cells to marrow stromal cells." Experimental hematology 33.3 (2005): 272-278.

SUMMARY OF INVENTION

Technical Problem

None of the existing anti-CCR1 antibodies disclosed in NPL 15, NPL 16, PTL 1, and the like have been developed as pharmaceuticals, and information on performance as antibody pharmaceuticals is not sufficient. Therefore, an object of the present invention is to provide a monoclonal antibody which binds to a human CCR1 and inhibits activation of the human CCR1, or an antibody fragment thereof, a hybridoma producing the antibody, a nucleic acid having a nucleotide sequence encoding the antibody or the antibody fragment, a transformant cell containing a vector containing the nucleic acid, a method for producing the antibody or the antibody fragment using the hybridoma or the transformant cell; a therapeutic agent and a diagnostic agent containing the antibody or the antibody fragment, and a method for treating and diagnosing a CCR1-related disease using the antibody or the antibody fragment.

Solution to Problem

As means for solving the above problems, the present invention provides a human CCR1 monoclonal antibody which binds to the extracellular region of a human CCR1 and inhibits activation of the human CCR1 by human CCL15.

That is, the present invention relates to the following (1) to (27).

(1) A monoclonal antibody or an antibody fragment thereof which binds to an extracellular region of a CCR1 and inhibits activation of the human CCR1 by a human CCL 15.

(2) The monoclonal antibody or the antibody fragment thereof according to (1), which inhibits migration of a human CCR1-expressing cell induced by the human CCL15.

(3) The monoclonal antibody or the antibody fragment thereof according to (1) or (2), which binds to at least one amino acid residue in an amino acid sequence of the extracellular loop 2 region of the human CCR1.

(4) The monoclonal antibody or the antibody fragment thereof according to any one of (1) to (3), wherein the monoclonal antibody is any one antibody selected from the following (a) to (n);

(a) an antibody in which complementarity determining regions (hereinafter, abbreviated as CDRs) 1 to 3 of a heavy chain variable region (hereinafter, abbreviated as VH) comprise the amino acid sequences of SEQ ID NOs: 69, 70, and 71, respectively, and in which the CDRs 1 to 3 of a light chain variable region (hereinafter, abbreviated as VL) comprise the amino acid sequences of SEQ ID NOs: 72, 73, and 74, respectively, (b) an antibody in which the CDRs 1 to 3 of VH comprise the amino acid sequences of SEQ ID NOs: 75, 76, and 77, respectively, and in which the CDRs 1 to 3 of VL comprise the amino acid sequences of SEQ ID NOs: 78, 79, and 80, respectively, (c) an antibody in which CDRs 1 to 3 of VH comprise the amino acid sequences of SEQ ID NOs: 81, 82, and 83, respectively, and in which the CDRs 1 to 3 of VL comprise the amino acid sequences of SEQ ID NOs: 84, 85, and 86, respectively, (d) an antibody in which the CDRs 1 to 3 of VH comprise the amino acid sequences of SEQ ID NOs: 87, 88, and 89, respectively, and in which the CDRs 1 to 3 of VL comprise the amino acid sequences of SEQ ID NOs: 90, 91, and 92, respectively, (e) an antibody in which the CDRs 1 to 3 of VH comprise the amino acid sequences of SEQ ID NOs: 93, 94, and 95, respectively, and in which the CDRs 1 to 3 of VL comprise the amino acid sequences of SEQ ID NOs: 96, 97, and 98, respectively, (f) an antibody in which the CDRs 1 to 3 of VH comprise the amino acid sequences of SEQ ID NOs: 99, 100, and 101, respectively, and in which the CDRs 1 to 3 of VL comprise the amino acid sequences of SEQ ID NOs: 102, 103, and 104, respectively, (g) an antibody in which the CDRs 1 to 3 of VH comprise the amino acid sequences of SEQ ID NOs: 105, 106, and 107, respectively, and in which the CDRs 1 to 3 of VL comprise the amino acid sequences of SEQ ID NOs: 108, 109, and 110, respectively, (h) an antibody in which the CDRs 1 to 3 of VH comprise the amino acid sequences of SEQ ID NOs: 111, 112, and 113, respectively, and in which the CDRs 1 to 3 of VL comprise the amino acid sequences of SEQ ID NOs: 114, 115, and 116, respectively, (i) an antibody in which the CDRs 1 to 3 of VH comprise the amino acid sequences of SEQ ID NOs: 117, 118, and 119, respectively, and in which the CDRs 1 to 3 of VL comprise the amino acid sequences of SEQ ID NOs: 120, 121, and 122, respectively, (j) an antibody in which the CDR1 of VH comprises the amino acid sequence of SEQ ID NO: 75, the CDR2 of VH comprises the amino acid sequence of SEQ ID NO: 76 or the amino acid sequence in which at least one modification selected from modifications of substituting Ile at a position 2 with Thr, Val at a position 9 with Ala, Phe at a position 14 with Ala, and Ile at a position 15 with Ala is introduced in the amino acid sequence of SEQ ID NO: 76, and the CDR3 of VH comprises the amino acid sequence of SEQ ID NO: 77 or the amino acid sequence in which at least one of modifications of substituting Tyr at a position 5 with Ala and Thr at a position 7 with Ala is introduced in the amino acid sequence of SEQ ID NO: 77, and in which the CDR1 of VL comprises the amino acid sequence of SEQ ID NO: 126 or the amino acid sequence in which a modification of substituting Phe at a position 15 with Ala is introduced in the amino acid sequence SEQ ID NO: 126, the CDR2 of VL comprises the amino acid sequence of SEQ ID NO: 127 or the amino acid sequence in which at least one of modifications of substituting Val at a position 2 with Ile, and Arg at a position 5 with Lys is introduced in the amino acid sequence of SEQ ID NO: 127, and the CDR3 of VL comprises the amino acid sequence of SEQ ID NO: 128, (k) an antibody in which the CDRs 1 to 3 of VH comprise the amino acid sequences of SEQ ID NOs: 75, 131, and 77, respectively, and in which the CDRs 1 to 3 of VL comprise the amino acid sequences of SEQ ID NOs: 126, 134, and 128, respectively, (l) an antibody which competes in binding to the human CCR1 with at least one of the antibodies according to (a) to (k), (m) an antibody which binds to an epitope comprising an epitope to which any one of the antibodies according to (a) to (k) binds, and (n) an antibody which binds to the same epitope to which any one of the antibodies according to (a) to (k) binds.

(5) The monoclonal antibody or the antibody fragment thereof according to any one of (1) to (4), wherein the monoclonal antibody is any one antibody selected from the following (a) to (j);

(a) an antibody in which VH comprises the amino acid sequence of SEQ ID NO: 51, and in which VL comprises the amino acid sequence of SEQ ID NO: 52, (b) an antibody in which VH comprises the amino acid sequence of SEQ ID NO: 53, and in which VL comprises the amino acid sequence of SEQ ID NO: 54, (c) an antibody in which VH comprises the amino acid sequence of SEQ ID NO: 55, and in which VL comprises the amino acid sequence of SEQ ID NO: 56, (d) an antibody in which VH comprises the amino acid sequence of SEQ ID NO: 57, and in which VL comprises the amino acid sequence of SEQ ID NO: 58, (e) an antibody in which VH comprises the amino acid sequence of SEQ ID NO: 59, and in which VL comprises the amino acid sequence of SEQ ID NO: 60, (f) an antibody in which VH comprises the amino acid sequence of SEQ ID NO: 61, and in which VL comprises the amino acid sequence of SEQ ID NO: 62, (g) an antibody in which VH comprises the amino acid sequence of SEQ ID NO: 63, and in which VL comprises the amino acid sequence of SEQ ID NO: 64, (h) an antibody in which VH comprises the amino acid sequence of SEQ ID NO: 65, and in which VL comprises the amino acid sequence of SEQ ID NO: 66, (i) an antibody in which VH comprises the amino acid sequence of SEQ ID NO: 67, and in which VL comprises the amino acid sequence of SEQ ID NO: 68, and (j) an antibody in which VH comprises the amino acid sequence of SEQ ID NO: 130, and in which VL comprises the amino acid sequence of SEQ ID NO: 133.

(6)

The monoclonal antibody or the antibody fragment thereof according to any one of (1) to (4), wherein the monoclonal antibody is any one antibody selected from the following (a) to (c);

(a) an antibody in which VH comprises the amino acid sequence of SEQ ID NO: 136 or the amino acid sequence in which at least one of amino acid modifications of substituting Glu at a position 6 with Gln, Leu at a position 20 with Ile, Gly at a position 27 with Phe, Val at a position 29 with Leu, Ser at a position 30 with Asn, Ile at a position 37 with Val, Ile at a position 48 with Leu, Val at a position 67 with Leu, Val at a position 71 with Lys, Thr at a position 73 with Asp, Asn at a position 76 with Ser, Phe at a position 78 with Val, Leu at a position 80 with Phe, Leu at a position 82 with Met, Val at a position 85 with Leu, Val at a position 92 with Ile, and Arg at a position 97 with Lys is introduced in the amino acid sequence of SEQ ID NO: 136, and in which VL comprises the amino acid sequence of SEQ ID NO: 135 or the amino acid sequence in which at least one of amino acid modifications of substituting Ile at a position 2 with Val, Pro at a position 15 with Leu, Gln at a position 50 with Lys, Tyr at a position 92 with Phe, and Val at a position 109 with Leu is introduced in the amino acid sequence of SEQ ID NO: 135, (b) an antibody in which VH comprises the amino acid sequence of SEQ ID NO: 146 or the amino acid sequence in which at least one of amino acid modifications of substituting Leu at a position 4 with Val, Gly at a position 44 with Arg, Ser at a position 49 with Ala, Ala at a position 92 with Gly, Val at a position 93 with Met, Ala at a position 97 with Thr, and Lys at a position 98 with Arg is introduced in the amino acid sequence of SEQ ID NO: 146, and in which VL comprises the amino acid sequence of SEQ ID NO: 145 or the amino acid sequence in which at least one of amino acid modifications of substituting Ile at a position 2 with Val, Ser at a position 15 with Leu, Ala at a position 19 with Val, Gln at a position 43 with Lys, Gln at a position 50 with Lys, and Val at a position 109 with Leu is introduced in the amino acid sequence of SEQ ID NO: 145, and (c) an antibody in which VH comprises the amino acid sequence of SEQ ID NO: 163 or the amino acid sequence in which at least one of amino acid modifications of substituting Asp at a position 42 with Glu, Lys at a position 87 with Arg, and Ala at a position 97 with Thr is introduced in the amino acid sequence of SEQ ID NO: 163, and in which VL comprises the amino acid sequence of SEQ ID NO: 162 or the amino acid sequence in which at least one of amino acid modifications of substituting Gln at a position 38 with His and Ala at a position 43 with Gly is introduced in the amino acid sequence of SEQ ID NO: 162.

(7) The monoclonal antibody or the antibody fragment thereof according to any one of (1) to (4) and (6), wherein the monoclonal antibody is any one antibody selected from the following (a) to (h);

(a) an antibody in which VH comprises the amino acid sequence of SEQ ID NO: 144, and in which VL comprises the amino acid sequence of SEQ ID NO: 135, (b) an antibody in which VH comprises the amino acid sequence of SEQ ID NO: 144, and in which VL comprises the amino acid sequence of SEQ ID NO: 137, (c) an antibody in which VH comprises the amino acid sequence of SEQ ID NO: 144, and in which VL comprises the amino acid sequence of SEQ ID NO: 138, (d) an antibody in which VH comprises the amino acid sequence of SEQ ID NO: 144, and in which VL comprises the amino acid sequence of SEQ ID NO: 139, (e) an antibody in which VH comprises the amino acid sequence of SEQ ID NO: 144, and in which VL comprises the amino acid sequence of SEQ ID NO: 140, (f) an antibody in which VH comprises the amino acid sequence of SEQ ID NO: 144, and in which VL comprises the amino acid sequence of SEQ ID NO: 141, (g) an antibody in which VH comprises the amino acid sequence of SEQ ID NO: 144, and in which VL comprises the amino acid sequence of SEQ ID NO: 142, and (h) an antibody in which VH comprises the amino acid sequence of SEQ ID NO: 143, and in which VL comprises the amino acid sequence of SEQ ID NO: 142.

(8) The monoclonal antibody or the antibody fragment thereof according to any one of (1) to (4) and (6), wherein the monoclonal antibody is any one antibody selected from the following (a) to (w);

(a) an antibody in which VH comprises the amino acid sequence of SEQ ID NO: 146, and in which VL comprises the amino acid sequence of SEQ ID NO: 145, (b) an antibody in which VH comprises the amino acid sequence of SEQ ID NO: 146, and in which VL comprises the amino acid sequence of SEQ ID NO: 147, (c) an antibody in which VH comprises the amino acid sequence of SEQ ID NO: 146, and in which VL comprises the amino acid sequence of SEQ ID NO: 148, (d) an antibody in which VH comprises the amino acid sequence of SEQ ID NO: 146, and in which VL comprises the amino acid sequence of SEQ ID NO: 149, (e) an antibody in which VH comprises the amino acid sequence of SEQ ID NO: 146, and in which VL comprises the amino acid sequence of SEQ ID NO: 150, (f) an antibody in which VH comprises the amino acid sequence of SEQ ID NO: 146, and in which VL comprises the amino acid sequence of SEQ ID NO: 151, (g) an antibody in which VH comprises the amino acid sequence of SEQ ID NO: 146, and in which VL comprises the amino acid sequence of SEQ ID NO: 152, (h) an antibody in which VH comprises the amino acid sequence of SEQ ID NO: 146, and in which VL comprises the amino acid sequence of SEQ ID NO: 153, (i) an antibody in which VH comprises the amino acid sequence of SEQ ID NO: 161, and in which VL comprises the amino acid sequence of SEQ ID NO: 145, (j) an antibody in which VH comprises the amino acid sequence of SEQ ID NO: 161, and in which VL comprises the amino acid sequence of SEQ ID NO: 147,

(k) an antibody in which VH comprises the amino acid sequence of SEQ ID NO: 161, and in which VL comprises the amino acid sequence of SEQ ID NO: 148, (l) an antibody in which VH comprises the amino acid sequence of SEQ ID NO: 161, and in which VL comprises the amino acid sequence of SEQ ID NO: 149, (m) an antibody in which VH comprises the amino acid sequence of SEQ ID NO: 161, and in which VL comprises the amino acid sequence of SEQ ID NO: 150, (n) an antibody in which VH comprises the amino acid sequence of SEQ ID NO: 161, and in which VL comprises the amino acid sequence of SEQ ID NO: 151, (o) an antibody in which VH comprises the amino acid sequence of SEQ ID NO: 161, and in which VL comprises the amino acid sequence of SEQ ID NO: 152, (p) an antibody in which VH comprises the amino acid sequence of SEQ ID NO: 161, and in which VL comprises the amino acid sequence of SEQ ID NO: 153, (q) an antibody in which VH comprises the amino acid sequence of SEQ ID NO: 154, and in which VL comprises the amino acid sequence of SEQ ID NO: 151, (r) an antibody in which VH comprises the amino acid sequence of SEQ ID NO: 155, and in which VL comprises the amino acid sequence of SEQ ID NO: 151, (s) an antibody in which VH comprises the amino acid sequence of SEQ ID NO: 156, and in which VL comprises the amino acid sequence of SEQ ID NO: 151, (t) an antibody in which VH comprises the amino acid sequence of SEQ ID NO: 157, and in which VL comprises the amino acid sequence of SEQ ID NO: 151, (u) an antibody in which VH comprises the amino acid sequence of SEQ ID NO: 158, and in which VL comprises the amino acid sequence of SEQ ID NO: 151, (v) an antibody in which VH comprises the amino acid sequence of SEQ ID NO: 159, and in which VL comprises the amino acid sequence of SEQ ID NO: 151, and (w) an antibody in which VH comprises the amino acid sequence of SEQ ID NO: 160, and in which VL comprises the amino acid sequence of SEQ ID NO: 151.

(9) The monoclonal antibody or the antibody fragment thereof according to any one of (1) to (4) and (6),
wherein the monoclonal antibody is any one antibody selected from the following (a) to (f);

(a) an antibody in which VH comprises the amino acid sequence of SEQ ID NO: 163, and in which VL comprises the amino acid sequence of SEQ ID NO: 162, (b) an antibody in which VH comprises the amino acid sequence of SEQ ID NO: 163, and in which VL comprises the amino acid sequence of SEQ ID NO: 164,

10

(c) an antibody in which VH comprises the amino acid sequence of SEQ ID NO: 165, and in which VL comprises the amino acid sequence of SEQ ID NO: 162, (d) an antibody in which VH comprises the amino acid sequence of SEQ ID NO: 165, and in which VL comprises the amino acid sequence of SEQ ID NO: 164, (e) an antibody in which VH comprises the amino acid sequence of SEQ ID NO: 166, and in which VL comprises the amino acid sequence of SEQ ID NO: 162, and (f) an antibody in which VH comprises the amino acid sequence of SEQ ID NO: 166, and in which VL comprises the amino acid sequence of SEQ ID NO: 164.

(10) The monoclonal antibody or the antibody fragment thereof according to any one of (1) to (9),
wherein the monoclonal antibody is a genetically recombinant antibody.

(11) The monoclonal antibody or the antibody fragment thereof according to (10),
wherein the genetically recombinant antibody is any one of genetically recombinant antibodies selected from a human chimeric antibody, a humanized antibody, and a human antibody.

(12) The antibody fragment according to any one of (1) to (11), which is any one of antibody fragments selected from Fab, Fab', (Fab')$_2$, a single chain antibody (scFv), a dimerized V region (diabody), a disulfide stabilized V region (dsFv), and a peptide comprising CDR.

(13) A hybridoma which produces the monoclonal antibody according to any one of (1) to (9).

(14) A nucleic acid comprising:
a nucleotide sequence which encodes the monoclonal antibody or the antibody fragment thereof according to any one of (1) to (12).

(15) A transformant cell comprising a vector comprising:
the nucleic acid according to (14).

(16) A method for producing the monoclonal antibody or the antibody fragment thereof according to any one of (1) to (12), the method comprising:
culturing the hybridoma according to (13) or the transformant cell according to (15); and
collecting the monoclonal antibody or the antibody fragment thereof according to any one of (1) to (12) from a culture solution.

(17) A reagent for detecting or measuring a human CCR1, comprising:
the monoclonal antibody or the antibody fragment thereof according to any one of (1) to (12).

(18) A diagnostic agent for a human CCR1-related disease, comprising:
the monoclonal antibody or the antibody fragment thereof according to any one of (1) to (12).

(19) The diagnostic agent according to (18),
wherein the human CCR1-related disease is a cancer, an autoimmune disease, or an inflammatory disease.

(20) A therapeutic agent for a human CCR1-related disease, comprising:
the monoclonal antibody or the antibody fragment thereof according to any one of (1) to (12) as an active ingredient.

(21) The therapeutic agent according to (20),
wherein the human CCR1-related disease is a cancer, an autoimmune disease, or an inflammatory disease.

(22) A method for diagnosing a human CCR1-related disease using the monoclonal antibody or the antibody fragment thereof according to any one of (1) to (12).

(23) A method for treating a human CCR1-related disease using the monoclonal antibody or the antibody fragment thereof according to any one of (1) to (12).

(24) Use of the monoclonal antibody or the antibody fragment thereof according to any one of (1) to (12) for producing a diagnostic agent for a human CCR1-related disease.

(25) Use of the monoclonal antibody or the antibody fragment thereof according to any one of (1) to (12) for producing a therapeutic agent for a human CCR1-related disease.

(26) The monoclonal antibody or the antibody fragment thereof according to any one of (1) to (12) for being used as a therapeutic agent for a human CCR1-related disease.

(27) The monoclonal antibody or the antibody fragment thereof according to any one of (1) to (12) for being used as a diagnostic agent for a human CCR1-related disease.

Advantageous Effects of Invention

The monoclonal antibody or the antibody fragment thereof of the present invention binds to the extracellular region of a human CCR1, and inhibits various reactions associated with human CCR1 activation. Therefore, the monoclonal antibody or the antibody fragment thereof of the present invention can be used as a therapeutic agent and a diagnostic agent for human CCR1-related diseases.

BRIEF DESCRIPTION OF DRAWINGS

In FIG. 1 (a) and FIG. 1 (b), a sample to which DPBS is added is denoted by DPBS, a sample to which the activated human CCL15 is not added is denoted by No ligand, and a sample to which the activated human CCL15 is added is denoted by hCCL15 (68aa). As the anti-human CCR1 antibody, a KM5907 antibody, a KM5908 antibody, a KM5909 antibody, a KM5911 antibody, a KM5915 antibody, a KM5916 antibody, a KM5954 antibody, a KM5955 antibody, and a KM5956 antibody are used.

In FIG. 2, a sample to which DPBS is added is denoted by DPBS, a sample to which the activated human CCL15 is not added is denoted by No ligand, and a sample to which the activated human CCL15 is added is denoted by hCCL15 (68aa). As the anti-human CCR1 antibody, a 2D4 antibody (Millennium), a 53504 antibody (R&D Technologies), a 141-2 antibody (MBL, #D063-3), a KM5908 antibody, and a KM5916 antibody are used.

In FIG. 3, a sample to which an antibody is not added is denoted by No mAb, a sample to which the activated human CCL15 is not added is denoted by No ligand, and a sample to which the activated human CCL15 is added is denoted by hCCL15. As the anti-human CCR1 antibody, a chKM5908 antibody and a chKM5908' antibody were used. The experiment was performed with N=3, and an average value and a standard deviation are indicated on a graph.

FIG. 4 illustrates results of measuring an activity of an anti-human CCR1 antibody to inhibit THP-1 migration by an activated human CCL15. A vertical axis in FIG. 4 indicates an amount of luminescence (relative light unit; RLU) when the number of cells that have moved to the lower layer of Transwell is measured by CellTiter-Glo. A horizontal axis of FIG. 4 indicates an antibody and a ligand added to the THP-1 cells and concentrations thereof. In FIG. 4, a sample to which an antibody is not added is denoted by No mAb, a sample to which the activated human CCL15 is not added is denoted by No ligand, and a sample to which the activated human CCL15 is added is denoted by hCCL15. As the anti-human CCR1 antibody, a chKM5908 antibody, a chKM5908' antibody, a chKM5908'mut02 antibody, a chKM5908'mut22 antibody, and a chKM5908'mut25 antibody are used. The experiment was performed with N=3, and an average value and a standard deviation are indicated on a graph.

FIG. 5 illustrates the amino acid sequences of VL of a mAb5-06 antibody not containing a signal sequence and VL (LV0, LV1a, LV1b, LV2a, LV2b, LV4, and LV5) of a mAb5-06 humanized antibody (hereinafter, referred to as a hzmAb5-06 antibody). A region surrounded by a frame in each sequence indicates the amino acid sequence of CDR. From top to bottom, SEQ ID NOs: 133, 135, 137, 138, 139, 140, 141, and 142 are illustrated.

FIG. 6 illustrates the amino acid sequences of VH of the mAb 5-06 antibody not containing a signal sequence and VH (HV0, HV14 and HV17) of the hzmAb 5-06 antibody. A region surrounded by a frame in each sequence indicates the amino acid sequence of CDR. From top to bottom, SEQ ID NOs: 130, 136, 143, and 144 are illustrated.

FIG. 7 illustrates the amino acid sequences of VL of a KM5907 antibody not containing a signal sequence and VL (LV0, LV1a, LV1b, LV1c, LV2a, LV2b, LV4, and LV6) of a KM5907 humanized antibody (hereinafter, referred to as a hzKM5907 antibody). A region surrounded by a frame in each sequence indicates the amino acid sequence of CDR. From top to bottom, SEQ ID NOs: 52, 145, 147, 148, 149, 150, 151, 152, and 153 are illustrated.

FIG. 8 illustrates the amino acid sequence of VH of the KM5907 antibody not containing a signal sequence and of VH (HV0, HV1, HV2a, HV2b, HV3a, HV3b, HV3c, HV4, and HV7) of the hzKM5907 antibody. A region surrounded by a frame in each sequence indicates the amino acid sequence of CDR. From top to bottom, SEQ ID NOs: 51, 146, 154, 155, 156, 157, 158, 159, 160, and 161 are illustrated.

FIG. 9 illustrates the amino acid sequences of VL of a KM5916 antibody not containing a signal sequence and VL (LV0 and LV1α) of a KM5916 humanized antibody (hereinafter, referred to as a hzKM5916 antibody). A region surrounded by a frame in each sequence indicates the amino acid sequence of CDR. From top to bottom, SEQ ID NOs: 62, 162, and 164 are illustrated.

FIG. 10 illustrates the amino acid sequences of VH of the Km5916 antibody not containing a signal sequence and VH (HV0, HV1, and HV3) of the hzKM5916 antibody. A region surrounded by a frame in each sequence indicates the amino acid sequence of CDR. From top to bottom, SEQ ID NOs: 61, 163, 165, and 166 are illustrated.

FIG. 11 illustrates results of measuring an activity of an anti-human CCR1 antibody to inhibit THP-1 migration by an activated human CCL15. A vertical axis in FIG. 11 indicates an amount of luminescence (relative light unit; RLU) when the number of cells that have moved to the lower layer of Transwell is measured by CellTiter-Glo. A horizontal axis of FIG. 11 indicates an antibody and a ligand added to the THP-1 cells and concentrations thereof. In FIG. 11, a sample to which an antibody is not added is denoted by No mAb, a sample to which the activated human CCL15 is not added is denoted by No ligand, and a sample to which the activated human CCL15 is added is denoted by hCCL15. As the anti-human CCR1 antibody, hzmAb5-06 LV5HV14, hzKM5907 LV2bHV3a, and hzKM5916 LV2HV0 are used. The experiment was performed with N=3, and an average value and a standard deviation are indicated on a graph.

DESCRIPTION OF EMBODIMENTS

Figure 1:
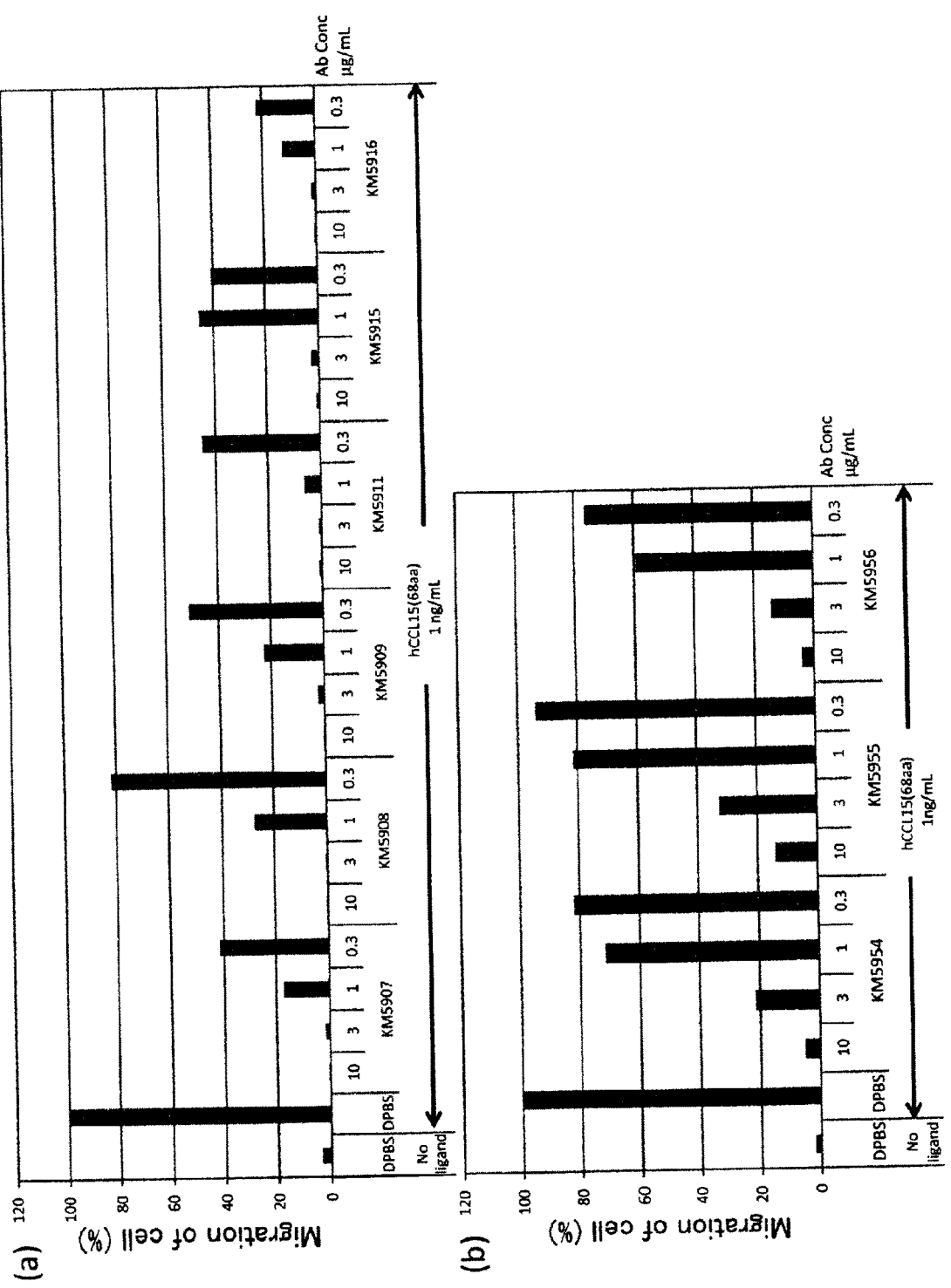
FIG. 1 illustrates results of measuring an activity of an anti-human CCR1 antibody to inhibit THIP-1 migration by an activated human CCL15. A vertical axis in FIG. 1(a) and FIG. 1(b) indicates THP-1 cell migration (%), and when DPBS and activated CCL15 were added, the number of cells that migrated to a lower layer of Transwell is set to 100%. A horizontal axis of FIG. 1(a) and FIG. 1(b) indicates an antibody and a ligand added to the THP-1 cells and concentrations thereof.

The present invention relates to a monoclonal antibody which binds to the extracellular region of human CCR1 and inhibits activation of the human CCR1 by human CCL15, or an antibody fragment thereof.

CCR1 is also referred to as CD 191, CKR-1, HM145, Macrophage inflammatory protein 1α receptor (MIP1αR), CMKBR1, SCYAR1, or the like. CCR1 is GPCR having a seven-transmembrane structure, and is a membrane protein consisting of 355 amino acids in total.

In GPCR containing CCR1, GPCR on the cell surface is activated by binding of a ligand, and the receptor-dependent signal is transmitted into the cell, and a calcium ion concentration in the cell is increased at the same time. As a result, it is known that the cells undergo cell migration, chemokine production, matrix metalloprotease MMP production, and the like.

That is, as a function of CCR1, when the ligand binds to CCR1 on the cell surface, a CCR1-dependent signal is transmitted into the cell, and the calcium ion concentration in the cell is increased at the same time. As a result, the cells undergo the cell migration, the chemokine production, the MMP production, and the like.

As ligands for the human CCR1, for example, human CCL3, CCL5, CCL8, CCL14, CCL15, CCL16, and CCL23 have been reported. As ligands for mouse CCR1, for example, mouse CCL3, CCL5, CCL7, and CCL9 have been reported.

The human CCL15 is a ligand included in the C-C chemokine family and consists of 92 amino acids in total. It has been known that the human CCL15 exhibits stronger activity than that of CCL15 as whole (hereinafter, in the present invention, referred to as whole CCL15) when an N-terminus thereof is composed by the action of proteases and becomes an activated form of about 68 amino acids

[hereinafter, referred to as activated human CCL15 or hCCL15 (68aa) in the present invention].

When the human CCL15 binds to the human CCR1 on the cell surface and the receptor is activated, a CCR1-dependent signal is transmitted into the cell, activation of phospholipase C (PLC), an increase in an intracellular calcium ion concentration, or activation of nuclear factor-κB (NF-κB) occurs. As a result, the cells undergo the cell migration or the like.

Examples of the monoclonal antibody of the present invention (hereinafter, also abbreviated as the antibody of the present invention) include an antibody that inhibits at least one of various reactions associated with human CCR1 activation by the human CCL15. Specific examples of the antibody of the present invention include an antibody that inhibits at least one reaction selected from CCR1-dependent signal transduction in human CCR1-expressing cells by the human CCL15, the activation of PLC, an increase in the intracellular calcium ion concentration, activation of NF-κB, and the migration of CCR1-expressing cells. Among these, the antibody of the present invention is preferably an antibody that inhibits the migration of the human CCR1-expressing cells derived by human CCL15.

As the antibody of the present invention, regarding the reaction associated with human CCR1 activation by the human CCL15, antibodies which inhibit preferably 5% or more, 10% or more, 20% or more, 30% or more, 40% or more, 50% or more, 60% or more, 70% or more, 80% or more, and 90% or more as compared to a control to which only human CCL15 is added and no antibody is added are exemplified. The concentration of the human CCL15 can be appropriately adjusted to a concentration at which the activity of the reaction when the human CCL15 is added becomes a maximum value depending on the measurement system. For example, in a case where the migration of the CCR1-expressing cells is measured by the method described in the examples of the present application, the concentration of CCL15 is preferably 1 ng/mL. In addition, the concentration of the antibody of the present invention can also be adjusted as appropriate by the measurement system. For example, in a case where the migration of the CCR1-expressing cells is measured by the method described in this example, the antibody concentration of the present invention is 0.3 μg/mL or more, is preferably 1 μg/mL or more, is more preferably 3 μg/mL or more, and is most preferably 10 μg/mL or more.

In the present invention, the human CCL15 may be any CCL15 of whole CCL15 and activated human CCL15 as long as it activates CCR1.

The human CCR1-expressing cells may be any cells as long as the human CCR1 is expressed on the cells, and examples include human cells, a human cell line, and the human CCR1 forcibly-expressing line.

Examples of the human cells expressing the human CCR1 include neutrophils, eosinophils, basophils, monocytes, macrophages, dendritic cells, NK cells, T cells, B cells, immature myeloid cells (iMC), and myeloid derived suppressor cells (MDSC).

Examples of the extracellular region of the human CCR1 include an N-terminus region containing the amino acid sequences at positions 1 to 31 from the N-terminus of the amino acid sequence of the human CCR1, an extracellular loop 1 region containing the amino acid sequences at positions 97 to 103, an extracellular loop 2 region containing the amino acid sequences at positions 172 to 195, and an extracellular loop 3 region containing the amino acid sequences at positions 266 to 278 [Cell 72.3 (1993): 415 to 425].

As the N-terminus region, the extracellular loop 1 region, the extracellular loop 2 region, and the extracellular loop 3 region, specifically, the amino acid sequences at positions 1 to 31, positions 97 to 103, positions 172 to 195, and positions 266 to 278 in the amino acid sequences of SEQ ID NO: 2 are exemplified, respectively.

The antibody of the present invention may be any antibody which binds to the extracellular region of the human CCR1 described above, and is preferably an antibody which binds to at least one amino acid residue in the amino acid sequences of the extracellular loop 2 region of the human CCR1. Examples of such an antibody include an antibody which binds to at least one amino acid residue in the amino acid sequences at positions 172 to 195 in the amino acid sequences of SEQ ID NO: 2.

More specifically, the antibody of the present invention includes any one antibody selected from the following (a) to (n);

(a) an antibody in which the CDRs 1 to 3 of VH include the amino acid sequences of SEQ ID NOs: 69, 70, and 71, respectively, and in which the CDRs 1 to 3 of VL include the amino acid sequences of SEQ ID NOs: 72, 73, and 74, respectively, (b) an antibody in which the CDRs 1 to 3 of VH include the amino acid sequences of SEQ ID NOs: 75, 76, and 77, respectively, and in which the CDRs 1 to 3 of VL include the amino acid sequences of SEQ ID NOs: 78, 79, and 80, respectively, (c) an antibody in which CDRs 1 to 3 of VH include the amino acid sequences of SEQ ID NOs: 81, 82, and 83, respectively, and in which the CDRs 1 to 3 of VL include the amino acid sequences of SEQ ID NOs: 84, 85, and 86, respectively, (d) an antibody in which the CDRs 1 to 3 of VH include the amino acid sequences of SEQ ID NOs: 87, 88, and 89, respectively, and in which the CDRs 1 to 3 of VL include the amino acid sequences of SEQ ID NOs: 90, 91, and 92, respectively, (e) an antibody in which the CDRs 1 to 3 of VH include the amino acid sequences of SEQ ID NOs: 93, 94, and 95, respectively, and in which the CDRs 1 to 3 of VL include the amino acid sequences of SEQ ID NOs: 96, 97, and 98, respectively, (f) an antibody in which the CDRs 1 to 3 of VH include the amino acid sequences of SEQ ID NOs: 99, 100, and 101, respectively, and in which the CDRs 1 to 3 of VL include the amino acid sequences of SEQ ID NOs: 102, 103, and 104, respectively, (g) an antibody in which the CDRs 1 to 3 of VH include the amino acid sequences of SEQ ID NOs: 105, 106, and 107, respectively, and in which the CDRs 1 to 3 of VL include the amino acid sequences of SEQ ID NOs: 108, 109, and 110, respectively, (h) an antibody in which the CDRs 1 to 3 of VH include the amino acid sequences of SEQ ID NOs: 111, 112, and 113, respectively, and in which the CDRs 1 to 3 of VL include the amino acid sequences of SEQ ID NOs: 114, 115, and 116, respectively, (i) an antibody in which the CDRs 1 to 3 of VH include the amino acid sequences of SEQ ID NOs: 117, 118, and 119, respectively, and in which the CDRs 1 to 3 of VL include the amino acid sequences of SEQ ID NOs: 120, 121, and 122, respectively, (j) an antibody in which the CDR1 of VH includes the amino acid sequence of SEQ ID NO: 75, the CDR2 of VH includes the amino acid sequence of SEQ ID NO: 76 or the amino acid sequence in which at least one modification selected from modifications of substituting Ile at a position 2 with Thr, the Val at a position 9 with Ala, Phe at a position 14 with Ala, and Ile at a position 15 with Ala is introduced in the amino acid sequence of SEQ ID NO: 76, and the CDR3 of VH includes the amino acid sequence of SEQ ID NO: 77 or the amino acid sequence in which at least one of modifications of substituting Tyr at a position 5 with Ala and Thr at a position 7 with Ala is introduced in the amino acid sequence of SEQ ID NO: 77, and in which the CDR1 of VL includes the amino acid sequence of SEQ ID NO: 126 or the amino acid sequence in which a modification of substituting Phe at a position 15 with Ala is introduced in the amino acid sequence SEQ ID NO: 126, the CDR2 of VL includes the amino acid sequence of SEQ ID NO: 127 or the amino acid sequence in which at least one modification from modifications of substituting Val at a position 2 with Ile, and Arg at a position 5 with Lys is introduced in the amino acid sequence of SEQ ID NO: 127, and the CDR3 of VL includes the amino acid sequence of SEQ ID NO: 128, (k) an antibody in which the CDRs 1 to 3 of VH include the amino acid sequences of SEQ ID NOs: 75, 131, and 77, respectively, and in which the CDRs 1 to 3 of VL include the amino acid sequences of SEQ ID NOs: 126, 134, and 128, respectively, (l) an antibody which competes in binding to the human CCR1 with at least one of the antibodies according to (a) to (k), (m) an antibody which binds to an epitope including an epitope to which any one of the antibodies according to (a) to (k) binds, and (n) an antibody which binds to the same epitope to which any one of the antibodies according to (a) to (k) binds.

The antibody of the present invention includes an antibody having amino acid sequences of CDRs 1 to 3 of VH and CDRs 1 to 3 of VL of antibody having homology of 90% or higher to amino acid sequences of CDRs 1 to 3 of VH and CDRs 1 to 3 of VL of any one antibody described in the above (a) to (k), respectively. The homology of 90% or higher is specifically homology of 91%, 92%, 93%, 94%, 95%, 96%, 97%, 98% or 99% or higher or the like.

In the present invention, an embodiment of the antibodies described in described in the above (a) to (i) includes a KM5907 antibody, a KM5908 antibody, a KM5909 antibody, a KM5911 antibody, a KM5915 antibody, a KM5916 antibody, a KM5954 antibody, a KM5955 antibody, and a KM5956 antibody which are mouse anti-human CCR1 monoclonal antibody, respectively. An embodiment of the antibodies described in the above (a) to (i) includes a chKM5907 antibody, a chKM5908 antibody, a chKM5909 antibody, a chKM5911 antibody, a chKM5915 antibody, a chKM5916 antibody, a chKM5954 antibody, a chKM5955 antibody, and a chKM5956 antibody which are anti-human CCR1 chimeric antibody. An embodiment of the antibodies described in the above (a) and (f) includes a hzKM5907 antibody and a hzKM5916 antibody which are humanized anti-human CCR1 antibodies, respectively. Embodiments of the antibodies described in the above (j) include a variant chKM5908' antibody and chKM5908' mut01-32 antibodies of an anti-human CCR1 chimeric antibody, and a humanized anti-human CCR1 antibody hzmAb5-06 antibody. Embodiments of the antibodies described in the above (k) include a variant chKM5908' mut22 antibody of an anti-human CCR1 chimeric antibody (also referred to as mAb5-06) and a humanized anti-human CCR1 antibody hzmAb5-06 antibody. Embodiments of the antibodies described in the above (a) to (k) include human antibodies having the amino acid sequences of CDRs 1 to 3 of VH and the CDRs 1 to 3 of VL of any one of the antibodies described in the above (a) to (k) and the like.

The antibody (l) of the present invention is referred to as a second antibody that inhibits the binding between the first antibody and the human CCR1 when the antibodies described in the above (a) to (k) are set as first antibodies. The antibody (m) of the present invention is referred to as a second antibody which binds to a second epitope including a first epitope in a case where the antibodies described in the above (a) to (k) are set as first antibodies, and an epitope to which the first antibody binds is set as the first epitope. In addition, the antibody (n) of the present invention is referred to as a second antibody which binds to a first epitope in a case where the antibodies described in the above (a) to (k) are set as first antibodies, and an epitope to which the first antibody binds is set as the first epitope.

Further, as the antibody of the present invention, specific examples thereof include any one antibody selected from the following (1)-(a) to (j), (2)-(a) to (c), (3)-(a) to (h), (4)-(a) to (w), and (5)-(a) to (f);

(1)-(a) an antibody in which VH includes the amino acid sequence of SEQ ID NO: 51, and in which VL includes the amino acid sequence of SEQ ID NO: 52, (1)-(b) an antibody in which VH includes the amino acid sequence of SEQ ID NO: 53, and in which VL includes the amino acid sequence of SEQ ID NO: 54, (1)-(c) an antibody in which VH includes the amino acid sequence of SEQ ID NO: 55, and in which VL includes the amino acid sequence of SEQ ID NO: 56, (1)-(d) an antibody in which VH includes the amino acid sequence of SEQ ID NO: 57, and in which VL includes the amino acid sequence of SEQ ID NO: 58, (1)-(e) an antibody in which VH includes the amino acid sequence of SEQ ID NO: 59, and in which VL includes the amino acid sequence of SEQ ID NO: 60, (1)-(f) an antibody in which VH includes the amino acid sequence of SEQ ID NO: 61, and in which VL includes the amino acid sequence of SEQ ID NO: 62, (1)-(g) an antibody in which VH includes the amino acid sequence of SEQ ID NO: 63, and in which VL includes the amino acid sequence of SEQ ID NO: 64, (1)-(h) an antibody in which VH includes the amino acid sequence of SEQ ID NO: 65, and in which VL includes the amino acid sequence of SEQ ID NO: 66, (1)-(i) an antibody in which VH includes the amino acid sequence of SEQ ID NO: 67, and in which VL includes the amino acid sequence of SEQ ID NO: 68, (1)-(j) an antibody in which VH includes the amino acid sequence of SEQ ID NO: 130, and in which VL includes the amino acid sequence of SEQ ID NO: 133, (2)-(a) an antibody in which VH includes the amino acid sequence of SEQ ID NO: 136 or the amino acid sequence in which at least one of amino acid modifications of substituting Glu at a position 6 with Gln, Leu at a position 20 with Ile, Gly at a position 27 with Phe, Val at a position 29 with Leu, Ser at a position 30 with Asn, Ile at a position 37 with Val, Ile at a position 48 with Leu, Val at a position 67 with Leu, Val at a position 71 with Lys, Thr at a position 73 with Asp, Asn at a position 76 with Ser, Phe at a position 78 with Val, Leu at a position 80 with Phe, Leu at a position 82 with Met, Val at a position 85 with Leu, Val at a position 92 with Ile, and Arg at a position 97 with Lys is introduced in the amino acid sequence of SEQ ID NO: 136, and in which VL includes the amino acid sequence of SEQ ID NO: 135 or the amino acid sequence in which at least one of amino acid modifications of substituting Ile at a position 2 with Val, Pro at a position 15 with Leu, Gln at a position 50 with Lys, Tyr at a position 92 with Phe, and Val at a position 109 with Leu is introduced in the amino acid sequence of SEQ ID NO: 135, (2)-(b) an antibody in which VH includes the amino acid sequence of SEQ ID NO: 146 or the amino acid sequence in which at least one of amino acid modifications of substituting Leu at a position 4 with Val, Gly at a position 44 with Arg, Ser at a position 49 with Ala, Ala at a position 92 with Gly, Val at a position 93 with Met, Ala at a position 97 with Thr, and Lys at a position 98 with Arg is introduced in the amino acid sequence of SEQ ID NO: 146, and in which VL includes the amino acid sequence of SEQ ID NO: 145 or the amino acid sequence in which at least one of amino acid modifications of substituting Ile at a position 2 with Val, Ser at a position 15 with Leu, Ala at a position 19 with Val, Gln at a position 43 with Lys, Gln at a position 50 is substituted with Lys, and Val at a position 109 is substituted with Leu is introduced in the amino acid sequence of SEQ ID NO: 145, (2)-(c) an antibody in which VH includes the amino acid sequence of SEQ ID NO: 163 or the amino acid sequence in which at least one of amino acid modifications of substituting Asp at a position 42 with Glu, Lys at a position 87 with Arg, and Ala at a position 97 with Thr is introduced in the amino acid sequence of SEQ ID NO: 163, and in which VL includes the amino acid sequence of SEQ ID NO: 162 or the amino acid sequence in which at least one of amino acid modifications of substituting Gln at a position 38 with His and Ala at a position 43 with Gly is introduced in the amino acid sequence of SEQ ID NO: 162, (3)-(a) an antibody in which VH includes the amino acid sequence of SEQ ID NO: 144, and in which VL includes the amino acid sequence of SEQ ID NO: 135, (3)-(b) an antibody in which VH includes the amino acid sequence of SEQ ID NO: 144, and in which VL includes the amino acid sequence of SEQ ID NO: 137, (3)-(c) an antibody in which VH includes the amino acid sequence of SEQ ID NO: 144, and in which VL includes the amino acid sequence of SEQ ID NO: 138, (3)-(d) an antibody in which VH includes the amino acid sequence of SEQ ID NO: 144, and in which VL includes the amino acid sequence of SEQ ID NO: 139, (3)-(e) an antibody in which VH includes the amino acid sequence of SEQ ID NO: 144, and in which VL includes the amino acid sequence of SEQ ID NO: 140, (3)-(f) an antibody in which VH includes the amino acid sequence of SEQ ID NO: 144, and in which VL includes the amino acid sequence of SEQ ID NO: 141, (3)-(g) an antibody in which VH includes the amino acid sequence of SEQ ID NO: 144, and in which VL includes the amino acid sequence of SEQ ID NO: 142, (3)-(h) an antibody in which VH includes the amino acid sequence of SEQ ID NO: 143, and in which VL includes the amino acid sequence of SEQ ID NO: 142, (4)-(a) an antibody in which VH includes the amino acid sequence of SEQ ID NO: 146, and in which VL includes the amino acid sequence of SEQ ID NO: 145, (4)-(b) an antibody in which VH includes the amino acid sequence of SEQ ID NO: 146, and in which VL includes the amino acid sequence of SEQ ID NO: 147, (4)-(c) an antibody in which VH includes the amino acid sequence of SEQ ID NO: 146, and in which VL includes the amino acid sequence of SEQ ID NO: 148, (4)-(d) an antibody in which VH includes the amino acid sequence of SEQ ID NO: 146, and in which VL includes the amino acid sequence of SEQ ID NO: 149, (4)-(e) an antibody in which VH includes the amino acid sequence of SEQ ID NO: 146, and in which VL includes the amino acid sequence of SEQ ID NO: 150, (4)-(f) an antibody in which VH includes the amino acid sequence of SEQ ID NO: 146, and in which VL includes the amino acid sequence of SEQ ID NO: 151, (4)-(g) an antibody in which VH includes the amino acid sequence of SEQ ID NO: 146, and in which VL includes the amino acid sequence of SEQ ID NO: 152, (4)-(h) an antibody in which VH includes the amino acid sequence of SEQ ID NO: 146, and in which VL includes the amino acid sequence of SEQ ID NO: 153, (4)-(i) an antibody in which VH includes the amino acid sequence of SEQ ID NO: 161, and in which VL includes the amino acid sequence of SEQ ID NO: 145, (4)-(j) an antibody in which VH includes the amino acid sequence of SEQ ID NO: 161, and in which VL includes the amino acid sequence of SEQ ID NO: 147, (4)-(k) an antibody in which VH includes the amino acid sequence of SEQ ID NO: 161, and in which VL includes the amino acid sequence of SEQ ID NO: 148, (4)-(l) an antibody in which VH includes the amino acid sequence of SEQ ID NO: 161, and in which VL includes the amino acid sequence of SEQ ID NO: 149, (4)-(m) an antibody in which VH includes the amino acid sequence of SEQ ID NO: 161, and in which VL includes the amino acid sequence of SEQ ID NO: 150, (4)-(n) an antibody in which VH includes the amino acid sequence of SEQ ID NO: 161, and in which VL includes the amino acid sequence of SEQ ID NO: 151, (4)-(o) an antibody in which VH includes the amino acid sequence of SEQ ID NO: 161, and in which VL includes the amino acid sequence of SEQ ID NO: 152, (4)-(p) an antibody in which VH includes the amino acid sequence of SEQ ID NO: 161, and in which VL includes the amino acid sequence of SEQ ID NO: 153, (4)-(q) an antibody in which VH includes the amino acid sequence of SEQ ID NO: 154, and in which VL includes the amino acid sequence of SEQ ID NO: 151, (4)-(r) an antibody in which VH includes the amino acid sequence of SEQ ID NO: 155, and in which VL includes the amino acid sequence of SEQ ID NO: 151, (4)-(s) an antibody in which VH includes the amino acid sequence of SEQ ID NO: 156, and in which VL includes the amino acid sequence of SEQ ID NO: 151, (4)-(t) an antibody in which VH includes the amino acid sequence of SEQ ID NO: 157, and in which VL includes the amino acid sequence of SEQ ID NO: 151, (4)-(u) an antibody in which VH includes the amino acid sequence of SEQ ID NO: 158, and in which VL includes the amino acid sequence of SEQ ID NO: 151, (4)-(v) an antibody in which VH includes the amino acid sequence of SEQ ID NO: 159, and in which VL includes the amino acid sequence of SEQ ID NO: 151, (4)-(w) an antibody in which VH includes the amino acid sequence of SEQ ID NO: 160, and in which VL includes the amino acid sequence of SEQ ID NO: 151, (5)-(a) an antibody in which VH includes the amino acid sequence of SEQ ID NO: 163, and in which VL includes the amino acid sequence of SEQ ID NO: 162, (5)-(b) an antibody in which VH includes the amino acid sequence of SEQ ID NO: 163, and in which VL includes the amino acid sequence of SEQ ID NO: 164, (5)-(c) an antibody in which VH includes the amino acid sequence of SEQ ID NO: 165, and in which VL includes the amino acid sequence of SEQ ID NO: 162, (5)-(d) an antibody in which VH includes the amino acid sequence of SEQ ID NO: 165, and in which VL includes the amino acid sequence of SEQ ID NO: 164, (5)-(e) an antibody in which VH includes the amino acid sequence of SEQ ID NO: 166, and in which VL includes the amino acid sequence of SEQ ID NO: 162, and (5)-(f) an antibody in which VH includes the amino acid sequence of SEQ ID NO: 166, and in which VL includes the amino acid sequence of SEQ ID NO: 164.

The antibody of the present invention includes an antibody having amino acid sequences of VH and VL of antibody having homology of 90% or higher to amino acid sequences of VH and VL of any one antibody described in the above (1)-(a) to (j), (2)-(a) to (c), (3)-(a) to (h), (4)-(a) to (w), and (5)-(a) to (f). The homology of 90% or higher is specifically homology of 91%, 92%, 93%, 94%, 95%, 96%, 97%, 98% or 99% or higher, or the like.

In the present invention, an embodiment of the antibodies described in described in the above (1)-(a) to (i) includes a KM5907 antibody, a KM5908 antibody, a KM5909 antibody, a KM5911 antibody, a KM5915 antibody, a KM5916 antibody, a KM5954 antibody, a KM5955 antibody, and a KM5956 antibody which are mouse anti-human CCR1 monoclonal antibody, respectively.

In the present invention, an embodiment of the antibodies described in the above (1)-(a) to (i) includes a chKM5907 antibody, a chKM5908 antibody, a chKM5909 antibody, a chKM5911 antibody, a chKM5915 antibody, a chKM5916 antibody, a chKM5954 antibody, a chKM5955 antibody, and a chKM5956 antibody which are anti-human CCR1 chimeric antibody, respectively. In addition, embodiments of the antibodies described in the above (1)-(j) include an anti-human CCR1 chimeric antibody variant chmAb5-06.

In the present invention, an embodiment of the antibodies described in the above (2)-(a) to (c) include a hzmAb5-06 antibody, a hzKM5907 antibody, and a hzKM5916 antibody which are humanized anti-human CCR1 antibody, respectively.

In the present invention, an embodiment of the antibodies described in the above (3)-(a) to (h) includes hzmAb5-06 LV0HV17 antibody, a hzmAb5-06 LV1aHV17 antibody, a hzmAb5-06 LV1bHV17 antibody, a hzmAb5-06 LV2aHV17 antibody, a hzmAb5-06 LV2bHV17 antibody, a hzmAb5-06 LV4HV17 antibody, a hzmAb5-06 LV5HV17 antibody, and a hzmAb5-06 LV5HV14 antibody which are humanized anti-human CCR1 antibody, respectively.

In the present invention, an embodiment of the antibodies described in the above (4)-(a) to (w) includes hzKM5907 LV0HV0 antibody, a hzKM5907 LV1aHV0 antibody, a hzKM5907 LV1bHV0 antibody, a hzKM5907 LV1cHV0 antibody, a hzKM5907 LV2aHV0 antibody, a hzKM5907 LV2bHV0 antibody, a hzKM5907 LV4HV0 antibody, a hzKM5907 LV6HV0 antibody, a hzKM5907 LV0HV7 antibody, a hzKM5907 LV1aHV7 antibody, a hzKM5907 LV1bHV7 antibody, a hzKM5907 LV1cHV7 antibody, a hzKM5907 LV2aHV7 antibody, a hzKM5907 LV2bHV7 antibody, a hzKM5907 LV4HV7 antibody, a hzKM5907 LV6HV7 antibody, a hzKM5907 LV2bHV1 antibody, a hzKM5907 LV2bHV2a antibody, a hzKM5907 LV2bHV2b antibody, a hzKM5907 LV2bHV3a antibody, a hzKM5907

LV2bHV3b antibody, a hzKM5907 LV2bHV3c antibody, and a hzKM5907 LV2bHV4 antibody which are humanized anti-human CCR1 antibody, respectively.

In the present invention, an embodiment of the antibodies described in the above (5)-(a) to (f) includes hzKM5916 LV0HV0 antibody, a hzKM5916 LV2HV0 antibody, a hzKM5916 LV0HV1 antibody, a hzKM5916 LV2HV1 antibody, a hzKM5916 LV0HV3 antibody, and a hzKM5916 LV2HV3 antibody which are humanized anti-human CCR1 antibody, respectively.

In the present invention, as the human CCR1, a polypeptide including an amino acid sequence of SEQ ID NO: 2 or an amino acid sequence of NCBI accession No. NP_001286, a polypeptide including an amino acid sequence in which one or more amino acids are deleted, substituted, or added in the amino acid sequence of SEQ ID NO: 2 or an amino acid sequence of NCBI accession No. NP_001286, and having a function of the human CCR1, and a polypeptide including an amino acid sequence having homology of 60% or higher, preferably 80% or higher, more preferably 90% or higher, and most preferably 95% or higher to an amino acid sequence of SEQ ID NO: 2 or an amino acid sequence of NCBI accession No. NP_001286, and having a function of the human CCR1 are exemplified.

The polypeptide including an amino acid sequence in which one or more amino acids are deleted, substituted, or added in the amino acid sequence of SEQ ID NO: 2 or an amino acid sequence of NCBI accession No. NP_001286, can be obtained by introducing a site-specific mutation, for example, to DNA that encodes a polypeptide containing the amino acid sequence of SEQ ID NO: 2 using the site-directed mutagenesis [Molecular Cloning, A Laboratory Manual, Second Edition, Cold Spring Harbor Laboratory Press (1989), Current Protocols in Molecular Biology, John Wiley & Sons (1987-1997), Nucleic acids Research, 10, 6487 (1982), Proc. Natl. Acad. Sci. USA, 79, 6409 (1982), Gene, 34, 315 (1985), Nucleic Acids Research, 13, 4431 (1985) and Proc. Natl. Acad. Sci. USA, 82, 488 (1985)] or the like.

The number of amino acids that are deleted, substituted or added is not particularly limited but is preferably one to tens, for example, 1 to 20, more preferably one to a few, for example, one to five amino acids.

Genes which encode human CCR1 are the nucleotide sequence of SEQ ID NO: 1 and the nucleotide sequence of NCBI accession No. NM_001295. A gene containing DNA which has a nucleotide sequence in which one or more bases are deleted, substituted or added in the nucleotide sequence of SEQ ID NO: 1 or the nucleotide sequence of NM_001295, and which encodes a polypeptide having a function of human CCR1, a gene containing DNA which has a nucleotide sequence having homology of at least 60% or higher, preferably a nucleotide sequence having homology of 80% or higher or further preferably a nucleotide sequence having homology of 95% or higher to the nucleotide sequence of SEQ ID NO: 1 or the nucleotide sequence of NM_001295 and which encodes a polypeptide having a function of human CCR1, a gene which contains DNA that hybridizes with DNA containing the nucleotide sequence of SEQ ID NO: 1 or the nucleotide sequence of NM_001295 under stringent conditions and which encodes a polypeptide having a function of human CCR1 and another gene are also included as the genes that encode human CCR1 in the present invention.

The DNA that hybridizes under stringent conditions means hybridizable DNA that is obtained by a colony hybridization method, a plaque hybridization method, a southern blot hybridization method, a DNA microarray method or the like using DNA containing the nucleotide sequence of SEQ ID NO: 1 or the nucleotide sequence of NM_001295 as a probe.

Specifically, it is possible to exemplify DNA that can be identified by washing a filter or a glass slide under the condition of 65° C. using a SSC solution of the concentration of 0.1 to 2 times (the composition of the SSC solution with the concentration of 1 time is 150 mmol/L sodium chloride and 15 mmol/L sodium citrate), after performing hybridization [Molecular Cloning, A Laboratory Manual, Second Edition, Cold Spring Harbor Laboratory Press (1989), Current Protocols in Molecular Biology, John Wiley & Sons (1987-1997) and DNA Cloning 1: Core Techniques, A Practical Approach, Second Edition, Oxford University, (1995)] at 65° C. in the presence of 0.7 to 1.0 mol/L sodium chloride using a filter or a glass slide on which DNA derived from a hybridized colony or plaque or a PCR product or DNA oligo having the sequence is fixed.

Examples of the hybridizable DNA include DNA having homology of at least 60% or higher, preferably DNA having homology of 80% or higher and further preferably DNA having homology of 95% or higher to the nucleotide sequence of SEQ ID NO: 1 or the nucleotide sequence of NM_001295.

Genetic polymorphism is often recognized in a nucleotide sequence of a gene that encodes a protein of a eukaryote. The genes that encode human CCR1 in the present invention also include genes in which small scale mutations arise in the nucleotide sequences by such polymorphism in the genes used in the present invention.

A value of homology in the present invention may be a value calculated using a homology detection program known to those skilled in the art unless particularly specified. Regarding a nucleotide sequence, there are a value calculated using a default parameter of BLAST [J. Mol. Biol., 215, 403 (1990)] and the like. Regarding an amino acid sequence, there are a value calculated using a default parameter of BLAST2 [Nucleic Acids Res., 25, 3389 (1997), Genome Res., 7, 649 (1997) and http://www.ncbi.nlm.nih.gov/Education/BLASTinfo/information3.htmL] and the like.

Regarding the default parameters, G (Cost to open gap) is 5 for a nucleotide sequence and 11 for an amino acid sequence, -E (Cost to extend gap) is 2 for a nucleotide sequence and 1 for an amino acid sequence, -q (Penalty for nucleotide mismatch) is -3, -r (reward for nucleotide match) is 1, -e (expect value) is 10, -W (wordsize) is 11 residues for a nucleotide sequence and 3 residues for an amino acid sequence, -y [Dropoff (X) for blast extensions in bits] is 20 for the blastn and 7 for programs other than the blastn, -X (X dropoff value for gapped alignment in bits) is 15, and -Z (final X dropoff value for gapped alignment in bits) is 50 for the blastn and 25 for programs other than the blastn (http://www.ncbi.nlm.nih.gov/blast/htmL/blastcgihelp.htmL).

A polypeptide containing partial sequence of the amino acid sequence of SEQ ID NO: 2 or an amino acid sequence of NCBI accession No. NP_001286 can be produced by a method known to those skilled in the art. Specifically, the polypeptide can be produced by deleting a part of DNA that encodes the amino acid sequence of SEQ ID NO: 2 and culturing a transformant into which an expression vector including the DNA has been introduced. In addition, the polypeptide having amino acid sequence in which one or more amino acids are deleted, substituted or added in the amino acid sequence of SEQ ID NO: 2 or an amino acid sequence of NCBI accession No. NP_001286 can be obtained by the same method as above. Furthermore, the polypeptide containing of the amino acid sequence of SEQ ID NO: 2 or the amino acid sequence of NCBI accession No. NP_001286, or the polypeptide containing an amino acid sequence in which one or more amino acids are deleted, substituted, or added in the amino acid sequence of SEQ ID NO: 2 or an amino acid sequence of NCBI accession No. NP_001286 can be produced also using a chemical synthesis method such as a fluorenylmethyloxycarbonyl (Fmoc) method or a t-butyloxycarbonyl (tBoc) method.

As the antibody of the present invention, a polyclonal antibody, a monoclonal antibody and an oligoclonal antibody are all included. A polyclonal antibody is a group of antibody molecules that are secreted by antibody-producing cells of different clones. A monoclonal antibody is an antibody that is secreted by antibody-producing cells of a single clone, recognizes only one epitope (also called an antigenic determinant), and the amino acid sequences (primary sequences) of the monoclonal antibodies are uniform. An oligoclonal antibody is a group of antibody molecules in which different monoclonal antibodies are mixed.

The monoclonal antibody of the present invention may be an antibody that is produced from a hybridoma or a genetically recombinant antibody that is produced by a transformant transformed with an expression vector containing the antibody genes.

The epitope may be a single amino acid sequence, a three-dimensional structure made of an amino acid sequence, an amino acid sequence modified after translation, a three-dimensional structure made of an amino acid sequence modified after translation which the monoclonal antibody recognizes and binds to or the like.

The amino acid sequence modified after translation may be an O-linked glycan in which sugar chains are attached to Tyr and Ser having OH substituents, an N-linked glycan in which sugar chains are attached to Gln and Asn having $NH_2$ substituents or an amino acid sequence in which a sulfuric acid molecule is attached to Tyr and Ser having OH substituents.

The fact that the antibody of the present invention binds to an extracellular region of human CCR1 can be confirmed by measuring the affinity of the antibody of the present invention to the human CCR1-expressing cells using ELISA, flow cytometry, surface plasmon resonance method or the like. Moreover, binding of the antibody can be confirmed also using a combination of known immunological detection methods [Monoclonal Antibodies-Principles and practice, Third edition, Academic Press (1996), Antibodies-A Laboratory Manual, Cold Spring Harbor Laboratory (1988) and A manual for monoclonal antibody experiments, Kodansha scientific books (1987)] and the like.

The amino acid residue or the epitope of the human CCR1 to which the antibody of the present invention binds can be identified by an antibody-binding test using a deletion variant of the human CCR1 in which some domains are lost, a mutant in which some domains are replaced with domains derived from another protein, a partial peptide fragment of the human CCR1 or the like. The antibody-binding test can also be conducted using expressing cells of the deletion variant or the mutant.

Alternatively, the amino acid residue or the epitope of human CCR1 to which the antibody of the present invention binds can also be identified by adding the antibody of the present invention to peptide fragments of human CCR1 obtained by decomposition using proteases and conducting epitope mapping using a known mass spectrometry.

The fact that the antibody of the present invention inhibits the activation of the human CCR1 by the human CCL15 can be confirmed by, as an index, at least one of the CCR1-dependent signal transduction in the human CCR1-expressing cells, the activation of PLC, the increase in the intracellular calcium ion concentration, the activation of NF-κB, and the migration of human CCR1-expressing cells.

The cell migration can be measured using the chemotaxis assay described below. For example, the human CCR1-expressing cells are added to the upper portion of the chemotaxis assay chamber, and each of 1) a negative control such as a medium or DPBS, 2) the human CCL15, and 3) the human CCL15 and the antibody of the present invention are added to the lower portion of the chamber. After culturing for a certain time, the number of the human CCR1-expressing cells present in the lower portion of the chamber is measured by an appropriate method. Regarding the obtained results, if the number of cells when the human CCL15 and the antibody of the present invention were added is smaller than that when human CCL15 is added under the condition that the number of cells when the human CCL15 was added was larger than the number of cells when the medium was added, the antibody of the present invention can be determined to inhibit the activation of the human CCR1 by the human CCL15.

Moreover, it can confirm that the antibody of the present invention inhibits activation of the human CCR1 by the human CCL15 as an index for the change of the calcium ion concentration in the human CCR1-expressing cells. The changes in the intracellular calcium ion concentration can be measured by a known method, for example, using an intracellular Ca measurement kit (produced by Wako) and the like, and can be measured according to the attached protocol.

As the confirmation method, for example, changes in the intracellular calcium ion concentration when the human CCR1-expressing cells are added with each of 1) a negative control such as medium or DPBS, 2) the human CCL15, and 3) the human CCL15 and the antibody of the present invention are measured according to the above method. If the intracellular calcium ion concentration when the human CCL15 and the antibody of the present invention were added is smaller than the intracellular calcium ion concentration when the human CCL15 is added under the condition that the intracellular calcium ion concentration when the human CCL15 was added was larger than the intracellular calcium ion concentration when the medium was added, the antibody of the present invention can be determined to inhibit the activation of the human CCR1 by the human CCL15.

The antibody molecule is also referred to as an immunoglobulin (hereinafter, referred to as Ig), and the human antibodies are classified into IgA1, IgA2, IgD, IgE, IgG1, IgG2, IgG3, IgG4, and IgM isotypes according to the difference in a molecular structure. IgG1, IgG2, IgG3, and IgG4 having relatively high amino acid sequence homology are collectively referred to as IgG.

The antibody molecule is composed of polypeptides called heavy chains (referred to as H chains below) and light chains (referred to as L chains below). H chain is composed of VH and a H chain constant region (also referred to as CH) from the N-terminus side, and L chain is composed of VL and a L chain constant region (also referred to as CL) from the N-terminus side. For CH, α, δ, ε, γ, and μ chains are known for each subclass. CH is further composed of a CH1 domain, a hinge domain, a CH2 domain and a CH3 domain from the N-terminus side. A domain is a functional structural unit which constitutes each of polypeptide of an antibody molecule. The CH2 domain and the CH3 domain are together called an Fc region or simply Fc. For CL, $C_\lambda$ chain and $C_\kappa$ chain are known.

The CH1 domain, the hinge domain, the CH2 domain, the CH3 domain and the Fc region in the present invention can be identified by the positions of the amino acid residues from the N-terminus according to the EU index [Kabat et al., Sequences of Proteins of Immunological Interest, US Dept. Health and Human Services (1991)]. Specifically, CH1 is identified as the amino acid sequence of from position 118 to position 215 according to the EU index, and the hinge is identified as the amino acid sequence of from position 216 to position 230 according to the EU index. CH2 is identified as the amino acid sequence of from position 231 to position 340 according to the EU index, and CH3 is identified as the amino acid sequence of from position 341 to position 447 according to the EU index.

As the antibody of the present invention, a recombinant mouse antibody, a recombinant rat antibody, a recombinant rabbit antibody, a human chimeric antibody (hereinafter simply abbreviated as a chimeric antibody), a humanized antibody (human complementarity determining region CDR-grafted antibody) produced in particular by genetic engineering, and a genetically recombinant antibody such as a human antibody are also included. In addition, the antibody of the present invention also includes a genetically recombinant antibody (also referred to as a VL-substituted antibody) produced by recombination of an H chain (or VH) and an L chain (or VL) derived from two different types of antibodies. The two different types of antibodies may be any of a hybridoma-derived monoclonal antibody, a chimeric antibody, a humanized antibody, and a human antibody. Furthermore, the antibody of the present invention includes a genetically recombinant antibody to which an appropriate amino acid residue substitution has been added in producing the above-described genetically recombinant antibody.

The chimeric antibody means an antibody consisting of VH and VL of an antibody other than a human (non-human animal) and CH and CL of a human antibody. As the non-human animal, any mouse, rat, hamster, rabbit or the like can be used as long as a hybridoma can be produced.

A hybridoma is a cell which is obtained by cell fusion of a B cell obtained by immunizing a non-human animal with an antigen and a myeloma cell derived from a mouse or the like and which produces a monoclonal antibody having a desired antigen specificity. Therefore, the variable region constituting the antibody produced by the hybridoma consists of the amino acid sequences of a non-human animal antibody.

A human chimeric antibody can be produced by obtaining cDNAs that encode VH and VL of the monoclonal antibody from a hybridoma derived from a non-human animal cell producing a monoclonal antibody, inserting the cDNAs into an expression vector for animal cells having DNA that encodes CH and CL of a human antibody, thereby constructing a human chimeric antibody expression vector, introducing the vector to an animal cell and expressing the antibody.

The chimeric antibody variant in the present invention is an antibody in which VL of one chimeric antibody is substituted with VL of another chimeric antibody (also referred to as a VL-substituted chimeric antibody), and/or an antibody in which one or more amino acid residues of VL or VH of the antibody is substituted with another amino acid residue.

A chimeric antibody variant can be produced by obtaining cDNAs that encode VH of the monoclonal antibody from a hybridoma derived from a non-human animal cell producing a monoclonal antibody, obtaining cDNAs that encode VL of the monoclonal antibody from a hybridoma derived from a non-human animal cell producing another monoclonal antibody, inserting the cDNAs into an expression vector for animal cells having DNA that encodes CH and CL of a human antibody, thereby constructing a human chimeric antibody expression vector combining VH and VL derived from different hybridoma clones, introducing the vector to an animal cell and expressing the antibody. In addition, DNA in which one or a plurality of amino acid residues are substituted with amino acid residues different from those obtained from the hybridoma with respect to the amino acid of VH or VL of the chimeric antibody or the VL-substituted chimeric antibody can be produced to be inserted into the expression vector. An antibody that can be similarly expressed and produced using this vector is also referred to as a chimeric antibody variant.

A humanized antibody is an antibody in which the amino acid sequences of CDRs of VH and VL of an antibody of a non-human animal are implanted to the corresponding CDRs of VH and VL of a human antibody. The region other than the CDRs of VH and VL is called a framework region (referred to as FR below).

A humanized antibody can be produced by constructing cDNA that encodes the amino acid sequence of VH formed from the amino acid sequences of CDRs of VH of an antibody of a non-human animal and the amino acid sequence of FR of VH of any human antibody and cDNA that encodes the amino acid sequence of VL formed from the amino acid sequences of CDRs of VL of an antibody of a non-human animal and the amino acid sequence of FR of VL of any human antibody, inserting the cDNAs to an expression vector for animal cells having DNA that encodes CH and CL of a human antibody, thereby constructing a humanized antibody expression vector, introducing the vector to an animal cell and expressing the antibody.

A human antibody is originally an antibody that naturally exists in the human body, but antibodies obtained from a human antibody phage library, and a human antibody-producing transgenic animal and the like which are produced by recent advances in genetic engineering, cell engineering, and developmental engineering are also included.

A human antibody can be obtained by immunizing a mouse having a human immunoglobulin gene (Tomizuka K. et al., Proc Natl Acad Sci USA. 97, 722-7, 2000) with a desired antigen. A human antibody can be obtained also without immunization by selecting a human antibody having a desired affinity using a phage display library obtained by amplifying antibody genes from human-derived B cells (Winter G. et al., Annu Rev Immunol. 12:433-55. 1994). Moreover, a human antibody can be obtained by producing cells which produce a human antibody having a desired affinity by immortalizing human B cells using EB virus (Rosen A. et al., Nature 267, 52-54.1977).

The antibodies existing in the human body can be obtained by, for example, immortalizing lymphocytes isolated from human peripheral blood by infecting EB virus or the like and then cloning to obtain lymphocytes that produce the antibody, and the antibodies can be purified from the culture in which the lymphocytes are cultured.

A human antibody phage library is a library in which antibody fragments such as Fab and scFv are expressed on the surface of phages by inserting an antibody gene prepared from a human B cell to phage genes. It is possible to collect phages on which antibody fragments having a desired antigen affinity are expressed using affinity to a substrate to which an antigen is fixed as an index from the library. The antibody fragments can be further converted to a human antibody molecule formed from two whole H chains and two whole L chains using a genetic engineering technique.

A human antibody-producing transgenic animal is an animal in which a human antibody gene is incorporated into the chromosomes of the host animal. Specifically, a human antibody-producing transgenic animal can be produced by introducing a human antibody gene to mouse ES cells, implanting the ES cells to an early embryo of another mouse and then causing development. A method for producing the human antibody from a human antibody-producing transgenic animal is performed in such a manner that a human antibody-producing hybridoma can be obtained and cultured by a conventional method for producing hybridoma with a mammal other than a human, and the human antibodies can be produced and accumulated in the culture.

The amino acid sequences of VH and VL of the antibody of the present invention may be any of the amino acid sequences of VH and VL of the humanized antibody in which the amino acid sequences of VH and VL of the human antibodies, the amino acid sequences of VH and VL of the non-human animal antibodies, or the CDRs of non-human animal antibodies are implanted into any human antibody framework.

The amino acid sequence of CL in the antibody of the present invention may be either an amino acid sequence of a human antibody or an amino acid sequence of a non-human animal antibody, and CG or C, of an amino acid sequence of a human antibody is preferable.

The CH of the antibody of the present invention may be any CH as long as it belongs to immunoglobulin, and preferably any of subclass belonging to IgG class, γ1 (IgG1), γ2 (IgG2), γ3 (IgG3) and γ4 (IgG4) can also be used.

As the antibodies of the present invention, an Fc fusion protein in which Fc and an antibody fragment are bound, an Fc fusion protein in which Fc and a naturally existing ligand or receptor are bound (also, referred to as immunoadhesin), and an Fc fusion protein in which a plurality of Fc regions are fused are also included in the present invention. In addition, in order to stabilize the antibody and to control the blood half-life, an Fc region with a modified amino acid residue can also be used in the antibody of the present invention.

The antibody or the antibody fragment thereof of the present invention includes an antibody containing any amino acid residue modified after translation. The modifications after translation include, for example, deletion of a lysine residue at the C-terminus of the H chain [lysine clipping] or conversion of a glutamine residue at the N-terminus of the polypeptide to pyroglutin (pyroGlu) [Beck et al, Analytical Chemistry, 85, 715-736 (2013)].

In the present invention, the antibody fragment is an antibody fragment having antigen affinity, which binds to the extracellular region of human CCR1 and inhibits activation of the human CCR1 by human CCL15. Examples of the antibody fragment in the present invention include Fab, Fab', F(ab')$_2$, scFv, diabody, dsFv, or a peptide containing a plurality of CDRs. Fab is an antibody fragment which has an antigen affinity and a molecular weight of approximately fifty thousand and in which about a half of the H chain in the N-terminus side and the entire L chain are linked to each other through disulfide bonds (S—S bonds) (cleaved at the $224^{th}$ amino acid residue in the H chain), of the fragments obtained by treating IgG antibody with proteases, papain.

F(ab')$_2$ is an antibody fragment which has an antigen affinity and a molecular weight of approximately hundred thousand and which is slightly larger than the one in which Fabs are bound through the S—S bond in the hinge region (cleaved at the $234^{th}$ amino acid residue in the H chain), of the fragments obtained by treating IgG with proteases, pepsin. Fab' is an antibody fragment which has an antigen affinity and a molecular weight of approximately fifty thousand and in which the S—S bond in the hinge region of the above F (ab')$_2$ is cleaved.

scFv is a VH-P-VL or VL-P-VH polypeptide in which one VH and one VL are linked using an appropriate peptide linker (P) such as a linker peptide of any number of connected linkers each having four Gly residues and one Ser residue (G4S) and is an antibody fragment having an antigen affinity.

Diabody is an antibody fragment in which scFvs having same or different antigen binding specificities form a dimer and is an antibody fragment having a divalent antigen affinity to a same antigen or specific antigen affinity to different antigens.

dsFv is a fragment in which polypeptides obtained by substituting one amino acid residue in VH and that in VL with cysteine residues are bound through the S—S bond between the cysteine residues.

A peptide containing CDR is configured by containing at least one or more regions of CDRs of VH or VL. In a peptide containing CDRs, the CDRs can be bound directly or through an appropriate peptide linker. Production can be performed by constructing DNA that encodes CDRs of VH and VL of the modified antibody of the present invention, inserting the DNA into an expression vector for a prokaryote or an expression vector for a eukaryote and introducing the expression vector into a prokaryote or a eukaryote for expression. In addition, a peptide containing CDR can also be produced by a chemical synthesis method such as the Fmoc method or the tBoc method.

The monoclonal antibody of the present invention includes derivatives of antibodies in which a radioisotope, a low molecular drug, a high molecular drug, a protein, or an antibody drug chemically or genetically bound to the monoclonal antibody or the antibody fragment thereof which binds to human CCR1 of the present invention.

The derivative of the antibody can be produced by binding a radioisotope, a low molecular drug, a high molecular weight drug, an immunostimulant, a protein, an antibody drug, or a nucleic acid drug to the N-terminus side or C-terminus side of the H chain or L chain, an appropriate substituent in the antibody molecule, the side chain or sugar chain, or the like of the monoclonal antibody or antibody fragment thereof binding to human CCR1 of the present invention by a chemical method [Introduction to Antibody Engineering, CHIJIN SHOKAN CO., LTD. (1994)].

Also, it can be produced by using a genetic engineering technique performed in such a manner that the DNA encoding the monoclonal antibody or the antibody fragment thereof which binds to the human CCR1 of the present invention and the DNA encoding the protein or antibody drug to be bound are ligated and inserted into an expression vector, and the expression vector is introduced into an appropriate host cell to be expressed.

Examples of the radioisotope include $^{111}$In, $^{131}$I, $^{125}$I, $^{90}$Y, $^{64}$Cu, $^{99}$Tc, $^{77}$Lu, and $^{211}$At. The radioisotope can be directly bound to the antibody by the chloramine T method or the like. Further, a substance that chelates a radioisotope may be bound to the antibody. Examples of a chelating agent include 1-isothiocyanate benzyl-3-methyl diethylenetriamine pentaacetic acid (MX-DTPA).

Examples of the drug of low molecule include anti-cancer drugs such as alkylating agents, nitrosoureas, antimetabolites, antibiotics, plant alkaloids, topoisomerase inhibitors, hormonal therapy agents, hormone antagonists, aromatase inhibitors, P-glycoprotein inhibitors, platinum complex derivatives, M cycle inhibitor or kinase inhibitors [Clinical oncology, Cancer and chemotherapy (1996)], anti-inflammatory agents such as steroids such as hydrocortisone or prednisone, nonsteroidal drugs such as aspirin or indomethacin, immune modulating drugs such as gold thiomalate or penicillamine, immunosuppressive drugs such as cyclophosphamide or azathioprine, antihistamine drugs such as chlorpheniramine maleate or clemastine [Inflammation and anti-inflammatory therapy, Ishiyaku Pub, Inc. (1982)] and the like.

Examples of the anti-cancer drugs include amifostine (Ethyol), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (Adriamycin), epirubicin, gemcitabine (Gemzar), daunorubicin, procarbazine, mitomycin, cytarabine, etoposide, methotrexate, 5-fluorouracil, fluorouracil, vinblastine, vincristine, bleomycin, daunomycin, peplomycin, estramustine, paclitaxel (Taxol), docetaxel (Taxotere), Aldesleukin, asparaginase, busulfan, carboplatin, oxaliplatin, nedaplatin, cladribine, camptothecin, 7-ethyl-10-hydroxycamptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacitidine, UFT, oxaloplatin, gefitinib (Iressa), imatinib (STI571), erlotinib, FMS-like tyrosine kinase 3 (Flt3) inhibitor, vascular endothelial growth factor receptor (VEGFR) inhibitor, fibroblast growth factor receptor (FGFR) inhibitor, epidermal growth factor receptor (EGFR) inhibitor such as Iressa or Tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestins, estrogens, anastrozole (Arimidex), Leuplin, Aspirin, indomethacin, celecoxib, penicillamine, gold thiomalate, chlorpheniramine maleate, chloropheniramine, clemastine, tretinoin, bexarotene, arsenic, bortezomib, allopurinol, calicheamicin, ibritumomab tiuxetan, targretin, ozogamine, clarithromycin, leucovorin, ketoconazole, aminoglutethimide, suramin, or maytansinoid, derivatives thereof and the like.

Examples of the method for binding a low molecular drug and an antibody include a method for binding between a drug and an amino group of the antibody via glutaraldehyde and a method for binding an amino group of the drug and a carboxyl group of the antibody via water-soluble carbodiimide.

Examples of the high molecular drug include polyethylene glycol (hereinafter, referred to as PEG), albumin, dextran, polyoxyethylene, a styrene maleic acid copolymer, polyvinyl pyrrolidone, a pyran copolymer, and hydroxypropyl methacrylamide. By binding these high molecular compounds to the antibody or the antibody fragment thereof, effects such of (1) improving stability against various chemical, physical, or biological factors, (2) significant prolongation of blood half-life, or (3) loss of immunogenicity or suppression of the antibody production are expected [Bioconjugate pharmaceuticals, Hirokawa-Shoten Ltd. (1993)].

For example, as a method for binding PEG and the antibody, a method for reacting with a PEGylation modifying reagent, and the like can be mentioned [Bioconjugate pharmaceuticals, Hirokawa-Shoten Ltd. (1993)]. Examples of the PEGylation modifying reagent include a modifier for 8-amino group of lysine (JP-A-S61-178926), a modifier for a carboxyl group of aspartic acid and glutamic acid (JP-A-S56-23587), or a modifier for a guanidino group of arginine (JP-A-H2-117920).

The immunostimulant may be a natural product known as an immunoadjuvant. Specific examples of drugs enhancing immunity include $\beta$ (1→3) glucan (for example, lentinan or schizophyllan) or $\alpha$-galactosylceramide (KRN7000).

Examples of the protein include cytokines, growth factors or toxin proteins that activate immunocompetent cells such as NK cells, macrophages, and neutrophils.

Examples of cytokines or growth factors include interferon (hereinafter, referred to as IFN)-$\alpha$, IFN-$\beta$, IFN-$\gamma$, interleukin (hereinafter, referred to as IL)-2, IL-12, IL-15, IL-18, IL-21, IL-23, a granulocyte colony stimulating factor (G-CSF), a granulocyte/macrophage colony stimulating factor (GM-CSF), or a macrophage colony stimulating factor (M-CSF). Examples of the toxin protein include ricin, diphtheria toxin, and ONTAK, and also include protein toxins in which mutations are introduced into the protein in order to regulate toxicity.

Examples of the antibody drug include antibodies to an antigen of which apoptosis is induced by the binding of an antibody, an antigen involved in tumor pathogenesis, an antigen that regulates an immune function, and an antigen involved in angiogenesis at the lesion site.

Examples of the antigen of which apoptosis is induced by antibody binding include a cluster of differentiation (hereinafter, referred to as CD) 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-Class II, or Epidermal Growth Factor Receptor (EGFR).

Examples of the antigen involved in tumor pathogenesis and the antigen of the antibody that regulates an immune function include CD4, CD40, a CD40 ligand, B7 family molecules (such as CD80, CD86, CD274, B7-DC, B7-H2, B7-H3, and B7-H4), B7 family molecule ligands (such as CD28, CTLA-4, ICOS, PD-1, and BTLA), OX-40, an OX-40 ligand, CD137, tumor necrosis factor (TNF) receptor family molecules (such as DR4, DR5, TNFR1, and TNFR2), TNF-related apoptosis-inducing ligand receptor (TRAIL) family molecules, receptor family of TRAIL family molecules (such as TRAIL-R1, TRAIL-R2, TRAIL-R3, or TRAIL-R4), a receptor activator of nuclear factor kappa B ligand (RANK), a RANK ligand, CD25, a folate receptor, cytokines [such as IL-1$\alpha$, IL-1$\beta$, IL-4, IL-5, IL-6, IL-10, IL-13, transforming growth factor (TGF) $\beta$, and TNF$\alpha$] or receptors for these cytokines, and chemokines (such as SLC, ELC, I-309, TARC, MDC, and CTACK) or receptors for these chemokines.

Examples of the antibody of antigen that inhibits angiogenesis at the lesion site include a vascular endothelial growth factor (VEGF), angiopoietin, a fibroblast growth factor (FGF), EGF, a hepatocyte growth factor (HGF), a platelet-derived growth factor (PDGF), an insulin-like growth factor (IGF), erythropoietin (EPO), TGF$\beta$, IL-8, ephrin, and SDF-1 or these receptors thereof.

The fusion antibody with protein or the antibody drug is expressed by ligating cDNA encoding an antibody contained in a protein or antibody drug to cDNA encoding the monoclonal antibody or the antibody fragment thereof to construct DNA encoding the fusion antibody, inserting the DNA into a prokaryotic or eukaryotic expression vector, and introducing the expression vector into a prokaryotic or eukaryotic organism, and thereby a fusion antibody can be produced.

Examples of the nucleic acid drug include pharmaceuticals containing nucleic acid such as small interference ribonucleic acid (siRNA) or microRNA that acts on a living body by controlling a function of a gene. For example, a conjugate with the nucleic acid drug that suppresses the master transcription factor RORγt of Th17 cells is conceivable.

In a case where the derivative of the antibody of the present invention is used for detection and measurement of the human CCR1 and diagnosis of the human CCR1-related disease, examples of the drug which binds to the antibody include a labeling substance used in usual immunological detection or measurement methods. Examples of the labeling substance include an enzyme such as alkaline phosphatase, peroxidase, or luciferase, a luminescent substance such as acridinium ester or lophine, and a fluorescent substance such as fluorescein isothiocyanate (FITC) or tetramethylrhodamine isothiocyanate (RITC).

The present invention also includes a composition containing a monoclonal antibody which binds to the human CCR1 or the antibody fragment thereof as an active ingredient.

In addition, the present invention relates to a therapeutic agent for the human CCR1-related disease including the monoclonal antibody which binds to the human CCR1 or the antibody fragment thereof as an active ingredient. In addition, the present invention relates to a method for treating the human CCR1-related disease including administering the monoclonal antibody which binds to the human CCR1 or the antibody fragment thereof.

The human CCR1-related disease may be any disease involving the human CCR1 or the human CCR1 ligand, and examples thereof include cancer, autoimmune diseases, and inflammatory diseases. Examples of cancer diseases include diffuse large B cell lymphoma, follicular lymphoma, B cell lymphoma, T cell lymphoma, plasma cell myeloma, acute myeloid leukemia, Hodgkin lymphoma, chronic lymphocytic leukemia, hairy Cellular leukemia, mantle cell lymphoma, follicular marginal zone lymphoma, small lymphocytic lymphoma, multiple myeloma, hepatocellular carcinoma, colorectal cancer, non-small cell lung cancer, oral squamous cell carcinoma, ovarian cancer, prostate cancer, breast cancer, glioma, and osteosarcoma. Examples of the autoimmune diseases or inflammatory diseases include rheumatoid arthritis, multiple sclerosis, chronic obstructive pulmonary disease, systemic lupus erythematosus, lupus nephritis, asthma, atopic dermatitis, inflammatory bowel disease, Crohn's disease, and Behcet's disease.

The therapeutic agent containing the antibody or the antibody fragment of the present invention may be an agent that contains only the antibody or the antibody fragment as an active ingredient, but the agent is generally preferably mixed with one or more pharmacologically acceptable carriers and provided as medicinal formulation that is produced by any method known in the technical field of pharmaceutical science.

As the route of administration, it is preferable to use the most effective route for the treatment, and examples include oral administration or parenteral administration such as intraoral, airway, intrarectal, subcutaneous, intramuscular, or intravenous administration. Intravenous or intraventricular administration or the like is particularly preferable. Examples of the form of administration include a spray, a capsule, a tablet, a powder, a granule, a syrup, an emulsion, a suppository, an injection, an ointment, a tape and the like.

The dose or the frequency of administration varies according to the desired therapeutic effect, administration method, treatment period, age, body weight and the like but is usually 10 μg/kg to 10 mg/kg per day for an adult.

The present invention relates to a reagent for detecting or measuring CCR1 containing a monoclonal antibody which binds to the human CCR1 or the antibody fragment thereof, or a method for detecting or measuring CCR1 using the monoclonal antibody which binds to the human CCR1 or the antibody fragment thereof. In the present invention, any known method can be used as a method for detecting or measuring the human CCR1. Examples thereof include an immunological detection or measurement method.

The immunological detection or measurement method is a method of detecting or measuring the amount of an antibody or the amount of an antigen using a labeled antigen or antibody. Examples of the immunological detection or measurement method include a radiolabeled immunoassay (RIA) method, an enzyme immunoassay (EIA or ELISA) method, a fluorescence immunoassay (FIA) method, a luminescent immunoassay method, a western blot method, and a physicochemical method.

The present invention includes a diagnostic agent for a CCR1-related disease, including the monoclonal antibody which binds to the human CCR1 or the antibody fragment thereof, or a method for diagnosing CCR1-related diseases, including detecting or measuring CCR1 using the monoclonal antibody which binds to the human CCR1 or the antibody fragment thereof. By using the monoclonal antibody or the antibody fragment thereof of the present invention so as to detect or measure a cell in which the human CCR1 is expressed according to the above method, diseases associated with the human CCR1 can be diagnosed.

In the present invention, a biological sample to be detected or measured for the human CCR1 is not particularly limited as long as it may contain the human CCR1 or cells expressing the human CCR1, such as tissue, cells, blood, plasma, serum, pancreatic juice, urine, feces, tissue fluid, or a culture solution.

The diagnostic agent containing the monoclonal antibody or the antibody fragment thereof of the present invention may contain a reagent for conducting an antigen-antibody reaction and a reagent for detecting the reaction, depending on the target diagnostic method. Examples of the reagent for performing the antigen-antibody reaction include a buffer and a salt. Examples of the reagent for detection include a labeled secondary antibody that recognizes the monoclonal antibody or an antibody fragment thereof, or a reagent that is used for usual immunological detection or measurement methods such as a substrate corresponding to the label.

The present invention also relates to the use of an anti-human CCR1 monoclonal antibody or the antibody fragment thereof for the production of the diagnostic agent or therapeutic agent for the CCR1-related diseases.

The method for producing the antibody of the present invention, the method for treating a disease, the method for diagnosing a disease are specifically explained below.

1. Production Method for Antibody (1) Preparation of Antigen

The human CCR1 or human CCR1-expressing cells serving as antigens can be obtained by introducing an expression vector containing cDNA encoding the full length of human CCR1 or a partial length thereof into *E. coli*, yeast, insect cells, or animal cells. In addition, the human CCR1 can also be obtained by purifying the human CCR1 from various human cell lines, human cells, human tissues, and the like that express the human CCR1 in a large amount. In addition, these human cell lines, human cells, human tissues, and the like can be used as antigens as they are. Furthermore, a synthetic peptide having a partial sequence of the human CCR1 can be prepared by a chemical synthesis method such as an Fmoc method or a tBoc method and used as an antigen. A known tag such as FLAG or His may be added to the C-terminus or N-terminus of the synthetic peptide having the human CCR1 or a partial sequence of the human CCR1.

The human CCR1 used in the present invention can be produced using the method described in Molecular Cloning, A Laboratory Manual, Second Edition, Cold Spring Harbor Laboratory Press (1989), Current Protocols In Molecular Biology, John Wiley & Sons (1987-1997) or the like or another method by expressing DNA that encodes the human CCR1 in a host cell, for example, by the following method.

First, a recombinant vector is produced by inserting the full-length cDNA containing the part that encodes the human CCR1 into downstream of a promoter in an appropriate expression vector. A DNA fragment of an appropriate length which contains the part encoding the polypeptide and which is prepared based on the full-length cDNA may be used in place of the full-length cDNA. Next, a transformant that produces the polypeptide can be obtained by introducing the obtained recombinant vector into a host cell suitable for the expression vector.

As the expression vector, any vector can be used as long as it can replicate autonomously or can be inserted into a chromosome in a host cell to be used and which contains a suitable promoter in the position that enables the transcription of DNA that encodes the polypeptide. As the host cell, any cell, such as a microorganism belonging to the genus *Escherichia* such as *E. coli*, yeast, an insect cell or an animal cell, can be used as long as it enables the expression of a target gene.

In a case where a prokaryote such as *E. coli* is used as a host cell, the recombinant vector is preferably a vector that can replicate autonomously in the prokaryote and that contains a promoter, a ribosomal binding sequence, DNA containing the part encoding human CCR1 and a transcription termination sequence. In addition, the transcription termination sequence is not essentially needed for the recombinant vector, but the transcription termination sequence is preferably placed immediately after the structural gene. Furthermore, the recombinant vector may contain a gene controlling the promoter.

As the recombinant vector, it is preferable to use a plasmid in which the distance between the Shine-Dalgarno sequence (also called SD sequence) that is a ribosomal binding sequence and the initiation codon is appropriately adjusted (to, for example, 6 to 18 nucleotides).

In addition, regarding the nucleotide sequence of DNA that encodes the human CCR1, a nucleotide can be substituted in a manner that the codon becomes optimum for the expression in a host, which enables the enhancement in the production rate of target human CCR1.

As the expression vector, any vector can be used as long as it can exhibit its function in a host cell to be used. Examples thereof include pBTrp2, pBTac1 and pBTac2 (produced by Roche Diagnostics K.K.), pKK233-2 (produced by Pharmacia), pSE280 (produced by Invitrogen), pGEMEX-1 (produced by Promega Corporation), pQE-8

(produced by QIAGEN), pKYP10 (JP-A-S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK (−) (produced by Stratagene Corporation), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), JP-A-S60-221091], pGKA2 [prepared from *Escherichia coli* IGKA2 (FERM BP-6798), JP-A-S60-221091], pTerm2 (U.S. Pat. Nos. 4,686,191, 4,939,094 and U.S. Pat. No. 160,735), pSupex, pUB110, pTP5, pC194, pEG400 [J. Bacteriol., 172, 2392 (1990)], pGEX (produced by Pharmacia), pET System (produced by Novagen), pME18SFL3 and the like.

As the promoter, any promoter may be used as long as it can exhibit its function in a host cell to be used. Examples thereof include promoters such as a trp promoter (Ptrp), a lac promoter, a PL promoter, a PR promoter or a T7 promoter, which are derived from *E. coli*, a phage or the like. In addition, examples thereof also include promoters such as a tandem promoter with two tandemly arrayed Ptrps, a tac promoter, a lacT7 promoter or a let I promoter, which are artificially designed and altered.

Examples of the host cell include *E. coli* XL1-Blue, *E. coli* XL2-Blue, *E. coli* DH1, *E. coli* MC1000, *E. coli* KY3276, *E. coli* W1485, *E. coli* JM109, *E. coli* HB101, *E. coli* No. 49, *E. coli* W3110, *E. coli* NY49, *E. coli* DH5α, and the like.

As a method for introducing a recombinant vector into a host cell, any method can be used as long as it is a method by which DNA is introduced into a host cell to be used. Examples thereof include a method using calcium ions [Proc. Natl. Acad. Sci. USA, 69, 2110 (1972), Gene, 17, 107 (1982) and Molecular & General Genetics, 168, 111 (1979)].

In a case of using an animal cell as a host, as the expression vector, any vector can be used as long as it can exhibit its function in the animal cell. Examples thereof include pcDNAI, pCDM8 (produced by Funakoshi Co., Ltd.), pAGE107 [JP-A-H3-22979; and Cytotechnology, 3, 133 (1990)], pAS3-3 (JP-A-H2-227075), pCDM8 [Nature, 329, 840 (1987)], pcDNAI/Amp (produced by Invitrogen), pcDNA3.1 (produced by Invitrogen), pREP4 (produced by Invitrogen), pAGE103 [J. Biochemistry, 101, 1307 (1987)], pAGE210, pME18SFL3, pKANTEX93 (International Publication No. 97/10354), N5KG1val (U.S. Pat. No. 6,001, 358), INPEP4 (produced by Biogen-IDEC), a transposon vector (International Publication No. 2010/143698) and the like.

As the promoter, any promoter can be used as long as it can exhibit its function in the animal cell. Examples thereof include a promoter of cytomegalovirus (CMV) immediate early (IE) gene, an early promoter of SV40, a retroviral promoter, a metallothionein promoter, a heat-shock promoter, a SRα promoter, a promoter of Moloney murine leukemia virus or an enhancer. In addition, an enhancer of a human CMV IE gene may be used together with the promoter.

Examples of the host cell include a human leukemia cell Namalwa, a monkey cell COS, a Chinese hamster ovary cell CHO [Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci., 60, 1275 (1968); Cell, 6, 121 (1975); and Molecular Cell Genetics, Appendix I, II (pp. 883-900)]; a CHO cell which lacks dihydrofolate reductase gene (referred to as dhfr below) (CHO/DG44 cell) [Proc. Natl. Acad. Sci. USA, 77, 4216 (1980)], CHO-K1 (ATCC CCL-61), DUkXB11 (ATCC CCL-9096), Pro-5 (ATCC CCL-1781), CHO-S (Life Technologies, Cat #11619), Pro-3, a rat myeloma cell YB2/3HL.P2.G11.16Ag.20 (also called YB2/0), a mouse myeloma cell NSO, a mouse myeloma cell SP2/0-Ag14, a Syrian hamster cell BHK, HBT5637 (JP-A-S63-000299) and the like.

As a method for introducing a recombinant vector into a host cell, any method can be used as long as it is a method by which DNA is introduced into an animal cell. Examples thereof include the electroporation [Cytotechnology, 3, 133 (1990)], the calcium phosphate transfection method (JP-A-H2-227075), the lipofection [Proc. Natl. Acad. Sci. USA, 84, 7413 (1987)] and the like.

The human CCR1 can be produced by culturing a transformant derived from a microorganism, an animal cell or the like having the recombinant vector into which DNA that encodes the human CCR1 obtained as above has been introduced in a medium, generating and accumulating the human CCR1 in the culture solution and then collecting the human CCR1 from the culture solution. A method for culturing the transformant in a medium can be performed according to a usual method used for a host culture.

In a case of expression in the cells derived from a eukaryote, the human CCR1 added with sugars or sugar chains can be obtained.

When culturing a microorganism that has been transformed by a recombinant vector using an inducible promoter, an inducer may be added to the medium if necessary. For example, isopropyl-β-D-thiogalactopyranoside or the like may be added to the medium for a case of culturing a microorganism that has been transformed by a recombinant vector using a lac promoter, and indoleacrylic acid or the like may be added to the medium for a case of culturing a microorganism that has been transformed by the recombinant vector using a trp promoter.

Examples of the medium in which the transformant obtained using an animal cell as a host is cultured include RPMI 1640 Medium [The Journal of the American Medical Association, 199, 519 (1967)], Eagle's MEM Medium [Science, 122, 501 (1952)], Dulbecco's Modified MEM Medium [Virology, 8, 396 (1959)], Medium 199 [Proc. Soc. Exp. Biol. Med., 73, 1 (1950)], Iscove's Modified Dulbecco's Medium (IMDM), which are generally used, or a medium in which fetal bovine serum (FBS) or the like is added to such a medium. Culture is usually performed under the conditions of pH 6 to 8 and 30° C. to 40° C. in the presence of 5% $CO_2$ for 1 to 7 days. In addition, during the culture, antibiotics such as kanamycin or penicillin may be added to the medium, if necessary.

Examples of the method for expressing a gene that encodes the human CCR1 include a method such as secretory production or fused protein expression [Molecular Cloning, A Laboratory Manual, Second Edition, Cold Spring Harbor Laboratory Press (1989)] in addition to direct expression.

Examples of the method for producing the human CCR1 include a method for producing in a host cell, a method for secretion out of a host cell and a method for producing on the outer membrane of a host cell. An appropriate method can be selected by changing the host cell to be used or the structure of the human CCR1 to be produced.

In a case where the human CCR1 is produced in a host cell or on the outer membrane of a host cell, the human CCR1 can be actively secreted outside the host cell using the method by Paulson et al. [J. Biol. Chem., 264, 17619 (1989)], the method by Lowe et al. [Proc. Natl. Acad. Sci., USA, 86, 8227 (1989) and Genes Develop., 4, 1288 (1990)] or the method described in JP-A-H05-336963, International Publication No. 94/23021 or the like. In addition, the amount of production of human CCR1 can also be increased using the gene amplification using dihydrofolate reductase gene or the like (JP-A-H2-227075).

The obtained human CCR1 can be isolated and purified as follows, for example. In a case where the human CCR1 is expressed in the cells in a dissolved state, the cells are collected by centrifugation after completing culture and suspended in an aquatic buffer solution, followed by crushing of the cells using an ultrasonic crusher, a French press, a Manton Gaulin homogenizer, a Dyno mill or the like, and therefore cell-free extract is obtained. A purified sample can be obtained from a supernatant obtained by centrifugation of the cell-free extract using a method such as a general method for isolation and purification of proteins, that is, a solvent extraction method, a salting-out method using ammonium sulfate or the like, a desalting method, a precipitation method using an organic solvent, anion-exchange chromatography using a resin such as Diethylaminoethyl (DEAE)-Sepharose or DIAION HPA-75 (produced by Mitsubishi Chemical Corporation), cation-exchange chromatography using a resin such as S-Sepharose FF (produced by Pharmacia), hydrophobic interaction chromatography method using a resin such as Butyl Sepharose or Phenyl Sepharose, a gel filtration method using molecular decoration, affinity chromatography, a chromatofocusing method, electrophoresis such as isoelectric focusing electrophoresis and the like alone or in combination.

In a case where the human CCR1 forms an insoluble complex and expressed in the cells, the cells are collected and then crushed in the same manner as above, followed by centrifugation, and then an insoluble complex of the human CCR1 is collected as a precipitated fraction. The collected insoluble complex of the human CCR1 is solubilized with a protein denaturant. A purified sample of the polypeptide can be obtained by the same method for isolation and purification as above, after returning the human CCR1 back to the normal three-dimensional structure through dilution or dialysis of the solubilized solution.

In a case where the human CCR1 or a derivative thereof such as a sugar-modified complex is extracellularly secreted, the human CCR1 or the derivative thereof such as a sugar-modified complex can be collected in a culture supernatant. By subjecting the culture to procedures using a method such as centrifugation as in the same manner as above, thereby obtaining a soluble fraction, and then using the same method for isolation and purification as above, a purified sample can be obtained from the soluble fraction.

In addition, the human CCR1 used in the present invention can be produced also by a chemical synthesis method such as the Fmoc method or the tBoc method. The human CCR1 can be also chemically synthesized using a peptide synthesizer manufactured by Advanced Chemtech, PerkinElmer, Inc., Pharmacia, Protein Technology Instrument, Inc., Shinseserubega Co., Perceptive, Shimadzu Corporation or the like.

(2) Immunization of Animal and Preparation of Antibody-Producing Cell for Fusion By immunizing a 3- to 20-week old animal such as a mouse, a rabbit or a hamster with the antigen obtained in (1), antibody-producing cells are collected from the spleen, lymph nodes or peripheral blood of the animal. A mouse CCR1 knockout mouse can also be used as the animal to be immunized.

Immunization is performed by administering the antigen, for example, together with an appropriate adjuvant such as Freund's complete adjuvant, aluminum hydroxide gel or *Bordetella pertussis* vaccine subcutaneously, intravenously or intraperitoneally to the animal. In a case where the antigen is a partial peptide, a conjugate of the antigen with a carrier protein such as BSA (bovine serum albumin) or KLH (Keyhole Limpet hemocyanin) is produced and used as an immunogen.

The administration of the antigen is performed 5 to 10 times every 1 to 2 weeks after the first administration. On the $3^{rd\ to}\ 7^{th}$ day after each administration, the blood is collected from a venous plexus of the fundus of the eye, and the antibody valency of the serum is measured using an enzyme immunoassay method [Antibodies—A Laboratory Manual, Cold Spring Harbor Laboratory (1988)] or the like. An animal in which the serum exhibited sufficient antibody valency with respect to the antigen used for the immunization is used as a supply source for the antibody-producing cells for fusion.

On the $3^{rd\ to}\ 7^{th}$ day after a final administration of the antigen, tissues including the antibody-producing cells such as the spleen are extracted from the immunized animal, and the antibody-producing cells are collected. In a case of using the spleen cells, the spleen is shredded and loosened, followed by centrifugation, and then erythrocytes are removed. The antibody-producing cells for fusion are thus obtained.

(3) Preparation of Myeloma Cells

As the myeloma cells, established cells obtained from a mouse are used, and for example, a 8-azaguanine resistant mouse (BALB/c derived) myeloma cell line, P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], P3-X63-Ag8 (X63) [Nature, 256, 495 (1975)] or the like is used.

The myeloma cells are subjected to subculturing with a normal medium [RPMI1640 medium supplemented with glutamine, 2-mercaptoethanol, gentamicin, FBS and 8-azaguanine] and subjected to subculturing with a normal medium 3 to 4 days before the cell fusion, and $2 \times 10^7$ or more cells are acquired on the day of the fusion.

(4) Cell Fusion and Preparation of Monoclonal Antibody-Producing Hybridoma

The antibody-producing cells for fusion obtained in (2) and the myeloma cells obtained in (3) are thoroughly washed with the Minimum Essential Medium (MEM) or PBS (disodium phosphate 1.83 g, monopotassium phosphate 0.21 g, salt 7.65 g, distilled water 1 liter, pH 7.2), mixed at cell numbers of antibody-producing cells for fusion: myeloma cells of 5 to 10:1 and centrifuged, and then the supernatant is removed. After the precipitated cell clusters are loosened thoroughly, a mixture of polyethylene glycol-1000 (PEG-1000), a MEM medium and dimethylsulfoxide is added thereto while stirring at 37° C. Furthermore, 1 to 2 mL of a MEM medium is added thereto every 1 to 2 minutes for several times, and then a MEM medium is added so that the total amount becomes 50 mL. After centrifugation, the supernatant is removed. The precipitated cell clusters are loosened gently, and then the antibody-producing cells for fusion are suspended gently in the HAT medium [normal medium supplemented with hypoxanthine, thymidine and aminopterin]. This suspension is cultured in a 5% $CO_2$ incubator at 37° C. for 7 to 14 days.

After culturing, a part of the culture supernatant is taken, and cell clusters which react with antigens containing the human CCR1 and do not react with antigens without the human CCR1 are selected by a method for selecting a hybridoma such as the binding assay described below. Next, after cloning by the limiting dilution method, a hybridoma which stably shows potent antibody valency is selected as a monoclonal antibody-producing hybridoma.

(5) Preparation of Purified Monoclonal Antibody

The monoclonal antibody-producing hybridoma obtained in (4) is intraperitoneally injected into an 8- to 10-week old mouse or nude mouse which has been treated by pristane treatment [by intraperitoneally administering 2,6,10,14-tetramethylpentadecane (Pristane) 0.5 mL and breeding for 2 weeks]. In 10 to 21 days, the hybridoma becomes an ascites tumor. The ascites are collected from this mouse, and the solid is removed by centrifugation. Then, by salting out with 40% to 50% ammonium sulfate and purifying by caprylic acid precipitation method, a DEAE-Sepharose column, a protein A-column or a gel filtration column, an IgG or IgM fraction is collected to obtain a purified monoclonal antibody.

Moreover, the monoclonal antibody-producing hybridoma obtained in (4) is cultured in RPMI1640 medium supplemented with 10% FBS or the like, and then the supernatant is removed by centrifugation. The hybridoma is suspended in a Hybridoma SFM medium and cultured for 3 to 7 days. A purified monoclonal antibody can also be obtained by centrifuging the obtained cell suspension, purifying from the obtained supernatant by a protein A-column or a protein G-column and collecting an IgG fraction. In this regard, 5% Daigo's GF21 can be added to the Hybridoma SFM medium.

The subclass of the antibody is determined by the enzyme immunoassay method using a subclass typing kit. The protein mass is determined by the Lowry method or by calculating from the absorbance at 280 nm.

(6) Selection of Monoclonal Antibody

The monoclonal antibody is selected, for example, by measuring the affinity of the antibody to human CCR1-expressing cells using flow cytometry as shown below. The human CCR1-expressing cells may be any cells as long as the human CCR1 is expressed on the cell surface, and examples include human cells, a human cell line, and the human CCR1 forcibly-expressing cell line obtained in (1).

After dispensing the human CCR1-expressing cells to a plate such as a 96-well plate, the substances to be tested such as serum, culture supernatants of hybridomas or purified monoclonal antibodies are dispensed as the first antibodies and reacted. The cells after the reaction are thoroughly washed with PBS containing 1% to 10% bovine serum albumin (BSA) (referred to as BSA-PBS below) or the like, and an anti-immunoglobulin antibody labeled with a fluorescent reagent or the like is then dispensed as the second antibody and reacted. After thoroughly washing with BSA-PBS or the like, the fluorescence amounts of the labeled antibody are measured using a flow cytometer, and a monoclonal antibody which specifically reacts with the human CCR1-expressing cells is thus selected.

In addition, an antibody which competes in binding to the human CCR1 with the antibody of the present invention can be obtained by adding an antibody to be tested to the assay system using flow cytometry described above and reacting. That is, by selecting an antibody which inhibits binding of the antibody of the present invention and the human CCR1 when the antibody to be tested is added by screening, a monoclonal antibody that competes with the antibody of the present invention in binding to the amino acid sequence of the human CCR1 or the three-dimensional structure thereof can be obtained.

In addition, an antibody which binds to an epitope containing the epitope to which the monoclonal antibody binding to the human CCR1 of the present invention binds can be obtained by identifying the epitope of an antibody obtained by the screening method described above by a known method, producing a synthetic peptide containing the identified epitope, a synthetic peptide which mimics the three-dimensional structure of the epitope or the like and immunizing.

In addition, an antibody which binds to the same epitope as the epitope to which the monoclonal antibody binding to the human CCR1 of the present invention binds can be obtained by identifying the epitope of an antibody obtained by the screening method described above, producing a partial synthetic peptide of the identified epitope, a synthetic peptide which mimics the three-dimensional structure of the epitope or the like and immunizing.

2. Production of Genetically Recombinant Antibody

As a production example of a genetically recombinant antibody, methods for producing a human chimeric antibody, a human chimeric antibody variant, and a humanized antibody are described below. Genetically recombinant mouse antibody, rat antibody, rabbit antibody, and the like can also be produced by the same method.

(1) Construction of Expression Vector for Genetically Recombinant Antibody

An expression vector for a genetically recombinant antibody is an expression vector for animal cells in which DNA that encodes CH and CL of a human antibody has been incorporated and can be constructed by cloning DNAs that encode CH and CL of a human antibody into an expression vector for animal cells.

As the C region of a human antibody, CH and CL of any human antibody can be used. For example, CH of γ1 subclass and CL of κ class of a human antibody and the like are used. As the DNAs that encode CH and CL of the human antibody, cDNA is used, and chromosomal DNA consisting of exons and introns can also be used. As the expression vector for animal cells, any vector can be used as long as it is capable of incorporating and expressing a gene that encodes the C region of a human antibody. For example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)] and the like are used. The promoter and the enhancer of the expression vector for animal cells are the early promoter of SV40 [J. Biochem., 101, 1307 (1987)], the Moloney murine leukemia virus LTR [Biochem. Biophys. Res. Commun., 149, 960 (1987)] or the promoter of immunoglobulin H chain [Cell, 41, 479 (1985)] and the enhancer [Cell, 33, 717 (1983)] or the like.

As the expression vector for the genetically recombinant antibody, an expression vector for a genetically recombinant antibody of a type in which the antibody H chains and L chains are on the same vector (tandem type) [J. Immunol. Methods, 167, 271 (1994)] is used from the viewpoints of ease of construction of the expression vector for the genetically recombinant antibody, ease of introduction into animal cells, balanced expression levels of the antibody H chains and L chains in animal cells and the like, and a type in which the antibody H chains and L chains are on different vectors can also be used. As the tandem type expression vector for a genetically recombinant antibody, pKANTEX93 (International Publication No. 97/10354), pEE18 [Hybridoma, 17, 559 (1998)] and the like are used.

(2) Acquisition of cDNA Encoding V Region of Antibody Derived from Animal Other than Human and Analysis of Amino Acid Sequence cDNA that encodes VH and VL of a non-human antibody can be obtained, and the amino acid sequence can be analyzed as follows.

mRNA is extracted from hybridoma cells producing a non-human antibody, and cDNA is synthesized. The synthesized cDNA is cloned into a vector such as a phage or a plasmid to produce a cDNA library. Recombinant phages or recombinant plasmids having cDNAs that encode VH or VL are isolated from the libraries using DNAs that encode the C region and the V region of the mouse antibody as probes. The entire nucleotide sequences of VH or VL of the target mouse antibody on the recombinant phages or the recombinant plasmids are determined, and then the entire amino acid sequences of VH or VL are deduced from the nucleotide sequences.

As the animal other than human which produces the hybridoma cells producing the non-human antibody, a mouse, a rat, a hamster, or a rabbit is used, but any animal can be used as long as hybridoma cells can be produced.

For the preparation of total RNA from hybridoma cells, the guanidine thiocyanate-cesium trifluoroacetate method [Methods in Enzymol., 154, 3 (1987)], a kit such as RNA easy Kit (manufactured by QIAGEN) or the like is used.

To prepare mRNA from total RNA, oligo (dT) immobilized cellulose column chromatography [Molecular Cloning, A Laboratory Manual, Second Edition, Cold Spring Harbor Laboratory Press (1989)], a kit such as Oligo-dT30 <Super> mRNA Purification (registered trademark) Kit (manufactured by Takara Bio Inc.) or the like is used. Furthermore, mRNA can also be prepared from hybridoma cells using a kit such as Fast Track mRNA Isolation (registered trademark) Kit (manufactured by Invitrogen) or QuickPrep mRNA Purification (registered trademark) Kit (manufactured by Pharmacia).

For the synthesis of cDNA and the production of a cDNA library, a known method [Molecular Cloning, A Laboratory Manual, Second Edition, Cold Spring Harbor Laboratory Press (1989) and Current Protocols in Molecular Biology, Supplement 1, John Wiley & Sons (1987-1997)], a kit such as SuperScript Plasmid System for cDNA Synthesis and Plasmid Cloning (manufactured by Invitrogen) or ZAP-cDNA Synthesis (registered trademark) Kit (manufactured by Stratagene) or the like is used.

When a cDNA library is produced, any vector capable of incorporating the cDNA can be used as a vector into which the cDNA synthesized using mRNA extracted from the hybridoma cells as a template is incorporated. For example, ZAP Express [Strategies, 5, 58 (1992)], pBluescript II SK (+) [Nucleic Acids Research, 17, 9494 (1989)], λZAPII (manufactured by Stratagene), λgt 10 and λgt 11 [DNA Cloning: A Practical Approach, I, 49 (1985)], Lambda Blue Mid (manufactured by Clontech Laboratories, Inc.), λExCell, pT7T3-18U (manufactured by Pharmacia), pCD2 [Mol. Cell. Biol., 3, 280 (1983)], pUC18 [Gene, 33, 103 (1985)] or the like is used.

Any Escherichia coli can be used as Escherichia coli into which a cDNA library constructed by a phage or a plasmid vector is introduced as long as the cDNA library can be introduced, expressed and maintained. For example, XL1-

Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], JM105 [Gene, 38, 275 (1985)] or the like is used.

For the selection of the cDNA clone that encodes VH or VL of the non-human antibody from the cDNA libraries, a colony hybridization method using an isotope- or fluorescently labeled probe, the plaque hybridization method [Molecular Cloning, A Laboratory Manual, Second Edition, Cold Spring Harbor Laboratory Press (1989)] or the like is used.

In addition, the cDNA that encodes VH or VL can also be prepared by preparing primers and performing the polymerase chain reaction method [referred to as PCR method below, Molecular Cloning, A Laboratory Manual, Second Edition, Cold Spring Harbor Laboratory Press (1989) and Current Protocols in Molecular Biology, Supplement 1, John Wiley & Sons (1987-1997)] using the cDNA synthesized from mRNA or a cDNA library as a template.

The selected cDNA is cleaved with an appropriate restriction enzyme or the like and then cloned into a plasmid such as pBluescript SK (−) (manufactured by Stratagene), and the nucleotide sequence of the cDNA is determined by a commonly used nucleotide sequence analysis method or the like. For the nucleotide sequence analysis method, for example, after performing a reaction such as the dideoxy method [Proc. Natl. Acad. Sci. USA, 74, 5463 (1977)], an automatic nucleotide sequence analyzer such as ABI PRISM3700 (manufactured by PE Biosystems) or A.L.F. DNA sequencer (manufactured by Pharmacia) or the like is used.

By deducing the entire amino acid sequences of VH and VL from the determined nucleotide sequences and comparing with the entire amino acid sequences of VH and VL of a known antibody [Sequences of Proteins of Immunological Interest, US Dept. Health and Human Services (1991)], it is confirmed whether the obtained cDNA encodes the complete amino acid sequences of VH and VL of an antibody containing a secretion signal sequence. Regarding the complete amino acid sequences of VH and VL of the antibody containing a secretion signal sequence, by comparing with the entire amino acid sequences of VH and VL of a known antibody [Sequences of Proteins of Immunological Interest, US Dept. Health and Human Services (1991)], the length of the secretion signal sequence and the N-terminus amino acid sequence can be deduced, and the subgroup to which they belong can be found. In addition, the amino acid sequences of the CDRs of VH and VL can also be determined by comparing with the amino acid sequences of VH and VL of a known antibody [Sequences of Proteins of Immunological Interest, US Dept. Health and Human Services (1991)].

Furthermore, using the obtained complete amino acid sequences of VH and VL, it is possible to confirm whether the complete amino acid sequences of VH and VL are new by carrying out homology search by the BLAST method [J. Mol. Biol., 215, 403 (1990)] or the like using any database such as SWISS-PROT or PIR-Protein.

(3) Construction of Human Chimeric Antibody Expression Vector or Human Chimeric Antibody Variant Expression Vector By cloning cDNAs that encode VH and VL of a non-human antibody in the upstream of the respective genes that encode CH and CL of a human antibody in the expression vector for a genetically recombinant antibody obtained in (1), a human chimeric antibody expression vector can be constructed.

By using cDNA encoding VH derived from a certain monoclonal antibody and cDNA encoding VL derived from another monoclonal antibody, a human chimeric antibody variant expression vector can be constructed.

In addition, the gene fragment is amplified by using a PCR primer that introduces the corresponding cDNA or the already produced human chimeric antibody expression vector as a PCR template into a point mutation at a desired amino acid modification site, and cloned and ligated to the vector obtained in (1), and thereby the human chimeric antibody variant expression vector can be constructed. In a case where there are a plurality of modification sites, gene fragments produced by artificial DNA synthesis can also be used.

In order to link the 3' terminus sides of the cDNAs that encode VH or VL of the non-human antibody with the respective 5' terminus sides of CH or CL of the human antibody, cDNAs of VH and VL in which the nucleotide sequences of the linking parts are designed to encode an appropriate amino acid and to become an appropriate restriction enzyme recognition sequence are produced. The produced cDNAs of VH and VL are cloned in the upstream of the respective genes that encode CH or CL of the human antibody in the expression vector for a genetically recombinant antibody obtained in (1) in a manner that they are expressed in an appropriate form, and therefore a human chimeric antibody expression vector or a human chimeric antibody variant expression vector is constructed.

In addition, each of the cDNAs that encode VH or VL of the non-human antibody can be amplified by the PCR method using synthetic DNA having an appropriate restriction enzyme recognition sequence at both ends and cloned into the expression vector for a genetically recombinant antibody obtained in (1).

(4) Construction of cDNA Encoding V Region of Humanized Antibody

A cDNA that encodes VH or VL of a humanized antibody can be constructed as follows.

The amino acid sequences of the FRs of VH and VL of the human antibody for the implanting of the amino acid sequences of the CDRs of VH and VL of a non-human antibody are selected. Any amino acid sequences derived from a human antibody can be used as the selected amino acid sequences of the FRs. For example, an amino acid sequence of FR of a human antibody registered in a database such as Protein Data Bank, a common amino acid sequence of the subgroups of FR of a human antibody [Sequences of Proteins of Immunological Interest, US Dept. Health and Human Services (1991)] or the like is used. In order to suppress a decrease in affinity of the antibody, an amino acid sequence of FR having as high homology (at least 60% or higher) as possible to the amino acid sequence of the FR of VH or VL of the original antibody is selected.

Next, the amino acid sequences of the CDRs of the original antibody are implanted to the respective selected amino acid sequences of the FRs of VH and VL of the human antibody, and the amino acid sequences of VH and VL of a humanized antibody are designed. By converting the designed amino acid sequences into DNA sequences in consideration of the use frequency of codons found in the nucleotide sequences of the antibody genes [Sequences of Proteins of Immunological Interest, US Dept. Health and Human Services (1991)], DNA sequences encoding the amino acid sequences of VH and VL of a humanized antibody are designed.

Based on the designed DNA sequences, several synthetic DNAs having lengths of around 100 bases are synthesized, and the PCR reaction is carried out using the DNAs. In this case, due to the reaction efficiency of the PCR reaction and the synthesizable lengths of DNAs, 6 synthetic DNAs are preferably designed for each of VH and VL. Furthermore, by introducing an appropriate restriction enzyme recognition sequence at the 5' or 3' terminus of the synthetic DNAs located at both ends, cDNA that encodes VH or VL of a humanized antibody can be easily cloned into the expression vector for a genetically recombinant antibody obtained in (1).

After the PCR reaction, the amplified products are each cloned into a plasmid such as pBluescript SK (−) (produced by Stratagene), and the nucleotide sequences are determined by the same method as the method described in (2). A plasmid having the DNA sequence that encodes the amino acid sequence of VH or VL of a desired humanized antibody is thus obtained.

Alternatively, the entire VH and the entire VL each synthesized as a long chain DNA based on the designed DNA sequences can also be used instead of the PCR amplified products. Moreover, by introducing an appropriate restriction enzyme recognition sequence at both ends of the synthesized long chain DNAs, cDNAs that encode VH and VL of the humanized antibody can be easily cloned into the expression vector for a genetically recombinant antibody obtained in (1).

(5) Modification of Amino Acid Sequence of V Region of Humanized Antibody

When only the CDRs of VH and VL of a non-human antibody are merely implanted into the FRs of VH and VL of the human antibody, the antigen affinity of the humanized antibody is lower than that of the original non-human antibody [BIO/TECHNOLOGY, 9, 266 (1991)]. In a humanized antibody, by identifying the amino acid residues directly related to antigen binding, the amino acid residues interacting with the amino acid residues of the CDRs and the amino acid residues which maintain the three-dimensional structure of the antibody and which are indirectly related to antigen binding, in the amino acid sequences of the FRs of VH and VL of a human antibody, and by substituting these amino acid residues with the amino acid residues of the original non-human antibody, the lowered antigen affinity can be increased.

In order to identify the amino acid residues of FR related to the antigen affinity, the three-dimensional structure of the antibody can be constructed and analyzed using X-ray crystallography [J. Mol. Biol., 112, 535 (1977)], computer modeling [Protein Engineering, 7, 1501 (1994)] or the like. Furthermore, a humanized antibody having necessary antigen affinity can be obtained by producing various types of variants for each antibody and repeatedly examining their correlation with the antigen affinity and through trial and error.

Amino acid residues of the FRs of VH and VL of a human antibody can be modified by carrying out the PCR reaction described in (4) using synthetic DNA for the modification. The nucleotide sequence of the amplified product after the PCR reaction is determined, and whether the intended modification has been carried out is confirmed by the method described in (2).

(6) Construction of Expression Vector for Humanized Antibody

By cloning the cDNAs that encode VH and VL of the constructed genetically recombinant antibody in the upstream of the respective genes that encode CH and CL of the human antibody in the expression vector for a genetically recombinant antibody obtained in (1), an expression vector for a humanized antibody can be constructed.

For example, the cDNAs are cloned in the upstream of the respective genes that encode CH and CL of the human antibody in the expression vector for a genetically recombinant antibody obtained in (1) in a manner that the cDNAs are expressed in an appropriate form by introducing an appropriate restriction enzyme recognition sequence at the 5' or 3' terminus of the synthetic DNAs located at both ends of the synthetic DNAs used for constructing VH and VL of the humanized antibody obtained in (4) and (5).

In addition, in a case of producing a genetically recombinant antibody such as the above-described chimeric antibody or the humanized antibody, by producing the antibody expression vector obtained by recombining H chain (or VH) and L chain (or VL) derived from two different types of antibodies, a vector for expressing a VL-substituted chimeric antibody can be constructed.

(7) Transient Expression of Genetically Recombinant Antibody

By transiently expressing genetically recombinant antibodies using the expression vectors of a genetically recombinant antibody obtained in (3) and (6) or modified expression vectors thereof, the antigen affinity of the produced various human chimeric antibodies and humanized antibodies can be efficiently evaluated.

As a host cell into which an expression vector is introduced, any cell can be used as long as it is a host cell capable of expressing a genetically recombinant antibody, but for example, COS-7 cells [American Type Culture Collection (ATCC) number: CRL1651] are used [Methods in Nucleic Acids Res., CRC press, 283 (1991)].

For introduction of an expression vector into COS-7 cells, the DEAE-dextran method [Methods in Nucleic Acids Res., CRC press (1991)], the lipofection method [Proc. Natl. Acad. Sci. USA, 84, 7413 (1987)] or the like is used.

After the introduction of the expression vector, the expression level and the antigen affinity of the genetically recombinant antibody in a culture supernatant are measured using the enzyme immunoassay method [Monoclonal Antibodies-Principles and practice, Third edition, Academic Press (1996), Antibodies-A Laboratory Manual, Cold Spring Harbor Laboratory (1988) and A manual for monoclonal antibody experiments, Kodansha scientific books (1987)] or the like.

(8) Acquisition of Transformant Stably Expressing Genetically Recombinant Antibody and Preparation of Genetically Recombinant Antibody By introducing the expression vector for a genetically recombinant antibody obtained in (3) or (6) into an appropriate host cell, a transformant stably expressing the genetically recombinant antibody can be obtained.

For the introduction of the expression vector into a host cell, the electroporation method [JP-A-H2-257891 and Cytotechnology, 3, 133 (1990)] or the like is used.

As the host cell into which the expression vector for a genetically recombinant antibody is introduced, any cell can be used as long as it is a host cell capable of expressing the genetically recombinant antibody. For example, CHO-K1 (ATCC CCL-61), DUKXB11 (ATCC CCL-9096), Pro-5 (ATCC CCL-1781), CHO-S (Life Technologies, Cat #11619), rat myeloma cells YB2/3HL.P2.G11.16Ag.20 (ATCC No. CRL1662, also called YB2/0), mouse myeloma cells NS0, mouse myeloma cells SP2/0-Ag14 (ATCC No. CRL1581), mouse P3X63-Ag8.653 cells (ATCC No. CRL1580), CHO cells in which the dihydroforate reductase gene (referred to as dhfr below) is deficient (CHO/DG44 cells) [Proc. Natl. Acad. Sci. USA, 77, 4216 (1980)] and the like are used.

In addition, a host cell in which the activity of a protein such as enzymes related to intracellular synthesis of sugar nucleotide GDP-fucose, a protein such as enzymes related to glycosylation modification in which the 1-position of fucose is α-bonded to the 6-position of N-acetylglucosamine at the reducing terminus of a N-glycoside-linked complex type sugar chain, a protein related to intracellular transport of sugar nucleotide GDP-fucose to the Golgi body or the like is reduced or lost, for example, CHO cells in which the α1,6-fucosyltransferase gene is deficient (International Publication No. 2005/035586 and International Publication No. 02/31140), Lec13 having lectin resistance [Somatic Cell and Molecular genetics, 12, 55 (1986)] and the like can also be used.

After the introduction of the expression vector, a transformant stably expressing a genetically recombinant antibody is selected by culturing the transformant in a medium for animal cell culture containing a drug such as G418 sulfate (referred to as G418 below) (JP-A-H2-257891).

As the medium for animal cell culture, RPMI 1640 medium (produced by Invitrogen), GIT medium (produced by Nippon Pharmaceutical Co., Ltd.), EX-CELL 301 medium (produced by Jay Earl H., Inc.), IMDM medium (produced by Invitrogen), Hybridoma-SFM medium (produced by Invitrogen), a medium in which various additives such as FBS are added to any of these media or the like is used. A genetically recombinant antibody is expressed and accumulated in a culture supernatant by culturing the obtained transformant in the medium. The expression level and the antigen affinity of the genetically recombinant antibody in the culture supernatant can be measured by the ELISA method or the like. In addition, the expression level of the genetically recombinant antibody produced by the transformant can be increased using the dhfr gene amplification system (JP-A-H2-257891) or the like.

The genetically recombinant antibody is purified using a protein A-column from the culture supernatant of the transformant [Monoclonal Antibodies—Principles and practice, Third edition, Academic Press (1996) and Antibodies—A Laboratory Manual, Cold Spring Harbor Laboratory (1988)]. In addition, a method used for purifying proteins, such as gel filtration, ion exchange chromatography and ultrafiltration, can also be combined.

The molecular weights of the H chains, the L chains or the whole antibody molecule of the purified genetically recombinant antibody can be measured using polyacrylamide gel electrophoresis [Nature, 227, 680 (1970)], western blotting method [Monoclonal Antibodies—Principles and practice, Third edition, Academic Press (1996) and Antibodies—A Laboratory Manual, Cold Spring Harbor Laboratory (1988)] or the like.

3. Activity Evaluation of Purified Monoclonal Antibody or Antibody Fragment Thereof The activity of the purified monoclonal antibody or the antibody fragment thereof of the present invention can be evaluated as follows.

The affinity of the antibody or the antibody fragment thereof of the present invention to the human CCR1 is measured by using the flow cytometry described in the above 1-(6). Moreover, the affinity can also be measured using a fluorescent antibody method [Cancer Immunol. Immunother., 36, 373 (1993)].

The activity of the antibody or the antibody fragment thereof of the present invention to inhibit the migration of the human CCR1-expressing cells by the human CCL15 can be measured using the chemotaxis assay described above.

The CDC activity or the ADCC activity to the human CCR1-expressing cells can be measured by a known measurement method [Cancer Immunol. Immunother., 36, 373 (1993); and Current protocols in Immunology, Chapter7. Immunologic studies in humans, Editor, John E, Coligan, et al., John Wiley & Sons, Inc., (1993)].

4. Method for Controlling Effector Activity of Antibody

As the method for controlling the effector activity of the monoclonal antibody of the present invention, a method for controlling the amount of α1,6-fucose (also called a core fucose) binding to N-acetylglucosamine (GlcNAc) present on the reducing terminal of the N-linked complex sugar chain that bind to the $297^{th}$ asparagine (Asn) in the Fc region of the antibody or the antibody fragment containing Fc (International Publication No. 2005/035586, International Publication No. 2002/31140 and International Publication No. 00/61739), a method for controlling by modifying an amino acid residue in the Fc region of the antibody are known. The effector activity of the monoclonal antibody of the present invention can be controlled using any of the methods.

The effector activity refers to the antibody-dependent activity that is caused through the Fc region of the antibody, and ADCC activity, CDC activity, Antibody-dependent phagocytosis (ADP activity) that is caused by phagocytes such as macrophages or dendritic cells and the like are known.

As the method for measuring the effector activity, for example, the effector activity can be measured by mixing inflammatory cells as targets, human peripheral blood mononuclear cells (PBMC) as effectors, and inflammatory cell-specific antibodies, incubating the mixture for around four hours and then measuring the released lactate dehydrogenase (LDH) as an index of the cytotoxicity. Alternatively, an antibody recognizing a blood cell-specific antigen such as CD20 is added to human whole blood, and after incubation, a decrease in the number of blood cells to be targeted can be measured as effector activity. Alternatively, for example, after mixing another target cell with the human whole blood, and further adding and incubating an antibody specific to the target cell, the decrease in the number of target cells can be measured as the effector activity. In any case, the effector activity can be measured by a LDH-release method, a $^{51}$Cr-release method, a flow cytometry method, or the like.

The effector activity of an antibody can be increased or decreased by controlling the core fucose content of the N-linked complex sugar chain of Fc of the antibody. Regarding the method for reducing the content of fucose which binds to the N-linked complex sugar chain binding to Fc of the antibody, an antibody thereof to which fucose is not bound can be obtained by expressing the antibody using CHO cells in which the α1,6-fucosyltransferase gene is deficient. An antibody to which fucose is not bound has high ADCC activity.

On the other hand, as the method for increasing the content of fucose which binds to the N-linked complex sugar chain binding to Fc of the antibody, an antibody to which fucose is bound can be obtained by expressing the antibody using host cells into which the α1,6-fucosyltransferase gene has been introduced. An antibody to which fucose is bound has lower ADCC than that of an antibody to which fucose is not bound.

Moreover, by modifying an amino acid residue in the Fc region of the antibody, the ADCC activity or the CDC activity can be increased or reduced. For example, the CDC activity of the antibody can be increased using the amino acid sequence of the Fc region described in US Patent Application Publication No. 2007/0148165.

Furthermore, the ADCC activity or the CDC activity can be increased or decreased by the amino acid modifications described in U.S. Pat. No. 6,737,056 specification, U.S. Pat. No. 7,297,775 specification or U.S. Pat. No. 7,317,091 specification. The antibody of the present invention also includes an antibody whose half-life in the blood is controlled by controlling the reactivity with Fc receptor, for example through the amino acid modifications described in JP-A-2013-165716, JP-A-2012-021004 or the like in accordance with the amino acid modifications or the sugar chain modifications in the constant region contained in the antibody.

Moreover, when a combination of the above methods is applied to one antibody, an antibody thereof whose effector activity of the antibody and the half-life in the blood are controlled can be obtained.

5. Method for Treating Disease Using Anti-Human CCR1 Monoclonal Antibody or Antibody Fragment of Present Invention The monoclonal antibody or the antibody fragment thereof of the present invention can be used for the treatment of any human CCR1-related disease as long as it is a disease related to CCR1, such as human CCR1-dependent cell migration and lesion.

The therapeutic agent containing the monoclonal antibody or the antibody fragment of the present invention may contain only the antibody or the antibody fragment as an active ingredient, but the agent is generally mixed with one or more pharmacologically acceptable carriers and provided as medicinal formulation that is produced by a method known in the technical field of pharmaceutical science.

Examples of the route of administration include oral administration or parenteral administration such as intraoral, airway, intrarectal, subcutaneous, intramuscular, or intravenous administration. Examples of the form of administration include a spray, a capsule, a tablet, a powder, a granule, a syrup, an emulsion, a suppository, an injection, an ointment, a tape and the like.

Formulations suitable for oral administration are emulsions, syrups, capsules, tablets, powders, granules and the like.

Liquid preparations such as emulsions or syrups are produced using water, sugars such as sucrose, sorbitol or fructose, glycols such as polyethylene glycol or propylene glycol, oils such as sesame oil, olive oil or soybean oil, preservatives such as p-hydroxybenzoic acid esters, flavors such as strawberry flavor or peppermint or the like as an additive.

The capsules, the tablets, the powders, the granules and the like are produced using excipients such as lactose, glucose, sucrose or mannitol, disintegrating agents such as starch or sodium alginate, lubricants such as magnesium stearate or talc, binders such as polyvinyl alcohol, hydroxypropyl cellulose or gelatin, surfactants such as a fatty acid ester, plasticizers such as glycerin or the like as an additive.

Formulations suitable for parenteral administration are injections, suppositories, sprays and the like. The injections are produced using a salt solution, a glucose solution, a carrier formed of a mixture of these solutions or the like. The suppositories are produced using carriers such as cocoa butter, hydrogenated fats or carboxylic acids.

The sprays are produced using a carrier which does not stimulate the oral and respiratory mucosa of a recipient and which enables dispersion of the monoclonal antibody or the antibody fragment of the present invention as fine particles and easy absorption or the like. As the carrier, for example, lactose, glycerin or the like is used. In addition, it can also be produced as an aerosol or a dry powder. Furthermore, also for the above parenteral preparations, the components exemplified as the additives for the formulations suitable for oral administration can also be added.

6. Method for Diagnosing Disease Using Anti-Human CCR1 Monoclonal Antibody or Antibody Fragment of Invention By using the monoclonal antibody or the antibody fragment thereof of the present invention so as to detect or measure the human CCR1 or a cell in which the human CCR1 is expressed, human CCR1-related diseases can be diagnosed.

The diagnosis of the cancer diseases, the autoimmune diseases, and the inflammatory diseases, which are the human CCR1-related diseases, can be performed by, for example, detecting or measuring the human CCR1 present in a patient by an immunological method. In addition, the diagnosis can be performed by detecting the human CCR1 expressed in the cells in a patient using the immunological method such as flow cytometry.

The immunological method is a method for detecting or measuring the amount of an antibody or the amount of an antigen using a labeled antigen, antibody or the like. For example, the radioactive material labeled immune antibody method, the enzyme immunoassay method, the fluorescence immunoassay method, the luminescent immunoassay method, the western blotting method, the physicochemical method or the like is used.

In the radioactive material labeled immune antibody method, for example, the antibody or the antibody fragment of the present invention is reacted with an antigen, cells expressing an antigen or the like and then reacted with an anti-immunoglobulin antibody or an antibody fragment thereof subjected to radiolabeling, followed by measurement with a scintillation counter or the like.

In the enzyme immunoassay method, for example, the antibody or the binding fragment of the present invention is reacted with an antigen, cells expressing an antigen or the like and then reacted with an anti-immunoglobulin antibody or a binding fragment thereof subjected to labeling with an enzyme or the like, followed by addition of a substrate and measurement of the absorbance of the reaction solution with an absorptiometer. For example, a sandwich ELISA method or the like is used. As a labeling substance used in the enzyme immunoassay method, a known [Enzyme Immunoassay Method, Igaku-Shoin Ltd. (1987)] enzyme label can be used.

For example, alkaline phosphatase label, peroxidase label, luciferase label, biotin label or the like is used. The sandwich ELISA method is a method in which after binding an antibody to a solid phase, a target antigen to be detected or to be measured is trapped, and then a second antibody is reacted with the trapped antigen. In the ELISA method, two kinds of antibodies or the antibody fragments which recognize the antigen to be detected or measured and which have different antigen recognition sites are prepared, and among these, a first antibody or an antibody fragment is adsorbed on a plate (for example, a 96-well plate) in advance, followed by labeling a second antibody or an antibody fragment with a fluorescent substance such as FITC, an enzyme such as peroxidase, biotin or the like. The plate on which the antibody is adsorbed is allowed to react with cells or a lysate thereof, tissues or a lysate thereof, a cell culture supernatant, serum, pleural effusion, ascites, intraocular fluid or the like separated from the living body and then to react with the labeled monoclonal antibody or the antibody fragment, followed by the detection reaction according to the labeling material. From a calibration curve prepared by serially diluting the antigen of a known concentration, the antigen concentration in the test sample is calculated. As the antibodies used in the sandwich ELISA method, either a polyclonal antibody or a monoclonal antibody may be used. Antibody fragments such as Fab, Fab' and F(ab)$_2$ may be used. The combination of the two kinds of antibodies used in the sandwich ELISA method may be a combination of monoclonal antibodies or antibody fragments thereof which recognize different epitopes or may be a combination of a polyclonal antibody and a monoclonal antibody or antibody fragments thereof.

In the fluorescence immunoassay method, measurement is carried out by the method described in documents [Monoclonal Antibodies-Principles and practice, Third edition, Academic Press (1996) and A manual for monoclonal antibody experiments, Kodansha scientific books (1987)] or the like. As the labeling substance used in the fluorescence immunoassay method, a known [Fluorescent Antibody Method, Soft Science (1983)] fluorescent label can be used. For example, FITC, RITC or the like is used.

In the luminescent immunoassay method, measurement is carried out by the method described in a document [Bioluminescence and Chemiluminescence, Clinical Test 42, Hirokawa-Shoten Ltd. (1998)] or the like. As the labeling substance used in the luminescent immunoassay method, a known luminescent label is used, and an acridinium ester, a lophine or the like is used.

In the western blotting method, measurement is carried out by after fractionating antigens, cells expressing an antigen or the like by SDS (sodium dodecyl sulfate)-PAGE (polyacrylamide gel) [Antibodies—A Laboratory Manual Cold Spring Harbor Laboratory (1988)], blotting the gel on a polyvinylidene fluoride (PVDF) membrane or a nitrocellulose membrane, reacting an antibody or an antibody fragment that recognizes the antigen with the membrane, further reacting it with an anti-mouse IgG antibody or a binding fragment subjected to labeling with a fluorescent substance such as FITC, labeling with an enzyme such as peroxidase, biotin labeling or the like and then visualizing the label.

An example is shown below. Cells or tissues expressing a polypeptide having the amino acid sequence of SEQ ID NO: 2 are lysed, and 0.1 to 30 µg as a protein amount per lane is subjected to electrophoresis by the SDS-PAGE method under reducing conditions. The electrophoresed proteins are transferred to a PVDF membrane and reacted with PBS containing 1% to 10% BSA (referred to as BSA-PBS below) for 30 minutes at room temperature to perform blocking operation. The monoclonal antibody of the present invention is reacted therewith, and the membrane is washed with PBS containing 0.05 to 0.1% Tween-20 (referred to as Tween-PBS below) and reacted with a goat anti-mouse IgG labeled with peroxidase for 2 hours at room temperature. By washing with Tween-PBS and detecting a band to which the monoclonal antibody is bound using ECL Western Blotting Detection Reagents (manufactured by Amersham) or the like, the polypeptide having the amino acid sequence of SEQ ID NO: 2 is detected. As the antibody used for detection by western blotting, an antibody capable of binding to a polypeptide that does not retain the natural three-dimensional structure is used.

The physicochemical method is carried out, for example, by binding the human CCR1, which is the antigen, with the monoclonal antibody or the antibody fragment of the present invention to form an aggregate and detecting the aggregate. As another physicochemical method, a capillary tube method, a one-dimensional immunodiffusion method, an immunoturbidimetric method, a latex immunoturbidimetric method [Outline of Clinical Examination Method, KANEHARA & Co., LTD. (1998)] or the like can also be used. In the latex immunoturbidimetric method, when a carrier such as a polystyrene latex having a particle size of approximately 0.1 to 1 µm sensitized with an antibody or an antigen is used to cause the antigen-antibody reaction with a corresponding antigen or antibody, the scattered light is increased in a reaction solution, and the transmitted light is decreased. The antigen concentration and the like in the test sample are measured by detecting this change as absorbance or integrating sphere turbidity.

For detection or measurement of cells expressing the human CCR1, a known immunological detection method can be used, but of known methods, the immunoprecipitation method, the immunocytostaining method, the immunohistochemical staining method, the fluorescent antibody staining method or the like is preferably used.

In the immunoprecipitation method, after reacting cells expressing the human CCR1 or the like with the monoclonal antibody or the antibody fragment of the present invention, a carrier having specific affinity to an immunoglobulin such as Protein G-Sepharose is added thereto, and therefore an antigen-antibody complex is precipitated. Alternatively, the method can also be carried out by the following method. The monoclonal antibody or the antibody fragment of the present invention described above is immobilized on a 96-well plate for ELISA and then blocked with BSA-PBS. When the antibody is an antibody which is not purified such as a hybridoma culture supernatant, for example, the hybridoma culture supernatant is dispensed and bound after immobilizing anti-mouse immunoglobulin, anti-rat immunoglobulin, protein-A, protein-G or the like on a 96-well plate for ELISA in advance and blocking the plate with BSA-PBS. Next, after discarding BSA-PBS and thoroughly washing with PBS, lysates of cells or tissues expressing human CCR1 are reacted therewith. Immunoprecipitates are extracted from the plate after thoroughly washing with a sample buffer for SDS-PAGE and detected by the above western blotting.

The immunocytostaining method or the immunohistochemical staining method is a method in which cells, tissues or the like expressing an antigen are treated with a surfactant, methanol or the like in order to improve passing of the antibody in some cases, then reacted with the monoclonal antibody of the present invention and further reacted with an anti-immunoglobulin antibody or a binding fragment thereof subjected to fluorescent labeling with FITC or the like, labeling with an enzyme such as peroxidase, biotin labeling or the like and in which the label is then visualized and observed with a microscope. In addition, detection can be carried out by the fluorescent antibody staining method in which a fluorescently-labeled antibody is reacted with cells and analyzed with a flow cytometer [Monoclonal Antibodies—Principles and practice, Third edition, Academic Press (1996) and A manual for monoclonal antibody experiments, Kodansha scientific books (1987)]. In particular, the monoclonal antibody or the antibody fragment thereof, binding to the human CCR1, of the present invention can detect cells in which the antigen is expressed and retains the natural three-dimensional structure by the fluorescent antibody staining method.

In addition, when the FMAT 8100 HTS system (produced by Applied Biosystems) or the like of the fluorescent antibody staining methods is used, the amount of an antigen or the amount of an antibody can be measured without separating the formed antibody-antigen complex from the free antibody or antigen that is not involved in formation of the antibody-antigen complex.

Hereinafter, the present invention will be explained in more detail by Examples, but the present invention is not limited to the following Examples.

EXAMPLES

[Example 1] Production of Expression Vectors for Human and Mouse CCR1s (1) Production of Each CCR1 Gene DNAs encoding the following 1 to 7 human or mouse CCR1 or CCR1-CCR3 chimeric receptors were synthesized (Genscript Japan). In the synthesis, restriction enzyme sites (BamHI and NotI) for incorporation into each vector and a Kozak sequence were added.

1. cDNA sequence (SEQ ID NO: 1) encoding human CCR1 (hereinafter, referred to as hCCR1)
2. cDNA sequence (SEQ ID NO: 3) encoding mouse CCR1 (hereinafter, referred to as mCCR1)
3. cDNA sequence (SEQ ID NO: 5) encoding human CCR3 (hereinafter, referred to as hCCR3)
4. cDNA sequence (SEQ ID NO: 6) encoding a chimeric receptor (hereinafter, referred to as NC3-hCCR1) in which the amino acid sequences at positions 1 to 31 in human CCR1 were substituted with the corresponding N-terminus amino acid sequence of human CCR3
5. cDNA sequence (SEQ ID NO: 7) encoding a chimeric receptor (hereinafter, referred to as NC3-mCCR1) in which the amino acid sequences at a position 1 to 31 in mouse CCR1 were substituted with the corresponding N-terminus amino acid sequence of human CCR3
6. cDNA sequence (SEQ ID NO: 8) encoding a chimeric receptor (hereinafter, referred to as hCCR3_EL2hCCR1) in which the amino acid sequences at a position 171 to 194 in human CCR3 are substituted with the amino acid sequences at a position 171 to 194 in human CCR1
7. cDNA sequence (SEQ ID NO: 9) encoding a chimeric receptor (hereinafter, referred to as hCCR3_EL2mCCR1) in which the amino acid sequences at a position 171 to 194 in human CCR3 are substituted with the amino acid sequences at a position 171 to 194 in mouse CCR1

(2) Production of Human CCR1 Expression Vector

DNA encoding hCCR1 synthesized in (1)-1 was treated with restriction enzymes BamHI and NotI (New England Biolab) to purify a DNA fragment. A Tol2 transposon vector (International Publication No. 2010/143698) (hereinafter, referred to as Tn-pMug-Hygro) was treated with the same restriction enzyme, mixed with a DNA fragment encoding CCR1, and then treated by DNA ligase (Takara Bio Inc.) to be ligated. The ligated DNA was introduced into an *E. coli* competent cell (Takara Bio Inc.), and an *E. coli* strain having the desired plasmid DNA was selected from colonies that had acquired drug resistance. This *Escherichia coli* strain was cultured again, and DNA for transfection was purified from a culture solution. (Hereinafter, the plasmid thus produced is referred to as hCCR1/Tn-pMug-Hygro.)

(3) Production of Various CCR1 Expression Vectors

In the same method as in (2) above, mCCR1, hCCR3, NC3-hCCR1, NC3-mCCR1, hCCR3_EL2hCCR1, and hCCR3_EL2mCCR1 synthesized in (1) were ligated to Tn-pMug-Hygro so as to construct an expression vector.

(Hereinafter, referred to as mCCR1/Tn-pMug-Hygro, hCCR3/Tn-pMug-Hygro, NC3-hCCR1/Tn-pMug-Hygro, NC3-mCCR1/Tn-pMug-Hygro, hCCR3_EL2hCCR1/Tn-pMug-Hygro, and hCCR3_EL2mCCR1/Tn-pMug-Hygro, respectively.)

(4) Production of mCCR1 Expression Vector

In the same method as in (2) above, the DNA encoding mCCR1 synthesized in (1) above was ligated to pCAG-IRES-neo which is a vector in which an internal ribosomal entry site (IRES) and a neomycin resistance gene were added to pCAGGS [Gene. 1991 Dec. 15; 108 (2):193-9.] so as to construct an expression vector (hereinafter, referred to as mCCR1/pCAG-IRES-neo).

[Example 2] Production of CCR1-Expressing Cell Line (1) Production of hCCR1-Expressing Cell An expressing cell line was obtained by co-introducing hCCR1/Tn-pMug-Hygro, which is the plasmid DNA, produced in Example 1, and a Tol2 transposase expression vector TPEX_pMug (International Publication No. 2013/005649) into CHO-S (Thermo Fisher Scientific Inc.). Gene introduction was performed using Fugene HD (Promega Corporation) as follows. Cells prepared to $1\times10^5$ cells/mL were seeded in 2.5 mL each in a 6-well plate, and 24 hours later, a mixture of hCCR1/Tn-pMug-Hygro, TPEX_pMug, and Fugene HD was added to a culture solution. 72 hours after the addition, 1 mg/mL hygromycin (Invitrogen) was added, and drug selection was performed for about 2 weeks. The cells that acquired drug resistance were collected, and expression analysis was performed by flow cytometry (FACS Calibur, BD Biosciences). As a result, the expression of the introduced hCCR1 was confirmed. This cell line is referred to as CHO-S-hCCR1.

(2) Production of Various CCR Expressing Cells mCCR1/Tn-pMug-Hygro, hCCR3/Tn-pMug-Hygro, NC3-hCCR1/Tn-pMug-Hygro, NC3-mCCR1/Tn-pMug-Hygro, hCCR3_EL2hCCR1/Tn-pMug-Hygro, and hCCR3_EL2mCCR1/Tn-pMug-Hygro produced in Example 1 were introduced to CHO-S cells in the same method as in (1) above so as to produce an expressing cell line. Hereinafter, these cell lines are referred to as CHO-S-mCCR1, CHO-S-hCCR3, CHO-S-NC3-hCCR1, CHO-S-NC3-mCCR1, CHO-S-hCCR3_EL2hCCR1, and CHO-S-hCCR3_EL2mCCR1, respectively.

(3) Production of RL33-hCCR1 Cell

An hCCR1-expressing cell line was obtained by co-introducing hCCR1/Tn-pMug-Hygro produced in Example 1, and the Tol2 transposase expression vector TPEX_pMug (International Publication No. 2013/005649) into a rabbit cell line RL-33 [Yoshii et al., Jpn J Med Sci Biol. 1977 June; 30 (3): 149-57]. Gene introduction was performed using Lipofectamine LTX (Thermo Fisher Scientific Inc.) as follows. Cells prepared to $1\times10^5$ cells/mL were seeded in 2 mL each in a 6-well plate, and a mixture of 2.5 μg of plasmid DNA and 5 μL of Lipofectamine LTX was added to the medium. 72 hours after the addition, 1 mg/mL hygromycin was added, and drug selection was performed for about 2 weeks. The cells that acquired drug resistance were collected, and expression analysis was performed by flow cytometry. As a result, the expression of the introduced hCCR1 was confirmed. This cell line is referred to as RL33-hCCR1.

(4) Production of RL33-mCCR1 Cell

An expressing cell line was produced by introducing mCCR1/pCAG-IRES-neo produced by Example 1 (4) into RL-33 in the same method as in (3) above. As a drug, G418 having 0.5 mg/mL was selected. This cell line is referred to as RL33-mCCR1.

[Example 3] Production of Anti-CCR1 Rabbit Polyclonal Antibody

An anti-CCR1 rabbit polyclonal antibody was produced by the following method. An N-terminus peptide (SEQ ID NO: 10) of the human CCR1 was synthesized, and two rabbits (New Zealand White) were immunized 5 times every 2 weeks. The immunization was carried out by subcutaneous injection at multiple locations on the back using Complete Freund's Adjuvant (CFA) only for the first time and Incomplete Freund's Adjuvant (IFA) for the second and subsequent times. The serum was collected from individuals whose the antibody valency increased after the immunization, and IgG was purified by affinity purification using a Protein A column (GE Healthcare). The anti-CCR1 rabbit polyclonal antibody thus produced was referred to as E5971.

[Example 4] Expression Analysis by Flow Cytometry (1) Confirmation of CCR1 Expression The CCR1-expressing cell line produced in Example 2 was stained with the anti-CCR1 rabbit polyclonal antibody E5971 produced in Example 3, and the expression of CCR1 was confirmed by flow cytometry (FCM). FCM analysis was performed as follows. Cells were seeded in a 96-well plate at $2\times10^5$ cells/well and washed with a staining buffer [3% FBS (Thermo Fisher Scientific Inc.)/DPBS (Nacalai Tesque)/0.1% sodium azide (Nacalai Tesque)]. The cells were treated with 10 μg/mL E5971 for 1 hour on ice, washed with the staining buffer, and then added with secondary antibody Alexa Fluor 647 goat Anti-Rabbit IgG (produced by Thermo Fisher Scientific Inc.) at a final concentration of 1 μg/mL, and treated for 30 minutes at room temperature. The cells were washed again with the staining buffer, suspended in the staining buffer, and analyzed using BD FACSCalibur (BD Biosciences). With this, it was confirmed that the introduced CCR1 was expressed in the produced CCR1-expressing cell line.

(2) Confirmation of CCR3 Expression

For CHO-S-hCCR3 produced in Example 2, the expression of CCR3 was confirmed by the same method as in (1) above. A commercially available anti-CCR3 antibody 444-11 antibody (MBL) was used as the primary antibody, and Alexa Fluor 647 goat Anti-mouse IgG (H+L) (Thermo Fisher Scientific Inc.) was used as the secondary antibody. With this, it was confirmed that the CCR3 introduced by CHO-S-hCCR3 was expressed.

[Example 5] Production of Monoclonal Antibody Using CCR1 Knockout Mouse

In order to obtain a mouse cross-linking antibody, a monoclonal antibody was produced using a commercially available CCR1 knockout (KO) mouse (B6.129S4-Ccr1$^{tm1Gao}$ N10+N5) (Taconic). Antibody production was performed according to the following procedure.

(1) Immunization

As an immunogen, CHO-S-hCCR1, CHO-S-mCCR1, RL33-hCCR1, and RL33-mCCR1 produced in Example 2 were used. $1\times10^7$ cells/mouse were used per immunization. Alum gel (ELS) (80 μL/animal) and pertussis vaccine (Nacalai Tesque) ($1\times10^7$ cells/animal) were added to 5 to 9 weeks old CCR1 KO mice as adjuvants only at the time of the first immunization so that the immunization was performed by intraperitoneal administration. All immunizations were prepared with PBS so that the dose was 500 μL/animal. The second immunization was performed 2 weeks after the first immunization and the third immunization was further performed after 1 week, and partial blood collection was performed 3 days later.

(2) Antiserum Evaluation (FCM)

Using the various CCR1-expressing cells produced in Example 2, the specific antibody valency in the serum was measured by FCM. The measurement was performed according to the following procedure. Each cell was prepared to be $1\times10^5$ cells/well with 1% BSA (Nacalai Tesque)-PBS (Nacalai Tesque) [including 0.02% EDTA (Nacalai Tesque), 0.05% NaN$_3$ (Nacalai Tesque) and dispensed to a U-shaped bottom of a 96-well cell culture plate at 50 μL/well. The serum collected from the immunized animal as a test sample was diluted with 1% BSA-PBS (0.02% EDTA, 0.05% NaN$_3$) so that the final concentration became 200-fold dilution, 1000-fold dilution, and 5000-fold dilution, and the diluted serum was dispensed at 50 μL/well and allowed to stand at 4° C. for 30 minutes. After performing centrifugation (2000 rpm for 2 minutes), a supernatant was aspirated, and a cell pellet was broken with a plate shaker. The mixture was dispensed with 1% BSA-PBS (0.02% EDTA, 0.05% NaN$_3$) at 200 μL/well, and subjected to the centrifugation again (2000 rpm for 2 minutes), then the supernatant was aspirated, and the cell pellet was broken with a plate shaker. Alexa Fluor 647 goat anti-mouse IgG (H+L) or Alexa Fluor 488 goat anti-mouse IgG (H+L) was prepared with 1% BSA-PBS (0.02% EDTA, 0.05% NaN$_3$) so that the final concentration became 300-fold, dispensed at 50 μL/well, and allowed to stand at 4° C. for 30 minutes in the dark. After performing centrifugation (2000 rpm for 2 minutes), a supernatant was aspirated, and a cell pellet was broken with a plate shaker. The mixture was dispensed with 1% BSA-PBS (0.02% EDTA, 0.05% NaN$_3$) at 200 μL/well, and subjected to the centrifugation again (2000 rpm for 2 minutes), then the supernatant was aspirated, and the cell pellet was broken with a plate shaker. 1% BSA-PBS (0.02% EDTA, 0.05% NaN$_3$) was dispensed thereto at 50 μL/well, and the fluorescence intensity was measured with a flow cytometer [FACSCanto (Trademark) II/BD]. With this, an individual in which an increase in the antibody valency was confirmed was selected, and a spleen was removed.

(3) Hybridoma Production by Cell Fusion

A mouse myeloma cell line P3-U1 (P3X63Ag8U.1, ATCC CRL-1597) was cultured in Esculon Cloning Medium (Aedia Co., Ltd.) and serum-free and then used as a parent line for the cell fusion. The spleen of the immunized animal was aseptically collected and hemolyzed with RED BLOOD CELL LYSING BUFFER (Sigma-Aldrich), then the cells were washed twice with PBS and mixed so that the number of spleen cells and P3-U1 satisfied spleen cells: P3-U1=8:1, and then the mixture was subjected to the centrifugation (1200 rpm for 5 minutes). After the cells of the obtained precipitate fraction were thoroughly loosened, 0.5 mL of a mixed solution of 1 g of polyethylene glycol-1000 (PEG-1000, Junsei Chemical Co., Ltd.), 1 mL of a MEM medium (Nacalai Tesque), and 0.35 mL of dimethyl sulfoxide (Sigma-Aldrich) was added thereto at 37° C. under the stirring, 1 mL of a MEM medium was added 5 times every minute, and then a MEM medium was added so that the total amount became 50 mL. After centrifuging the cell suspension (900 rpm for 5 minutes) and gently loosening the cells of the obtained precipitate fraction, the spleen cells were suspended in a cell concentration of $1.5 \times 10^7$ cells/9 mL with an Escron cloning medium supplemented with HAT SUPPLEMENT (Thermo Fisher Scientific Inc.). A 96-well culture plate was pre-dispensed with a HAT-added cloning medium at 100 μL/well, and the cell suspension was dispensed at 100 μL/well into the plate, and cultured for 8 to 10 days in a $CO_2$ incubator (5% $CO_2$ at 37° C.).

(4) Hybridoma Screening

The affinity of the antibody contained in the hybridoma culture supernatant to CCR1 was evaluated by FCM. The hybridoma culture supernatant was used as a test sample, and staining and measurement were performed in the same procedure as in (2) above.

(5) Hybridoma Subcloning

The cells in the wells that were positive in the screening were subcloned and cultured in a cloning medium for about 7 to 10 days.

(6) Determination of Antibody Subclass

The subclass of each antibody was determined by FCM using a subclass specific secondary antibody. The procedure for staining and measurement was performed in the same manner as in (2) above. The hybridoma culture supernatant was used as a test sample. As an antibody for detection, an Alexa Fluor 488 goat anti-mouse IgG (H+L) (Thermo Fisher Scientific Inc.), and the respective subclass specific antibodies (Alexa Fluor 488 goat anti-mouse IgG1 (Thermo Fisher Scientific Inc.), Alexa Fluor 488 goat anti-mouse IgG2a (Thermo Fisher Scientific Inc.), Alexa Fluor 488 goat anti-mouse IgG2b (Thermo Fisher Scientific Inc.), and Alexa Fluor 488 goat anti-mouse IgG3 (Thermo Fisher Scientific Inc.) were used.

(7) Antibody Purification from Hybridoma Culture Supernatant

The antibody was purified from a culture supernatant of the hybridoma cloned as described above. For purification, Protein G Sepharose 4Fast Flow (GE Healthcare) was used. The culture supernatant was centrifuged to remove the precipitate and filtered through a filter. A column was packed with 400 μL of carrier and a buffer was substituted with DPBS. The culture supernatant was added, and the antibody was adsorbed to a carrier, followed by washing twice with 10 mL of DPBS. 0.4 mL of IgG Elution Buffer (Thermo Fisher Scientific Inc.) was added and eluted, and immediately after that, neutralized with 0.1 mL of 1 M Tris-HCl (Nippon Gene Co., Ltd.) pH 8.6. Desalination and buffer substitution with DPBS were performed using a NAP column (GE Healthcare) and used for the subsequent analysis. Table 1 indicates the clone name, origin, and subclass of the produced antibody.

TABLE 1

| Names of Antibodies | Origin | Subclass |
| --- | --- | --- |
| KM5907 | Mouse | IgG1 |
| KM5908 | Mouse | IgG2a |
| KM5909 | Mouse | IgG1 |
| KM5911 | Mouse | IgG2b |
| KM5915 | Mouse | IgG2b |
| KM5916 | Mouse | IgG2b |
| KM5954 | Mouse | IgG2a |
| KM5955 | Mouse | IgG2a |
| KM5956 | Mouse | IgG2a |

[Example 6] THP-1 Migration (Chemotaxis) Assay

A human monocytic leukemia cell line THP-1 has been known as a human cell line expressing CCR1. This cell is known to exhibit chemotaxis to a concentration gradient of CCR1 ligands such as CCL3, CCL5, CCL15 or CCL23, and a migration assay using THP-1 is a system widely used as an evaluation system for CCR1 inhibitors. Therefore, the anti-human CCR1 antibody obtained in Example 5 was also evaluated using this experimental system to inhibit the activation of human CCR1 by human CCL15.

The method for migration assay is described below. THP-1 cells were obtained from ATCC. The THP-1 cells were cultured for 3 days in the presence of 5 μM All-trans-retinoic acid (ATRA) (Wako Pure Chemical Industries, Ltd.), induced to differentiate, collected, and washed in an assay medium [1% FBS (Thermo Fisher Scientific Inc.)/RPMI1640 (Nacalai Tesque)] heated to 37° C., and then resuspended in the same medium. $1 \times 10^6$ cells/mL were prepared, and the cells were dispensed at 100 μL/well on an upper layer of Transwell (Corning, #3421) having a pore size of 5 μm. In a lower layer, an assay medium added with 1 ng/mL recombinant human CCL15 (68aa) (R & D technologies, #628-LK) as a chemoattractant was placed, and cultured for 4 to 6 hours in a 5% $CO_2$ incubator at 37° C., and then the number of cells that migrated to the lower layer was quantified with Celltiter-Glo (Promega Corporation).

When evaluating the cell migration of the purified antibody using this measurement system, 90 μL of the cell suspension and 10 μL of the purified antibody solution were previously mixed in a 1.5 mL tube and incubated at 37° C. for 1 hour, and the cells were then dispensed into the upper layer of Trasnwell. The antibody was used for the measurement after adjusting the final concentration to 0.3, 1, 3, and 10 μg/mL.

The obtained results are illustrated in FIGS. 1(a) and 1(b). As illustrated in FIGS. 1(a) and 1(b), the KM5907 antibody, the KM5908 antibody, the KM5909 antibody, the KM5911 antibody, the KM5915 antibody, the KM5916 antibody, the KM5954 antibody, the KM5955 antibody, and the KM5956 antibody which are mouse anti-human CCR1 monoclonal antibody and were obtained in Example 5 inhibited THP-1 migration induced by activated CCL15 in a concentration-dependent manner.

From the above, it was revealed that the mouse anti-human CCR1 monoclonal antibody of the present invention is an antibody that inhibits the activation of the human CCR1 by the human CCL15.

[Example 7] Determination of Human CCR1
Binding Region of Anti-Human CCR1 Antibody The binding region of the human CCR1 of the mouse anti-human CCR1 monoclonal antibody obtained in Example 5 was examined by FCM using CCR1-CCR3 chimeric receptor-expressing cells. The measurement was performed in the same method as in Example 4.

As the CCR1-CCR3 chimeric receptor-expressing cells, CHO-S-hCCR3, CHO-S-NC3-hCCR1, CHO-S-NC3-mCCR1, and CHO-S-hCCR3_EL2hCCR1 produced in Example 2 were used. Moreover, CHO-S was used as a negative control.

As test antibodies, each hybridoma culture supernatant diluted 10-fold, an existing mouse anti-human CCR1 monoclonal antibody 53504 antibody (R & D Technologies), and a mouse anti-human CCR3 monoclonal antibody 444-11 antibody (MBL) were used.

Regarding the measurement results, the fluorescence intensity when a certain cell was stained with a certain test antibody (each hybridoma culture supernatant, 53504 antibody or 444-11 antibody) and a secondary antibody was divided by the fluorescence intensity when the cell was stained only with the secondary antibody. When the obtained numerical value was 10 or more, it was determined that the test antibody bound to the cell, and when it was less than 10, it was determined that the test antibody did not bind to the cell. In Table 2, the results are indicated as A and B, respectively.

TABLE 2

| | Cells | | | | |
|---|---|---|---|---|---|
| Antibodies | CHO-S-NC3-hCCR1 | CHO-S-NC3-mCCR1 | CHO-S-hCCR3 | CHO-S-_hCCR3 EL2hCCR1 | CHO-S |
| KM5907 | A | A | B | A | B |
| KM5908 | A | A | B | A | B |
| KM5909 | A | A | B | A | B |
| KM5911 | A | A | B | A | B |
| KM5915 | A | A | B | A | B |
| KM5916 | A | A | B | A | B |
| KM5954 | A | A | B | A | B |
| KM5955 | A | B | B | A | B |
| KM5956 | A | A | B | A | B |
| 53504 antibody (R&D) | A | B | B | B | B |
| 444-11 antibody (MBL) | B | B | A | B | B |

From Table 2, the KM5907 antibody, the KM5908 antibody, the KM5909 antibody, the KM5911 antibody, the KM5915 antibody, the KM5916 antibody, the KM5954 antibody, the KM5955 antibody, and a KM5956 antibody which are mouse anti-human CCR1 monoclonal antibody bound to both CHO-NC3-hCCR1 and CHO-S-hCCR3_EL2hCCR1 without binding to CHO-S-hCCR3. Therefore, it was revealed that any of the mouse anti-human CCR1 monoclonal antibodies of the present invention binds to the extracellular loop 2 of the human CCR1.

[Example 8] Chemotaxis Assay Using Existing Anti-Human CCR1 Antibody and Anti-Human CCR1 Antibody (1) Preparation of Existing Mouse Anti-Human CCR1 Monoclonal Antibody 2D4 Antibody A hybridoma (LS-125-2D4-11-10-1) producing 2D4 antibody (U.S. Pat. No. 6,756,035), which is an existing anti-human CCR1 antibody, was obtained from ATCC. This hybridoma was cultured using Hybridoma-SFM (Thermo Fisher Scientific Inc.), and the antibody was purified from the culture supernatant. For purification, Protein G Sepharose 4Fast Flow (GE Healthcare) was used. The culture supernatant was centrifuged, and the obtained culture supernatant was filtered with a filter. A column was packed with 400 μL of carrier and a buffer was substituted with DPBS. The culture supernatant was added to the column, and the antibody was adsorbed on the carrier, followed by washing twice with 10 mL of DPBS. 0.4 mL of IgG Elution Buffer (Thermo Scientific) was added to the column to elute the antibody, and the antibody solution was immediately neutralized with 0.1 mL of 1 M Tris-Cl (Nacalai Tesque) at pH 8.6. Desalination of the antibody solution and buffer substitution with DPBS were performed using a NAP column (GE Healthcare) and used for the subsequent analysis.

The purified 2D4 antibody was subjected to SDS-PAGE under reducing conditions by a conventional method, and it was confirmed that the antibody was purified.

Further, the affinity of the 2D4 antibody to the human CCR1 was confirmed by FCM according to the method described in Example 4. The 2D4 antibody was reacted at 0.1 and 1 μg/mL, and as the cells, CHO-S-hCCR1 as human CCR1-expressing cells and CHO-S as a negative control were used. As a result, the 2D4 antibody did not bind to CHO-S but bound to CHO-S-hCCR1 in a concentration-dependent manner. Therefore, it was confirmed that the purified 2D4 antibody has affinity to human CCR1 in the same manner as the commercially available 141-2 antibody (MBL) and 53504 antibody (R & D Systems).

(2) Chemotaxis Assay

The activity of inhibiting the activation of the human CCR1 for the existing anti-human CCR1 antibody and the KM5908 antibody and the KM5916 antibody which are mouse anti-human CCR1 antibody monoclonal antibody and were obtained in Example 5 as measured based on the method described in Example 6, and the results obtained were compared for each antibody.

As the existing anti-human CCR1 antibody, the 2D4 antibody produced in (1) and the commercially available 141-2 antibody and 53504 antibody were used.

Figure 2:
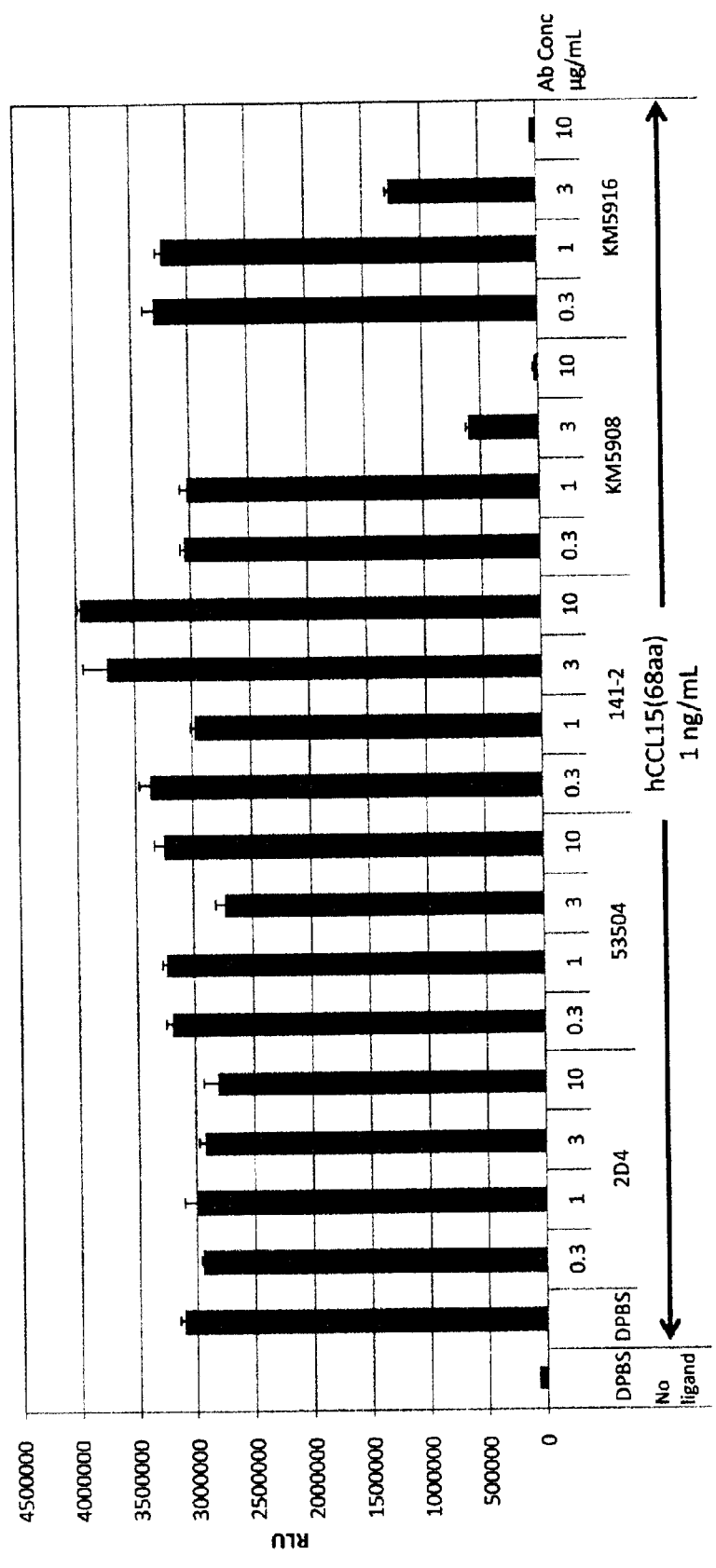
FIG. 2 illustrates results of measuring an activity of an anti-human CCR1 antibody to inhibit THP-1 migration by an activated human CCL15. A vertical axis in FIG. 2 indicates an amount of luminescence (relative light unit; RLU) when the number of cells that have moved to the lower layer of Transwell is measured by CellTiter-Glo. A horizontal axis of FIG. 2 indicates an antibody and a ligand added to the THP-1 cells and concentrations thereof.

The obtained results are indicated in FIG. 2. As illustrated in FIG. 2, the 2D4 antibody, the 141-2 antibody, and the 53504 antibody which are existing anti-human CCR1 antibody did not inhibit the migration of THP-1 cells induced by activated CCL15; whereas the KM5908 antibody and the KM5916 antibody which are mouse anti-human CCR1 monoclonal antibody of the present invention both inhibited the migration of the cells in a concentration-dependent manner.

As described in Example 6, all of the anti-human CCR1 antibodies obtained in Example 5 inhibited the migration of THP-1 cells induced by activated CCL15 in an antibody concentration-dependent manner under the same experimental conditions as in this Example [FIGS. 1 (a) and 1 (b)].

Therefore, the existing anti-human CCR1 antibody does not inhibit the activation of the human CCR1 by the human CCL15; whereas, the KM5907 antibody, the KM5908 antibody, the KM5909 antibody, the KM5911 antibody, the KM5915 antibody, the KM5916 antibody, the KM5954 antibody, the KM5955 antibody, and the KM5956 antibody, which are mouse anti-human CCR1 monoclonal antibody and were obtained in Example 5, are all antibodies that inhibit the activation of the human CCR1 by the human CCL15.

[Example 9] Production of Genetically Recombinant Antibody (1) Cloning and Sequencing of Antibody Variable Region Genes Total RNA was extracted from the hybridoma cloned in Example 5 using Trizol (Life Technologies), and the antibody gene was amplified by a 5'-RACE method. SMARTer RACE Kit (Clontech) was used for the synthesis of RACE cDNA. Antibody variable region fragments were amplified by PCR using primers specific for the sequences added in the RACE cDNA synthesis process and primers for mouse Ig gamma chain or kappa chain amplification (SEQ ID NOs: 11 to 14) and cloned to confirm the nucleotide sequence of the DNA fragment.

Regarding each anti-human CCR1 antibody obtained in Example 5, Table 3 indicates SEQ ID NOs representing the nucleotide sequences encoding the amino acid sequences of the variable region of the heavy chain and the light chain, the amino acid sequences deduced from the nucleotide sequences, and the amino acid sequences obtained by removing the signal sequence from the amino acid sequences. Further, Table 4 indicates SEQ ID NOs representing the amino acid sequences of CDRs of the respective antibodies of the present invention.

(Life Technologies). The procedure was as follows according to the attached manual. Expi293F cells (Thermo Fisher Scientific Inc.) were cultured at a density of $2 \times 10^6$ cells/mL for 24 hours at 37° C., and then $1.25 \times 10^8$ cells per reaction were added to 42.5 mL of Expi293 Expression Medium

TABLE 3

| Antibodies | VH | | | VL | | Amino acid |
| | Nucleotide sequence | Amino acid sequence | Amino acid sequences obtained by removing signal sequence | Nucleotide sequence | Amino acid sequence | sequences obtained by removing signal sequence |
|---|---|---|---|---|---|---|
| KM5907 | SEQ ID NO: 15 | SEQ ID NO: 16 | SEQ ID NO: 51 | SEQ ID NO: 17 | SEQ ID NO: 18 | SEQ ID NO: 52 |
| KM5908 | SEQ ID NO: 19 | SEQ ID NO: 20 | SEQ ID NO: 53 | SEQ ID NO: 21 | SEQ ID NO: 22 | SEQ ID NO: 54 |
| KM5909 | SEQ ID NO: 23 | SEQ ID NO: 24 | SEQ ID NO: 55 | SEQ ID NO: 25 | SEQ ID NO: 26 | SEQ ID NO: 56 |
| KM5911 | SEQ ID NO: 27 | SEQ ID NO: 28 | SEQ ID NO: 57 | SEQ ID NO: 29 | SEQ ID NO: 30 | SEQ ID NO: 58 |
| KM5915 | SEQ ID NO: 31 | SEQ ID NO: 32 | SEQ ID NO: 59 | SEQ ID NO: 33 | SEQ ID NO: 34 | SEQ ID NO: 60 |
| KM5916 | SEQ ID NO: 35 | SEQ ID NO: 36 | SEQ ID NO: 61 | SEQ ID NO: 37 | SEQ ID NO: 38 | SEQ ID NO: 62 |
| KM5954 | SEQ ID NO: 39 | SEQ ID NO: 40 | SEQ ID NO: 63 | SEQ ID NO: 41 | SEQ ID NO: 42 | SEQ ID NO: 64 |
| KM5955 | SEQ ID NO: 43 | SEQ ID NO: 44 | SEQ ID NO: 65 | SEQ ID NO: 45 | SEQ ID NO: 46 | SEQ ID NO: 66 |
| KM5956 | SEQ ID NO: 47 | SEQ ID NO: 48 | SEQ ID NO: 67 | SEQ ID NO: 49 | SEQ ID NO: 50 | SEQ ID NO: 68 |

TABLE 4

| | VH | | | VL | | |
| | CDR1 | CDR2 | CDR3 | CDR1 | CDR2 | CDR3 |
|---|---|---|---|---|---|---|
| KM5907 | SEQ ID NO: 69 | SEQ ID NO: 70 | SEQ ID NO: 71 | SEQ ID NO: 72 | SEQ ID NO: 73 | SEQ ID NO: 74 |
| KM5908 | SEQ ID NO: 75 | SEQ ID NO: 76 | SEQ ID NO: 77 | SEQ ID NO: 78 | SEQ ID NO: 79 | SEQ ID NO: 80 |
| KM5909 | SEQ ID NO: 81 | SEQ ID NO: 82 | SEQ ID NO: 83 | SEQ ID NO: 84 | SEQ ID NO: 85 | SEQ ID NO: 86 |
| KM5911 | SEQ ID NO: 87 | SEQ ID NO: 88 | SEQ ID NO: 89 | SEQ ID NO: 90 | SEQ ID NO: 91 | SEQ ID NO: 92 |
| KM5915 | SEQ ID NO: 93 | SEQ ID NO: 94 | SEQ ID NO: 95 | SEQ ID NO: 96 | SEQ ID NO: 97 | SEQ ID NO: 98 |
| KM5916 | SEQ ID NO: 99 | SEQ ID NO: 100 | SEQ ID NO: 101 | SEQ ID NO: 102 | SEQ ID NO: 103 | SEQ ID NO: 104 |
| KM5954 | SEQ ID NO: 105 | SEQ ID NO: 106 | SEQ ID NO: 107 | SEQ ID NO: 108 | SEQ ID NO: 109 | SEQ ID NO: 110 |
| KM5955 | SEQ ID NO: 111 | SEQ ID NO: 112 | SEQ ID NO: 113 | SEQ ID NO: 114 | SEQ ID NO: 115 | SEQ ID NO: 116 |
| KM5956 | SEQ ID NO: 117 | SEQ ID NO: 118 | SEQ ID NO: 119 | SEQ ID NO: 120 | SEQ ID NO: 121 | SEQ ID NO: 122 |

(2) Production of Expression Vector of Chimeric Antibody

Regarding each anti-human CCR1 antibody produced in Example 5, a chimeric antibody in which the constant region was substituted with a human IgG4 constant region (human IgG4PE_R409K) containing amino acid modifications of S228P, L235E, and R409K was produced by the method described below. A nucleotide sequence encoding the amino acid sequence in the variable region of each antibody by PCR using a primer added with a nucleotide sequence for homologous recombination was amplified by using the plasmid DNA into which the nucleotide sequence encoding the amino acid sequence in the variable region of each antibody produced in (1) was cloned, as a template. Using In-Fusion HD Cloning Kit (Clontech), the nucleotide sequence was ligated to a vector (hereinafter, referred to as N5KG4PE R409K vector) in which the nucleotide sequence encoding the constant region of the human IgG1 in the N5KG4PE R409K vector [N5KG1 vector (U.S. Pat. No. 6,001,358)] was substituted with the nucleotide sequence encoding the constant region of mutant human IgG4 containing the above-mentioned amino acid modification so as to produce an expression vector for the chimeric antibody. The experimental procedure was performed in accordance with the manual attached to the kit.

(3) Production and Purification of Chimeric Antibody

A chimeric antibody was produced using the expression vector produced in (2) and an Expi293 Expression System (Thermo Fisher Science Inc.). 50 µg of plasmid DNA and Expifectamin 293 Reagent (Thermo Fisher Scientific Inc.) were added to Opti-MEM (Thermo Fisher Scientific Inc.), and after standing for 30 minutes, the plasmid solution was added to the above cell solution. Further, after culturing overnight, ExpiFectamin 293 Transfection Enhancer was added to the cell solution (the culture volume was 50 mL in total). After culturing the cell solution for 7 to 10 days, the culture supernatants were collected.

For purification of the antibody, Protein G Sepharose 4Fast Flow (GE Healthcare) was used. The collected culture supernatant was centrifuged, and the obtained culture supernatant was filtered with a filter. A column was packed with 400 µL of carrier and a buffer was substituted with DPBS. The culture supernatant was added to the column, and the antibody was adsorbed on the carrier, and the column was washed twice with 10 mL of DPBS. 0.4 mL of IgG Elution Buffer (Thermo Scientific) was added to the column to elute the antibody, and 0.1 mL of 1 M Tris-Cl at pH 8.6 was immediately added to the antibody solution to neutralize the antibody solution. The antibody solution was desalted using a NAP column (GE Healthcare) and used for the subsequent analysis.

The obtained chimeric antibodies of a KM5907 antibody, a KM5908 antibody, a KM5909 antibody, a KM5911 antibody, a KM5915 antibody, a KM5916 antibody, a KM5954 antibody, a KM5955 antibody, and a KM5956 antibody which are mouse anti-human CCR1 monoclonal antibody are referred to as a chKM5907 antibody, a chKM5908 antibody, a chKM5909 antibody, a chKM5911 antibody, a chKM5915 antibody, a chKM5916 antibody, a chKM5954 antibody, a chKM5955 antibody, and a chKM5956 antibody, respectively.

[Example 10] Evaluation of Affinity of Chimeric Antibody

Regarding the chimeric antibodies of a chKM5907 antibody, a chKM5908 antibody, a chKM5909 antibody, a chKM5911 antibody, a chKM5915 antibody, a chKM5916 antibody, a chKM5954 antibody, a chKM5955 antibody, and a chKM5956 antibody produced in Example 9, the affinity to human and mouse CCR1 was measured by FCM in accordance with the method described in Example 4. As the human CCR1-expressing cells and mouse CCR1-expressing cells, CHO-S-hCCR1 and CHO-S-mCCR1 produced in Example 2 were used, respectively. As a result, it was found that the chKM5955 antibody bound to the human CCR1. It was found that other chimeric antibodies bound to both human and mouse CCR1s.

[Example 11] Chemotaxis Assay Using Chimeric Antibody

Regarding the chimeric antibodies of a chKM5907 antibody, a chKM5908 antibody, a chKM5909 antibody, a chKM5911 antibody, a chKM5915 antibody, a chKM5916 antibody, a chKM5954 antibody, a chKM5955 antibody, and a chKM5956 antibody produced in Example 9, the activity of inhibiting human CCR1 activation was measured in accordance with the method described in Example 6. As a result, it was found that all of the chimeric antibodies inhibit the migration of THP-1 by the activated human CCL15.

[Example 12] Production of chKM5908 Antibody Variant Having Substituted VL

For further improvement of the chKM5908 antibody, Production of an antibody in which VL of the chKM5908 antibody was substituted with VL of another anti-CCR1 chimeric antibody was examined. Based on the mouse anti-human CCR1 antibody obtained by the method described in Example 5, a plurality of types of VLs of the chimeric antibody produced by the method described in Example 10 were examined as VL to be substituted. Among these, the Production of a chKM5908 antibody variant selected by criteria such as THP-1 migration activity and having VL substituted with that of the chKM5914 antibody will be described below.
(1) Design of VL-Substituted Chimeric Antibody
VL of the chKM5914 to be substituted was selected because of its high homology with the amino acid sequence of VL of the chKM5908. A nucleotide sequence encoding the amino acid sequence of VL of the chKM5914 antibody, and an amino acid sequence including a signal sequence and an amino acid sequence obtained by removing the signal sequence from the amino acid sequence, which are deduced from the nucleotide sequences, are shown in SEQ ID NOs: 123, 124, and 125, respectively. In addition, the amino acid sequences of CDRs 1 to 3 of VL of the chKM5914 antibody are shown in SEQ ID NOs: 126 to 128, respectively.
(2) Production of Expression Vector
A nucleotide sequence encoding the amino acid sequence in the VL variable region of each antibody by PCR using a primer added with a nucleotide sequence for homologous recombination was amplified by using the plasmid DNA into which the nucleotide sequence encoding the amino acid sequence in the VL variable region of the chKM5914 antibody was cloned, as a template. The chKM5908 VH variable region was similarly amplified. By using In-Fusion HD Cloning Kit (Clontech), the nucleotide sequence was ligated to an N5hK vector (L chain expression vector) or N5hG4PE_R409K vector (H chain expression vector) to produce an expression vector for the chimeric antibody. The experimental procedure was performed in accordance with the manual attached to the kit. E. coli DH5a competent cells (Takara Bio Inc.) were transformed, and the sequence of the obtained plasmid was confirmed. E. coli colonies producing a plasmid with the correct nucleotide sequence inserted were selected, and a plasmid was prepared using a NucleoBond Xtra Midi EF kit (Takara Bio Inc.).
(3) Production and Purification of VL-Substituted Chimeric Antibody
A target VL-substituted chimeric antibody was transiently expressed using an Expi293 Expression System Kit (Life Technologies). The method for introducing the plasmid was performed in accordance with the attached document. The light chain expression vector and the heavy chain expression vector were mixed and introduced at a ratio of 1:2. The cells after introduction of the plasmid were cultured in 120 mL of a culture solution under the conditions of 37° C., 5% $CO_2$, and 125 rpm for 3 days. Thereafter, the cell culture suspension was centrifuged, and the culture supernatant was collected through a 0.2 μm filter (Thermo Scientific). A purified antibody was obtained from the culture supernatant by affinity purification using MabSelect SuRe (GE Healthcare).

Specifically, after the resin with which the column was filled was equilibrated with PBS, the culture supernatant was added to the column, washed twice with PBS, washed once with a wash buffer 1 (PBS with 1M NaCl), and washed once with a wash buffer 2 (20 mM citric acid, 50 mM NaCl, pH 5.0), and then, the antibody was eluted using an elution buffer (20 mM citric acid, 50 mM NaCl, pH 3.4).

The obtained antibody solution was neutralized by adding 1/10 amount of neutralization buffer (1M phosphate-NaOH, pH 7.0), and the solvent of the antibody solution was substituted with PBS using NAP25 (GE Healthcare). The antibody solution after the buffer substitution was concentrated by ultrafiltration using Amicon Ultra-4 Centrifugal Filter Units (Millipore), the absorbance $A_{280}$ was measured using Nanodrop (Thermo Scientific), and the concentration of the antibody solution measured and adjusted. The chimeric antibody variant containing VH of the chKM5908 antibody and VL of the chKM5914 antibody thus obtained is referred to as a chKM5908' antibody in the following description.

[Example 13] Evaluation of Antigen Affinity and THP-1 Migration Inhibitory Activity of chKM5908' Antibody The antigen affinity of the chKM5908' antibody, which is a VL-substituted chimeric antibody, was measured by flow cytometry using the CHO-S-hCCR1 cells produced in Example 2. The cells were collected by centrifugation, the supernatant was removed, and the cells were suspended in PBS (Staining Medium, hereinafter, abbreviated as SM) containing 2% fetal bovine serum (FBS), 0.05% $NaN_3$, and 1 mM EDTA. Next, the cells were seeded in a 96-well plate so that the number of cells is $1 \times 10^5$ per well, and the chKM5908' antibody was added at each final concentration of 10,000, 2,000, 400, 80, 16, and 3.2 ng/mL, and the reaction was performed at 4° C. for 60 minutes. After washing the cells with SM, Goat F (ab')₂ Anti-Human IgG PE (γ chain specific) (Southern Biotech) diluted 500-fold with SM was added and reacted at 4° C. for 60 minutes. After washing the cells with SM, the cells were resuspended in 50 μL of SM, and the fluorescence intensity was measured by the flow cytometry (FACS Canto II, BD Biosciences).

The data was analyzed by FlowJo 7.65 (Tommy Digital Biology Co., Ltd.), and the binding strength was compared from the Geomean value at each concentration. As a result, the chKM5908' antibody was found to have the affinity equivalent to that of chKM5908 on CHO-S-hCCR1 cells.

Figure 3:
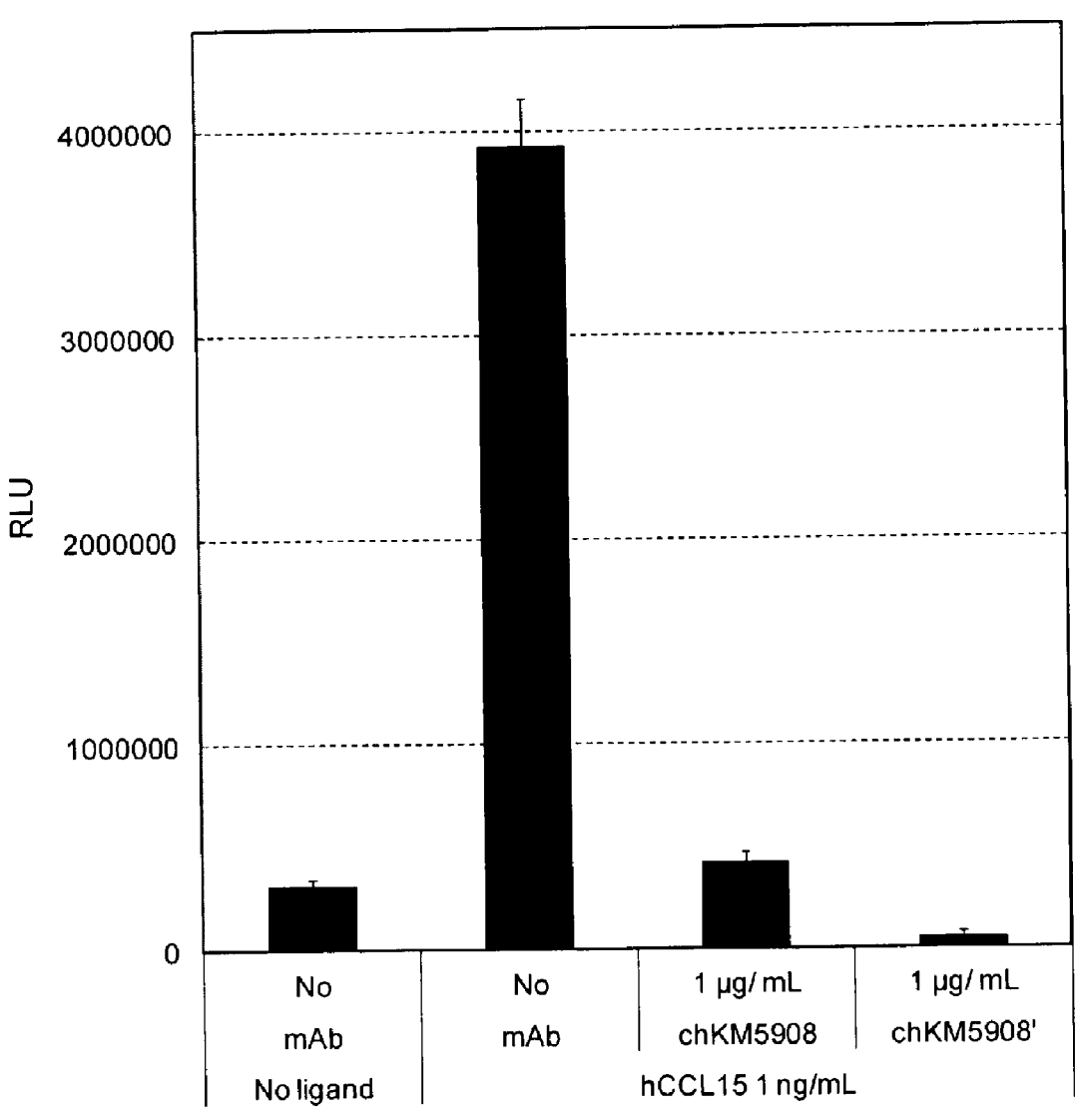
FIG. 3 illustrates results of measuring an activity of an anti-human CCR1 antibody to inhibit THP-1 migration by an activated human CCL15. A vertical axis in FIG. 3 indicates an amount of luminescence (relative light unit; RLU) when the number of cells that have moved to the lower layer of Transwell is measured by CellTiter-Glo. A horizontal axis of FIG. 3 indicates an antibody and a ligand added to the THP-1 cells and concentrations thereof.

Further, the chKM5908' antibody was measured for THP-1 migration inhibitory activity by the method described in Example 6. The antibody concentration was added at a concentration of 1 μg/mL. As a result, as illustrated in FIG. 3, it was found that the chKM5908' antibody has a THP-1 migration inhibitory activity equal to or higher than that of the chKM5908 antibody.

[Example 14] Production and Evaluation of CDR Modified chKM5908' Antibody Variant (1) Production and Evaluation of Chimeric Antibody Variants with Modified CDR Amino Acids An attempt was made to further modify the CDR based on the chKM5908' antibody. Table 5 indicates the modified VH of the designed chKM5908 VH. Table 6 illustrates the modified VL of the designed chKM5914 VL. Further, Table 7 indicates CDR-modified chimeric antibody variants obtained by combining these.

TABLE 5

| Modified VH | Modified CDR | Amino acid sequence before modification | Modified site | Amino acid residue after modification |
|---|---|---|---|---|
| 5908VH-m1 | VH CDR2 | SEQ ID NO: 76 | Isoleucine at position 2 | Threonine |
| 5908VH-m2 | VH CDR2 | SEQ ID NO: 76 | Valine at position 9 | Alanine |
| 5908VH-m3 | VH CDR2 | SEQ ID NO: 76 | Phenylalanine at position 14 | Alanine |
| 5908VH-m4 | VH CDR2 | SEQ ID NO: 76 | Isoleucine at position 15 | Alanine |
| 5908VH-m5 | VH CDR3 | SEQ ID NO: 77 | Tyrosine at position 5 | Alanine |
| 5908VH-m6 | VH CDR3 | SEQ ID NO: 77 | Threonine at position 7 | Alanine |
| 5908VH-m7 | VH CDR2 | SEQ ID NO: 76 | Isoleucine at position 2 | Threonine |
| | VH CDR2 | SEQ ID NO: 76 | Valine at position 9 | Alanine |
| | VH CDR2 | SEQ ID NO: 76 | Isoleucine at position 15 | Alanine |
| 5908VH-m8 | VH CDR2 | SEQ ID NO: 76 | Isoleucine at position 2 | Threonine |
| | VH CDR2 | SEQ ID NO: 76 | Isoleucine at position 15 | Alanine |
| | VH CDR3 | SEQ ID NO: 77 | Tyrosine at position 5 | Alanine |
| | VH CDR3 | SEQ ID NO: 77 | Threonine at position 7 | Alanine |
| 5908VH-m9 | VH CDR2 | SEQ ID NO: 76 | Isoleucine at position 2 | Threonine |
| | VH CDR2 | SEQ ID NO: 76 | Isoleucine at position 15 | Alanine |
| | VH CDR3 | SEQ ID NO: 77 | Threonine at position 7 | Alanine |
| 5908VH-m10 | VH CDR2 | SEQ ID NO: 76 | Isoleucine at position 2 | Threonine |
| | VH CDR2 | SEQ ID NO: 76 | Isoleucine at position 15 | Alanine |
| 5908VH-m11 | VH CDR2 | SEQ ID NO: 76 | Isoleucine at position 2 | Threonine |
| | VH CDR3 | SEQ ID NO: 77 | Tyrosine at position 5 | Alanine |
| | VH CDR3 | SEQ ID NO: 77 | Threonine at position 7 | Alanine |
| 5908VH-m12 | VH CDR2 | SEQ ID NO: 77 | Isoleucine at position 2 | Threonine |
| | VH CDR3 | SEQ ID NO: 77 | Tyrosine at position 5 | Alanine |

TABLE 6

| Modified VH | Modified CDR | Amino acid sequence before modification | Modified site | Amino acid residue after modification |
|---|---|---|---|---|
| 5914VL-m1 | VL CDR1 | SEQ ID NO: 126 | Phenylalanine at position 15 | Alanine |
| 5914VL-m2 | VL CDR2 | SEQ ID NO: 127 | Valine at position 2 | Isoleucine |
| 5914VL-m3 | VL CDR2 | SEQ ID NO: 127 | Arginine at position 5 | Lysine |
| 5914VL-m4 | VL CDR1 | SEQ ID NO: 126 | Phenylalanine at position 15 | Alanine |
| | VL CDR2 | SEQ ID NO: 127 | Valine at position 2 | Isoleucine |

TABLE 7

| Antibodies | VH | VL |
|---|---|---|
| chKM5908' | 5908VH | 5914VL |
| chKM5908' mut01 | 5908VH | 5914VL-m1 |
| chKM5908' mut02 | 5908VH | 5914VL-m2 |
| chKM5908' mut03 | 5908VH | 5914VL-m3 |
| chKM5908' mut04 | 5908VH | 5914VL-m4 |
| chKM5908' mut05 | 5908VH-m1 | 5914VL |
| chKM5908' mut06 | 5908VH-m2 | 5914VL |
| chKM5908' mut07 | 5908VH-m3 | 5914VL |
| chKM5908' mut08 | 5908VH-m4 | 5914VL |
| chKM5908' mut09 | 5908VH-m5 | 5914VL |
| chKM5908' mut10 | 5908VH-m6 | 5914VL |
| chKM5908' mut11 | 5908VH-m7 | 5914VL |
| chKM5908' mut12 | 5908VH-m8 | 5914VL |
| chKM5908' mut13 | 5908VH-m9 | 5914VL |
| chKM5908' mut14 | 5908VH-m10 | 5914VL |
| chKM5908' mut15 | 5908VH-m11 | 5914VL |
| chKM5908' mut16 | 5908VH-m12 | 5914VL |
| chKM5908' mut17 | 5908VH-m1 | 5914VL-m1 |
| chKM5908' mut18 | 5908VH-m3 | 5914VL-m1 |
| chKM5908' mut19 | 5908VH-m7 | 5914VL-m1 |
| chKM5908' mut20 | 5908VH-m8 | 5914VL-m1 |
| chKM5908' mut21 | 5908VH-m1 | 5914VL-m2 |
| chKM5908' mut22 | 5908VH-m3 | 5914VL-m2 |
| chKM5908' mut23 | 5908VH-m7 | 5914VL-m2 |
| chKM5908' mut24 | 5908VH-m8 | 5914VL-m2 |
| chKM5908' mut25 | 5908VH-m1 | 5914VL-m3 |
| chKM5908' mut26 | 5908VH-m3 | 5914VL-m3 |
| chKM5908' mut27 | 5908VH-m7 | 5914VL-m3 |
| chKM5908' mut28 | 5908VH-m8 | 5914VL-m3 |
| chKM5908' mut29 | 5908VH-m1 | 5914VL-m4 |
| chKM5908' mut30 | 5908VH-m3 | 5914VL-m4 |
| chKM5908' mut31 | 5908VH-m7 | 5914VL-m4 |
| chKM5908' mut32 | 5908VH-m8 | 5914VL-m4 |

The nucleotide sequence necessary for expressing these chimeric antibody variants was produced by total synthesis or by assembly PCR using primers into which the corresponding mutation was introduced, and introduced into the expression vector by using the method described in Example 12-(2) so as to produce a necessary plasmid. Next, a chimeric antibody variant was obtained by using the method described in Example 12-(3).

For each of the obtained CDR-modified chimeric antibody variants, the antigen affinity was measured using the method described in Example 13, and those exhibiting the fluorescence intensity 10 times or more than that of an isotype control chimeric antibody [an antibody produced according to the method described in Example 12-(3) using a vector encoding VL and VH of DNP-1 antibody (GenBank Accession No.: VL U16688, VH U116687) described in Mol Immunol. 1996 June; 33 (9):759-68, hereinafter, referred to as chDNP1)] were determined to be bound to the human CCR1. As a result, it was found that all of the CDR-modified chimeric antibody variants exhibited the affinity to the human CCR1 from an antibody concentration of at least 80 ng/mL.

Further, the THP-1 migration inhibitory activity was evaluated for each CDR-modified antibody using the method described in Example 13. As a result, all of the CDR-modified chimeric antibody variants were found to inhibit THP-1 migration by the activated human CCL15.

For chKM5908'mut02, chKM5908'mut22, and chKM5908'mut25, further, THP-1 migration inhibitory activity was measured under the conditions of the antibody concentrations at 10, 3, 1, 0.75, 0.5, 0.3, 0.1, and 0.05 μg/mL. The results are indicated in FIG. 4.

As illustrated in FIG. 4, all antibodies inhibited the THP-1 cell migration in an antibody concentration-dependent manner. Further, it was revealed that chKM5908'mut22 had an inhibitory activity equivalent to or higher than that of chKM5908', chKM5908'mut02, and chKM5908'mut25.

In the following description, chKM5908'mut22 is referred to as mAb5-06. Table 8 indicates each of SEQ ID NO of the nucleotide sequence and amino acid sequence of VH and VL of mAb 5-06, and the amino acid sequences of CDRs 1 to 3 of VH and VL.

TABLE 8

| | Nucleotide sequence | Amino acid sequence | CDR1 amino acid sequence | CDR2 amino acid sequence | CDR3 amino acid sequence |
|---|---|---|---|---|---|
| VH | SEQ ID NO: 129 | SEQ ID NO: 130 | SEQ ID NO: 75 | SEQ ID NO: 131 | SEQ ID NO: 77 |
| VL | SEQ ID NO: 132 | SEQ ID NO: 133 | SEQ ID NO: 126 | SEQ ID NO: 134 | SEQ ID NO: 128 |

[Example 15] Design of Light and Heavy Chain Variable Regions of Humanized Antibodies of mAb 5-06, chKM5907, and chKM5916

(1) Design of Amino Acid Sequences of VL and VH of mAb 5-06 Humanized Antibody

Various amino acid sequences of VL and VH of the mAb 5-06 humanized antibody were designed by the method described below. In the following description, the term "hzmAb5-06 antibody" is used as a general term for mAb5-06 humanized antibodies having various amino acid sequences of VL and VH. For each of VL and VH, homology of the amino acid sequence of FR of the mAb 5-06 antibody was compared with that of the human FR consensus sequence reported in Kabat et al. [Sequences of Proteins of Immunological Interest, US Dept. Health and Human Services (1991)]. As a result, a human subgroup L chain II (hSGLII) and a human subgroup H chain II (hSGHII) had the highest homology with the amino acid sequences of FRs of VL and VH of the mAb 5-06 antibody, respectively.

Therefore, the amino acid sequences of CDRs 1 to 3 of the mAb5-06 VL represented by SEQ ID NOs: 126, 134, and 128, respectively, are implanted into appropriate positions in the amino acid sequence of FR of hSGLII to design hzmAb5-06 LV0 (SEQ ID NO: 135). Therefore, the amino acid sequences of CDRs 1 to 3 of the mAb5-06 VH represented by SEQ ID NOs: 75, 131, and 77 are implanted into appropriate positions in the amino acid sequence of FR of hSGHII to design hzmAb5-06 HV0 (SEQ ID NO: 136).

HzmAb5-06 LV0 and hzmAb5-06 HV0 designed as described above are the amino acid sequences obtained by implanting only the amino acid sequence of CDR derived from mAb 5-06, which is a CDR variant of mouse-derived antibody, into the amino acid sequence of FR of the selected human antibody. However, in general, in a case of producing a humanized antibody, the biological activity of the humanized antibody is often reduced simply by implanting the amino acid sequence of CDR of a rodent-derived antibody to the amino acid sequence of FR of the human antibody. In order to avoid such a decrease in the affinity, together with the implanting of the amino acid sequence of CDR, the modifying of the amino acid residue which is considered to affect the affinity of the antibody among the amino acid residues of FR that differ between human antibodies and rodent antibodies has been performed. Therefore, also in this example, the amino acid residues of FR that are considered to affect the affinity of the antibody were identified and modified as follows.

In the following description, the above-designed antibodies having hzmAb5-06 LV0 and hzmAb5-06 HV0 in VL and VH, respectively, are referred to as a hzmAb5-06 LV0HV0 antibody or referred to as a simply hzmAb5-06 LV0HV0, respectively. Other hzmAb5-06 antibodies are described in a same method. The three-dimensional structure of the variable region of the hzmAb5-06 LV0HV0 antibody was constructed using a computer modeling technique.

Discovery Studio (BIOVIA) was used for the Production of three-dimensional structure coordinates and the display of the three-dimensional structure. A computer model of the three-dimensional structure of the variable region of mAb 5-06 antibody was also constructed in the same manner. Further, in the amino acid sequences of FRs of VL and VH of the hzmAb5-06 LV0HV0 antibodies, the amino acid sequence in which an amino acid residue different from the mAb5-06 antibody was substituted with an amino acid residue present at the same site of the mAb5-06 antibody was created and a three-dimensional structural model was constructed in the same way. The three-dimensional structures of the variable regions of these produced mAb5-06 antibodies, hzmAb5-06 LV0HV0 antibody, and the variant were compared, and the amino acid residues predicted to affect the affinity of the antibody were identified.

As a result, among the amino acid residues of FRs of the variable region of the hzmAb5-06 LV0HV0 antibody, as an amino acid residue that change the three-dimensional structure of the antigen-binding site and is considered to affect the affinity of the antibody, Ile at a position 2, Pro at a position 15, Gln at a position 50, Tyr at a position 92, and Val at a position 109 in the amino acid sequences represented by SEQ ID NO: 135 were selected in VL, and Glu at a position 6, Leu at a position 20, Gly at a position 27, Val at a position 29, Ser at a position 30, Ile at a position 37, Ile at a position 48, Val at a position 67, Val at a position 71, Thr at a position 73, Asn at a position 76, Phe at a position 78, Leu at a position 80, Leu at a position 82, Val at a position 85, Val at a position 92, and Arg at a position 97 in the amino acid sequences represented by SEQ ID NO: 136 were selected in VH. Among these selected amino acid residues, at least one or more amino acid residues are substituted with an amino acid residue present at the same site of the mAb5-06 antibody, and VL and VH of the humanized antibody having various modifications are designed.

Specifically, for VL, in the amino acid sequences of SEQ ID NO: 135, at least one modification from amino acid modifications in which Ile at a position 2 was substituted with Val, Pro at a position 15 was substituted with Leu, Gln at a position 50 was substituted with Lys, Tyr at a position 92 was substituted with Phe, and Val at a position 109 was substituted with Leu was introduced. As a result, as VL of the hzmAb5-06 antibody, the hzmAb5-06 LV0 (SEQ ID NO: 135), LV1a (SEQ ID NO: 137), LV1b (SEQ ID NO: 138), LV2a (SEQ ID NO: 139), LV2b (SEQ ID NO: 140), LV4 (SEQ ID NO: 141), and LV5 (SEQ ID NO: 142) are designed, and the respective amino acid sequences are illustrated in FIG. 5.

For VH, in the amino acid sequences of SEQ ID NO: 136, at least one modification from amino acid modifications in which Glu at a position 6 was substituted with Gln, Leu at a position 20 was substituted with Ile, Gly at a position 27 was substituted with Phe, Val at a position 29 was substituted with Leu, and Ser at a position 30 was substituted with Asn, Ile at a position 37 was substituted with Val, Ile at a position 48 was substituted with Leu, Val at a position 67 was substituted with Leu, Val at a position 71 was substituted with Lys, Thr at a position 73 was substituted with Asp, Asn at a position 76 was substituted with Ser, Phe at a position 78 was substituted with Val, Leu at a position 80 was substituted with Phe, Leu at a position 82 was substituted with Met, Val at a position 85 was substituted with Leu, Val at a position 92 was substituted with Ile, and Arg at a position 97 was substituted with Lys was introduced. As a result, as VH of the hzmAb5-06 antibody, the hzmAb5-06 HV0 (SEQ ID NO: 136), HV14 (SEQ ID NO: 143), and HV17 (SEQ ID NO: 144) are designed, and the respective amino acid sequences are illustrated in FIG. 6.

(2) Design of Amino Acid Sequences of VL and VH of chKM5907 Humanized Antibody

The various amino acid sequences of VL and VH of the chKM5907 humanized antibody were also designed in the same method as in Example 15 (1). In the following description, the term "hzKM5907 antibody" is used as a general term for chKM5907 humanized antibodies having various amino acid sequences of VL and VH. hzKM5907 LV0 (SEQ ID NO: 145) was designed by implanting the amino acid sequences (SEQ ID NOs: 72, 73 and 74, respectively) of CDRs 1 to 3 of VL of the KM5907 antibody into an appropriate position of the amino acid sequence of FR of VL of the human antibody represented by GenBank accession number ABG38363.1, (immunoglobulin light chain variable region, partial [Homo sapiens]).

In addition, hzKM5907 HV0 (SEQ ID NO: 146) was designed by implanting the amino acid sequences (SEQ ID NOs: 69, 70, and 71, respectively) of CDRs 1 to 3 of VH of the KM5907 antibody into an appropriate position of the amino acid sequence of FR of the human antibody to which human heavy chain V region germline VH3-23 (FRs 1 to 3) and hSGHI (FR4) were bound.

The amino acid residues of FR that are considered to affect the affinity of the hzKM5907 antibody were also selected for VL and VH in the same method as the case of the hzmAb5-06 antibody. Among these selected amino acid residues, at least one or more amino acid sequences are substituted with an amino acid residue present at the same site of Km5907 antibody, and VL and VH of the humanized antibody having various modifications are designed.

Specifically, for VL, in the amino acid sequences of SEQ ID NO: 145, at least one modification from amino acid modifications in which Ile at a position 2 was substituted with Val, Ser at a position 15 was substituted with Leu, Ala at a position 19 was substituted with Val, Gln at a position 43 was substituted with Lys, Gln at a position 50 was substituted with Lys, and Val at a position 109 was substituted with Leu was introduced. As a result, as VL of the hzKM5907 antibody, the hzKM5907 LV0 (SEQ ID NO: 145), LV1a (SEQ ID NO: 147), LV1b (SEQ ID NO: 148), LV1c (SEQ ID NO: 149), LV2a (SEQ ID NO: 150), LV2b (SEQ ID NO: 151), LV4 (SEQ ID NO: 152), and LV6 (SEQ ID NO: 153) are designed, and the respective amino acid sequences are illustrated in FIG. 7.

In addition, for VH, in the amino acid sequences of SEQ ID NO: 146, at least one modification from amino acid modifications in which Leu at a position 4 was substituted with Val, Gly at a position 44 was substituted with Arg, Ser at a position 49 was substituted with Ala, Ala at a position 92 was substituted with Gly, Val at a position 93 was substituted with Met, Ala at a position 97 was substituted with Thr, and Lys at a position 98 was substituted with Arg was introduced. As a result, as VH of the hzKM5907 antibody, the hzKM5907 HV0 (SEQ ID NO: 146), HV1 (SEQ ID NO: 154), HV2a (SEQ ID NO: 155), HV2b (SEQ ID NO: 156), HV3a (SEQ ID NO: 157), HV3b (SEQ ID NO: 158), HV3c (SEQ ID NO: 159), HV4 (SEQ ID NO: 160), and HV7 (SEQ ID NO: 161) are designed, and the respective amino acid sequences are illustrated in FIG. 8.

In the following description, an antibody having hzKM5907 LV0 and hzKM5907 HV0 in VL and VH, respectively, is referred to as a hzKM5907 LV0HV0 antibody or hzKM5907 LV0HV0. Other hzKM5907 antibodies are described in a same method.

(3) Design of Amino Acid Sequences of VL and VH of chKM5916 Humanized Antibody

The amino acid sequences of various VLs and VHs of the chKM5916 humanized antibody were also designed in the same method as in Example 15 (1). In the following description, the term "hzKM5916 antibody" is used as a general term for chKM5916 humanized antibodies having various amino acid sequences of VL and VH. hzKM5916 LV0 (SEQ ID NO: 162) was designed by implanting the amino acid sequences (SEQ ID NOs: 102, 103, and 104, respectively) of CDRs 1 to 3 of VL of the KM5916 antibody into an appropriate position of the amino acid sequence of FR of VL of the human antibody represented by PIR accession number S52789 (Ig kappa chain V region-human (fragment)).

In addition, hzKM5916 HV0 (SEQ ID NO: 163) was designed by implanting the amino acid sequences (SEQ ID NOs: 99, 100, and 101, respectively) of CDRs 1 to 3 of VH of the KM5916 antibody into an appropriate position of the amino acid sequence of FR of VH of the human antibody represented by GenBank accession number AAX82494.1 (anti-*Plasmodium falciparum* merozoite surface, protein 3 immunoglobulin heavy chain variable region, partial [*Homo sapiens*]).

The amino acid residues of FR that are considered to affect the affinity of the hzKM5916 antibody were also selected for VL and VH in the same method as the case of the hzmAb5-06 antibody. Among these selected amino acid residues, at least one or more amino acid sequences are substituted with an amino acid residue present at the same site of KM5916 antibody, and VL and VH of the humanized antibody having various modifications are designed.

Specifically, for VL, in the amino acid sequence of SEQ ID NO: 162, at least one modification from amino acid modifications in which Gln at a position 38 was substituted with His, and Ala at a position 43 was substituted with Gly was introduced. As a result, as VL of the hzKM5916 antibody, the hzKM5916 LV0 (SEQ ID NO: 162) and LV2 (SEQ ID NO: 164) are designed, and the respective amino acid sequences are illustrated in FIG. 9.

In addition, for VH, in the amino acid sequences of SEQ ID NO: 163, at least one modification from amino acid modifications in which Asp at a position 42 was substituted with Glu, Lys at a position 87 was substituted with Arg, and Ala at a position 97 was substituted with Thr was introduced. As a result, as VH of the hzKM5916 antibody, the hzKM5907 HV0 (SEQ ID NO: 163), HV1 (SEQ ID NO: 165), and HV3 (SEQ ID NO: 166) are designed, and the respective amino acid sequences are illustrated in FIG. 10.

In the following description, an antibody having hzKM5916 LV0 and hzKM5916 HV0 in VL and VH, respectively, is referred to as a KM5916 LV0HV0 antibody or hzKM5916 LV0HV0. Other hzKM5916 antibodies are described in a same method.

(4) Design of Variable Region Gene of Humanized Antibody

The nucleotide sequence encoding the amino acid sequences of the variable regions of the humanized antibodies (hzmAb5-06 antibody, hzKM5907 antibody, and hzKM5916 antibody) indicated in Table 9 was designed by using codons frequently used in animal cells.

TABLE 9

| Humanized antibody | | VL amino acid sequence | VH amino acid sequence |
|---|---|---|---|
| hzmAb5-06 | LV0HV17 | SEQ ID NO: 135 | SEQ ID NO: 144 |
| | LV1aHV17 | SEQ ID NO: 137 | SEQ ID NO: 144 |
| | LV1bHV17 | SEQ ID NO: 138 | SEQ ID NO: 144 |
| | LV2aHV17 | SEQ ID NO: 139 | SEQ ID NO: 144 |
| | LV2bHV17 | SEQ ID NO: 140 | SEQ ID NO: 144 |
| | LV4HV17 | SEQ ID NO: 141 | SEQ ID NO: 144 |
| | LV5HV17 | SEQ ID NO: 142 | SEQ ID NO: 144 |
| | LV5HV14 | SEQ ID NO: 142 | SEQ ID NO: 143 |
| hzmAb5907 | LV0HV0 | SEQ ID NO: 145 | SEQ ID NO: 146 |
| | LV1aHV0 | SEQ ID NO: 147 | SEQ ID NO: 146 |
| | LV1bHV0 | SEQ ID NO: 148 | SEQ ID NO: 146 |
| | LV1cHV0 | SEQ ID NO: 149 | SEQ ID NO: 146 |
| | LV2aHV0 | SEQ ID NO: 150 | SEQ ID NO: 146 |
| | LV2bHV0 | SEQ ID NO: 151 | SEQ ID NO: 146 |
| | LV4HV0 | SEQ ID NO: 152 | SEQ ID NO: 146 |
| | LV6HV0 | SEQ ID NO: 153 | SEQ ID NO: 146 |
| | LV0HV7 | SEQ ID NO: 145 | SEQ ID NO: 161 |
| | LV1aHV7 | SEQ ID NO: 147 | SEQ ID NO: 161 |
| | LV1bHV7 | SEQ ID NO: 148 | SEQ ID NO: 161 |
| | LV1cHV7 | SEQ ID NO: 149 | SEQ ID NO: 161 |
| | LV2aHV7 | SEQ ID NO: 150 | SEQ ID NO: 161 |
| | LV2bHV7 | SEQ ID NO: 151 | SEQ ID NO: 161 |
| | LV4HV7 | SEQ ID NO: 152 | SEQ ID NO: 161 |
| | LV6HV7 | SEQ ID NO: 153 | SEQ ID NO: 161 |
| | LV2bHV1 | SEQ ID NO: 151 | SEQ ID NO: 154 |
| | LV2bHV2a | SEQ ID NO: 151 | SEQ ID NO: 155 |
| | LV2bHV2b | SEQ ID NO: 151 | SEQ ID NO: 156 |
| | LV2bHV3a | SEQ ID NO: 151 | SEQ ID NO: 157 |
| | LV2bHV3b | SEQ ID NO: 151 | SEQ ID NO: 158 |
| | LV2bHV3c | SEQ ID NO: 151 | SEQ ID NO: 159 |
| | LV2bHV4 | SEQ ID NO: 151 | SEQ ID NO: 160 |
| hzmAb5916 | LV0HV0 | SEQ ID NO: 162 | SEQ ID NO: 163 |
| | LV2HV0 | SEQ ID NO: 164 | SEQ ID NO: 163 |
| | LV0HV1 | SEQ ID NO: 162 | SEQ ID NO: 165 |
| | LV2HV1 | SEQ ID NO: 164 | SEQ ID NO: 165 |
| | LV0HV3 | SEQ ID NO: 162 | SEQ ID NO: 166 |
| | LV2HV3 | SEQ ID NO: 164 | SEQ ID NO: 166 |

[Example 16] Production of Evaluation of Humanized Antibody

The nucleotide sequence designed in Example 15-(4) was introduced into an expression vector using the method described in Example 12-(2) to produce a necessary plasmid. However, a pCI-OtCMV_hK vector having a signal sequence and a human x chain constant region sequence was used as a VL expression vector, and a pCI-OtCAG_hG4PE (R409K) vector having a signal sequence and a human γ chain constant region sequence was used as a VH expression vector.

Next, a modified antibody was obtained using the method described in Example 12-(3). After confirming the quality by SDS-PAGE, the antigen affinity was measured using the method described in Example 13, and those exhibiting the fluorescence intensity 10 times or more that of an isotype control humanized antibody [an antibody designed according to the method described in Example 15 based on chDNP1 (using a consensus sequence as the human FR sequence), produced according to the method described in Example 12-(3), and has VL and VH consisting of an amino acid sequences of SEQ ID NOs: 167 and 168, respectively. Hereinafter referred to as hzDNP1)] were determined to bind to the human CCR1. As a result, it was found that all of the humanized antibodies exhibited the affinity to the human CCR1 from an antibody concentration of at least 80 ng/mL.

Next, the THP-1 migration inhibitory activity was evaluated for all the produced humanized antibodies. As a result, it was found that all humanized antibodies had THP-1 migration inhibitory activity. For hzmAb5-06 LV5HV14, hzKM5907 LV2bHV3a and hzKM5916 LV2HV0, the THP-1 migration inhibitory activity was evaluated under the conditions of the antibody concentrations at 10, 3, 1, 0.75, 0.5, 0.3, 0.1, and 0.05 μg/mL. As a result, as illustrated in FIG. 11, it was found that all humanized antibodies exhibited the THP-1 migration inhibitory activity at antibody concentrations of 0.3 μg/mL or more.

While the present invention has been described in detail and with reference to specific embodiments, it will be apparent to those skilled in the art that various changes and modifications can be made without departing from the spirit and scope of the present invention. This application is based on a Japanese patent application filed on Jul. 18, 2017 (Japanese Patent Application No. 2017-139157), which is incorporated by reference in the entirety thereof. Also, all references cited herein are incorporated as a whole.

SEQUENCE LISTING FREE TEXT

Definition of SEQ ID NO: 6-artificial sequence: nucleotide sequence of NC3-hCCR1

Definition of SEQ ID NO: 7-artificial sequence: nucleotide sequence of NC3-mCCR1

Definition of SEQ ID NO: 8-artificial sequence: nucleotide sequence of hCCR3_EL2hCCR1

Definition of SEQ ID NO: 9-artificial sequence: nucleotide sequence of hCCR3_EL2mCCR1

Definition of SEQ ID NO: 10-artificial sequence: amino acid sequence of N-terminus hCCR1 peptide Definition of SEQ ID NO: 11-artificial sequence: nucleotide sequence of primer_mouse_gamma_r1

Definition of SEQ ID NO: 12-artificial sequence: nucleotide sequence of primer_mouse_gamma_r2

Definition of SEQ ID NO: 13-artificial sequence: nucleotide sequence of primer_mouse_kappa_r1

Definition of SEQ ID NO: 14-artificial sequence: nucleotide sequence of primer_mouse_kappa_r2

Definition of SEQ ID NO: 51-artificial sequence: amino acid sequence of KM5907 VH excluding signal sequence Definition of SEQ ID NO: 52-artificial sequence: amino acid sequence of KM5907 VL excluding signal sequence Definition of SEQ ID NO: 53-artificial sequence: amino acid sequence of KM5908 VH excluding signal sequence Definition of SEQ ID NO: 54-artificial sequence: amino acid sequence of KM5908 VL excluding signal sequence Definition of SEQ ID NO: 55-artificial sequence: amino acid sequence of KM5909 VH excluding signal sequence Definition of SEQ ID NO: 56-artificial sequence: amino acid sequence of KM5909 VL excluding signal sequence Definition of SEQ ID NO: 57-artificial sequence: amino acid sequence of KM5911 VH excluding signal sequence Definition of SEQ ID NO: 58-artificial sequence: amino acid sequence of KM5911 VL excluding signal sequence Definition of SEQ ID NO: 59-artificial sequence: amino acid sequence of KM5915 VH excluding signal sequence Definition of SEQ ID NO: 60-artificial sequence: amino acid sequence of KM5915 VL excluding signal sequence Definition of SEQ ID NO: 61-artificial sequence: amino acid sequence of KM5916 VH excluding signal sequence Definition of SEQ ID NO: 62-artificial sequence: amino acid sequence of KM5916 VL excluding signal sequence Definition of SEQ ID NO: 63-artificial sequence: amino acid sequence of KM5954 VH excluding signal sequence Definition of SEQ ID NO: 64-artificial sequence: amino acid sequence of KM5954 VL excluding signal sequence Definition of SEQ ID NO: 65-artificial sequence: amino acid sequence of KM5955 VH excluding signal sequence Definition of SEQ ID NO: 66-artificial sequence: amino acid sequence of KM5955 VL excluding signal sequence Definition of SEQ ID NO: 67-artificial sequence: amino acid sequence of KM5956 VH excluding signal sequence Definition of SEQ ID NO: 68-artificial sequence: amino acid sequence of KM5956 VL excluding signal sequence Definition of SEQ ID NO: 69-artificial sequence: amino acid sequence of KM5907 VH CDR1

Definition of SEQ ID NO: 70-artificial sequence: amino acid sequence of KM5907 VH CDR2

Definition of SEQ ID NO: 71-artificial sequence: amino acid sequence of KM5907 VH CDR3

Definition of SEQ ID NO: 72-artificial sequence: amino acid sequence of KM5907 VL CDR1

Definition of SEQ ID NO: 73-artificial sequence: amino acid sequence of KM5907 VL CDR2

Definition of SEQ ID NO: 74-artificial sequence: amino acid sequence of KM5907 VL CDR3

Definition of SEQ ID NO: 75-artificial sequence: amino acid sequence of KM5908 VH CDR1

Definition of SEQ ID NO: 76-artificial sequence: amino acid sequence of KM5908 VH CDR2

Definition of SEQ ID NO: 77-artificial sequence: amino acid sequence of KM5908 VH CDR3

Definition of SEQ ID NO: 78-artificial sequence: amino acid sequence of KM5908 VL CDR1

Definition of SEQ ID NO: 79-artificial sequence: amino acid sequence of KM5908 VL CDR2

Definition of SEQ ID NO: 80-artificial sequence: amino acid sequence of KM5908 VL CDR3

Definition of SEQ ID NO: 81-artificial sequence: amino acid sequence of KM5909 VH CDR1

Definition of SEQ ID NO: 82-artificial sequence: amino acid sequence of KM5909 VH CDR2

Definition of SEQ ID NO: 83-artificial sequence: amino acid sequence of KM5909 VH CDR3

Definition of SEQ ID NO: 84-artificial sequence: amino acid sequence of KM5909 VL CDR1

Definition of SEQ ID NO: 85-artificial sequence: amino acid sequence of KM5909 VL CDR2

Definition of SEQ ID NO: 86-artificial sequence: amino acid sequence of KM5909 VL CDR3

Definition of SEQ ID NO: 87-artificial sequence: amino acid sequence of KM5911 VH CDR1

Definition of SEQ ID NO: 88-artificial sequence: amino acid sequence of KM5911 VH CDR2

Definition of SEQ ID NO: 89-artificial sequence: amino
acid sequence of KM5911 VH CDR3
Definition of SEQ ID NO: 90-artificial sequence: amino
acid sequence of KM5911 VL CDR1
Definition of SEQ ID NO: 91-artificial sequence: amino
acid sequence of KM5911 VL CDR2
Definition of SEQ ID NO: 92-artificial sequence: amino
acid sequence of KM5911 VL CDR3
Definition of SEQ ID NO: 93-artificial sequence: amino
acid sequence of KM5915 VH CDR1
Definition of SEQ ID NO: 94-artificial sequence: amino
acid sequence of KM5915 VH CDR2
Definition of SEQ ID NO: 95-artificial sequence: amino
acid sequence of KM5915 VH CDR3
Definition of SEQ ID NO: 96-artificial sequence: amino
acid sequence of KM5915 VL CDR1
Definition of SEQ ID NO: 97-artificial sequence: amino
acid sequence of KM5915 VL CDR2
Definition of SEQ ID NO: 98-artificial sequence: amino
acid sequence of KM5915 VL CDR3
Definition of SEQ ID NO: 99-artificial sequence: amino
acid sequence of KM5916 VH CDR1
Definition of SEQ ID NO: 100-artificial sequence: amino
acid sequence of KM5916 VH CDR2
Definition of SEQ ID NO: 101-artificial sequence: amino
acid sequence of KM5916 VH CDR3
Definition of SEQ ID NO: 102-artificial sequence: amino
acid sequence of KM5916 VL CDR1
Definition of SEQ ID NO: 103-artificial sequence: amino
acid sequence of KM5916 VL CDR2
Definition of SEQ ID NO: 104-artificial sequence: amino
acid sequence of KM5916 VL CDR3
Definition of SEQ ID NO: 105-artificial sequence: amino
acid sequence of KM5954 VH CDR1
Definition of SEQ ID NO: 106-artificial sequence: amino
acid sequence of KM5954 VH CDR2
Definition of SEQ ID NO: 107-artificial sequence: amino
acid sequence of KM5954 VH CDR3
Definition of SEQ ID NO: 108-artificial sequence: amino
acid sequence of KM5954 VL CDR1
Definition of SEQ ID NO: 109-artificial sequence: amino
acid sequence of KM5954 VL CDR2
Definition of SEQ ID NO: 110-artificial sequence: amino
acid sequence of KM5954 VL CDR3
Definition of SEQ ID NO: 111-artificial sequence: amino
acid sequence of KM5955 VH CDR1
Definition of SEQ ID NO: 112-artificial sequence: amino
acid sequence of KM5955 VH CDR2
Definition of SEQ ID NO: 113-artificial sequence: amino
acid sequence of KM5955 VH CDR3
Definition of SEQ ID NO: 114-artificial sequence: amino
acid sequence of KM5955 VL CDR1
Definition of SEQ ID NO: 115-artificial sequence: amino
acid sequence of KM5955 VL CDR2
Definition of SEQ ID NO: 116-artificial sequence: amino
acid sequence of KM5955 VL CDR3
Definition of SEQ ID NO: 117-artificial sequence: amino
acid sequence of KM5956 VH CDR1
Definition of SEQ ID NO: 118-artificial sequence: amino
acid sequence of KM5956 VH CDR2
Definition of SEQ ID NO: 119-artificial sequence: amino
acid sequence of KM5956 VH CDR3
Definition of SEQ ID NO: 120-artificial sequence: amino
acid sequence of KM5956 VL CDR1
Definition of SEQ ID NO: 121-artificial sequence: amino
acid sequence of KM5956 VL CDR2

Definition of SEQ ID NO: 122-artificial sequence: amino
acid sequence of KM5956 VL CDR3
Definition of SEQ ID NO: 125-artificial sequence: amino
acid sequence of chKM5914 VL excluding signal
sequence
Definition of SEQ ID NO: 126-artificial sequence: amino
acid sequence of chKM5914 VL CDR1
Definition of SEQ ID NO: 127-artificial sequence: amino
acid sequence of chKM5914 VL CDR2
Definition of SEQ ID NO: 128-artificial sequence: amino
acid sequence of chKM5914 VL CDR3
Definition of SEQ ID NO: 129-artificial sequence:
nucleotide sequence of mAb5-06 VH
Definition of SEQ ID NO: 130-artificial sequence: amino
acid sequence of mAb5-06 VH
Definition of SEQ ID NO: 131-artificial sequence: amino
acid sequence of mAb5-06 VH CDR2
Definition of SEQ ID NO: 132-artificial sequence:
nucleotide sequence of mAb5-06 VL
Definition of SEQ ID NO: 133-artificial sequence: amino
acid sequence of mAb5-06 VL
Definition of SEQ ID NO: 134-artificial sequence: amino
acid sequence of mAb5-06 VL CDR2
Definition of SEQ ID NO: 135-artificial sequence: amino
acid sequence of hzmAb5-06 LV0
Definition of SEQ ID NO: 136-artificial sequence: amino
acid sequence of hzmAb5-06 HV0
Definition of SEQ ID NO: 137-artificial sequence: amino
acid sequence of hzmAb5-06 LV1a
Definition of SEQ ID NO: 138-artificial sequence: amino
acid sequence of hzmAb5-06 LV1b
Definition of SEQ ID NO: 139-artificial sequence: amino
acid sequence of hzmAb5-06 LV2a
Definition of SEQ ID NO: 140-artificial sequence: amino
acid sequence of hzmAb5-06 LV2b
Definition of SEQ ID NO: 141-artificial sequence: amino
acid sequence of hzmAb5-06 LV4
Definition of SEQ ID NO: 142-artificial sequence: amino
acid sequence of hzmAb5-06 LV5
Definition of SEQ ID NO: 143-artificial sequence: amino
acid sequence of hzmAb5-06 HV14
Definition of SEQ ID NO: 144-artificial sequence: amino
acid sequence of hzmAb5-06 HV17
Definition of SEQ ID NO: 145-artificial sequence: amino
acid sequence of hzKM5907 LV0
Definition of SEQ ID NO: 146-artificial sequence: amino
acid sequence of hzKM5907 HV0
Definition of SEQ ID NO: 147-artificial sequence: amino
acid sequence of hzKM5907 LV1a
Definition of SEQ ID NO: 148-artificial sequence: amino
acid sequence of hzKM5907 LV1b
Definition of SEQ ID NO: 149-artificial sequence: amino
acid sequence of hzKM5907 LV1c
Definition of SEQ ID NO: 150-artificial sequence: amino
acid sequence of hzKM5907 LV2a
Definition of SEQ ID NO: 151-artificial sequence: amino
acid sequence of hzKM5907 LV2b
Definition of SEQ ID NO: 152-artificial sequence: amino
acid sequence of hzKM5907 LV4
Definition of SEQ ID NO: 153-artificial sequence: amino
acid sequence of hzKM5907 LV6
Definition of SEQ ID NO: 154-artificial sequence: amino
acid sequence of hzKM5907 HV1
Definition of SEQ ID NO: 155-artificial sequence: amino
acid sequence of hzKM5907 HV2a
Definition of SEQ ID NO: 156-artificial sequence: amino
acid sequence of hzKM5907 HV2b Definition of SEQ ID NO: 157-artificial sequence: amino
    acid sequence of hzKM5907 HV3a
Definition of SEQ ID NO: 158-artificial sequence: amino
    acid sequence of hzKM5907 HV3b
Definition of SEQ ID NO: 159-artificial sequence: amino
    acid sequence of hzKM5907 HV3c
Definition of SEQ ID NO: 160-artificial sequence: amino
    acid sequence of hzKM5907 HV4
Definition of SEQ ID NO: 161-artificial sequence: amino
    acid sequence of hzKM5907 HV7
Definition of SEQ ID NO: 162-artificial sequence: amino
    acid sequence of hzKM5916 LV0
Definition of SEQ ID NO: 163-artificial sequence: amino
    acid sequence of hzKM5916 HV0

Definition of SEQ ID NO: 164-artificial sequence: amino
    acid sequence of hzKM5916 LV2
Definition of SEQ ID NO: 165-artificial sequence: amino
    acid sequence of hzKM5916 HV1
Definition of SEQ ID NO: 166-artificial sequence: amino
    acid sequence of hzKM5916 HV3
Definition of SEQ ID NO: 167-artificial sequence: amino
    acid sequence of hzDNP1 VL
Definition of SEQ ID NO: 168-artificial sequence: amino
    acid sequence of hzDNP1 VH

[Sequence Table]

PRCD36A_9.txt

---

```
                        SEQUENCE LISTING

Sequence total quantity: 188
SEQ ID NO: 1                moltype = DNA  length = 1068
FEATURE                     Location/Qualifiers
source                      1..1068
                            mol_type = genomic DNA
                            organism = Homo sapiens
CDS                         1..1068
                            protein_id = 169
                            translation = METPNTTEDYDTTTEFDYGDATPCQKVNERAFGAQLLPPLYSLVFV
                              IGLVGNILVVLVLVQYKRLKNMTSIYLLNLAISDLLFLFTLPFWIDYKLKDDWVFGDAM
                              CKILSGFYYTGLYSEIFFIILLTIDRYLAIVHAVFALRARTVTFGVITSIIIWALAILA
                              SMPGLYFSKTQWEFTHHTCSLHFPHESLREWKLFQALKLNLFGLVLPLLVMIICYTGII
                              KILLRRPNEKKSKAVRLIFVIMIIFFLFWTPYNLTILISVFQDFLFTHECEQSRHLDLA
                              VQVTEVIAYTHCCVNPVIYAFVGERFRKYLRQLFHRRVAVHLVKWLPFLSVDRLERVSS
                              TSPSTGEHELSAGF
SEQUENCE: 1
atggaaactc caaacaccac agaggactat gacacgacca cagagtttga ctatggggat  60
gcaactccgt gccagaaggt gaacgagagg gcctttgggg cccaactgct gccccctctg  120
tactccttgg tatttgtcat tggcctggtt ggaaacatcc tggtggtcct ggtccttgtg  180
caatacaaga ggctaaaaaa catgaccagc atctacctcc tgaacctggc catttctgac  240
ctgctcttcc tgttcacgct tcccttctgg atcgactaca agttgaagga tgactgggtt  300
tttggtgatg ccatgtgtaa gatcctctct gggttttatt acacaggctt gtacagcgag  360
atcttttca tcatcctgct gacgattgac aggtacctgg ccatcgtcca cgccgtgttt  420
gccttgcggg cacggaccgt cacttttggt gtcatcacca gcatcatcat ttgggccctg  480
gccatcttgg cttccatgcc aggcttatac ttttccaaga cccaatggga attcactcac  540
cacacctgca gccttcactt tcctcacgaa agcctacgag agtggaagct gtttcaggct  600
ctgaaactga acctctttgg gctggtattg cctttgttgg tcatgatcat ctgctacaca  660
gggattataa agattctgct aagacgacca aatgagaaga aatccaaagc tgtccgtttg  720
attttgtca tcatgatcat cttttttctc ttttggaccc cctacaattt gactatactt  780
atttctgttt ccaagacttt cctgttcacc catgagtgtg agcagagcag acatttggac  840
ctggctgtgc aagtgacgga ggtgatcgcc tacacgcact gctgtgtcaa cccagtgatc  900
tacgccttcg ttggtgagag gttccggaag tacctgcggc agttgttcca caggcgtgtg  960
gctgtgcacc tggttaaatg gctccccttc ctctccgtgg acaggctgga gagggtcagc  1020
tccacatctc cctccacagg ggagcatgaa ctctctgctg ggttctga  1068

SEQ ID NO: 2                moltype = AA  length = 355
FEATURE                     Location/Qualifiers
source                      1..355
                            mol_type = protein
                            organism = Homo sapiens
SEQUENCE: 2
METPNTTEDY DTTTEFDYGD ATPCQKVNER AFGAQLLPPL YSLVFVIGLV GNILVVLVLV  60
QYKRLKNMTS IYLLNLAISD LLFLFTLPFW IDYKLKDDWV FGDAMCKILS GFYYTGLYSE  120
IFFIILLTID RYLAIVHAVF ALRARTVTFG VITSIIIWAL AILASMPGLY FSKTQWEFTH  180
HTCSLHFPHE SLREWKLFQA LKLNLFGLVL PLLVMIICYT GIIKILLRRP NEKKSKAVRL  240
IFVIMIIFFL FWTPYNLTIL ISVFQDFLFT HECEQSRHLD LAVQVTEVIA YTHCCVNPVI  300
YAFVGERFRK YLRQLFHRRV AVHLVKWLPF LSVDRLERVS STSPSTGEHE LSAGF  355

SEQ ID NO: 3                moltype = DNA  length = 1068
FEATURE                     Location/Qualifiers
source                      1..1068
                            mol_type = genomic DNA
                            organism = Mus musculus
CDS                         1..1068
                            protein_id = 170
                            translation = MEISDFTEAYPTTTEFDYGDSTPCQKTAVRAFGAGLLPPLYSLVFI
                              IGVVGNVLVILVLMQHRRLQSMTSIYLFNLAVSDLVFLFTLPFWIDYKLKDDWIFGDAM
                              CKLLSGFYYLGLYSEIFFIILLTIDRYLAIVHAVFALRARTVTFGIITSIITWALAILA
                              SMPALYFFKAQWEFTHRTCSPHFPYKSLKQWKRFQALKLNLLGLILPLLVMIICYAGII
                              RILLRRPSEKKVKAVRLIFAITLLFFLLWTPYNLSVFVSAFQDVLFTNQCEQSKQLDLA
```

```
                     MQVTEVIAYTHCCVNPIIYVFVGERFWKYLRQLFQRHVAIPLAKWLPFLSVDQLERTSS
                     ISPSTGEHELSAGF
SEQUENCE: 3
atggagattt cagatttcac agaagcctac cccacaacta cagaatttga ctatggggac   60
tccactccat gccaaaagac tgctgtaaga gcctttgggg ctggactcct gcccccctg    120
tattctctag tgttcatcat tggagtggtg ggcaatgtcc tagtgattct ggtgctcatg   180
cagcatagga ggcttcaaag catgaccagc atctacctgt tcaacctggc tgtctctgat   240
ctggtcttcc tttcacttt accttctctgg attgactaca agttgaaaga cgactggatt    300
tttggtgatg ccatgtgcaa gcttctctct gggtttatt acctgggtt atacagtgag     360
atcttcttta tcatcctgtt gacgattgac agatacctgg ccattgtcca tgctgtgttt   420
gccctgaggg cccgaactgt tactctttggc atcatcacca gtattatcac ctgggcccta   480
gccatccttag cttccatgcc tgccttatac ttttttaagg cccagtggga gttcactcac   540
cgtacctgta gccctcattt cccctacaag agcctgaagc agtggaagag gtttcaagct    600
ctaaagctaa acctgcttgg actaattttg cctctgttag tcatgataat ctgctatgca   660
gggatcatca gaattctgct cagaagaccc agtgagaaga aggtcaaagc cgtgcgtctg    720
atatttgcta ttactcttct attcttcctc ctctggaccc cctacaatct gagtgtattt   780
gtttctgctt ccaagatgt tctattcacc aatcagtgtg agcagagtaa gcaactggac    840
ctggccatgc aggtgactga ggtgattgcc tacaccact gttgtgtcaa cccaatcatt    900
tatgtttttg tgggtgaacg gttctggaag taccttcggc agctgtttca aaggcatgtg   960
gctataccac tggcaaaatg gctgcccttc ctctctgtgg accaactaga aaggaccagt   1020
tctatatctc catccacagg agaacatgag ctctctgctg gcttctga              1068

SEQ ID NO: 4          moltype = AA   length = 355
FEATURE               Location/Qualifiers
source                1..355
                      mol_type = protein
                      organism = Mus musculus
SEQUENCE: 4
MEISDFTEAY PTTTEFDYGD STPCQKTAVR AFGAGLLPPL YSLVFIIGVV GNVLVILVLM   60
QHRRLQSMTS IYLFNLAVSD LVFLFTLPFW IDYKLKDDWI FGDAMCKLLS GFYYLGLYSE    120
IFFIILLTID RYLAIVHAVF ALRARTVTFG IITSIITWAL AILASMPALY FFKAQWEFTH   180
RTCSPHFPYK SLKQWKRFQA LKLNLLGLIL PLLVMIICYA GIIRILLRRP SEKKVKAVRL    240
IFAITLLFFL LWTPYNLSVF VSAFQDVLFT NQCEQSKQLD LAMQVTEVIA YTHCCVNPII    300
YVFVGERFWK YLRQLFQRHV AIPLAKWLPF LSVDQLERTS SISPSTGEHE LSAGF          355

SEQ ID NO: 5          moltype = DNA   length = 1068
FEATURE               Location/Qualifiers
source                1..1068
                      mol_type = genomic DNA
                      organism = Homo sapiens
SEQUENCE: 5
atgacaacct cactagatac agttgagacc tttggtacca catcctacta tgatgacgtg   60
ggcctgctct gtgaaaaagc tgataccaga gcactgatgg cccagtttgt gccccgctg    120
tactccctgg tgttcactgt gggcctcttg ggcaatgtgg tggtggtgat gatcctcata   180
aaatacagga ggctccgaat tatgaccaac atctacctgc tcaacctggc catttcggac   240
ctgctcttcc tcgtcaccct tccattctgg atacactatg tcaggggca taactgggtt    300
tttggccatg gcatgtgtaa gctcctctca gggtttatc acacaggctt gtacagcgag    360
atcttttttca taatcctgct gacaatcgac aggtacctgg ccattgtcca tgctgtgttt   420
gcccttcgag cccggactgt cacttttggt gtcatcacca gcatcgtcac ctggggcctg   480
gcagtgctag cagctcttcc tgaatttatc ttctatgaga ctgaagagtt gtttgaagag   540
actctttgca gtgctcttta cccagaggat acagtatata gctggaggca tttccacact   600
ctgagaatga ccatcttctg tctcgttctc cctctgctcg ttatggccat ctgctacaca   660
ggaatcatca aaacgctgct gaggtgcccc agtaaaaaaa agtacaaggc catccggctc   720
attttttgtca tcatggcggt gttttttcatt ttctggacac cctacaatgt ggctatcctt   780
ctctcttcct atcaatccat cttatttgga aatgactgtg agcggagcaa gcatctggac   840
ctggtcatgc tggtgacaga ggtgatcgcc tactcccact gctgcatgaa cccggtgatc   900
tacgcctttg ttggagagag gttccggaag tacctgcgcc acttcttcca caggcacttg   960
ctcatgcacc tgggcagata catcccattc cttcctagtg agaagctgga aagaaccagc   1020
tctgtctctc catccacagc agagccggaa ctctctattg tgtttttag                1068

SEQ ID NO: 6          moltype = DNA   length = 1068
FEATURE               Location/Qualifiers
misc_feature          1..1068
                      note = Description of the artificial sequence : nucleotide
                       sequence of NC3-hCCR1
source                1..1068
                      mol_type = other DNA
                      organism = synthetic construct
SEQUENCE: 6
atgacaacct cactagatac agttgagacc tttggtacca catcctacta tgatgacgtg   60
ggcctgctct gtgaaaaagc tgataccaga gcatttgggg cccaactgct gcccccctg    120
tactccttgta tatttgtcat tggcctggtt ggaaacatcc tggtggtcct ggtccttgtg   180
caatacaaga ggctaaaaaa catgaccagc atctacctcc tgaacctggc catttctgac   240
ctgctcttcc tgttcacgct tccctttctgg atcgactaca agttgaaaga tgactgggtt    300
tttggtgatg ccatgtgtaa gatcctctct gggtttttatt acacaggctt gtacagcgag   360
atctttttca tcatcctgct gacgattgac aggtacctgg ccatcgtcca cgccgtgttt   420
gccttgcggg cacggaccgt cacttttggt gtcatcacca gcatcatcat ttgggccctg   480
gccatccttg cttccatgcc aggcttatac ttttttccaaga cccaatggga attcactcac   540
cacacctgca gccttcactt tcctcacgaa agcctacgag agtggaagct gtttcaggct    600
```

-continued

```
ctgaaactga acctctttgg gctggtattg cctttgttgg tcatgatcat ctgctacaca    660
gggattataa agattctgct aagacgacca aatgagaaga aatccaaagc tgtccgtttg    720
attttttgtca tcatgatcat ctttttttctc ttttggaccc cctacaattt gactatactt    780
atttctgttt tccaagactt cctgttcacc catgagtgtg agcagagcag acatttggac    840
ctggctgtgc aagtgacgga ggtgatcgcc tacacgcact gctgtgtcaa cccagtgatc    900
tacgccttcg ttggtgagag gttccggaag tacctgcggc agttgttcca caggcgtgtg    960
gctgtgcacc tggttaaatg gctcccctttc ctctccgtgg acaggctgga gagggtcagc   1020
tccacatctc cctccacagg ggagcatgaa ctctctgctg ggttctga                 1068
```

```
SEQ ID NO: 7            moltype = DNA  length = 1068
FEATURE                 Location/Qualifiers
misc_feature            1..1068
                        note = Description of the artificial sequence : nucleotide
                         sequence of NC3-mCCR1
source                  1..1068
                        mol_type = other DNA
                        organism = synthetic construct
SEQUENCE: 7
atgacaacct cactagatac agttgagacc tttggtacca catcctacta tgatgacgtg     60
ggcctgctct gtgaaaaagc tgataccaga gcatttgggg ctggactcct gcccccccctg    120
tattctctag tgttcatcat tggagtggtg ggcaatgtcc tagtgattct ggtgctcatg    180
cagcatagga ggcttcaaag catgaccagc atctacctgt tcaacctggc tgtctctgat    240
ctggtcttcc tttttcacttt accttttctgg attgactaca agttgaaaga cgactggatt    300
tttggtgatg ccatgtgcaa gcttctctct gggttttatt acctgggtttt atacagtgag    360
atcttcttta tcatcctgtt gacgattgac agatacctgg ccattgtcca tgctgtgtttt    420
gccctgaggg cccgaactgt tacttttggc atcatccagt ctgggcccta                480
gccatcttag cttccatgcc tgccttatac tttttttaagg cccagtggga gttcactcac    540
cgtacctgta gccctcattt cccctacaag agcctgaagc agtggaagag gtttcaagct    600
ctaaagctaa accttcttgg actaattttg cctctgttag tcatgataat ctgctatgca    660
gggatcatca gaattctgct cagaagaccc agtgagaaga aggtcaaagc cgtcgtctg    720
atatttgcta ttactcttct attcttcctc ctctggaccc cctacaatct gagtgtattt    780
gtttctgctt tccaagatgt tctattcacc aatcagtgtg agcagagtaa gcaactggac    840
ctggccatgc aggtgactga ggtgattgcc tacacccact gttgtgtcaa cccaatcatt    900
tatgtttttg tgggtgaacg gttctggaag taccttcggc agctgtttca aaggcatgtg    960
gctataccac tggcaaaatg gctgcccttc ctctctgtgg accaactaga aaggaccagt   1020
tctatatctc catccacagg agaacatgag ctctctgctg gcttctga                 1068
```

```
SEQ ID NO: 8            moltype = DNA  length = 1068
FEATURE                 Location/Qualifiers
misc_feature            1..1068
                        note = Description of the artificial sequence : nucleotide
                         sequence of hCCR3_EL2hCCR1
source                  1..1068
                        mol_type = other DNA
                        organism = synthetic construct
SEQUENCE: 8
atgacaacct cactagatac agttgagacc tttggtacca catcctacta tgatgacgtg     60
ggcctgctct gtgaaaaagc tgataccaga gcactgatgg cccagtttgt gcccccgctg    120
tactccctgg tgttcactgt gggcctcttg ggcaatgtgg tggtggtgat gatcctcata    180
aaatacagga ggctccgaat tatgaccaac atctacctgc tcaacctggc catttcggac    240
ctgctcttcc tcgtcaccct tccattctgg atacactatg tcaggggggca taactggttt    300
tttggccatg gcatgtgtaa gctcctctca gggtttttatc acacaggctt gtacagcgag    360
atcttttttca taatcctgct gacaatcgac aggtacctgg ccattgtcca tgctgtgtttt    420
gcccttcgag cccggactgt cactttttggt gtcatcacca gcatcgtcac ctggggcctg    480
gcagtgctag cagctcttcc tgaattttatc ttttccaaga cccaatggga attcactcac    540
cacacctgca gccttcactt tcctcacgaa agcctacgag agtggaggca tttccacact    600
ctgagaatga ccatcttctg tctcgttctc cctctgctcg ttatggccat ctgctacaca    660
ggaatcatca aaacgctgct gaggtgcccc agtaaaaaaa agtacaaggc catccggctc    720
atttttgtca tcatggcggt gttttttcatt ttctggacac cctacaatgt gctatccttt    780
ctctcttcct atcaatccat cttatttgga aatgactgtg agcggagcaa gcatctggac    840
ctggtcatgc tggtgacaga ggtgatcgcc tactcccact gctgcatgaa cccggtgatc    900
tacgccttttg ttggagagag gttccggaag tacctgcgcc acttcttcca caggcacttg    960
ctcatgcacc tgggcagata catcccattc cttcctagtg agaagctgga aagaaccagc   1020
tctgtctctc catccacagc agagccggaa ctctctattg tgtttttag                1068
```

```
SEQ ID NO: 9            moltype = DNA  length = 1068
FEATURE                 Location/Qualifiers
misc_feature            1..1068
                        note = Description of the artificial sequence : nucleotide
                         sequence of hCCR3_EL2mCCR1
source                  1..1068
                        mol_type = other DNA
                        organism = synthetic construct
SEQUENCE: 9
atgacaacct cactagatac agttgagacc tttggtacca catcctacta tgatgacgtg     60
ggcctgctct gtgaaaaagc tgataccaga gcactgatgg cccagtttgt gcccccgctg    120
tactccctgg tgttcactgt gggcctcttg ggcaatgtgg tggtggtgat gatcctcata    180
aaatacagga ggctccgaat tatgaccaac atctacctgc tcaacctggc catttcggac    240
ctgctcttcc tcgtcaccct tccattctgg atacactatg tcaggggggca taactgggtt    300
```

```
tttggccatg gcatgtgtaa gctcctctca gggtttatc acacaggctt gtacagcgag    360
atctttttca taatcctgct gacaatcgac aggtacctgg ccattgtcca tgctgtgttt    420
gcccttcgag cccggactgt cactttggt gtcatcacca gcatcgtcac ctggggcctg    480
gcagtgctag cagctcttcc tgaatttatc tttttaagg cccagtggga gttcactcac    540
cgtacctgta gccctcattt cccctacaag agcctgaaca agtggaggca tttccacact    600
ctgagaatga ccatcttctg tctcgttctc cctctgctcg ttatggccat ctgctacaca    660
ggaatcatca aaacgctgct gaggtgcccc agtaaaaaaa agtacaaggc catccggctc    720
attttttgtca tcatggcggt gttttttcatt ttctggacac cctacaatgt ggctatcctt    780
ctctcttcct atcaatccat cttatttgga aatgactgtg agcggagcaa gcatctggac    840
ctggtcatgc tggtgacaga ggtgatcgcc tactcccact gctgcatgca cccggtgatc    900
tacgcctttg ttggagagag gttccggaag tacctgcgcc acttcttcca caggcacttg    960
ctcatgcacc tgggcagata catcccattc cttcctagtg agaagctgga aagaaccagc   1020
tctgtctctc catccacagc agagccggaa ctctctattg tgttttag                 1068
```

```
SEQ ID NO: 10          moltype = AA   length = 22
FEATURE                Location/Qualifiers
REGION                 1..22
                       note = Description of the artificial sequence : amino acid
                        sequence of N-terminal hCCR1 peptide
source                 1..22
                       mol_type = protein
                       organism = synthetic construct
SEQUENCE: 10
CTTEDYDTTT EFDYGDATPA QK                                                22

SEQ ID NO: 11          moltype = DNA   length = 30
FEATURE                Location/Qualifiers
misc_feature           1..30
                       note = Description of the artificial sequence : primer
                        mouse_gamma_r1
source                 1..30
                       mol_type = other DNA
                       organism = synthetic construct
SEQUENCE: 11
gcacacyrct ggacagggat ccagagttcc                                        30

SEQ ID NO: 12          moltype = DNA   length = 22
FEATURE                Location/Qualifiers
misc_feature           1..22
                       note = Description of the artificial sequence : primer
                        mouse_gamma_r2
source                 1..22
                       mol_type = other DNA
                       organism = synthetic construct
SEQUENCE: 12
cckyggtsyt gctggcyggg tg                                                22

SEQ ID NO: 13          moltype = DNA   length = 30
FEATURE                Location/Qualifiers
misc_feature           1..30
                       note = Description of the artificial sequence : primer
                        mouse_kappa_r1
source                 1..30
                       mol_type = other DNA
                       organism = synthetic construct
SEQUENCE: 13
gaagcacacg actgaggcac ctccagatgt                                        30

SEQ ID NO: 14          moltype = DNA   length = 30
FEATURE                Location/Qualifiers
misc_feature           1..30
                       note = Description of the artificial sequence :
                        primer_mouse_kappa_r2
source                 1..30
                       mol_type = other DNA
                       organism = synthetic construct
SEQUENCE: 14
gtaggtgctg tctttgctgt cctgatcagt                                        30

SEQ ID NO: 15          moltype = DNA   length = 411
FEATURE                Location/Qualifiers
source                 1..411
                       mol_type = genomic DNA
                       organism = Mus musculus
CDS                    1..411
                       protein_id = 171
                       translation = MNFGLSLIFLALILKGVQCEVQVVESGGNLVKPGGSLKLSCSASGF
                        TFSRYGMSWVRQTPDKRLEWVASISATFTYTYYTDNVKGRFTISRDNAKNTLYLQMSSL
                        RSEDTGMYYCTRQDNYAWFDSWGQGTLVTVSA
```

```
SEQUENCE: 15
atgaacttcg ggctcagctt gattttcctt gcccttattt taaaaggtgt ccagtgtgag    60
gtgcaggtgg tggagtctgg gggaaactta gtgaaacctg gagggtccct gaaactttcc   120
tgttcagcct ctggattcac tttcagtcgc tatggcatgt cctgggttcg ccagactcca   180
gacaagaggc tggagtgggt cgcatccatt agtgctactt ttacttacac ctactataca   240
gacaatgtga aggggcgttt caccatctcc agagacaatg ccaagaacac cctgtaccta   300
caaatgagca gtctgaggtc tgaggacaca ggcatgtatt actgtacaag acaagataat   360
tacgcctggt ttgattcctg gggccaaggg actctggtca ctgtctctgc a           411

SEQ ID NO: 16              moltype = AA   length = 137
FEATURE                    Location/Qualifiers
source                     1..137
                           mol_type = protein
                           organism = Mus musculus
SEQUENCE: 16
MNFGLSLIFL ALILKGVQCE VQVVESGGNL VKPGGSLKLS CSASGFTFSR YGMSWVRQTP    60
DKRLEWVASI SATFTYTYYT DNVKGRFTIS RDNAKNTLYL QMSSLRSEDT GMYYCTRQDN   120
YAWFDSWGQG TLVTVSA                                                  137

SEQ ID NO: 17              moltype = DNA   length = 393
FEATURE                    Location/Qualifiers
source                     1..393
                           mol_type = genomic DNA
                           organism = Mus musculus
CDS                        1..393
                           protein_id = 172
                           translation = MKLPVRLLVLMFWIPVSNSDVLMTQTPLSLPVSLGDQVSISCRSSQ
                            SIVHSNGNTFLEWYLKKPGQSPKLLIYKVSSRFSGVPDRFSGSGSGTDFTLKIRRVEAD
                            DLGVYYCFQGSHIPWTFGGGTNLEIK
SEQUENCE: 17
atgaagttgc ctgttaggct gttggtgctg atgttctgga ttcctgtttc caacagtgat    60
gttttgatga cccaaactcc actctccctg cctgtcagtc ttggagatca agtctccatc   120
tcctgcagat ctagtcagag tattgtgcat agtaatggaa acaccttttt agaatggtac   180
ctgaagaaac caggccagtc tccaaagctc ctgatctata agtttccag ccgattttct    240
ggggtcccag acaggttcag tggcagtgga tcagggacag atttcacact caagatcagg   300
agagtggagg ctgacgatct gggagtttat tactgctttc aaggttcaca tattccgtgg   360
acgttcggtg gaggcaccaa cctggaaatc aaa                               393

SEQ ID NO: 18              moltype = AA   length = 131
FEATURE                    Location/Qualifiers
source                     1..131
                           mol_type = protein
                           organism = Mus musculus
SEQUENCE: 18
MKLPVRLLVL MFWIPVSNSD VLMTQTPLSL PVSLGDQVSI SCRSSQSIVH SNGNTFLEWY    60
LKKPGQSPKL LIYKVSSRFS GVPDRFSGSG SGTDFTLKIR RVEADDLGVY YCFQGSHIPW   120
TFGGGTNLEI K                                                        131

SEQ ID NO: 19              moltype = DNA   length = 414
FEATURE                    Location/Qualifiers
source                     1..414
                           mol_type = genomic DNA
                           organism = Mus musculus
CDS                        1..414
                           protein_id = 173
                           translation = MAVLVLLFCLVTFPSCVLSQVQLKQSGPGLVQPSQSLSITCTVSGF
                            SLNNYGVHWVRQPPGKGLEWLGVIWSAGTTVYNAAFISRLSISKDDSKSQVFFKMNSLQ
                            AGDTAIYYCAKDGSRYYTAMDYWGQGTSVTVSS
SEQUENCE: 19
atggctgtcc tggtgctgct cttctgcctg gtgacattcc caagctgtgt cctatcccag    60
gtgcagctga gcagtcagg acctggccta gtgcagccct cacagagtct gtccatcacc    120
tgcacagtct ctggtttctc attaaataac tatggtgtac actgggttcg ccagcctcca   180
ggaaagggtc tggagtggct gggagtgata tggagtgctg gaaccacagt ctataatgct   240
gctttcatat ccagactgag catcagcaag gacgactcca agagccaagt tttctttaaa   300
atgaacagtc tgcaagctgg tgacactgcc atatatact gtgccaaaga cggtagtaga    360
tattatactg ctatggacta ctggggtcaa ggaacctcag tcaccgtctc ctca         414

SEQ ID NO: 20              moltype = AA   length = 138
FEATURE                    Location/Qualifiers
source                     1..138
                           mol_type = protein
                           organism = Mus musculus
SEQUENCE: 20
MAVLVLLFCL VTFPSCVLSQ VQLKQSGPGL VQPSQSLSIT CTVSGFSLNN YGVHWVRQPP    60
GKGLEWLGVI WSAGTTVYNA AFISRLSISK DDSKSQVFFK MNSLQAGDTA IYYCAKDGSR   120
YYTAMDYWGQ GTSVTVSS                                                 138

SEQ ID NO: 21              moltype = DNA   length = 393
FEATURE                    Location/Qualifiers
```

```
source                    1..393
                          mol_type = genomic DNA
                          organism = Mus musculus
CDS                       1..393
                          protein_id = 174
                          translation = MKLPVRLLVLMFWIPATSSDVVMTQTPRSLPVSLGDQASISCRSRQ
                             SLIHSNGITFLHWYLQKAGQSPKLLIYKVSNRFSGVPDRFSGSGSGTDFTLRISRVEAE
                             DLGVYFCSQGTHVPPTFGGGTKLEIK
SEQUENCE: 21
atgaagttgc ctgttaggct gttggtgctg atgttctgga ttcctgctac cagcagtgat   60
gttgtgatga cccaaactcc tcgctccctg cctgtcagtc ttggagatca agcctccatc   120
tcttgcagat ctcgtcagag ccttattcac agtaatggaa tcacctttt acattggtac    180
ctgcagaagg caggccagtc tccaaagctc ctgatctaca agtttccaa ccgattttct     240
ggggtcccag acaggttcag tggcagtgga tcaggacagc atttcacact caggatcagc   300
agagtggagg ctgaggatct gggagtttat ttctgctctc aaggtacaca tgttcctccc   360
acgttcggtg gaggcaccaa gctggaaatc aaa                                393

SEQ ID NO: 22            moltype = AA   length = 131
FEATURE                  Location/Qualifiers
source                   1..131
                         mol_type = protein
                         organism = Mus musculus
SEQUENCE: 22
MKLPVRLLVL MFWIPATSSD VVMTQTPRSL PVSLGDQASI SCRSRQSLIH SNGITFLHWY   60
LQKAGQSPKL LIYKVSNRFS GVPDRFSGSG SGTDFTLRIS RVEAEDLGVY FCSQGTHVPP   120
TFGGGTKLEI K                                                        131

SEQ ID NO: 23            moltype = DNA   length = 414
FEATURE                  Location/Qualifiers
source                   1..414
                         mol_type = genomic DNA
                         organism = Mus musculus
CDS                      1..414
                         protein_id = 175
                         translation = MNFGLSLIFLALILKGVQCEVQLVESGGDLVKPGGSLKLSCAASGF
                            TLSNYGMSWVRQTPDKRLEWVASISIGNYIYYLDSVKGRFTIYRDNAKNTLFLQMRSLK
                            SEDTAMYHCARQGNDYDWFTYWGQGTLVTVSAA
SEQUENCE: 23
atgaacttcg ggctcagctt gattttcctt gcccttattt taaaaggtgt ccagtgtgag   60
gtgcagctgg tggagtctgg gggagactta gtgaagcctg agggtccct gaaactctcc    120
tgtgcagcct ctggattcac cttaagtaat tatggcatgt cttgggttcg ccagactcca   180
gacaagaggc tggaatgggt cgcatccatt agtattggca attacatcta ttatctagac   240
agtgtgaagg ggcgattcac catctacaga gacaatgcca agaacaccct gttcctgcaa   300
atgaggagtc tgaagtctga ggacacagcc atgtatcact gtgcaagaca ggggaatgat   360
tacgactggt ttacttactg gggccaaggg actctggtca ctgtctctgc agcc          414

SEQ ID NO: 24            moltype = AA   length = 138
FEATURE                  Location/Qualifiers
source                   1..138
                         mol_type = protein
                         organism = Mus musculus
SEQUENCE: 24
MNFGLSLIFL ALILKGVQCE VQLVESGGDL VKPGGSLKLS CAASGFTLSN YGMSWVRQTP   60
DKRLEWVASI SIGNYIYYLD SVKGRFTIYR DNAKNTLFLQ MRSLKSEDTA MYHCARQGND   120
YDWFTYWGQG TLVTVSAA                                                 138

SEQ ID NO: 25            moltype = DNA   length = 393
FEATURE                  Location/Qualifiers
source                   1..393
                         mol_type = genomic DNA
                         organism = Mus musculus
CDS                      1..393
                         protein_id = 176
                         translation = MKLPVRLLVLMFWIPVSSSDVLMTQTPLSLPVSLGDQASISCRSSQ
                            SVVHTNGNTYLEWYLQKPGQSPKLLIYKVSNRFSGVPDRFSGSGSGTDFTLKINRVEAE
                            DLGVYYCFQGSHLPWTFGGGTKLEIK
SEQUENCE: 25
atgaagttgc ctgttagact gttggtgctg atgttctgga ttcctgtttc cagcagtgat   60
gttttgatga cccaaactcc actctccctg cctgtcagtc ttggagatca agcctccatc   120
tcttgcagat ctagtcagag cgttgtacat actaatggaa acacctattt agagtggtac   180
ctgcagaaac aggccagtc tccaaagctc ctgatctaca agtttccaa ccgattttct      240
ggggtcccag acaggttcag tggcagtgga tcaggacag atttcacact caagatcaac    300
agagtggagg ctgaggatct gggagtttat tactgctttc aaggttcaca tcttccgtgg   360
acgttcggtg gaggcaccaa actggagatc aaa                                393

SEQ ID NO: 26            moltype = AA   length = 131
FEATURE                  Location/Qualifiers
source                   1..131
                         mol_type = protein
```

```
                              organism = Mus musculus
SEQUENCE: 26
MKLPVRLLVL MFWIPVSSSD VLMTQTPLSL PVSLGDQASI SCRSSQSVVH TNGNTYLEWY   60
LQKPGQSPKL LIYKVSNRFS GVPDRFSGSG SGTDFTLKIN RVEAEDLGVY YCFQGSHLPW  120
TFGGGTKLEI K                                                       131

SEQ ID NO: 27           moltype = DNA  length = 420
FEATURE                 Location/Qualifiers
source                  1..420
                        mol_type = genomic DNA
                        organism = Mus musculus
CDS                     1..420
                        protein_id = 177
                        translation = MNFGLRLIFLVLTLKGVQCDVKLVESGEGLVKPGGSLKLSCAASGF
                         TFSRNAMSWVRQTPEKRMEWVAYISSGGDYIYYADTVKGRFTVSRDNARNTLYLRMSSL
                         KSEDTAMYYCTRFSYGYAKNALDYWGQGTSVTVSS
SEQUENCE: 27
atgaacttcg ggctcagatt gattttcctt gtccttactt taaaaggtgt ccagtgtgac   60
gtgaagttgg tggagtctgg ggaaggctta gtgaagcctg gagggtccct gaaactctcc  120
tgtgctgcct ctggattcac gttcagcaga aatgccatgt cttgggttcg ccagactcca  180
gagaagagga tggagtgggt cgcatacatt agtagtggtg gtgattacat ctactatgca  240
gacactgtga agggccgatt caccgtctcc agagacaatg ccaggaacac cctgtacctg  300
cgaatgagca gtctgaagtc tgaggacaca gccatgtatt actgtacaag attctcctat  360
ggttacgcaa aaaatgctct ggactactgg ggtcaaggaa cctcagtcac cgtctcctca  420

SEQ ID NO: 28           moltype = AA  length = 140
FEATURE                 Location/Qualifiers
source                  1..140
                        mol_type = protein
                        organism = Mus musculus
SEQUENCE: 28
MNFGLRLIFL VLTLKGVQCD VKLVESGEGL VKPGGSLKLS CAASGFTFSR NAMSWVRQTP   60
EKRMEWVAYI SSGGDYIYYA DTVKGRFTVS RDNARNTLYL RMSSLKSEDT AMYYCTRFSY  120
GYAKNALDYW GQGTSVTVSS                                              140

SEQ ID NO: 29           moltype = DNA  length = 378
FEATURE                 Location/Qualifiers
source                  1..378
                        mol_type = genomic DNA
                        organism = Mus musculus
CDS                     1..378
                        protein_id = 178
                        translation = MRPSIQFLGLLLFWLHGAQCDIQMTQSPSSLSASLGGKVTITCKAS
                         QDIKKYIAWYQHKPGKGPRLLIHYTSSLQPGIPSRFSGSGSGRDYSFSISNLEPEDIAT
                         YYCLQYDYLMTFGGGTKLEIK
SEQUENCE: 29
atgagaccgt ctattcagtt cctggggctc ttgttgttct ggcttcatgg tgctcagtgt   60
gacatccaga tgacacagtc tccatcctca ctgtctgcat ctttgggagg caaagtcacc  120
atcacttgca aggcaagcca agacattaag aagtatatag cttggtacca acacaagcct  180
ggaaaaggtc ctaggctgct catacattac acatcttcat tacagccagg catcccatca  240
aggttcagtg gaagtgggtc tgggagagat tattccttca gcatcagcaa cctggagcct  300
gaggatattg caacttatta ttgtctacag tatgattatc ttatgacgtt cggtggaggc  360
accaagctgg aaatcaaa                                                378

SEQ ID NO: 30           moltype = AA  length = 126
FEATURE                 Location/Qualifiers
source                  1..126
                        mol_type = protein
                        organism = Mus musculus
SEQUENCE: 30
MRPSIQFLGL LLFWLHGAQC DIQMTQSPSS LSASLGGKVT ITCKASQDIK KYIAWYQHKP   60
GKGPRLLIHY TSSLQPGIPS RFSGSGSGRD YSFSISNLEP EDIATYYCLQ YDYLMTFGGG  120
TKLEIK                                                             126

SEQ ID NO: 31           moltype = DNA  length = 414
FEATURE                 Location/Qualifiers
source                  1..414
                        mol_type = genomic DNA
                        organism = Mus musculus
CDS                     1..414
                        protein_id = 179
                        translation = MNFGLSLIFLALILKGVQCEVQLVESGGDLVKPGGSLKLSCAASGF
                         TFSNYGMSWVRQTPDKRLEWVASISIGSYIYYLDSVKGRFTIYRDNAKNTLFLQMRSLK
                         SEDTAMYHCARQGNDYDWFAYWGQGTLVTVSAA
SEQUENCE: 31
atgaacttcg ggctcagctt gattttcctt gcccttattt taaaaggtgt ccagtgtgag   60
gtgcagctgg tggagtctgg gggagactta gtgaagcctg gagggtccct gaaactctcc  120
tgtgcagcct ctggattcac cttcagtaac tatggcatgt cttgggttcg ccagactcca  180
gacaagaggc tggagtgggt cgcatccatt agtattggca gttacatcta ttatctagac  240
```

-continued

```
agtgtgaagg ggcgattcac catctacaga gacaatgcca agaacaccct gttcctgcaa   300
atgaggagtc tgaagtctga ggacacagcc atgtatcact gtgcaagaca ggggaatgat   360
tacgactggt ttgcttactg gggccaaggg actctggtca ctgtctctgc agcc         414

SEQ ID NO: 32              moltype = AA   length = 138
FEATURE                    Location/Qualifiers
source                     1..138
                           mol_type = protein
                           organism = Mus musculus
SEQUENCE: 32
MNFGLSLIFL ALILKGVQCE VQLVESGGDL VKPGGSLKLS CAASGFTFSN YGMSWVRQTP   60
DKRLEWVASI SIGSYIYYLD SVKGRFTIYR DNAKNTLFLQ MRSLKSEDTA MYHCARQGND   120
YDWFAYWGQG TLVTVSAA                                                 138

SEQ ID NO: 33              moltype = DNA   length = 393
FEATURE                    Location/Qualifiers
source                     1..393
                           mol_type = genomic DNA
                           organism = Mus musculus
CDS                        1..393
                           protein_id = 180
                           translation = MKLPVRLLVLMFWIPASSSDVLMTQTPLSLPVSLGDQASISCRSSQ
                             NIVHTNGNTYLEWYLQKPGQSPKLLIYKVSNRFSGVPDRFSGSGSGTDFTLKISRVEAE
                             DLGVYYCFQGSHLPWTFGGGTKLEIK
SEQUENCE: 33
atgaagttgc ctgttagact gttggtgctg atgttctgga ttcctgcttc cagcagtgat   60
gttttgatga cccaaactcc actctccctg cctgtcagtc ttggagatca agcctccatc   120
tcttgcagat ctagtcagaa cattgtacat actaatggaa acacctattt agagtggtac   180
ctgcagaaac aggccagtc tccaaagctc ctgatctaca agtttccaa ccgattttct     240
ggggtcccag acaggttcag tggcagtgga tcagggacag atttcacact caagatcagc   300
agagtggagg ctgaggatct gggagtttat tactgctttc aaggttcaca tcttccgtgg   360
acgttcggtg gaggcaccaa gctggagatc aaa                               393

SEQ ID NO: 34              moltype = AA   length = 131
FEATURE                    Location/Qualifiers
source                     1..131
                           mol_type = protein
                           organism = Mus musculus
SEQUENCE: 34
MKLPVRLLVL MFWIPASSSD VLMTQTPLSL PVSLGDQASI SCRSSQNIVH TNGNTYLEWY   60
LQKPGQSPKL LIYKVSNRFS GVPDRFSGSG SGTDFTLKIS RVEAEDLGVY YCFQGSHLPW   120
TFGGGTKLEI K                                                        131

SEQ ID NO: 35              moltype = DNA   length = 420
FEATURE                    Location/Qualifiers
source                     1..420
                           mol_type = genomic DNA
                           organism = Mus musculus
CDS                        1..420
                           protein_id = 181
                           translation = MNFGLRLILLVLTLKGVQCDVKLVESGEGLVKPGGSLKLSCAASGF
                             TFSRNAMSWVRQTPEKRLEWVAYISSGSDYIYYADTVKGRFTVSRDNARNTLYLQMTSL
                             RSEDTAMYFCTRFSYGYGKNAPDYWGQGTSVTVSS
SEQUENCE: 35
atgaacttcg ggctcagatt gattctcctt gtccttactt taaaaggtgt ccaatgtgac   60
gtgaagctgg tggagtctgg ggaaggctta gtgaagcctg agggtccct gaaactctcc    120
tgtgcagcct ctggattcac gttcagcaga aatgccatgt cttgggttcg ccagactcca   180
gagaagaggc tggagtgggt cgcatacatt agtagtggta gtgattacat ctactatgca   240
gacactgtga agggccgatt cactgtctcc agagacaatg ccaggaacac cctgtacctg   300
caaatgacca gtctgaggtc tgaggacaca gccatgtatt tctgtacaag attctcgtat   360
ggttacggga aaaatgctcc ggactactgg ggtcaaggaa cctcagtcac cgtctcctca   420

SEQ ID NO: 36              moltype = AA   length = 140
FEATURE                    Location/Qualifiers
source                     1..140
                           mol_type = protein
                           organism = Mus musculus
SEQUENCE: 36
MNFGLRLILL VLTLKGVQCD VKLVESGEGL VKPGGSLKLS CAASGFTFSR NAMSWVRQTP   60
EKRLEWVAYI SSGSDYIYYA DTVKGRFTVS RDNARNTLYL QMTSLRSEDT AMYFCTRFSY   120
GYGKNAPDYW GQGTSVTVSS                                               140

SEQ ID NO: 37              moltype = DNA   length = 378
FEATURE                    Location/Qualifiers
source                     1..378
                           mol_type = genomic DNA
                           organism = Mus musculus
CDS                        1..378
                           protein_id = 182
```

-continued

```
                     translation = MRPSIQFLGLLLFWLHGTQCDIQMTQSPSSLSASLGGKVTITCKAS
                     QDINKYIAWYQHKPGQGPRLLIHYTSSLQPGIPSRFSGSGSGRDYSFSISNLEPEDIAT
                     YYCLQYDYTMTFGGGTKLEIR
SEQUENCE: 37
atgagaccgt ctattcagtt cctgggcctc ttgttgttct ggcttcatgg tactcagtgt   60
gacatccaga tgacacagtc accatcctca ctgtctgcat ctctgggagg caaagtcacc   120
atcacttgca aggcaagcca agacattaac aagtatatag cgtggtacca acacaagcct   180
ggacaaggtc ctaggctgct catacattac acatcttcat tacagccagg catcccatca   240
aggttcagtg gaagtgggtc tgggagagat tattccttca gcatcagcaa cctggagcct   300
gaagatattg caacttatta ttgtctacag tatgattata ctatgacgtt cggtggaggc   360
accaagctgg aaatcaga                                                 378

SEQ ID NO: 38          moltype = AA   length = 126
FEATURE                Location/Qualifiers
source                 1..126
                       mol_type = protein
                       organism = Mus musculus
SEQUENCE: 38
MRPSIQFLGL LLFWLHGTQC DIQMTQSPSS LSASLGGKVT ITCKASQDIN KYIAWYQHKP   60
GQGPRLLIHY TSSLQPGIPS RFSGSGSGRD YSFSISNLEP EDIATYYCLQ YDYTMTFGGG   120
TKLEIR                                                              126

SEQ ID NO: 39          moltype = DNA   length = 429
FEATURE                Location/Qualifiers
source                 1..429
                       mol_type = genomic DNA
                       organism = Mus musculus
CDS                    1..429
                       protein_id = 183
                       translation = MAVLALLLCLVTFPSCALSQVQLKESGPGLVAPSQSLSITCTVSGF
                       SLPRYTITWVRQPPGKGLEWLGLIRTGGGTIYNSALKSRLSISKDNSKSQVFLKMNSLQ
                       SGDTARYYCARNGAYYSKSGSYWYFDVWGTGTTVTVSS
SEQUENCE: 39
atggctgtcc tggcgctact cctctgcctg gtgactttcc caagctgtgc cctgtcccag   60
gtgcagctga aggagtcagg acctggcctg gtggcgccct cacaaagcct gtccatcaca   120
tgcactgtct ctgggttctc attgcccaga tatactataa cctgggttcg ccagccacca   180
ggaaagggtc tggagtggct tggattaata aggactggtg gaggcacaat ttataattca   240
gctctcaaat ccagactgag catcagcaaa gacaactcca agagtcaagt tttcttgaaa   300
atgaacagtc tgcaaagtgg tgacacagcc aggtactact gtgccagaaa tggagcctac   360
tatagtaagt ccggttctta ctggtacttc gatgtctggg gcacagggac cacggtcacc   420
gtctcctca                                                          429

SEQ ID NO: 40          moltype = AA   length = 143
FEATURE                Location/Qualifiers
source                 1..143
                       mol_type = protein
                       organism = Mus musculus
SEQUENCE: 40
MAVLALLLCL VTFPSCALSQ VQLKESGPGL VAPSQSLSIT CTVSGFSLPR YTITWVRQPP   60
GKGLEWLGLI RTGGGTIYNS ALKSRLSISK DNSKSQVFLK MNSLQSGDTA RYYCARNGAY   120
YSKSGSYWYF DVWGTGTTVT VSS                                           143

SEQ ID NO: 41          moltype = DNA   length = 384
FEATURE                Location/Qualifiers
source                 1..384
                       mol_type = genomic DNA
                       organism = Mus musculus
CDS                    1..384
                       protein_id = 184
                       translation = MDFQVQIFSFLLISASVIMSRGQIVLTQSPAIMSVSLGEEITLTCS
                       ASSSVSYMHWYQQKSGTSPKLLIYSTSNLASGVPSRFSGSGSGTFYSLTISSVEAEDAA
                       DYYCHQWSSHPCTFGGGTKLEIK
SEQUENCE: 41
atggattttc aggtgcagat tttcagcttc ctgctaatca gtgcctcagt cataatgtcc   60
agaggacaaa ttgttctcac ccagtctcca gcaatcatgt ctgtatctct aggggaggag   120
atcaccctaa cctgcagtgc cagctcgagt gtaagttaca tgcactggta ccagcagaag   180
tcaggcactc tccccaaact cttgatttat agcacatcca acctggcttc tggagtccct   240
tctcgcttca gtggcagtgg gtctgggacc ttttattctc tcacaatcag cagtgtggag   300
gctgaagatg ctgccgatta ttactgtcat cagtggagta tcatccatg cacgttcgga   360
gggggaacca agctggaaat aaaa                                          384

SEQ ID NO: 42          moltype = AA   length = 128
FEATURE                Location/Qualifiers
source                 1..128
                       mol_type = protein
                       organism = Mus musculus
SEQUENCE: 42
MDFQVQIFSF LLISASVIMS RGQIVLTQSP AIMSVSLGEE ITLTCSASSS VSYMHWYQQK   60
SGTSPKLLIY STSNLASGVP SRFSGSGSGT FYSLTISSVE AEDAADYYCH QWSSHPCTFG   120
```

```
GGTKLEIK                                                                128

SEQ ID NO: 43              moltype = DNA   length = 417
FEATURE                   Location/Qualifiers
source                    1..417
                          mol_type = genomic DNA
                          organism = Mus musculus
CDS                       1..417
                          protein_id = 185
                          translation = MDSRLNLVFLVLILKGVQCEVQLVESGGGLVKPGGSLKLSCAASGF
                          TLRDFGMHWVRQVPEKGLEWVAYISSGRTAISYVDKVKGRFTISRDNAKNTLFLQMTSL
                          RSEDTAMYYCARRPYSKSYAMDYWGQGTSVTVSS
SEQUENCE: 43
atggactcca ggctcaattt agttttcctt gtcctatttt taaaaggtgt ccagtgtgag  60
gtgcaactgg tggagtctgg gggaggctta gtgaagcctg gagggtccct gaaactctcc  120
tgtgcagcct ctggattcac tctcagggac tttggaatgc actgggttcg acaggtccca  180
gagaaggggc tggagtgggt tgcatatatc agtagtggca ggactgccat ctcctatgta  240
gacaaagtga agggccgatt caccatctcc agagacaatg ccaagaacac cctgttcctg  300
caaatgacca gtctgaggtc tgaggacacg gccatgtatt actgtgcaag gaggccctat  360
agtaagtctt atgctatgga ctactggggt caaggaacct cagtcaccgt ctcctca      417

SEQ ID NO: 44              moltype = AA   length = 139
FEATURE                   Location/Qualifiers
source                    1..139
                          mol_type = protein
                          organism = Mus musculus
SEQUENCE: 44
MDSRLNLVFL VLILKGVQCE VQLVESGGGL VKPGGSLKLS CAASGFTLRD FGMHWVRQVP  60
EKGLEWVAYI SSGRTAISYV DKVKGRFTIS RDNAKNTLFL QMTSLRSEDT AMYYCARRPY  120
SKSYAMDYWG QGTSVTVSS                                                139

SEQ ID NO: 45              moltype = DNA   length = 396
FEATURE                   Location/Qualifiers
source                    1..396
                          mol_type = genomic DNA
                          organism = Mus musculus
CDS                       1..396
                          protein_id = 186
                          translation = MKLPVLLVVLLLFTSPASSSDVVLTQTPLSLPVNIGDQASISCKSI
                          KSLLNSDGFTYLDWYLQKPGQSPQLLIYLVSNRFSGVPDRFSGSGSGTDFTLKIRRVEA
                          EDLGVYYCFQSNYLPLTFGAGTKLELK
SEQUENCE: 45
atgaagctgc ctgttctgct agtggtgctg ctattgttca cgagtccagc ctcaagcagt  60
gatgttgttc tgacccaaac tccactctct ctgcctgtca atattggaga ccaagcctct  120
atctcttgca gtctattaa gagtcttctg aatagtgatg gattcactta tttggactgg  180
tatctgcaga agccaggcca gtctccacag ctcctaatat atttggtttc taatcgattt  240
tctggagttc cagacaggtt cagtggcagt gggtcaggaa cagatttcac actcaagatc  300
agaagagtgg aggctgagga tttgggagtt tattattgct tccagagtaa ctatcttcct  360
ctcacgttcg gtgctgggac caagctggag ctgaaa                            396

SEQ ID NO: 46              moltype = AA   length = 132
FEATURE                   Location/Qualifiers
source                    1..132
                          mol_type = protein
                          organism = Mus musculus
SEQUENCE: 46
MKLPVLLVVL LLFTSPASSS DVVLTQTPLS LPVNIGDQAS ISCKSIKSLL NSDGFTYLDW  60
YLQKPGQSPQ LLIYLVSNRF SGVPDRFSGS GSGTDFTLKI RRVEAEDLGV YYCFQSNYLP  120
LTFGAGTKLE LK                                                       132

SEQ ID NO: 47              moltype = DNA   length = 429
FEATURE                   Location/Qualifiers
source                    1..429
                          mol_type = genomic DNA
                          organism = Mus musculus
CDS                       1..429
                          protein_id = 187
                          translation = MAVLALLLCLVTFPSCALSQVQLKESGPGLVAPSQSLSITCTVSGF
                          SLARYTITWVRQPPGKGLEWLGLIRTGGGTIYNSALKSRLSISKDNSKSQVFLKMNSLQ
                          SGDTARYYCARNGAYYSNSGSYWYFDVWGTGTTVTVSS
SEQUENCE: 47
atggctgtcc tggcgctact cctctgcctg gtgactttcc caagctgtgc cctgtcccag  60
gtgcagctga aggagtcagg acctggcctg gtggcgccct cacaaagcct gtccatcaca  120
tgcactgtct ctgggttctc attggccagg tatactataa cctgggttcg ccagccacca  180
ggaaagggtc tggagtggct ggattaata aggactggtg gaggcacaat ttataattca  240
gctctcaaat ccagactgag catcagcaaa gacaactcca agagtcaagt tttcttaaaa  300
atgaacagtc tgcaaagtgg tgacacagcc aggtactact gtgccagaaa tggagcctac  360
tatagtaact ccggttctta ctggtacttc gatgtctggg gcacagggac cacggtcacc  420
gtctcctca                                                          429
```

-continued

```
SEQ ID NO: 48              moltype = AA  length = 143
FEATURE                    Location/Qualifiers
source                     1..143
                           mol_type = protein
                           organism = Mus musculus
SEQUENCE: 48
MAVLALLLCL VTFPSCALSQ VQLKESGPGL VAPSQSLSIT CTVSGFSLAR YTITWVRQPP  60
GKGLEWLGLI RTGGGTIYNS ALKSRLSISK DNSKSQVFLK MNSLQSGDTA RYYCARNGAY  120
YSNSGSYWYF DVWGTGTTVT VSS                                          143

SEQ ID NO: 49              moltype = DNA  length = 384
FEATURE                    Location/Qualifiers
source                     1..384
                           mol_type = genomic DNA
                           organism = Mus musculus
CDS                        1..384
                           protein_id = 188
                           translation = MDFQVQIFSFLLISASVMMSRGQIVLTQSPAIMSASLGEEITLTCS
                            ASSSVTYMHWYQQKSGTSPKLLIYSTSNLASGVPSRFSGSGSGTFYSLTISSVEAEDAA
                            DYYCHQWSSHPCTFGGGAKLEIK
SEQUENCE: 49
atggatttc aggtgcagat tttcagcttc ctgctaatca gtgcctcagt catgatgtcc  60
agaggacaaa ttgttctcac ccagtctcca gcaatcatgt ctgcatctct aggggaggag  120
atcaccctaa cctgcagtgc cagctcgagt gtaacttaca tgcactggta ccagcagaag  180
tcaggcactt ctcccaaact cttgatttat agcacatcca acctggcttc tggagtccct  240
tctcgcttca gtggcagtgg gtctgggacc ttttattctc tcacaatcag cagtgtggag  300
gctgaagatg ctgccgatta ttactgtcat cagtggagta gtcatccatg cacgttcgga  360
ggggggccaa agctggaaat aaaa                                         384

SEQ ID NO: 50              moltype = AA  length = 128
FEATURE                    Location/Qualifiers
source                     1..128
                           mol_type = protein
                           organism = Mus musculus
SEQUENCE: 50
MDFQVQIFSF LLISASVMMS RGQIVLTQSP AIMSASLGEE ITLTCSASSS VTYMHWYQQK  60
SGTSPKLLIY STSNLASGVP SRFSGSGSGT FYSLTISSVE AEDAADYYCH QWSSHPCTFG  120
GGAKLEIK                                                           128

SEQ ID NO: 51              moltype = AA  length = 118
FEATURE                    Location/Qualifiers
REGION                     1..118
                           note = Description of the artificial sequence : amino acid
                            sequence of KM5907 VH excluding signal sequence
source                     1..118
                           mol_type = protein
                           organism = synthetic construct
SEQUENCE: 51
EVQVVESGGN LVKPGGSLKL SCSASGFTFS RYGMSWVRQT PDKRLEWVAS ISATFTYTYY  60
TDNVKGRFTI SRDNAKNTLY LQMSSLRSED TGMYYCTRQD NYAWFDSWGQ GTLVTVSA    118

SEQ ID NO: 52              moltype = AA  length = 112
FEATURE                    Location/Qualifiers
REGION                     1..112
                           note = Description of the artificial sequence : amino acid
                            sequence of KM5907 VL excluding signal sequence
source                     1..112
                           mol_type = protein
                           organism = synthetic construct
SEQUENCE: 52
DVLMTQTPLS LPVSLGDQVS ISCRSSQSIV HSNGNTFLEW YLKKPGQSPK LLIYKVSSRF  60
SGVPDRFSGS GSGTDFTLKI RRVEADDLGV YYCFQGSHIP WTFGGGTNLE IK          112

SEQ ID NO: 53              moltype = AA  length = 119
FEATURE                    Location/Qualifiers
REGION                     1..119
                           note = Description of the artificial sequence : amino acid
                            sequence of KM5908 VH excluding signal sequence
source                     1..119
                           mol_type = protein
                           organism = synthetic construct
SEQUENCE: 53
QVQLKQSGPG LVQPSQSLSI TCTVSGFSLN NYGVHWVRQP PGKGLEWLGV IWSAGTTVYN  60
AAFISRLSIS KDDSKSQVFF KMNSLQAGDT AIYYCAKDGS RYYTAMDYWG QGTSVTVSS   119

SEQ ID NO: 54              moltype = AA  length = 112
FEATURE                    Location/Qualifiers
REGION                     1..112
```

-continued

```
                          note = Description of the artificial sequence : amino acid
                           sequence of KM5908 VL excluding signal sequence
source                    1..112
                          mol_type = protein
                          organism = synthetic construct
SEQUENCE: 54
DVVMTQTPRS LPVSLGDQAS ISCRSRQSLI HSNGITFLHW YLQKAGQSPK LLIYKVSNRF   60
SGVPDRFSGS GSGTDFTLRI SRVEAEDLGV YFCSQGTHVP PTFGGGTKLE IK           112

SEQ ID NO: 55            moltype = AA  length = 119
FEATURE                  Location/Qualifiers
REGION                   1..119
                         note = Description of the artificial sequence : amino acid
                          sequence of KM5909 VH excluding signal sequence
source                   1..119
                         mol_type = protein
                         organism = synthetic construct
SEQUENCE: 55
EVQLVESGGD LVKPGGSLKL SCAASGFTLS NYGMSWVRQT PDKRLEWVAS ISIGNYIYYL   60
DSVKGRFTIY RDNAKNTLFL QMRSLKSEDT AMYHCARQGN DYDWFTYWGQ GTLVTVSAA    119

SEQ ID NO: 56            moltype = AA  length = 112
FEATURE                  Location/Qualifiers
REGION                   1..112
                         note = Description of the artificial sequence : amino acid
                          sequence of KM5909 VL excluding signal sequence
source                   1..112
                         mol_type = protein
                         organism = synthetic construct
SEQUENCE: 56
DVLMTQTPLS LPVSLGDQAS ISCRSSQSVV HTNGNTYLEW YLQKPGQSPK LLIYKVSNRF   60
SGVPDRFSGS GSGTDFTLKI NRVEAEDLGV YYCFQGSHLP WTFGGGTKLE IK           112

SEQ ID NO: 57            moltype = AA  length = 121
FEATURE                  Location/Qualifiers
REGION                   1..121
                         note = Description of the artificial sequence : amino acid
                          sequence of KM5911 VH excluding signal sequence
source                   1..121
                         mol_type = protein
                         organism = synthetic construct
SEQUENCE: 57
DVKLVESGEG LVKPGGSLKL SCAASGFTFS RNAMSWVRQT PEKRMEWVAY ISSGGDYIYY   60
ADTVKGRFTV SRDNARNTLY LRMSSLKSED TAMYYCTRFS YGYAKNALDY WGQGTSVTVS   120
S                                                                    121

SEQ ID NO: 58            moltype = AA  length = 106
FEATURE                  Location/Qualifiers
REGION                   1..106
                         note = Description of the artificial sequence : amino acid
                          sequence of KM5911 VL excluding signal sequence
source                   1..106
                         mol_type = protein
                         organism = synthetic construct
SEQUENCE: 58
DIQMTQSPSS LSASLGGKVT ITCKASQDIK KYIAWYQHKP GKGPRLLIHY TSSLQPGIPS   60
RFSGSGSGRD YSFSISNLEP EDIATYYCLQ YDYLMTFGGG TKLEIK                  106

SEQ ID NO: 59            moltype = AA  length = 119
FEATURE                  Location/Qualifiers
REGION                   1..119
                         note = Description of the artificial sequence : amino acid
                          sequence of KM5915 VH excluding signal sequence
source                   1..119
                         mol_type = protein
                         organism = synthetic construct
SEQUENCE: 59
EVQLVESGGD LVKPGGSLKL SCAASGFTFS NYGMSWVRQT PDKRLEWVAS ISIGSYIYYL   60
DSVKGRFTIY RDNAKNTLFL QMRSLKSEDT AMYHCARQGN DYDWFAYWGQ GTLVTVSAA    119

SEQ ID NO: 60            moltype = AA  length = 112
FEATURE                  Location/Qualifiers
REGION                   1..112
                         note = Description of the artificial sequence : amino acid
                          sequence of KM5915 VL excluding signal sequence
source                   1..112
                         mol_type = protein
                         organism = synthetic construct
SEQUENCE: 60
```

-continued

```
DVLMTQTPLS LPVSLGDQAS ISCRSSQNIV HTNGNTYLEW YLQKPGQSPK LLIYKVSNRF   60
SGVPDRFSGS GSGTDFTLKI SRVEAEDLGV YYCFQGSHLP WTFGGGTKLE IK           112

SEQ ID NO: 61              moltype = AA  length = 121
FEATURE                    Location/Qualifiers
REGION                     1..121
                           note = Description of the artificial sequence : amino acid
                            sequence of KM5916 VH excluding signal sequence
source                     1..121
                           mol_type = protein
                           organism = synthetic construct
SEQUENCE: 61
DVKLVESGEG LVKPGGSLKL SCAASGFTFS RNAMSWVRQT PEKRLEWVAY ISSGSDYIYY   60
ADTVKGRFTV SRDNARNTLY LQMTSLRSED TAMYFCTRFS YGYGKNAPDY WGQGTSVTVS   120
S                                                                    121

SEQ ID NO: 62              moltype = AA  length = 106
FEATURE                    Location/Qualifiers
REGION                     1..106
                           note = Description of the artificial sequence : amino acid
                            sequence of KM5916 VL excluding signal sequence
source                     1..106
                           mol_type = protein
                           organism = synthetic construct
SEQUENCE: 62
DIQMTQSPSS LSASLGGKVT ITCKASQDIN KYIAWYQHKP GQGPRLLIHY TSSLQPGIPS   60
RFSGSGSGRD YSFSISNLEP EDIATYYCLQ YDYTMTFGGG TKLEIR                  106

SEQ ID NO: 63              moltype = AA  length = 124
FEATURE                    Location/Qualifiers
REGION                     1..124
                           note = Description of the artificial sequence : amino acid
                            sequence of KM5954 VH excluding signal sequence
source                     1..124
                           mol_type = protein
                           organism = synthetic construct
SEQUENCE: 63
QVQLKESGPG LVAPSQSLSI TCTVSGFSLP RYTITWVRQP PGKGLEWLGL IRTGGGTIYN   60
SALKSRLSIS KDNSKSQVFL KMNSLQSGDT ARYYCARNGA YYSKSGSYWY FDVWGTGTTV   120
TVSS                                                                 124

SEQ ID NO: 64              moltype = AA  length = 106
FEATURE                    Location/Qualifiers
REGION                     1..106
                           note = Description of the artificial sequence : amino acid
                            sequence of KM5954 VL excluding signal sequence
source                     1..106
                           mol_type = protein
                           organism = synthetic construct
SEQUENCE: 64
QIVLTQSPAI MSVSLGEEIT LTCSASSSVS YMHWYQQKSG TSPKLLIYST SNLASGVPSR   60
FSGSGSGTFY SLTISSVEAE DAADYYCHQW SSHPCTFGGG TKLEIK                  106

SEQ ID NO: 65              moltype = AA  length = 120
FEATURE                    Location/Qualifiers
REGION                     1..120
                           note = Description of the artificial sequence : amino acid
                            sequence of KM5955 VH excluding signal sequence
source                     1..120
                           mol_type = protein
                           organism = synthetic construct
SEQUENCE: 65
EVQLVESGGG LVKPGGSLKL SCAASGFTLR DFGMHWVRQV PEKGLEWVAY ISSGRTAISY   60
VDKVKGRFTI SRDNAKNTLF LQMTSLRSED TAMYYCARRP YSKSYAMDYW GQGTSVTVSS   120

SEQ ID NO: 66              moltype = AA  length = 112
FEATURE                    Location/Qualifiers
REGION                     1..112
                           note = Description of the artificial sequence : amino acid
                            sequence of KM5955 VL excluding signal sequence
source                     1..112
                           mol_type = protein
                           organism = synthetic construct
SEQUENCE: 66
DVVLTQTPLS LPVNIGDQAS ISCKSIKSLL NSDGFTYLDW YLQKPGQSPQ LLIYLVSNRF   60
SGVPDRFSGS GSGTDFTLKI RRVEAEDLGV YYCFQSNYLP LTFGAGTKLE LK           112

SEQ ID NO: 67              moltype = AA  length = 124
FEATURE                    Location/Qualifiers
```

-continued

```
REGION                    1..124
                          note = Description of the artificial sequence : amino acid
                           sequence of KM5956 VH excluding signal sequence
source                    1..124
                          mol_type = protein
                          organism = synthetic construct
SEQUENCE: 67
QVQLKESGPG LVAPSQSLSI TCTVSGFSLA RYTITWVRQP PGKGLEWLGL IRTGGGTIYN   60
SALKSRLSIS KDNSKSQVFL KMNSLQSGDT ARYYCARNGA YYSNSGSYWY FDVWGTGTTV  120
TVSS                                                                124

SEQ ID NO: 68             moltype = AA  length = 106
FEATURE                   Location/Qualifiers
REGION                    1..106
                          note = Description of the artificial sequence : amino acid
                           sequence of KM5956 VL excluding signal sequence
source                    1..106
                          mol_type = protein
                          organism = synthetic construct
SEQUENCE: 68
QIVLTQSPAI MSASLGEEIT LTCSASSSVT YMHWYQQKSG TSPKLLIYST SNLASGVPSR   60
FSGSGSGTFY SLTISSVEAE DAADYYCHQW SSHPCTFGGG AKLEIK                  106

SEQ ID NO: 69             moltype = AA  length = 5
FEATURE                   Location/Qualifiers
REGION                    1..5
                          note = Description of the artificial sequence : amino acid
                           sequence of KM5907 VH CDR1
source                    1..5
                          mol_type = protein
                          organism = synthetic construct
SEQUENCE: 69
RYGMS                                                                 5

SEQ ID NO: 70             moltype = AA  length = 17
FEATURE                   Location/Qualifiers
REGION                    1..17
                          note = Description of the artificial sequence : amino acid
                           sequence of KM5907 VH CDR2
source                    1..17
                          mol_type = protein
                          organism = synthetic construct
SEQUENCE: 70
SISATFTYTY YTDNVKG                                                   17

SEQ ID NO: 71             moltype = AA  length = 9
FEATURE                   Location/Qualifiers
REGION                    1..9
                          note = Description of the artificial sequence : amino acid
                           sequence of KM5907 VH CDR3
source                    1..9
                          mol_type = protein
                          organism = synthetic construct
SEQUENCE: 71
QDNYAWFDS                                                             9

SEQ ID NO: 72             moltype = AA  length = 16
FEATURE                   Location/Qualifiers
REGION                    1..16
                          note = Description of the artificial sequence : amino acid
                           sequence of KM5907 VL CDR1
source                    1..16
                          mol_type = protein
                          organism = synthetic construct
SEQUENCE: 72
RSSQSIVHSN GNTFLE                                                    16

SEQ ID NO: 73             moltype = AA  length = 7
FEATURE                   Location/Qualifiers
REGION                    1..7
                          note = Description of the artificial sequence : amino acid
                           sequence of KM5907 VL CDR2
source                    1..7
                          mol_type = protein
                          organism = synthetic construct
SEQUENCE: 73
KVSSRFS                                                               7

SEQ ID NO: 74             moltype = AA  length = 9
```

```
FEATURE           Location/Qualifiers
REGION            1..9
                  note = Description of the artificial sequence : amino acid
                   sequence of KM5907 VL CDR3
source            1..9
                  mol_type = protein
                  organism = synthetic construct
SEQUENCE: 74
FQGSHIPWT                                                                 9

SEQ ID NO: 75     moltype = AA   length = 5
FEATURE           Location/Qualifiers
REGION            1..5
                  note = Description of the artificial sequence : amino acid
                   sequence of KM5908 VH CDR1
source            1..5
                  mol_type = protein
                  organism = synthetic construct
SEQUENCE: 75
NYGVH                                                                     5

SEQ ID NO: 76     moltype = AA   length = 16
FEATURE           Location/Qualifiers
REGION            1..16
                  note = Description of the artificial sequence : amino acid
                   sequence of KM5908 VH CDR2
source            1..16
                  mol_type = protein
                  organism = synthetic construct
SEQUENCE: 76
VIWSAGTTVY NAAFIS                                                         16

SEQ ID NO: 77     moltype = AA   length = 11
FEATURE           Location/Qualifiers
REGION            1..11
                  note = Description of the artificial sequence : amino acid
                   sequence of KM5908 VH CDR3
source            1..11
                  mol_type = protein
                  organism = synthetic construct
SEQUENCE: 77
DGSRYYTAMD Y                                                              11

SEQ ID NO: 78     moltype = AA   length = 16
FEATURE           Location/Qualifiers
REGION            1..16
                  note = Description of the artificial sequence : amino acid
                   sequence of KM5908 VL CDR1
source            1..16
                  mol_type = protein
                  organism = synthetic construct
SEQUENCE: 78
RSRQSLIHSN GITFLH                                                         16

SEQ ID NO: 79     moltype = AA   length = 7
FEATURE           Location/Qualifiers
REGION            1..7
                  note = Description of the artificial sequence : amino acid
                   sequence of KM5908 VL CDR2
source            1..7
                  mol_type = protein
                  organism = synthetic construct
SEQUENCE: 79
KVSNRFS                                                                   7

SEQ ID NO: 80     moltype = AA   length = 9
FEATURE           Location/Qualifiers
REGION            1..9
                  note = Description of the artificial sequence : amino acid
                   sequence of KM5908 VL CDR3
source            1..9
                  mol_type = protein
                  organism = synthetic construct
SEQUENCE: 80
SQGTHVPPT                                                                 9

SEQ ID NO: 81     moltype = AA   length = 5
FEATURE           Location/Qualifiers
REGION            1..5
```

```
                              note = Description of the artificial sequence : amino acid
                                sequence of KM5909 VH CDR1
source                        1..5
                              mol_type = protein
                              organism = synthetic construct
SEQUENCE: 81
NYGMS                                                                              5

SEQ ID NO: 82                 moltype = AA   length = 16
FEATURE                       Location/Qualifiers
REGION                        1..16
                              note = Description of the artificial sequence : amino acid
                                sequence of KM5909 VH CDR2
source                        1..16
                              mol_type = protein
                              organism = synthetic construct
SEQUENCE: 82
SISIGNYIYY LDSVKG                                                                  16

SEQ ID NO: 83                 moltype = AA   length = 10
FEATURE                       Location/Qualifiers
REGION                        1..10
                              note = Description of the artificial sequence : amino acid
                                sequence of KM5909 VH CDR3
source                        1..10
                              mol_type = protein
                              organism = synthetic construct
SEQUENCE: 83
QGNDYDWFTY                                                                         10

SEQ ID NO: 84                 moltype = AA   length = 16
FEATURE                       Location/Qualifiers
REGION                        1..16
                              note = Description of the artificial sequence : amino acid
                                sequence of KM5909 VL CDR1
source                        1..16
                              mol_type = protein
                              organism = synthetic construct
SEQUENCE: 84
RSSQSVVHTN GNTYLE                                                                  16

SEQ ID NO: 85                 moltype = AA   length = 7
FEATURE                       Location/Qualifiers
REGION                        1..7
                              note = Description of the artificial sequence : amino acid
                                sequence of KM5909 VL CDR2
source                        1..7
                              mol_type = protein
                              organism = synthetic construct
SEQUENCE: 85
KVSNRFS                                                                            7

SEQ ID NO: 86                 moltype = AA   length = 9
FEATURE                       Location/Qualifiers
REGION                        1..9
                              note = Description of the artificial sequence : amino acid
                                sequence of KM5909 VL CDR3
source                        1..9
                              mol_type = protein
                              organism = synthetic construct
SEQUENCE: 86
FQGSHLPWT                                                                          9

SEQ ID NO: 87                 moltype = AA   length = 5
FEATURE                       Location/Qualifiers
REGION                        1..5
                              note = Description of the artificial sequence : amino acid
                                sequence of KM5911 VH CDR1
source                        1..5
                              mol_type = protein
                              organism = synthetic construct
SEQUENCE: 87
RNAMS                                                                              5

SEQ ID NO: 88                 moltype = AA   length = 17
FEATURE                       Location/Qualifiers
REGION                        1..17
                              note = Description of the artificial sequence : amino acid
                                sequence of KM5911 VH CDR2
```

-continued

```
source                  1..17
                        mol_type = protein
                        organism = synthetic construct
SEQUENCE: 88
YISSGGDYIY YADTVKG                                               17

SEQ ID NO: 89           moltype = AA   length = 12
FEATURE                 Location/Qualifiers
REGION                  1..12
                        note = Description of the artificial sequence : amino acid
                         sequence of KM5911 VH CDR3
source                  1..12
                        mol_type = protein
                        organism = synthetic construct
SEQUENCE: 89
FSYGYAKNAL DY                                                    12

SEQ ID NO: 90           moltype = AA   length = 5
FEATURE                 Location/Qualifiers
REGION                  1..5
                        note = Description of the artificial sequence : amino acid
                         sequence of KM5911 VL CDR1
source                  1..5
                        mol_type = protein
                        organism = synthetic construct
SEQUENCE: 90
KASQD                                                            5

SEQ ID NO: 91           moltype = AA   length = 6
FEATURE                 Location/Qualifiers
REGION                  1..6
                        note = Description of the artificial sequence : amino acid
                         sequence of KM5911 VL CDR2
source                  1..6
                        mol_type = protein
                        organism = synthetic construct
SEQUENCE: 91
YTSSLQ                                                           6

SEQ ID NO: 92           moltype = AA   length = 8
FEATURE                 Location/Qualifiers
REGION                  1..8
                        note = Description of the artificial sequence : amino acid
                         sequence of KM5911 VL CDR3
source                  1..8
                        mol_type = protein
                        organism = synthetic construct
SEQUENCE: 92
LQYDYLMT                                                         8

SEQ ID NO: 93           moltype = AA   length = 5
FEATURE                 Location/Qualifiers
REGION                  1..5
                        note = Description of the artificial sequence : amino acid
                         sequence of KM5915 VH CDR1
source                  1..5
                        mol_type = protein
                        organism = synthetic construct
SEQUENCE: 93
NYGMS                                                            5

SEQ ID NO: 94           moltype = AA   length = 16
FEATURE                 Location/Qualifiers
REGION                  1..16
                        note = Description of the artificial sequence : amino acid
                         sequence of KM5915 VH CDR2
source                  1..16
                        mol_type = protein
                        organism = synthetic construct
SEQUENCE: 94
SISIGSYIYY LDSVKG                                                16

SEQ ID NO: 95           moltype = AA   length = 10
FEATURE                 Location/Qualifiers
REGION                  1..10
                        note = Description of the artificial sequence : amino acid
                         sequence of KM5915 VH CDR3
source                  1..10
                        mol_type = protein
```

```
                          organism = synthetic construct
SEQUENCE: 95
QGNDYDWFAY                                                            10

SEQ ID NO: 96             moltype = AA   length = 16
FEATURE                   Location/Qualifiers
REGION                    1..16
                          note = Description of the artificial sequence : amino acid
                           sequence of KM5915 VL CDR1
source                    1..16
                          mol_type = protein
                          organism = synthetic construct
SEQUENCE: 96
RSSQNIVHTN GNTYLE                                                     16

SEQ ID NO: 97             moltype = AA   length = 7
FEATURE                   Location/Qualifiers
REGION                    1..7
                          note = Description of the artificial sequence : amino acid
                           sequence of KM5915 VL CDR2
source                    1..7
                          mol_type = protein
                          organism = synthetic construct
SEQUENCE: 97
KVSNRFS                                                               7

SEQ ID NO: 98             moltype = AA   length = 9
FEATURE                   Location/Qualifiers
REGION                    1..9
                          note = Description of the artificial sequence : amino acid
                           sequence of KM5915 VL CDR3
source                    1..9
                          mol_type = protein
                          organism = synthetic construct
SEQUENCE: 98
FQGSHLPWT                                                             9

SEQ ID NO: 99             moltype = AA   length = 5
FEATURE                   Location/Qualifiers
REGION                    1..5
                          note = Description of the artificial sequence : amino acid
                           sequence of KM5916 VH CDR1
source                    1..5
                          mol_type = protein
                          organism = synthetic construct
SEQUENCE: 99
RNAMS                                                                 5

SEQ ID NO: 100            moltype = AA   length = 17
FEATURE                   Location/Qualifiers
REGION                    1..17
                          note = Description of the artificial sequence : amino acid
                           sequence of KM5916 VH CDR2
source                    1..17
                          mol_type = protein
                          organism = synthetic construct
SEQUENCE: 100
YISSGSDYIY YADTVKG                                                    17

SEQ ID NO: 101            moltype = AA   length = 12
FEATURE                   Location/Qualifiers
REGION                    1..12
                          note = Description of the artificial sequence : amino acid
                           sequence of KM5916 VH CDR3
source                    1..12
                          mol_type = protein
                          organism = synthetic construct
SEQUENCE: 101
FSYGYGKNAP DY                                                         12

SEQ ID NO: 102            moltype = AA   length = 11
FEATURE                   Location/Qualifiers
REGION                    1..11
                          note = Description of the artificial sequence : amino acid
                           sequence of KM5916 VL CDR1
source                    1..11
                          mol_type = protein
                          organism = synthetic construct
SEQUENCE: 102
```

-continued

```
KASQDINKYI A                                                          11

SEQ ID NO: 103          moltype = AA  length = 7
FEATURE                 Location/Qualifiers
REGION                  1..7
                        note = Description of the artificial sequence : amino acid
                          sequence of KM5916 VL CDR2
source                  1..7
                        mol_type = protein
                        organism = synthetic construct
SEQUENCE: 103
YTSSLQP                                                               7

SEQ ID NO: 104          moltype = AA  length = 8
FEATURE                 Location/Qualifiers
REGION                  1..8
                        note = Description of the artificial sequence : amino acid
                          sequence of KM5916 VL CDR3
source                  1..8
                        mol_type = protein
                        organism = synthetic construct
SEQUENCE: 104
LQYDYTMT                                                              8

SEQ ID NO: 105          moltype = AA  length = 5
FEATURE                 Location/Qualifiers
REGION                  1..5
                        note = Description of the artificial sequence : amino acid
                          sequence of KM5954 VH CDR1
source                  1..5
                        mol_type = protein
                        organism = synthetic construct
SEQUENCE: 105
RYTIT                                                                 5

SEQ ID NO: 106          moltype = AA  length = 16
FEATURE                 Location/Qualifiers
REGION                  1..16
                        note = Description of the artificial sequence : amino acid
                          sequence of KM5954 VH CDR2
source                  1..16
                        mol_type = protein
                        organism = synthetic construct
SEQUENCE: 106
LIRTGGGTIY NSALKS                                                     16

SEQ ID NO: 107          moltype = AA  length = 16
FEATURE                 Location/Qualifiers
REGION                  1..16
                        note = Description of the artificial sequence : amino acid
                          sequence of KM5954 VH CDR3
source                  1..16
                        mol_type = protein
                        organism = synthetic construct
SEQUENCE: 107
NGAYYSKSGS YWYFDV                                                     16

SEQ ID NO: 108          moltype = AA  length = 10
FEATURE                 Location/Qualifiers
REGION                  1..10
                        note = Description of the artificial sequence : amino acid
                          sequence of KM5954 VL CDR1
source                  1..10
                        mol_type = protein
                        organism = synthetic construct
SEQUENCE: 108
SASSSVSYMH                                                            10

SEQ ID NO: 109          moltype = AA  length = 7
FEATURE                 Location/Qualifiers
REGION                  1..7
                        note = Description of the artificial sequence : amino acid
                          sequence of KM5954 VL CDR2
source                  1..7
                        mol_type = protein
                        organism = synthetic construct
SEQUENCE: 109
STSNLAS                                                               7
```

-continued

```
SEQ ID NO: 110         moltype = AA   length = 9
FEATURE                Location/Qualifiers
REGION                 1..9
                       note = Description of the artificial sequence : amino acid
                        sequence of KM5954 VL CDR3
source                 1..9
                       mol_type = protein
                       organism = synthetic construct
SEQUENCE: 110
HQWSSHPCT                                                                    9

SEQ ID NO: 111         moltype = AA   length = 5
FEATURE                Location/Qualifiers
REGION                 1..5
                       note = Description of the artificial sequence : amino acid
                        sequence of KM5955 VH CDR1
source                 1..5
                       mol_type = protein
                       organism = synthetic construct
SEQUENCE: 111
DFGMH                                                                        5

SEQ ID NO: 112         moltype = AA   length = 17
FEATURE                Location/Qualifiers
REGION                 1..17
                       note = Description of the artificial sequence : amino acid
                        sequence of KM5955 VH CDR2
source                 1..17
                       mol_type = protein
                       organism = synthetic construct
SEQUENCE: 112
YISSGRTAIS YVDKVKG                                                           17

SEQ ID NO: 113         moltype = AA   length = 11
FEATURE                Location/Qualifiers
REGION                 1..11
                       note = Description of the artificial sequence : amino acid
                        sequence of KM5955 VH CDR3
source                 1..11
                       mol_type = protein
                       organism = synthetic construct
SEQUENCE: 113
RPYSKSYAMD Y                                                                 11

SEQ ID NO: 114         moltype = AA   length = 16
FEATURE                Location/Qualifiers
REGION                 1..16
                       note = Description of the artificial sequence : amino acid
                        sequence of KM5955 VL CDR1
source                 1..16
                       mol_type = protein
                       organism = synthetic construct
SEQUENCE: 114
KSIKSLLNSD GFTYLD                                                            16

SEQ ID NO: 115         moltype = AA   length = 7
FEATURE                Location/Qualifiers
REGION                 1..7
                       note = Description of the artificial sequence : amino acid
                        sequence of KM5955 VL CDR2
source                 1..7
                       mol_type = protein
                       organism = synthetic construct
SEQUENCE: 115
LVSNRFS                                                                      7

SEQ ID NO: 116         moltype = AA   length = 9
FEATURE                Location/Qualifiers
REGION                 1..9
                       note = Description of the artificial sequence : amino acid
                        sequence of KM5955 VL CDR3
source                 1..9
                       mol_type = protein
                       organism = synthetic construct
SEQUENCE: 116
FQSNYLPLT                                                                    9

SEQ ID NO: 117         moltype = AA   length = 5
FEATURE                Location/Qualifiers
```

```
REGION                    1..5
                          note = Description of the artificial sequence : amino acid
                           sequence of KM5956 VH CDR1
source                    1..5
                          mol_type = protein
                          organism = synthetic construct
SEQUENCE: 117
RYTIT                                                                      5

SEQ ID NO: 118            moltype = AA  length = 16
FEATURE                   Location/Qualifiers
REGION                    1..16
                          note = Description of the artificial sequence : amino acid
                           sequence of KM5956 VH CDR2
source                    1..16
                          mol_type = protein
                          organism = synthetic construct
SEQUENCE: 118
LIRTGGGTIY NSALKS                                                          16

SEQ ID NO: 119            moltype = AA  length = 16
FEATURE                   Location/Qualifiers
REGION                    1..16
                          note = Description of the artificial sequence : amino acid
                           sequence of KM5956 VH CDR3
source                    1..16
                          mol_type = protein
                          organism = synthetic construct
SEQUENCE: 119
NGAYYSNSGS YWYFDV                                                          16

SEQ ID NO: 120            moltype = AA  length = 10
FEATURE                   Location/Qualifiers
REGION                    1..10
                          note = Description of the artificial sequence : amino acid
                           sequence of KM5956 VL CDR1
source                    1..10
                          mol_type = protein
                          organism = synthetic construct
SEQUENCE: 120
SASSSVTYMH                                                                 10

SEQ ID NO: 121            moltype = AA  length = 7
FEATURE                   Location/Qualifiers
REGION                    1..7
                          note = Description of the artificial sequence : amino acid
                           sequence of KM5956 VL CDR2
source                    1..7
                          mol_type = protein
                          organism = synthetic construct
SEQUENCE: 121
STSNLAS                                                                    7

SEQ ID NO: 122            moltype = AA  length = 9
FEATURE                   Location/Qualifiers
REGION                    1..9
                          note = Description of the artificial sequence : amino acid
                           sequence of KM5956 VL CDR3
source                    1..9
                          mol_type = protein
                          organism = synthetic construct
SEQUENCE: 122
HQWSSHPCT                                                                  9

SEQ ID NO: 123            moltype = DNA  length = 393
FEATURE                   Location/Qualifiers
source                    1..393
                          mol_type = genomic DNA
                          organism = Mus musculus
SEQUENCE: 123
atgaagttgc gtgttaggct gttggtgctg atgttctgga ttcctgcttc caccggtgat   60
gttgtgatga cccaaactcc actctccctg cctgtcagtc ttggagatca agcctccatc  120
tttttgcagat ctagtcagag ccttgtacac aggaatggaa tcacctttt tcattggtac  180
ctgcagaagc caggccagtc tccaaaactc ctgatctaca aagtctccaa ccgattttct  240
ggggtcccag acaggttcag tggcagtgga tcaggacag atttcacact caagatcagc  300
agggtggcgc ctgacgatct gggagtttat ttctgctctc aaggaacaca tgttcctccc  360
actttcggtg gaggcaccaa gctggaaatc aaa                                393

SEQ ID NO: 124            moltype = AA  length = 131
```

-continued

```
FEATURE                 Location/Qualifiers
source                  1..131
                        mol_type = protein
                        organism = Mus musculus
SEQUENCE: 124
MKLRVRLLVL MFWIPASTGD VVMTQTPLSL PVSLGDQASI FCRSSQSLVH RNGITFFHWY  60
LQKPGQSPKL LIYKVSNRFS GVPDRFSGSG SGTDFTLKIS RVAPDDLGVY FCSQGTHVPP  120
TFGGGTKLEI K                                                        131

SEQ ID NO: 125          moltype = AA  length = 112
FEATURE                 Location/Qualifiers
REGION                  1..112
                        note = description of the artificial sequence: amino acid
                         sequence of KM5914 VL excluding signal sequence
source                  1..112
                        mol_type = protein
                        organism = synthetic construct
SEQUENCE: 125
DVVMTQTPLS LPVSLGDQAS IFCRSSQSLV HRNGITFFHW YLQKPGQSPK LLIYKVSNRF  60
SGVPDRFSGS GSGTDFTLKI SRVAPDDLGV YFCSQGTHVP PTFGGGTKLE IK          112

SEQ ID NO: 126          moltype = AA  length = 16
FEATURE                 Location/Qualifiers
REGION                  1..16
                        note = description of the artificial sequence: amino acid
                         sequence of KM5914 VL CDR1
source                  1..16
                        mol_type = protein
                        organism = synthetic construct
SEQUENCE: 126
RSSQSLVHRN GITFFH                                                   16

SEQ ID NO: 127          moltype = AA  length = 7
FEATURE                 Location/Qualifiers
REGION                  1..7
                        note = description of the artificial sequence: amino acid
                         sequence of KM5914 VL CDR2
source                  1..7
                        mol_type = protein
                        organism = synthetic construct
SEQUENCE: 127
KVSNRFS                                                             7

SEQ ID NO: 128          moltype = AA  length = 9
FEATURE                 Location/Qualifiers
REGION                  1..9
                        note = description of the artificial sequence: amino acid
                         sequence of KM5914 VL CDR3
source                  1..9
                        mol_type = protein
                        organism = synthetic construct
SEQUENCE: 128
SQGTHVPPT                                                           9

SEQ ID NO: 129          moltype = DNA  length = 357
FEATURE                 Location/Qualifiers
misc_feature            1..357
                        note = description of the artificial sequence: nucleotide
                         sequence of mAb5-06 VH
source                  1..357
                        mol_type = other DNA
                        organism = synthetic construct
SEQUENCE: 129
caggtgcagc tgaagcagtc aggacctggc ctagtgcagc cctcacagag tctgtccatc  60
acctgcacag tctctggttt ctcattaaat aactatggtg tacactgggt tcgccagcct  120
ccaggaaagg gtctggagtg gctgggagtg atatggagtg ctggaaccac agtctataat  180
gctgctgcca tatccagact gagcatcagc aaggacgact ccaagagcca agttttcttt  240
aaaatgaaca gtctgcaagc tggtgacact gccatatact actgtgccaa agacggtagt  300
agatattata ctgctatgga ctactggggt caaggaacct cagtcaccgt ctcctca     357

SEQ ID NO: 130          moltype = AA  length = 119
FEATURE                 Location/Qualifiers
REGION                  1..119
                        note = description of the artificial sequence: amino acid
                         sequence of mAb5-06 VH
source                  1..119
                        mol_type = protein
                        organism = synthetic construct
SEQUENCE: 130
```

```
QVQLKQSGPG LVQPSQSLSI TCTVSGFSLN NYGVHWVRQP PGKGLEWLGV IWSAGTTVYN  60
AAAISRLSIS KDDSKSQVFF KMNSLQAGDT AIYYCAKDGS RYYTAMDYWG QGTSVTVSS   119

SEQ ID NO: 131          moltype = AA  length = 16
FEATURE                 Location/Qualifiers
REGION                  1..16
                        note = description of the artificial sequence: amino acid
                         sequence of mAb5-06 VH CDR2
source                  1..16
                        mol_type = protein
                        organism = synthetic construct
SEQUENCE: 131
VIWSAGTTVY NAAAIS                                                       16

SEQ ID NO: 132          moltype = DNA  length = 336
FEATURE                 Location/Qualifiers
misc_feature            1..336
                        note = description of the artificial sequence: nucleotide
                         sequence of mAb5-06 VL
source                  1..336
                        mol_type = other DNA
                        organism = synthetic construct
SEQUENCE: 132
gatgttgtga tgacccaaac tccactctcc ctgcctgtca gtcttggaga tcaagcctcc  60
atctttgca gatctagtca gagccttgta cacaggaatg gaatcacctt ttttcattgg   120
tacctgcaga agccaggcca gtctccaaaa ctcctgatct acaaaatctc caaccgattt   180
tctggggtcc cagacaggtt cagtggcagt ggatcaggga cagatttcac actcaagatc   240
agcagggtgg cgcctgacga tctgggagtt tatttctgct ctcaaggaac acatgttcct   300
cccacttcg gtggaggcac caagctggaa atcaaa                              336

SEQ ID NO: 133          moltype = AA  length = 112
FEATURE                 Location/Qualifiers
REGION                  1..112
                        note = description of the artificial sequence: amino acid
                         sequence of mAb5-06 VL
source                  1..112
                        mol_type = protein
                        organism = synthetic construct
SEQUENCE: 133
DVVMTQTPLS LPVSLGDQAS IFCRSSQSLV HRNGITFFHW YLQKPGQSPK LLIYKISNRF  60
SGVPDRFSGS GSGTDFTLKI SRVAPDDLGV YFCSQGTHVP PTFGGGTKLE IK           112

SEQ ID NO: 134          moltype = AA  length = 7
FEATURE                 Location/Qualifiers
REGION                  1..7
                        note = description of the artificial sequence: amino acid
                         sequence of mAb5-06 VL CDR2
source                  1..7
                        mol_type = protein
                        organism = synthetic construct
SEQUENCE: 134
KISNRFS                                                                 7

SEQ ID NO: 135          moltype = AA  length = 112
FEATURE                 Location/Qualifiers
REGION                  1..112
                        note = description of the artificial sequence: amino acid
                         sequence of hzmAb5-06 LV0
source                  1..112
                        mol_type = protein
                        organism = synthetic construct
SEQUENCE: 135
DIVMTQSPLS LPVTPGEPAS ISCRSSQSLV HRNGITFFHW YLQKPGQSPQ LLIYKISNRF  60
SGVPDRFSGS GSGTDFTLKI SRVEAEDVGV YYCSQGTHVP PTFGQGTKVE IK           112

SEQ ID NO: 136          moltype = AA  length = 119
FEATURE                 Location/Qualifiers
REGION                  1..119
                        note = description of the artificial sequence: amino acid
                         sequence of hzmAb5-06 HV0
source                  1..119
                        mol_type = protein
                        organism = synthetic construct
SEQUENCE: 136
QVQLQESGPG LVKPSQTLSL TCTVSGGSVS NYGVHWIRQP PGKGLEWIGV IWSAGTTVYN  60
AAAISRVTIS VDTSKNQFSL KLSSVTAADT AVYYCARDGS RYYTAMDYWG QGTLVTVSS   119

SEQ ID NO: 137          moltype = AA  length = 112
FEATURE                 Location/Qualifiers
```

-continued

```
REGION                    1..112
                          note = description of the artificial sequence: amino acid
                           sequence of hzmAb5-06 LV1a
source                    1..112
                          mol_type = protein
                          organism = synthetic construct
SEQUENCE: 137
DIVMTQSPLS LPVTPGEPAS ISCRSSQSLV HRNGITFFHW YLQKPGQSPK LLIYKISNRF   60
SGVPDRFSGS GSGTDFTLKI SRVEAEDVGV YYCSQGTHVP PTFGQGTKVE IK          112

SEQ ID NO: 138            moltype = AA  length = 112
FEATURE                   Location/Qualifiers
REGION                    1..112
                          note = description of the artificial sequence: amino acid
                           sequence of hzmAb5-06 LV1b
source                    1..112
                          mol_type = protein
                          organism = synthetic construct
SEQUENCE: 138
DIVMTQSPLS LPVTLGEPAS ISCRSSQSLV HRNGITFFHW YLQKPGQSPQ LLIYKISNRF   60
SGVPDRFSGS GSGTDFTLKI SRVEAEDVGV YYCSQGTHVP PTFGQGTKVE IK          112

SEQ ID NO: 139            moltype = AA  length = 112
FEATURE                   Location/Qualifiers
REGION                    1..112
                          note = description of the artificial sequence: amino acid
                           sequence of hzmAb5-06 LV2a
source                    1..112
                          mol_type = protein
                          organism = synthetic construct
SEQUENCE: 139
DIVMTQSPLS LPVTLGEPAS ISCRSSQSLV HRNGITFFHW YLQKPGQSPK LLIYKISNRF   60
SGVPDRFSGS GSGTDFTLKI SRVEAEDVGV YYCSQGTHVP PTFGQGTKVE IK          112

SEQ ID NO: 140            moltype = AA  length = 112
FEATURE                   Location/Qualifiers
REGION                    1..112
                          note = description of the artificial sequence: amino acid
                           sequence of hzmAb5-06 LV2b
source                    1..112
                          mol_type = protein
                          organism = synthetic construct
SEQUENCE: 140
DIVMTQSPLS LPVTPGEPAS ISCRSSQSLV HRNGITFFHW YLQKPGQSPK LLIYKISNRF   60
SGVPDRFSGS GSGTDFTLKI SRVEAEDVGV YFCSQGTHVP PTFGQGTKVE IK          112

SEQ ID NO: 141            moltype = AA  length = 112
FEATURE                   Location/Qualifiers
REGION                    1..112
                          note = description of the artificial sequence: amino acid
                           sequence of hzmAb5-06 LV4
source                    1..112
                          mol_type = protein
                          organism = synthetic construct
SEQUENCE: 141
DIVMTQSPLS LPVTLGEPAS ISCRSSQSLV HRNGITFFHW YLQKPGQSPK LLIYKISNRF   60
SGVPDRFSGS GSGTDFTLKI SRVEAEDVGV YFCSQGTHVP PTFGQGTKLE IK          112

SEQ ID NO: 142            moltype = AA  length = 112
FEATURE                   Location/Qualifiers
REGION                    1..112
                          note = description of the artificial sequence: amino acid
                           sequence of hzmAb5-06 LV5
source                    1..112
                          mol_type = protein
                          organism = synthetic construct
SEQUENCE: 142
DVVMTQSPLS LPVTLGEPAS ISCRSSQSLV HRNGITFFHW YLQKPGQSPK LLIYKISNRF   60
SGVPDRFSGS GSGTDFTLKI SRVEAEDVGV YFCSQGTHVP PTFGQGTKLE IK          112

SEQ ID NO: 143            moltype = AA  length = 119
FEATURE                   Location/Qualifiers
REGION                    1..119
                          note = description of the artificial sequence: amino acid
                           sequence of hzmAb5-06 HV14
source                    1..119
                          mol_type = protein
                          organism = synthetic construct
SEQUENCE: 143
```

```
QVQLQQSGPG LVKPSQTLSI TCTVSGFSLN NYGVHWVRQP PGKGLEWLGV IWSAGTTVYN   60
AAAISRLTIS KDTSKNQVSF KMSSLTAADT AVYYCAKDGS RYYTAMDYWG QGTLVTVSS   119

SEQ ID NO: 144          moltype = AA  length = 119
FEATURE                 Location/Qualifiers
REGION                  1..119
                        note = description of the artificial sequence: amino acid
                         sequence of hzmAb5-06 HV17
source                  1..119
                        mol_type = protein
                        organism = synthetic construct
SEQUENCE: 144
QVQLQQSGPG LVKPSQTLSI TCTVSGFSLN NYGVHWVRQP PGKGLEWLGV IWSAGTTVYN   60
AAAISRLTIS KDDSKSQVSF KMSSLTAADT AIYYCAKDGS RYYTAMDYWG QGTLVTVSS   119

SEQ ID NO: 145          moltype = AA  length = 112
FEATURE                 Location/Qualifiers
REGION                  1..112
                        note = description of the artificial sequence: amino acid
                         sequence of hzKM5907 LV0
source                  1..112
                        mol_type = protein
                        organism = synthetic construct
SEQUENCE: 145
DIVMTQTPLS LPVTSGEPAS ISCRSSQSIV HSNGNTFLEW YLQKPGQSPQ LLIYKVSSRF   60
SGVPDRFSGS GSGTDFTLKI SRVEAEDVGV YYCFQGSHIP WTFGGGTKVE IK        112

SEQ ID NO: 146          moltype = AA  length = 118
FEATURE                 Location/Qualifiers
REGION                  1..118
                        note = description of the artificial sequence: amino acid
                         sequence of hzKM5907 HV0
source                  1..118
                        mol_type = protein
                        organism = synthetic construct
SEQUENCE: 146
EVQLLESGGG LVQPGGSLRL SCAASGFTFS RYGMSWVRQA PGKGLEWVSS ISATFTYTYY   60
TDNVKGRFTI SRDNSKNTLY LQMNSLRAED TAVYYCAKQD NYAWFDSWGQ GTLVTVSS   118

SEQ ID NO: 147          moltype = AA  length = 112
FEATURE                 Location/Qualifiers
REGION                  1..112
                        note = description of the artificial sequence: amino acid
                         sequence of hzKM5907 LV1a
source                  1..112
                        mol_type = protein
                        organism = synthetic construct
SEQUENCE: 147
DIVMTQTPLS LPVTSGEPAS ISCRSSQSIV HSNGNTFLEW YLKKPGQSPQ LLIYKVSSRF   60
SGVPDRFSGS GSGTDFTLKI SRVEAEDVGV YYCFQGSHIP WTFGGGTKVE IK        112

SEQ ID NO: 148          moltype = AA  length = 112
FEATURE                 Location/Qualifiers
REGION                  1..112
                        note = description of the artificial sequence: amino acid
                         sequence of hzKM5907 LV1b
source                  1..112
                        mol_type = protein
                        organism = synthetic construct
SEQUENCE: 148
DIVMTQTPLS LPVTSGEPAS ISCRSSQSIV HSNGNTFLEW YLQKPGQSPK LLIYKVSSRF   60
SGVPDRFSGS GSGTDFTLKI SRVEAEDVGV YYCFQGSHIP WTFGGGTKVE IK        112

SEQ ID NO: 149          moltype = AA  length = 112
FEATURE                 Location/Qualifiers
REGION                  1..112
                        note = description of the artificial sequence: amino acid
                         sequence of hzKM5907 LV1c
source                  1..112
                        mol_type = protein
                        organism = synthetic construct
SEQUENCE: 149
DIVMTQTPLS LPVTSGEPVS ISCRSSQSIV HSNGNTFLEW YLQKPGQSPQ LLIYKVSSRF   60
SGVPDRFSGS GSGTDFTLKI SRVEAEDVGV YYCFQGSHIP WTFGGGTKVE IK        112

SEQ ID NO: 150          moltype = AA  length = 112
FEATURE                 Location/Qualifiers
REGION                  1..112
                        note = description of the artificial sequence: amino acid
```

-continued

```
                              sequence of hzKM5907 LV2a
source                        1..112
                              mol_type = protein
                              organism = synthetic construct
SEQUENCE: 150
DIVMTQTPLS LPVTSGEPAS ISCRSSQSIV HSNGNTFLEW YLKKPGQSPK LLIYKVSSRF   60
SGVPDRFSGS GSGTDFTLKI SRVEAEDVGV YYCFQGSHIP WTFGGGTKVE IK          112

SEQ ID NO: 151                moltype = AA  length = 112
FEATURE                       Location/Qualifiers
REGION                        1..112
                              note = description of the artificial sequence: amino acid
                                sequence of hzKM5907 LV2b
source                        1..112
                              mol_type = protein
                              organism = synthetic construct
SEQUENCE: 151
DIVMTQTPLS LPVTSGEPVS ISCRSSQSIV HSNGNTFLEW YLKKPGQSPQ LLIYKVSSRF   60
SGVPDRFSGS GSGTDFTLKI SRVEAEDVGV YYCFQGSHIP WTFGGGTKVE IK          112

SEQ ID NO: 152                moltype = AA  length = 112
FEATURE                       Location/Qualifiers
REGION                        1..112
                              note = description of the artificial sequence: amino acid
                                sequence of hzKM5907 LV4
source                        1..112
                              mol_type = protein
                              organism = synthetic construct
SEQUENCE: 152
DIVMTQTPLS LPVTLGEPVS ISCRSSQSIV HSNGNTFLEW YLKKPGQSPK LLIYKVSSRF   60
SGVPDRFSGS GSGTDFTLKI SRVEAEDVGV YYCFQGSHIP WTFGGGTKVE IK          112

SEQ ID NO: 153                moltype = AA  length = 112
FEATURE                       Location/Qualifiers
REGION                        1..112
                              note = description of the artificial sequence: amino acid
                                sequence of hzKM5907 LV6
source                        1..112
                              mol_type = protein
                              organism = synthetic construct
SEQUENCE: 153
DVVMTQTPLS LPVTLGEPAS ISCRSSQSIV HSNGNTFLEW YLKKPGQSPK LLIYKVSSRF   60
SGVPDRFSGS GSGTDFTLKI SRVEAEDVGV YYCFQGSHIP WTFGGGTKLE IK          112

SEQ ID NO: 154                moltype = AA  length = 118
FEATURE                       Location/Qualifiers
REGION                        1..118
                              note = description of the artificial sequence: amino acid
                                sequence of hzKM5907 HV1
source                        1..118
                              mol_type = protein
                              organism = synthetic construct
SEQUENCE: 154
EVQLLESGGG LVQPGGSLRL SCAASGFTFS RYGMSWVRQA PGKRLEWVSS ISATFTYTYY   60
TDNVKGRFTI SRDNSKNTLY LQMNSLRAED TAVYYCAKQD NYAWFDSWGQ GTLVTVSS   118

SEQ ID NO: 155                moltype = AA  length = 118
FEATURE                       Location/Qualifiers
REGION                        1..118
                              note = description of the artificial sequence: amino acid
                                sequence of hzKM5907 HV2a
source                        1..118
                              mol_type = protein
                              organism = synthetic construct
SEQUENCE: 155
EVQLLESGGG LVQPGGSLRL SCAASGFTFS RYGMSWVRQA PGKRLEWVSS ISATFTYTYY   60
TDNVKGRFTI SRDNSKNTLY LQMNSLRAED TAVYYCARQD NYAWFDSWGQ GTLVTVSS   118

SEQ ID NO: 156                moltype = AA  length = 118
FEATURE                       Location/Qualifiers
REGION                        1..118
                              note = description of the artificial sequence: amino acid
                                sequence of hzKM5907 HV2b
source                        1..118
                              mol_type = protein
                              organism = synthetic construct
SEQUENCE: 156
EVQLLESGGG LVQPGGSLRL SCAASGFTFS RYGMSWVRQA PGKGLEWVAS ISATFTYTYY   60
TDNVKGRFTI SRDNSKNTLY LQMNSLRAED TAVYYCARQD NYAWFDSWGQ GTLVTVSS   118
```

-continued

```
SEQ ID NO: 157               moltype = AA   length = 118
FEATURE                      Location/Qualifiers
REGION                       1..118
                             note = description of the artificial sequence: amino acid
                              sequence of hzKM5907 HV3a
source                       1..118
                             mol_type = protein
                             organism = synthetic construct
SEQUENCE: 157
EVQLLESGGG LVQPGGSLRL SCAASGFTFS RYGMSWVRQA PGKRLEWVSS ISATFTYTYY   60
TDNVKGRFTI SRDNSKNTLY LQMNSLRAED TGVYYCARQD NYAWFDSWGQ GTLVTVSS    118

SEQ ID NO: 158               moltype = AA   length = 118
FEATURE                      Location/Qualifiers
REGION                       1..118
                             note = description of the artificial sequence: amino acid
                              sequence of hzKM5907 HV3b
source                       1..118
                             mol_type = protein
                             organism = synthetic construct
SEQUENCE: 158
EVQLLESGGG LVQPGGSLRL SCAASGFTFS RYGMSWVRQA PGKRLEWVAS ISATFTYTYY   60
TDNVKGRFTI SRDNSKNTLY LQMNSLRAED TAVYYCTKQD NYAWFDSWGQ GTLVTVSS    118

SEQ ID NO: 159               moltype = AA   length = 118
FEATURE                      Location/Qualifiers
REGION                       1..118
                             note = description of the artificial sequence: amino acid
                              sequence of hzKM5907 HV3c
source                       1..118
                             mol_type = protein
                             organism = synthetic construct
SEQUENCE: 159
EVQLLESGGG LVQPGGSLRL SCAASGFTFS RYGMSWVRQA PGKRLEWVSS ISATFTYTYY   60
TDNVKGRFTI SRDNSKNTLY LQMNSLRAED TGVYYCTKQD NYAWFDSWGQ GTLVTVSS    118

SEQ ID NO: 160               moltype = AA   length = 118
FEATURE                      Location/Qualifiers
REGION                       1..118
                             note = description of the artificial sequence: amino acid
                              sequence of hzKM5907 HV4
source                       1..118
                             mol_type = protein
                             organism = synthetic construct
SEQUENCE: 160
EVQLLESGGG LVQPGGSLRL SCAASGFTFS RYGMSWVRQA PGKGLEWVAS ISATFTYTYY   60
TDNVKGRFTI SRDNSKNTLY LQMNSLRAED TGVYYCTRQD NYAWFDSWGQ GTLVTVSS    118

SEQ ID NO: 161               moltype = AA   length = 118
FEATURE                      Location/Qualifiers
REGION                       1..118
                             note = description of the artificial sequence: amino acid
                              sequence of hzKM5907 HV7
source                       1..118
                             mol_type = protein
                             organism = synthetic construct
SEQUENCE: 161
EVQVLESGGG LVQPGGSLRL SCAASGFTFS RYGMSWVRQA PGKRLEWVAS ISATFTYTYY   60
TDNVKGRFTI SRDNSKNTLY LQMNSLRAED TGMYYCTRQD NYAWFDSWGQ GTLVTVSS    118

SEQ ID NO: 162               moltype = AA   length = 106
FEATURE                      Location/Qualifiers
REGION                       1..106
                             note = description of the artificial sequence: amino acid
                              sequence of hzKM5916 LV0
source                       1..106
                             mol_type = protein
                             organism = synthetic construct
SEQUENCE: 162
DIQMTQSPSS LSASVGDRVT ITCKASQDIN KYIAWYQQKP GKAPKLLIHY TSSLQPGVPS   60
RFSGSGSGTD FSFTISSLQP EDLATYYCLQ YDYTMTFGGG TKVEIK              106

SEQ ID NO: 163               moltype = AA   length = 121
FEATURE                      Location/Qualifiers
REGION                       1..121
                             note = description of the artificial sequence: amino acid
                              sequence of hzKM5916 HV0
source                       1..121
```

-continued

```
                              mol_type = protein
                              organism = synthetic construct
SEQUENCE: 163
QVQLQESGGG LVKPGGSLKL SCAASGFTFS RNAMSWVRQT PDKRLEWVAY ISSGSDYIYY  60
ADTVKGRFTI SRDNAKNTLY LQMSSLKSED TAMYYCARFS YGYGKNAPDY WGQGTMVTVS  120
S                                                                  121

SEQ ID NO: 164        moltype = AA   length = 106
FEATURE               Location/Qualifiers
REGION                1..106
                      note = description of the artificial sequence: amino acid
                       sequence of hzKM5916 LV2
source                1..106
                      mol_type = protein
                      organism = synthetic construct
SEQUENCE: 164
DIQMTQSPSS LSASVGDRVT ITCKASQDIN KYIAWYQHKP GKGPKLLIHY TSSLQPGVPS  60
RFSGSGSGTD FSFTISSLQP EDLATYYCLQ YDYTMTFGGG TKVEIK               106

SEQ ID NO: 165        moltype = AA   length = 121
FEATURE               Location/Qualifiers
REGION                1..121
                      note = description of the artificial sequence: amino acid
                       sequence of hzKM5916 HV1
source                1..121
                      mol_type = protein
                      organism = synthetic construct
SEQUENCE: 165
QVQLQESGGG LVKPGGSLKL SCAASGFTFS RNAMSWVRQT PDKRLEWVAY ISSGSDYIYY  60
ADTVKGRFTI SRDNAKNTLY LQMSSLKSED TAMYYCTRFS YGYGKNAPDY WGQGTMVTVS  120
S                                                                  121

SEQ ID NO: 166        moltype = AA   length = 121
FEATURE               Location/Qualifiers
REGION                1..121
                      note = description of the artificial sequence: amino acid
                       sequence of hzKM5916 HV3
source                1..121
                      mol_type = protein
                      organism = synthetic construct
SEQUENCE: 166
QVQLQESGGG LVKPGGSLKL SCAASGFTFS RNAMSWVRQT PEKRLEWVAY ISSGSDYIYY  60
ADTVKGRFTI SRDNAKNTLY LQMSSLRSED TAMYYCTRFS YGYGKNAPDY WGQGTMVTVS  120
S                                                                  121

SEQ ID NO: 167        moltype = AA   length = 112
FEATURE               Location/Qualifiers
REGION                1..112
                      note = description of the artificial sequence: amino acid
                       sequence of hzDNP1 VL
source                1..112
                      mol_type = protein
                      organism = synthetic construct
SEQUENCE: 167
DIVMTQSPLS LPVTPGEPAS ISCRSSQSLA NSYGNTYLSW YLQKPGQSPQ LLIYRVSNTF  60
SGVPDRFSGS GSGTDFTLKI SRVEAEDVGV YYCLQGTHQP YTFGQGTKVE IK          112

SEQ ID NO: 168        moltype = AA   length = 117
FEATURE               Location/Qualifiers
REGION                1..117
                      note = description of the artificial sequence: amino acid
                       sequence of hzDNP1 VH
source                1..117
                      mol_type = protein
                      organism = synthetic construct
SEQUENCE: 168
QVQLQESGPG LVKPSQTLSL TCTVSGGSVS SGYWNWIRQP PGKGLEWIGY ISYSGSTYYN  60
PSLKSRVTIS VDTSKNQFSL KLSSVTAADT AVYYCARWGV RHYFDYWGQG TLVTVSS      117

SEQ ID NO: 169        moltype = AA   length = 355
FEATURE               Location/Qualifiers
source                1..355
                      mol_type = protein
                      organism = Homo sapiens
SEQUENCE: 169
METPNTTEDY DTTTEFDYGD ATPCQKVNER AFGAQLLPPL YSLVFVIGLV GNILVVLVLV  60
QYKRLKNMTS IYLLNLAISD LLFLFTLPFW IDYKLKDDWV FGDAMCKILS GFYYTGLYSE  120
IFFIILLTID RYLAIVHAVF ALRARTVTFG VITSIIIWAL AILASMPGLY FSKTQWEFTH  180
HTCSLHFPHE SLREWKLFQA LKLNLFGLVL PLLVMIICYT GIIKILLRRP NEKKSKAVRL  240
```

-continued

```
IFVIMIIFFL FWTPYNLTIL ISVFQDFLFT HECEQSRHLD LAVQVTEVIA YTHCCVNPVI    300
YAFVGERFRK YLRQLFHRRV AVHLVKWLPF LSVDRLERVS STSPSTGEHE LSAGF          355

SEQ ID NO: 170          moltype = AA  length = 355
FEATURE                 Location/Qualifiers
source                  1..355
                        mol_type = protein
                        organism = Mus musculus
SEQUENCE: 170
MEISDFTEAY PTTTEFDYGD STPCQKTAVR AFGAGLLPPL YSLVFIIGVV GNVLVILVLM     60
QHRRLQSMTS IYLFNLAVSD LVFLFTLPFW IDYKLKDDWI FGDAMCKLLS GFYYLGLYSE    120
IFFIILLTID RYLAIVHAVF ALRARTVTFG IITSIITWAL AILASMPALY FFKAQWEFTH    180
RTCSPHFPYK SLKQWKRFQA LKLNLLGLIL PLLVMIICYA GIIRILLRRP SEKKVKAVRL    240
IFAITLLFFL LWTPYNLSVF VSAFQDVLFT NQCEQSKQLD LAMQVTEVIA YTHCCVNPII    300
YVFVGERFWK YLRQLFQRHV AIPLAKWLPF LSVDQLERTS SISPSTGEHE LSAGF          355

SEQ ID NO: 171          moltype = AA  length = 137
FEATURE                 Location/Qualifiers
source                  1..137
                        mol_type = protein
                        organism = Mus musculus
SEQUENCE: 171
MNFGLSLIFL ALILKGVQCE VQVVESGGNL VKPGGSLKLS CSASGFTFSR YGMSWVRQTP     60
DKRLEWVASI SATFTYTYYT DNVKGRFTIS RDNAKNTLYL QMSSLRSEDT GMYYCTRQDN    120
YAWFDSWGQG TLVTVSA                                                    137

SEQ ID NO: 172          moltype = AA  length = 131
FEATURE                 Location/Qualifiers
source                  1..131
                        mol_type = protein
                        organism = Mus musculus
SEQUENCE: 172
MKLPVRLLVL MFWIPVSNSD VLMTQTPLSL PVSLGDQVSI SCRSSQSIVH SNGNTFLEWY     60
LKKPGQSPKL LIYKVSSRFS GVPDRFSGSG SGTDFTLKIR RVEADDLGVY YCFQGSHIPW    120
TFGGGTNLEI K                                                          131

SEQ ID NO: 173          moltype = AA  length = 138
FEATURE                 Location/Qualifiers
source                  1..138
                        mol_type = protein
                        organism = Mus musculus
SEQUENCE: 173
MAVLVLLFCL VTFPSCVLSQ VQLKQSGPGL VQPSQSLSIT CTVSGFSLNN YGVHWVRQPP     60
GKGLEWLGVI WSAGTTVYNA AFISRLSISK DDSKSQVFFK MNSLQAGDTA IYYCAKDGSR    120
YYTAMDYWGQ GTSVTVSS                                                   138

SEQ ID NO: 174          moltype = AA  length = 131
FEATURE                 Location/Qualifiers
source                  1..131
                        mol_type = protein
                        organism = Mus musculus
SEQUENCE: 174
MKLPVRLLVL MFWIPATSSD VVMTQTPRSL PVSLGDQASI SCRSRQSLIH SNGITFLHWY     60
LQKAGQSPKL LIYKVSNRFS GVPDRFSGSG SGTDFTLRIS RVEAEDLGVY FCSQGTHVPP    120
TFGGGTKLEI K                                                          131

SEQ ID NO: 175          moltype = AA  length = 138
FEATURE                 Location/Qualifiers
source                  1..138
                        mol_type = protein
                        organism = Mus musculus
SEQUENCE: 175
MNFGLSLIFL ALILKGVQCE VQLVESGGDL VKPGGSLKLS CAASGFTLSN YGMSWVRQTP     60
DKRLEWVASI SIGNYIYYLD SVKGRFTIYR DNAKNTLFLQ MRSLKSEDTA MYHCARQGND    120
YDWFTYWGQG TLVTVSAA                                                   138

SEQ ID NO: 176          moltype = AA  length = 131
FEATURE                 Location/Qualifiers
source                  1..131
                        mol_type = protein
                        organism = Mus musculus
SEQUENCE: 176
MKLPVRLLVL MFWIPVSSSD VLMTQTPLSL PVSLGDQASI SCRSSQSVVH TNGNTYLEWY     60
LQKPGQSPKL LIYKVSNRFS GVPDRFSGSG SGTDFTLKIN RVEAEDLGVY YCFQGSHLPW    120
TFGGGTKLEI K                                                          131

SEQ ID NO: 177          moltype = AA  length = 140
FEATURE                 Location/Qualifiers
source                  1..140
```

```
                        mol_type = protein
                        organism = Mus musculus
SEQUENCE: 177
MNFGLRLIFL VLTLKGVQCD VKLVESGEGL VKPGGSLKLS CAASGFTFSR NAMSWVRQTP    60
EKRMEWVAYI SSGGDYIYYA DTVKGRFTVS RDNARNTLYL RMSSLKSEDT AMYYCTRFSY   120
GYAKNALDYW GQGTSVTVSS                                               140

SEQ ID NO: 178          moltype = AA  length = 126
FEATURE                 Location/Qualifiers
source                  1..126
                        mol_type = protein
                        organism = Mus musculus
SEQUENCE: 178
MRPSIQFLGL LLFWLHGAQC DIQMTQSPSS LSASLGGKVT ITCKASQDIK KYIAWYQHKP    60
GKGPRLLIHY TSSLQPGIPS RFSGSGSGRD YSFSISNLEP EDIATYYCLQ YDYLMTFGGG   120
TKLEIK                                                              126

SEQ ID NO: 179          moltype = AA  length = 138
FEATURE                 Location/Qualifiers
source                  1..138
                        mol_type = protein
                        organism = Mus musculus
SEQUENCE: 179
MNFGLSLIFL ALILKGVQCE VQLVESGGDL VKPGGSLKLS CAASGFTFSN YGMSWVRQTP    60
DKRLEWVASI SIGSYIYYLD SVKGRFTIYR DNAKNTLFLQ MRSLKSEDTA MYHCARQGND   120
YDWFAYWGQG TLVTVSAA                                                 138

SEQ ID NO: 180          moltype = AA  length = 131
FEATURE                 Location/Qualifiers
source                  1..131
                        mol_type = protein
                        organism = Mus musculus
SEQUENCE: 180
MKLPVRLLVL MFWIPASSSD VLMTQTPLSL PVSLGDQASI SCRSSQNIVH TNGNTYLEWY    60
LQKPGQSPKL LIYKVSNRFS GVPDRFSGSG SGTDFTLKIS RVEAEDLGVY YCFQGSHLPW   120
TFGGGTKLEI K                                                        131

SEQ ID NO: 181          moltype = AA  length = 140
FEATURE                 Location/Qualifiers
source                  1..140
                        mol_type = protein
                        organism = Mus musculus
SEQUENCE: 181
MNFGLRLILL VLTLKGVQCD VKLVESGEGL VKPGGSLKLS CAASGFTFSR NAMSWVRQTP    60
EKRLEWVAYI SSGSDYIYYA DTVKGRFTVS RDNARNTLYL QMTSLRSEDT AMYFCTRFSY   120
GYGKNAPDYW GQGTSVTVSS                                               140

SEQ ID NO: 182          moltype = AA  length = 126
FEATURE                 Location/Qualifiers
source                  1..126
                        mol_type = protein
                        organism = Mus musculus
SEQUENCE: 182
MRPSIQFLGL LLFWLHGTQC DIQMTQSPSS LSASLGGKVT ITCKASQDIN KYIAWYQHKP    60
GQGPRLLIHY TSSLQPGIPS RFSGSGSGRD YSFSISNLEP EDIATYYCLQ YDYTMTFGGG   120
TKLEIR                                                              126

SEQ ID NO: 183          moltype = AA  length = 143
FEATURE                 Location/Qualifiers
source                  1..143
                        mol_type = protein
                        organism = Mus musculus
SEQUENCE: 183
MAVLALLLCL VTFPSCALSQ VQLKESGPGL VAPSQSLSIT CTVSGFSLPR YTITWVRQPP    60
GKGLEWLGLI RTGGGTIYNS ALKSRLSISK DNSKSQVFLK MNSLQSGDTA RYYCARNGAY   120
YSKSGSYWYF DVWGTGTTVT VSS                                           143

SEQ ID NO: 184          moltype = AA  length = 128
FEATURE                 Location/Qualifiers
source                  1..128
                        mol_type = protein
                        organism = Mus musculus
SEQUENCE: 184
MDFQVQIFSF LLISASVIMS RGQIVLTQSP AIMSVSLGEE ITLTCSASSS VSYMHWYQQK    60
SGTSPKLLIY STSNLASGVP SRFSGSGSGT FYSLTISSVE AEDAADYYCH QWSSHPCTFG   120
GGTKLEIK                                                            128

SEQ ID NO: 185          moltype = AA  length = 139
FEATURE                 Location/Qualifiers
```

-continued

```
source                    1..139
                          mol_type = protein
                          organism = Mus musculus
SEQUENCE: 185
MDSRLNLVFL VLILKGVQCE VQLVESGGGL VKPGGSLKLS CAASGFTLRD FGMHWVRQVP  60
EKGLEWVAYI SSGRTAISYV DKVKGRFTIS RDNAKNTLFL QMTSLRSEDT AMYYCARRPY  120
SKSYAMDYWG QGTSVTVSS                                                139

SEQ ID NO: 186            moltype = AA   length = 132
FEATURE                   Location/Qualifiers
source                    1..132
                          mol_type = protein
                          organism = Mus musculus
SEQUENCE: 186
MKLPVLLVVL LLFTSPASSS DVVLTQTPLS LPVNIGDQAS ISCKSIKSLL NSDGFTYLDW  60
YLQKPGQSPQ LLIYLVSNRF SGVPDRFSGS GSGTDFTLKI RRVEAEDLGV YYCFQSNYLP  120
LTFGAGTKLE LK                                                       132

SEQ ID NO: 187            moltype = AA   length = 143
FEATURE                   Location/Qualifiers
source                    1..143
                          mol_type = protein
                          organism = Mus musculus
SEQUENCE: 187
MAVLALLLCL VTFPSCALSQ VQLKESGPGL VAPSQSLSIT CTVSGFSLAR YTITWVRQPP  60
GKGLEWLGLI RTGGGTIYNS ALKSRLSISK DNSKSQVFLK MNSLQSGDTA RYYCARNGAY  120
YSNSGSYWYF DVWGTGTTVT VSS                                           143

SEQ ID NO: 188            moltype = AA   length = 128
FEATURE                   Location/Qualifiers
source                    1..128
                          mol_type = protein
                          organism = Mus musculus
SEQUENCE: 188
MDFQVQIFSF LLISASVMMS RGQIVLTQSP AIMSASLGEE ITLTCSASSS VTYMHWYQQK  60
SGTSPKLLIY STSNLASGVP SRFSGSGSGT FYSLTISSVE AEDAADYYCH QWSSHPCTFG  120
GGAKLEIK                                                            128
```

The invention claimed is:

1. A method for diagnosing a CC chemokine receptor 1 (CCR1)-related cancer in a human subject, comprising:

detecting CCR1 in a biological sample of the human subject with a monoclonal antibody or antibody fragment thereof, whereby the subject is diagnosed as having the CCR1-related cancer when CCR1 is detected, wherein the monoclonal antibody or antibody fragment thereof binds to an extracellular region of a human CCR1 and inhibits activation of the human CCR1 by a human CC chemokine ligand 15 (CCL15), and wherein the monoclonal antibody is any one antibody selected from the following (a) to (n);

(a) an antibody in which the CDRs 1 to 3 of VH comprise the amino acid sequences of SEQ ID NOs: 75, 76, and 77, respectively, and in which the CDRs 1 to 3 of VL comprise the amino acid sequences of SEQ ID NOs: 78, 79, and 80, respectively, (b) an antibody in which the CDR1 of VH comprises the amino acid sequence of SEQ ID NO: 75, the CDR2 of VH comprises the amino acid sequence of SEQ ID NO: 76 or the amino acid sequence in which at least one modification selected from modifications of substituting Ile at a position 2 with Thr, Val at a position 9 with Ala, Phe at a position 14 with Ala, and Ile at a position 15 with Ala is introduced in the amino acid sequence of SEQ ID NO: 76, and the CDR3 of VH comprises the amino acid sequence of SEQ ID NO: 77 or the amino acid sequence in which at least one of modifications of substituting Tyr at a position 5 with Ala and Thr at a position 7 with Ala is introduced in the amino acid sequence of SEQ ID NO: 77, and in which the CDR1 of VL comprises the amino acid sequence of SEQ ID NO: 126 or the amino acid sequence in which a modification of substituting Phe at a position 15 with Ala is introduced in the amino acid sequence SEQ ID NO: 126, the CDR2 of VL comprises the amino acid sequence of SEQ ID NO: 127 or the amino acid sequence in which at least one of modifications of substituting Val at a position 2 with Ile, and Arg at a position 5 with Lys is introduced in the amino acid sequence of SEQ ID NO: 127, and the CDR3 of VL comprises the amino acid sequence of SEQ ID NO: 128, (c) an antibody in which the CDRs 1 to 3 of VH comprise the amino acid sequences of SEQ ID NOs: 75, 131, and 77, respectively, and in which the CDRs 1 to 3 of VL comprise the amino acid sequences of SEQ ID NOs: 126, 134, and 128, respectively, (d) an antibody in which VH comprises the amino acid sequence of SEQ ID NO: 53, and in which VL comprises the amino acid sequence of SEQ ID NO: 54, (e) an antibody in which VH comprises the amino acid sequence of SEQ ID NO: 130, and in which VL comprises the amino acid sequence of SEQ ID NO: 133, (f) an antibody in which VH comprises the amino acid sequence of SEQ ID NO: 136 or the amino acid sequence in which at least one of amino acid modifications of substituting Glu at a position 6 with Gln, Leu at a position 20 with Ile, Gly at a position 27 with Phe, Val at a position 29 with Leu, Ser at a position 30 with Asn, Ile at a position 37 with Val, Ile at a position 48 with Leu, Val at a position 67 with Leu, Val at a position 71 with Lys, Thr at a position 73 with Asp, Asn at a position 76 with Ser, Phe at a position 78 with Val, Leu at a position 80 with Phe, Leu at a position 82 with Met, Val at a position 85 with Leu, Val at a position 92 with Ile, and Arg at a position 97 with Lys is introduced in the amino acid sequence of SEQ ID NO: 136, and in which VL comprises the amino acid sequence of SEQ ID NO: 135 or the amino acid sequence in which at least one of amino acid modifications of substituting Ile at a position 2 with Val, Pro at a position 15 with Leu, Gln at a position 50 with Lys, Tyr at a position 92 with Phe, and Val at a position 109 with Leu is introduced in the amino acid sequence of SEQ ID NO: 135, (g) an antibody in which VH comprises the amino acid sequence of SEQ ID NO: 144, and in which VL comprises the amino acid sequence of SEQ ID NO: 135, (h) an antibody in which VH comprises the amino acid sequence of SEQ ID NO: 144, and in which VL comprises the amino acid sequence of SEQ ID NO: 137, (i) an antibody in which VH comprises the amino acid sequence of SEQ ID NO: 144, and in which VL comprises the amino acid sequence of SEQ ID NO: 138, (j) an antibody in which VH comprises the amino acid sequence of SEQ ID NO: 144, and in which VL comprises the amino acid sequence of SEQ ID NO: 139, (k) an antibody in which VH comprises the amino acid sequence of SEQ ID NO: 144, and in which VL comprises the amino acid sequence of SEQ ID NO: 140, (l) an antibody in which VH comprises the amino acid sequence of SEQ ID NO: 144, and in which VL comprises the amino acid sequence of SEQ ID NO: 141, (m) an antibody in which VH comprises the amino acid sequence of SEQ ID NO: 144, and in which VL comprises the amino acid sequence of SEQ ID NO: 142, and (n) an antibody in which VH comprises the amino acid sequence of SEQ ID NO: 143, and in which VL comprises the amino acid sequence of SEQ ID NO: 142.

2. A method for treating a CCR1-related cancer in a human subject having CCR1-related cancer, comprising:

administering to the human subject a therapeutically-effective amount of a monoclonal antibody or antibody fragment thereof, thereby treating the CCR1-related cancer in the subject, wherein the monoclonal antibody or antibody fragment thereof binds to an extracellular region of a human CCR1 and inhibits activation of the human CCR1 by a human CC chemokine ligand 15 (CCL15), and wherein the monoclonal antibody is any one antibody selected from the following (a) to (n);

(a) an antibody in which the CDRs 1 to 3 of VH comprise the amino acid sequences of SEQ ID NOs: 75, 76, and 77, respectively, and in which the CDRs 1 to 3 of VL comprise the amino acid sequences of SEQ ID NOs: 78, 79, and 80, respectively, (b) an antibody in which the CDR1 of VH comprises the amino acid sequence of SEQ ID NO: 75, the CDR2 of VH comprises the amino acid sequence of SEQ ID NO: 76 or the amino acid sequence in which at least one modification selected from modifications of substituting Ile at a position 2 with Thr, Val at a position 9 with Ala, Phe at a position 14 with Ala, and Ile at a position 15 with Ala is introduced in the amino acid sequence of SEQ ID NO: 76, and the CDR3 of VH comprises the amino acid sequence of SEQ ID NO: 77 or the amino acid sequence in which at least one of modifications of substituting Tyr at a position 5 with Ala and Thr at a position 7 with Ala is introduced in the amino acid sequence of SEQ ID NO: 77, and in which the CDR1 of VL comprises the amino acid sequence of SEQ ID NO: 126 or the amino acid sequence in which a modification of substituting Phe at a position 15 with Ala is introduced in the amino acid sequence SEQ ID NO: 126, the CDR2 of VL comprises the amino acid sequence of SEQ ID NO: 127 or the amino acid sequence in which at least one of modifications of substituting Val at a position 2 with Ile, and Arg at a position 5 with Lys is introduced in the amino acid sequence of SEQ ID NO: 127, and the CDR3 of VL comprises the amino acid sequence of SEQ ID NO: 128, (c) an antibody in which the CDRs 1 to 3 of VH comprise the amino acid sequences of SEQ ID NOs: 75, 131, and 77, respectively, and in which the CDRs 1 to 3 of VL comprise the amino acid sequences of SEQ ID NOs: 126, 134, and 128, respectively, (d) an antibody in which VH comprises the amino acid sequence of SEQ ID NO: 53, and in which VL comprises the amino acid sequence of SEQ ID NO: 54, (e) an antibody in which VH comprises the amino acid sequence of SEQ ID NO: 130, and in which VL comprises the amino acid sequence of SEQ ID NO: 133, (f) an antibody in which VH comprises the amino acid sequence of SEQ ID NO: 136 or the amino acid sequence in which at least one of amino acid modifications of substituting Glu at a position 6 with Gln, Leu at a position 20 with Ile, Gly at a position 27 with Phe, Val at a position 29 with Leu, Ser at a position 30 with Asn, Ile at a position 37 with Val, Ile at a position 48 with Leu, Val at a position 67 with Leu, Val at a position 71 with Lys, Thr at a position 73 with Asp, Asn at a position 76 with Ser, Phe at a position 78 with Val, Leu at a position 80 with Phe, Leu at a position 82 with Met, Val at a position 85 with Leu, Val at a position 92 with Ile, and Arg at a position 97 with Lys is introduced in the amino acid sequence of SEQ ID NO: 136, and in which VL comprises the amino acid sequence of SEQ ID NO: 135 or the amino acid sequence in which at least one of amino acid modifications of substituting Ile at a position 2 with Val, Pro at a position 15 with Leu, Gln at a position 50 with Lys, Tyr at a position 92 with Phe, and Val at a position 109 with Leu is introduced in the amino acid sequence of SEQ ID NO: 135, (g) an antibody in which VH comprises the amino acid sequence of SEQ ID NO: 144, and in which VL comprises the amino acid sequence of SEQ ID NO: 135, (h) an antibody in which VH comprises the amino acid sequence of SEQ ID NO: 144, and in which VL comprises the amino acid sequence of SEQ ID NO: 137, (i) an antibody in which VH comprises the amino acid sequence of SEQ ID NO: 144, and in which VL comprises the amino acid sequence of SEQ ID NO: 138, (j) an antibody in which VH comprises the amino acid sequence of SEQ ID NO: 144, and in which VL comprises the amino acid sequence of SEQ ID NO: 139, (k) an antibody in which VH comprises the amino acid sequence of SEQ ID NO: 144, and in which VL comprises the amino acid sequence of SEQ ID NO: 140, (l) an antibody in which VH comprises the amino acid sequence of SEQ ID NO: 144, and in which VL comprises the amino acid sequence of SEQ ID NO: 141, (m) an antibody in which VH comprises the amino acid sequence of SEQ ID NO: 144, and in which VL comprises the amino acid sequence of SEQ ID NO: 142, and (n) an antibody in which VH comprises the amino acid sequence of SEQ ID NO: 143, and in which VL comprises the amino acid sequence of SEQ ID NO: 142.

3. The method of claim 1, wherein the monoclonal antibody is any one antibody selected from the following (a) to (c):

(a) an antibody in which the CDRs 1 to 3 of VH comprise the amino acid sequences of SEQ ID NOs: 75, 76, and 77, respectively, and in which the CDRs 1 to 3 of VL comprise the amino acid sequences of SEQ ID NOs: 78, 79, and 80, respectively, (b) an antibody in which the CDR1 of VH comprises the amino acid sequence of SEQ ID NO: 75, the CDR2 of VH comprises the amino acid sequence of SEQ ID NO: 76 or the amino acid sequence in which at least one modification selected from modifications of substituting Ile at a position 2 with Thr, Val at a position 9 with Ala, Phe at a position 14 with Ala, and Ile at a position 15 with Ala is introduced in the amino acid sequence of SEQ ID NO: 76, and the CDR3 of VH comprises the amino acid sequence of SEQ ID NO: 77 or the amino acid sequence in which at least one of modifications of substituting Tyr at a position 5 with Ala and Thr at a position 7 with Ala is introduced in the amino acid sequence of SEQ ID NO: 77, and in which the CDR1 of VL comprises the amino acid sequence of SEQ ID NO: 126 or the amino acid sequence in which a modification of substituting Phe at a position 15 with Ala is introduced in the amino acid sequence SEQ ID NO: 126, the CDR2 of VL comprises the amino acid sequence of SEQ ID NO: 127 or the amino acid sequence in which at least one of modifications of substituting Val at a position 2 with Ile, and Arg at a position 5 with Lys is introduced in the amino acid sequence of SEQ ID NO: 127, and the CDR3 of VL comprises the amino acid sequence of SEQ ID NO: 128, and (c) an antibody in which the CDRs 1 to 3 of VH comprise the amino acid sequences of SEQ ID NOs: 75, 131, and 77, respectively, and in which the CDRs 1 to 3 of VL comprise the amino acid sequences of SEQ ID NOs: 126, 134, and 128, respectively.

4. The method of claim 2, wherein the monoclonal antibody is any one antibody selected from the following (a) to (c):

(a) an antibody in which the CDRs 1 to 3 of VH comprise the amino acid sequences of SEQ ID NOs: 75, 76, and 77, respectively, and in which the CDRs 1 to 3 of VL comprise the amino acid sequences of SEQ ID NOs: 78, 79, and 80, respectively, (b) an antibody in which the CDR1 of VH comprises the amino acid sequence of SEQ ID NO: 75, the CDR2 of VH comprises the amino acid sequence of SEQ ID NO: 76 or the amino acid sequence in which at least one modification selected from modifications of substituting Ile at a position 2 with Thr, Val at a position 9 with Ala, Phe at a position 14 with Ala, and Ile at a position 15 with Ala is introduced in the amino acid sequence of SEQ ID NO: 76, and the CDR3 of VH comprises the amino acid sequence of SEQ ID NO: 77 or the amino acid sequence in which at least one of modifications of substituting Tyr at a position 5 with Ala and Thr at a position 7 with Ala is introduced in the amino acid sequence of SEQ ID NO: 77, and in which the CDR1 of VL comprises the amino acid sequence of SEQ ID NO: 126 or the amino acid sequence in which a modification of substituting Phe at a position 15 with Ala is introduced in the amino acid sequence SEQ ID NO: 126, the CDR2 of VL comprises the amino acid sequence of SEQ ID NO: 127 or the amino acid sequence in which at least one of modifications of substituting Val at a position 2 with Ile, and Arg at a position 5 with Lys is introduced in the amino acid sequence of SEQ ID NO: 127, and the CDR3 of VL comprises the amino acid sequence of SEQ ID NO: 128, and (c) an antibody in which the CDRs 1 to 3 of VH comprise the amino acid sequences of SEQ ID NOs: 75, 131, and 77, respectively, and in which the CDRs 1 to 3 of VL comprise the amino acid sequences of SEQ ID NOs: 126, 134, and 128, respectively.

5. The method of claim 1, wherein the monoclonal antibody is any one antibody selected from the following (d) or (e):

(d) an antibody in which VH comprises the amino acid sequence of SEQ ID NO: 53, and in which VL comprises the amino acid sequence of SEQ ID NO: 54, and (e) an antibody in which VH comprises the amino acid sequence of SEQ ID NO: 130, and in which VL comprises the amino acid sequence of SEQ ID NO: 133.

6. The method of claim 2, wherein the monoclonal antibody is any one antibody selected from the following (d) or (e):

(d) an antibody in which VH comprises the amino acid sequence of SEQ ID NO: 53, and in which VL comprises the amino acid sequence of SEQ ID NO: 54, and (e) an antibody in which VH comprises the amino acid sequence of SEQ ID NO: 130, and in which VL comprises the amino acid sequence of SEQ ID NO: 133.

7. The method of claim 1, wherein the monoclonal antibody is the following (f):

(f) an antibody in which VH comprises the amino acid sequence of SEQ ID NO: 136 or the amino acid sequence in which at least one of amino acid modifications of substituting Glu at a position 6 with Gln, Leu at a position 20 with Ile, Gly at a position 27 with Phe, Val at a position 29 with Leu, Ser at a position 30 with Asn, Ile at a position 37 with Val, Ile at a position 48 with Leu, Val at a position 67 with Leu, Val at a position 71 with Lys, Thr at a position 73 with Asp, Asn at a position 76 with Ser, Phe at a position 78 with Val, Leu at a position 80 with Phe, Leu at a position 82 with Met, Val at a position 85 with Leu, Val at a position 92 with Ile, and Arg at a position 97 with Lys is introduced in the amino acid sequence of SEQ ID NO: 136, and in which VL comprises the amino acid sequence of SEQ ID NO: 135 or the amino acid sequence in which at least one of amino acid modifications of substituting Ile at a position 2 with Val, Pro at a position 15 with Leu, Gln at a position 50 with Lys, Tyr at a position 92 with Phe, and Val at a position 109 with Leu is introduced in the amino acid sequence of SEQ ID NO: 135.

8. The method of claim 2, wherein the monoclonal antibody is the following (f):

(f) an antibody in which VH comprises the amino acid sequence of SEQ ID NO: 136 or the amino acid sequence in which at least one of amino acid modifications of substituting Glu at a position 6 with Gln, Leu at a position 20 with Ile, Gly at a position 27 with Phe, Val at a position 29 with Leu, Ser at a position 30 with Asn, Ile at a position 37 with Val, Ile at a position 48 with Leu, Val at a position 67 with Leu, Val at a position 71 with Lys, Thr at a position 73 with Asp, Asn at a position 76 with Ser, Phe at a position 78 with Val, Leu at a position 80 with Phe, Leu at a position 82 with Met, Val at a position 85 with Leu, Val at a position 92 with Ile, and Arg at a position 97 with Lys is introduced in the amino acid sequence of SEQ ID NO: 136, and in which VL comprises the amino acid sequence of SEQ ID NO: 135 or the amino acid sequence in which at least one of amino acid modifications of substituting Ile at a position 2 with Val, Pro at a position 15 with Leu, Gln at a position 50 with Lys, Tyr at a position 92 with Phe, and Val at a position 109 with Leu is introduced in the amino acid sequence of SEQ ID NO: 135.

9. The method of claim 1, wherein the monoclonal antibody is any one antibody selected from the following (g) to (n):

(g) an antibody in which VH comprises the amino acid sequence of SEQ ID NO: 144, and in which VL comprises the amino acid sequence of SEQ ID NO: 135, (h) an antibody in which VH comprises the amino acid sequence of SEQ ID NO: 144, and in which VL comprises the amino acid sequence of SEQ ID NO: 137, (i) an antibody in which VH comprises the amino acid sequence of SEQ ID NO: 144, and in which VL comprises the amino acid sequence of SEQ ID NO: 138, (j) an antibody in which VH comprises the amino acid sequence of SEQ ID NO: 144, and in which VL comprises the amino acid sequence of SEQ ID NO: 139, (k) an antibody in which VH comprises the amino acid sequence of SEQ ID NO: 144, and in which VL comprises the amino acid sequence of SEQ ID NO: 140, (l) an antibody in which VH comprises the amino acid sequence of SEQ ID NO: 144, and in which VL comprises the amino acid sequence of SEQ ID NO: 141, (m) an antibody in which VH comprises the amino acid sequence of SEQ ID NO: 144, and in which VL comprises the amino acid sequence of SEQ ID NO: 142, and (n) an antibody in which VH comprises the amino acid sequence of SEQ ID NO: 143, and in which VL comprises the amino acid sequence of SEQ ID NO: 142.

10. The method of claim 2, wherein the monoclonal antibody is any one antibody selected from the following (g) to (n):

(g) an antibody in which VH comprises the amino acid sequence of SEQ ID NO: 144, and in which VL comprises the amino acid sequence of SEQ ID NO: 135, (h) an antibody in which VH comprises the amino acid sequence of SEQ ID NO: 144, and in which VL comprises the amino acid sequence of SEQ ID NO: 137, (i) an antibody in which VH comprises the amino acid sequence of SEQ ID NO: 144, and in which VL comprises the amino acid sequence of SEQ ID NO: 138, (j) an antibody in which VH comprises the amino acid sequence of SEQ ID NO: 144, and in which VL comprises the amino acid sequence of SEQ ID NO: 139, (k) an antibody in which VH comprises the amino acid sequence of SEQ ID NO: 144, and in which VL comprises the amino acid sequence of SEQ ID NO: 140, (l) an antibody in which VH comprises the amino acid sequence of SEQ ID NO: 144, and in which VL comprises the amino acid sequence of SEQ ID NO: 141, (m) an antibody in which VH comprises the amino acid sequence of SEQ ID NO: 144, and in which VL comprises the amino acid sequence of SEQ ID NO: 142, and (n) an antibody in which VH comprises the amino acid sequence of SEQ ID NO: 143, and in which VL comprises the amino acid sequence of SEQ ID NO: 142.

11. The method of claim 1, wherein the monoclonal antibody is a genetically recombinant antibody.

12. The method of claim 2, wherein the monoclonal antibody is a genetically recombinant antibody.

13. The method of claim 11, wherein the genetically recombinant antibody is any one of genetically recombinant antibodies selected from a human chimeric antibody, a humanized antibody, and a human antibody.

14. The method of claim 12, wherein the genetically recombinant antibody is any one of genetically recombinant antibodies selected from a human chimeric antibody, a humanized antibody, and a human antibody.

15. The method of claim 1, wherein the antibody fragment is any one of antibody fragments selected from Fab, Fab', (Fab')$_2$, a single chain antibody (scFv), a dimerized V region (diabody), a disulfide stabilized V region (dsFv), and a peptide comprising CDR.

16. The method of claim 2, wherein the antibody fragment is any one of antibody fragments selected from Fab, Fab', (Fab')$_2$, a single chain antibody (scFv), a dimerized V region (diabody), a disulfide stabilized V region (dsFv), and a peptide comprising CDR.

* * * * *